United States Patent
Vitti et al.

(12) 
(10) Patent No.: US 12,280,093 B2
(45) Date of Patent: *Apr. 22, 2025

(54) USE OF A VEGF RECEPTOR-BASED FUSION PROTEIN ANTAGONIST TO TREAT NONPROLIFERATIVE DIABETIC RETINOPATHY

(71) Applicant: REGENERON PHARMACEUTICALS, INC., Tarrytown, NY (US)

(72) Inventors: Robert L. Vitti, Old Tappan, NJ (US); Alyson J. Berliner, New York, NY (US); Karen Chu, White Plains, NY (US)

(73) Assignee: REGENRON PHARMACEUTICALS, INC., Tarrytown, NY (US)

( * ) Notice: Subject to any disclaimer, the term of this patent is extended or adjusted under 35 U.S.C. 154(b) by 292 days.

This patent is subject to a terminal disclaimer.

(21) Appl. No.: 17/148,039

(22) Filed: Jan. 13, 2021

(65) Prior Publication Data
US 2021/0205410 A1 Jul. 8, 2021

Related U.S. Application Data

(63) Continuation of application No. 16/204,262, filed on Nov. 29, 2018, now Pat. No. 10,973,879.
(Continued)

(51) Int. Cl.
*C07K 14/71* (2006.01)
*A61K 9/00* (2006.01)
(Continued)

(52) U.S. Cl.
CPC .......... *A61K 38/179* (2013.01); *A61K 9/0019* (2013.01); *A61K 47/65* (2017.08); *A61P 27/02* (2018.01)

(58) Field of Classification Search
None
See application file for complete search history.

(56) References Cited

U.S. PATENT DOCUMENTS 6,171,586 B1 1/2001 Lam et al.
6,833,349 B2 12/2004 Xia et al.
(Continued)

FOREIGN PATENT DOCUMENTS

CA 2480809 10/2003
CN 1304427 C 3/2007
(Continued)

OTHER PUBLICATIONS

Ziemssen et al., Initiation of intravitreal aflibercept injection treatment in patients with diabetic macular edema_ a review of VIVID-DME and VISTA-DME data, Int. J. Retin. Vitr. 2:16, 7 pages, doi.org/10.1186/s40942-016-0041-z, Jul. 11, 2016.*
(Continued)

*Primary Examiner* — Claire Kaufman
(74) *Attorney, Agent, or Firm* — Arnold & Porter Kaye Scholer LLP

(57) ABSTRACT

The present invention provides methods for treating or preventing diabetic retinopathy, e.g., nonproliferative diabetic retinopathy, by sequentially administering multiple doses of a VEGF antagonist to a patient. The methods of the present invention include the administration of a 2 mg aflibercept by intravitreal injection q8 weeks after three or five initial monthly doses (2q8) or 2 mg q16 weeks after three initial monthly doses and one 8-week interval (2q16). Moreover, the present invention provides methods for reversing or halting the progression NPDR to PDR (e.g., such that the DRSS is reduced by 2 or 3 levels) or preventing the occurrence or reoccurrence of a vision threatening
(Continued)

complication by administering aflibercept according to the dosing regimens set forth herein.

33 Claims, 32 Drawing Sheets

Specification includes a Sequence Listing.

Related U.S. Application Data

(60) Provisional application No. 62/748,782, filed on Oct. 22, 2018, provisional application No. 62/644,425, filed on Mar. 17, 2018, provisional application No. 62/593,033, filed on Nov. 30, 2017.

(51) Int. Cl.
  *A61K 38/17* (2006.01)
  *A61K 47/65* (2017.01)
  *A61P 27/02* (2006.01)

(56) References Cited

U.S. PATENT DOCUMENTS

| | | |
|---|---|---|
| 6,897,294 B2 | 5/2005 | Davis-Smyth et al. |
| 7,070,959 B1 | 7/2006 | Papdopoulos et al. |
| 7,087,411 B2 | 8/2006 | Daly et al. |
| 7,300,563 B2 | 11/2007 | Diaddario, Jr. |
| 7,300,653 B2 | 11/2007 | Wiegand et al. |
| 7,303,746 B2 | 12/2007 | Wiegand |
| 7,303,747 B2 | 12/2007 | Wiegand |
| 7,303,748 B2 | 12/2007 | Wiegand |
| 7,306,799 B2 | 12/2007 | Wiegand |
| 7,374,757 B2 | 5/2008 | Papadopoulos et al. |
| 7,374,758 B2 | 5/2008 | Papadopoulos et al. |
| 7,378,095 B2 | 5/2008 | Cao et al. |
| 7,396,664 B2 | 7/2008 | Daly et al. |
| 7,482,002 B2 | 1/2009 | Cedarbaum |
| 7,521,049 B2 | 4/2009 | Wiegand et al. |
| 7,531,173 B2 | 5/2009 | Wiegand et al. |
| 7,608,261 B2 | 10/2009 | Furfine et al. |
| 7,750,138 B2 | 7/2010 | Fang et al. |
| 7,951,585 B2 | 5/2011 | Ke |
| 7,972,598 B2 | 7/2011 | Daly et al. |
| 8,029,791 B2 | 10/2011 | Papadopoulos et al. |
| 8,092,803 B2 | 1/2012 | Furfine et al. |
| 8,216,575 B2 | 7/2012 | Yu |
| 8,343,737 B2 | 1/2013 | Papadopoulos et al. |
| 8,647,842 B2 | 2/2014 | Papadopoulos et al. |
| 9,254,338 B2 | 2/2016 | Yancopoulos |
| 9,657,084 B2 | 5/2017 | Ke et al. |
| 9,669,069 B2 | 6/2017 | Yancopoulos |
| 10,130,681 B2 | 11/2018 | Yancopoulos |
| 10,406,226 B2 | 9/2019 | Dix et al. |
| 10,464,992 B2 | 11/2019 | Furfine et al. |
| 10,828,345 B2 | 11/2020 | Yancopoulos |
| 10,857,205 B2 | 12/2020 | Yancopoulos |
| 10,888,601 B2 | 1/2021 | Yancopoulos |
| 10,925,927 B2* | 2/2021 | Brockmeyer ........ A61K 9/0019 |
| 11,066,458 B2 | 7/2021 | Furfine et al. |
| 11,084,865 B2 | 8/2021 | Furfine et al. |
| 11,253,572 B2 | 2/2022 | Yancopoulos |
| 11,559,564 B2 | 1/2023 | Yancopoulos |
| 11,707,506 B2 | 7/2023 | Yancopoulos |
| 11,707,560 B2 | 7/2023 | Klewinghaus |
| 11,730,794 B2 | 8/2023 | Yancopoulos |
| 2003/0113316 A1 | 6/2003 | Kaisheva et al. |
| 2003/0138417 A1 | 7/2003 | Kaisheva et al. |
| 2003/0171320 A1 | 9/2003 | Guyer |
| 2004/0197324 A1 | 10/2004 | Liu et al. |
| 2004/0213787 A1 | 10/2004 | Sleeman et al. |
| 2004/0266688 A1 | 12/2004 | Nayak |
| 2005/0032699 A1 | 2/2005 | Holash et al. |
| 2005/0163798 A1 | 7/2005 | Papadopoulos et al. |
| 2005/0250203 A1 | 11/2005 | Wiegand |
| 2005/0260203 A1 | 11/2005 | Wiegand et al. |
| 2005/0281822 A1 | 12/2005 | Cedarbaum et al. |
| 2006/0030000 A1 | 2/2006 | Alitalo et al. |
| 2006/0058234 A1 | 3/2006 | Daly et al. |
| 2006/0172944 A1 | 8/2006 | Wiegand et al. |
| 2006/0217311 A1 | 9/2006 | Dix et al. |
| 2007/0190058 A1 | 8/2007 | Shams |
| 2008/0220004 A1 | 9/2008 | Wiegand et al. |
| 2009/0264358 A1 | 10/2009 | Yu |
| 2010/0160233 A1 | 6/2010 | Bissery et al. |
| 2013/0295094 A1 | 11/2013 | Yancopoulos |
| 2016/0130337 A1 | 5/2016 | Gekkieva et al. |
| 2018/0339018 A1 | 11/2018 | Yancopoulos |
| 2019/0046609 A1 | 2/2019 | Yancopoulos |
| 2019/0247463 A1 | 8/2019 | Yancopoulos |
| 2019/0290725 A1 | 9/2019 | Vitti et al. |
| 2019/0343918 A1 | 11/2019 | Graham et al. |
| 2019/0388539 A1 | 12/2019 | Dix et al. |
| 2020/0017572 A1 | 1/2020 | Furfine et al. |

FOREIGN PATENT DOCUMENTS

| | | |
|---|---|---|
| CN | 100502945 C | 6/2009 |
| CN | 100567325 C | 12/2009 |
| CN | 102233132 B | 10/2013 |
| CN | 102380096 B | 4/2014 |
| CN | 103212075 B | 6/2017 |
| CN | 107115294 A | 9/2017 |
| EP | 2663325 | 11/2013 |
| EP | 3222285 A1 | 9/2017 |
| JP | 2010-509369 | 3/2010 |
| KR | 10-2014-0043313 A | 4/2014 |
| WO | WO 97/04801 | 2/1997 |
| WO | WO 2000/075319 | 12/2000 |
| WO | WO2002/060489 | 8/2002 |
| WO | WO 2004/106378 A2 | 12/2004 |
| WO | WO 2005/000895 | 1/2005 |
| WO | WO 2006/047325 | 5/2006 |
| WO | WO 2007/022101 A2 | 2/2007 |
| WO | WO 2008/063932 | 5/2008 |
| WO | WO 2012/097019 | 7/2012 |
| WO | WO 2014/203183 | 12/2014 |
| WO | 1 2016/085750 A1 | 6/2016 |
| WO | WO 2016/203313 | 12/2016 |
| WO | WO 2017/053807 A2 | 3/2017 |
| WO | WO 2017/091706 | 6/2017 |

OTHER PUBLICATIONS

Sobolewska et al., pH of anti-VEGF agents in the human vitreous_ low impact of very different formulations, Int. J. Retin. Vitr. 3:22, 6 pages, DOI 10.1186/s40942-017-0075-xm Jun. 2017.*

Arakawa et al., Biotechnology applications of amino acids in protein purification and formulations, AMino Acids 33:587-605, 2007.*

Singh et al., Clinical and angiographic characterization of choroidal neovascularization in diabetic retinopathy. European J. Ophthalmol. 31(2):584-591. doi:10.1177/1120672120902027, Abstract only, 2021.*

A Phase 3, Double Masked, Randomized Study Of The Efficacy And Safety Of Aflibercept In Patients With Moderately Severe To Severe NPDR—Week 100 Results, slide deck presented by Charles Wycoff, Angiogenesis, Exudation, And Degeneration meeting (Feb. 8, 2020).

Anonymous, "Highlights of Prescribing Information" (Dec. 1, 2016) Retrieved from the Internet: URL: https://web.archive.org/web. 20161206164049if_/https://www.regeneron.com/sites/default/files/ EYLEA_FPI.pdf [retrieved on Mar. 7, 2019] the whole document, p. 1 right column, paragraph 1 2.5; p. 2 left hand column.

Anonymous, "Archive History for NCT02718326", (Aug. 24, 2017) Retrieved from the Internet: URL: https://clinicaltrials. gov.ct2/ history/NCT02718326?V_7=View#StudyPageTop [retrieved on Mar. 7, 2019] the whole document.

Association for Research in Vision and Ophthalmology (ARVO) 2018 Program Summary Book, 2018 Annual Meeting (Apr. 29-May 3, 2018—Honolulu, HI).

(56) References Cited

OTHER PUBLICATIONS

Avitabile et al., "Aflibercept in the treatment of diabetic macular edema: a review and consensus paper." Eur. J. Ophthalmol. 27(6):627-639, published online Oct. 2017.
Brown, Poster: Intravitreal Aflibercept Injection (IAI) for Moderately Severe to Severe Nonproliferative Diabetic Retinopathy (NPDR): The Phase 3 Panorama Study—Association for Research in Vision and Ophthalmology (ARVO) Annual Meeting (Apr. 29-May 3, 2018—Honolulu, HI).
Brown, Abstract PO213: Intravitreal Aflibercept Injection for Moderately Severe to Severe Nonproliferative Diabetic Retinopathy, Annual 2018 Meeting—American Academy of Opthamology (AAO) (Oct. 28, 2018).
Brown, Abstract: Diabetic Retinopathy (NPDR): The Phase 3 Panorama Study, 2018 Annual Meeting—(Association for Research in Vision and Ophthalmology (ARVO) (Apr. 29-May 3, 2018—Honolulu, HI).
Brown et al., Poster: Intravitreal Aflibercept Injection (IAI) for Moderately Severe to Severe Nonproliferative Diabetic Retinopathy (NPDR): The Phase 3 Panorama Study, Assoc. for Res. in Vision and Ophthalmology (ARVO), 2018 Annual Meeting, Honolulu, HI (Apr. 29, 2018-May 3, 2018).
Brown, Abstract: Intravitreal Aflibercept Injection (IAI) for Moderately Severe to Severe Nonproliferative Diabetic Retinopathy (NPDR) (No. 30055820), American Acad. of Opthamol.(AAO), 2018 Annual Meeting, Chicago (Oct. 27-30, 2018).
Brown, Poster: Intravitreal Aflibercept Injection for Moderately Severe to Severe Nonproliferative Diabetic Retinopathy, American Acad. of Opthamol.(AAO), 2018 Annual Meeting, Chicago (Oct. 27-30, 2018).
Brown, Abstract: Intravitreal Aflibercept Injection (IAI) for Moderately Severe to Severe Nonproliferative Diabetic Retinopathy (NPDR): The Phase 3 Panorama Study, Assoc. for Res. in Vision and Ophthalmology (ARVO), 2018 Annual Meeting, Honolulu, HI (Apr. 29, 2018-May 3, 2018).
Brown, Abstract: Treatment of Moderately Severe to Severe Nonproliferative Diabetic Retinopathy with Intravitreal Aflibercept Injection: Results from the Phase 3 Panorama Study, 2019 Macula Society Meeting; Bonita Springs, FL (2018).
Clark, Abstract: Treatment of Moderately Severe to Severe Nonproliferative Diabetic Retinopathy with Intravitreal Aflibercept Injection, American Acad. of Opthamol.(AAO), 2018.
ClinicalTrials.gov, Vascular Endothelial Growth Factor (VEGF) Trap-Eye: Investigation of Efficacy and Safety in Wet Age-Related Macular Degeneration (Amd) (View 2), Retrieved online URL:https://clinicaltrials.gov/di2/show/study/NCT00637377, on Jul. 13, 2020, Dec. 12, 2014.
clinicaltrials.gov Panorama posting NCT02718326 (Mar. 23, 2016).
clinicaltrials.gov Panorama posting NCT02718326 (May 2, 2016).
clinicaltrials.gov Panorama posting NCT02718326 (Oct. 21, 2016).
clinicaltrials.gov Panorama posting NCT02718326 (Nov. 29, 2016).
clinicaltrials.gov Panorama posting NCT02718326 (May 10, 2017).
clinicaltrials.gov Panorama posting NCT02718326 (Jul. 6, 2017).
clinicaltrials.gov Panorama posting NCT02718326 (Aug. 24, 2017).
clinicaltrials.gov Panorama posting NCT02718326 (May 18, 2018).
clinicaltrials.gov Panorama posting NCT02718326 (Nov. 19, 2019).
Cui et al., "Comparison of effectiveness and safety between conbercept and ranibizumab for treatment of neovascular age-related macular degeneration. A retrospective case-controlled non-inferiority multiple center study." Eye, 32:391-399, published online Sep. 2017.
De Oliveira Dias et al., "Fusion proteins for treatment of retinal diseases: aflibercept, ziv-aflibercept, and conbercept," Int. J. Retina Vitreous, 2(3)1-9 (2016).
Do et al., "The Da Vinci study: Phase 2 primary results of VEGF Trap-Eye in patients with diabetic macular edema," Ophthalmol., 118:1819-1825 (2011).
Event Brief of Q1 2016 Regeneron Pharmaceuticals Inc Earnings Call—Final, FD (Fair Disclosure) Wire (May 5, 2016).
Event Brief of Q1 2017 Regeneron Pharmaceuticals Inc Earnings Call—Final, FD (Fair Disclosure) Wire (May 4, 2017).
Event Brief of Q4 2016 Regeneron Pharmaceuticals Inc Earnings Call—Final, FD (Fair Disclosure) Wire (Feb. 9, 2017).
Event Brief of Q4 2018 Regeneron Pharmaceuticals Inc Earnings Call—Final, FD (Fair Disclosure) Wire (Feb. 6, 2019).
Eylea® (aflibercept) Injection Demonstrates Positive Topline Results in Phase 3 Non-Proliferative Diabetic Retinopathy Trial; Expect U.S. regulatory submission for diabetic retinopathy later this year, PR Newswire (Mar. 19, 2018).
Eylea® (aflibercept) Injection Improves Diabetic Retinopathy and Reduces Vision-Threatening Complications in Phase 3 Trial, Global English (Middle East and North Africa Financial Network) (Oct. 25, 2018).
Eylea Prescribing Information (May 2016).
Eylea Prescribing Information (May 2017).
Eylea Prescribing Information (Nov. 2011).
FDA to Review EYLEA (aflibercept) Injection for the Treatment of Diabetic Retinopathy, PR Newswire (Sep. 13, 2018).
Heier et al, Abstract: Intravitreal Aflibercept Injection for Moderately Severe to Severe Nonproliferative Diabetic Retinopathy: The Phase 3 Panorama Study, The Retina Society, 2018 Annual Meeting, San Francisco, CA (Sep. 12-15, 2018).
Heier, Presentation: Intravitreal Aflibercept Injection for Moderately Severe to Severe Nonproliferative Diabetic Retinopathy: The Phase 3 Panorama Study, Retina Society Annual Meeting (2018).
Higgins, Presentation: The Phase 3 Panorama Study of Intravitreal Aflibercept for Moderately Severe to Severe Non-Proliferative Diabetic Retinopathy, American Acad. of Opthamol.(AAO), 2018.
Higgins, Abstract: The Phase 3 Panorama Study of Intravitreal Aflibercept for Moderately Severe to Severe Non-Proliferative Diabetic Retinopathy, American Acad. of Opthamol.(AAO), 2018 Annual Meeting, Chicago (Oct. 27-30, 2018).
Intravitreal Aflibercept for Moderately Severe to Severe Non-Proliferative Diabetic Retinopathy (NPDR) The Phase 3 Panorama Study, slide deck presented by Charles Wycoff, American Society of Retinal Specialists, 2018 Annual Meeting (Jun. 24, 2018).
Intravitreal Aflibercept for Moderately Severe to Severe Non-Proliferative Diabetic Retinopathy (NPDR) The Phase 3 Panorama Study, slide deck presented by Charles Wycoff, Angiogenesis, Exudation, And Degeneration meeting (Feb. 9, 2019) & Association for Research in Vision and Ophthalmology (ARVO) Annual Meeting (Apr. 29, 2019).
Lim, Abstract: Intravitreal Aflibercept Injection for Nonproliferative Diabetic Retinopathy: Year 2 Results from the Panorama Study, Assoc. for Res. in Vision and Ophthalmology (ARVO), 2018 Annual Meeting, Honolulu, HI (Apr. 29, 2018-May 3, 2018).
One-Year Results from Positive Phase 3 Eylea Trial in Diabetic Retinopathy Presented at Angiogenesis Symposium, Pharma & Healthcare Monitor Worldwide (Feb. 11, 2019).
One-Year Results from Positive Phase 3 Eylea Trial in Diabetic Retinopathy Presented at Angiogenesis Symposium, Global English (Middle East and North Africa Financial Network) (Feb. 9, 2019).
Q1 2018 Regeneron Pharmaceuticals Inc Earnings Call—Final, FD (Fair Disclosure) Wire (May 3, 2018).
Q1 2016 Regeneron Pharmaceuticals Inc Earnings Call—Final, FD (Fair Disclosure) Wire (May 5, 2016).
Q1 2017 Regeneron Pharmaceuticals Inc Earnings Call—Final, FD (Fair Disclosure) Wire (May 4, 2017).
Q1 2019 Regeneron Pharmaceuticals Inc Earnings Call—Final, FD (Fair Disclosure) Wire (May 7, 2019).
Q2 2019 Regeneron Pharmaceuticals Inc Earnings Call—Final, FD (Fair Disclosure) Wire (Aug. 6, 2019).
Q2 2017 Regeneron Pharmaceuticals Inc Earnings Call—Final, FD (Fair Disclosure) Wire (Aug. 3, 2017).
Q2 2018 Regeneron Pharmaceuticals Inc Earnings Call—Final, FD (Fair Disclosure) Wire (Aug. 2, 2018).
Q3 2017 Regeneron Pharmaceuticals Inc Earnings Call—Final, FD (Fair Disclosure) Wire (Nov. 8, 2017).
Q3 2018 Regeneron Pharmaceuticals Inc Earnings Call—Final, FD (Fair Disclosure) Wire (Nov. 6, 2018).
Q4 2015 Regeneron Pharmaceuticals Inc Earnings Call—Final, FD (Fair Disclosure) Wire (Feb. 9, 2016).
Q4 2016 Regeneron Pharmaceuticals Inc Earnings Call—Final, FD (Fair Disclosure) Wire (Feb. 9, 2017).

(56) References Cited

OTHER PUBLICATIONS

Q4 2019 Regeneron Pharmaceuticals Inc Earnings Call—Final, FD (Fair Disclosure) Wire (Feb. 6, 2020).
Q4 2018 Regeneron Pharmaceuticals Inc Earnings Call—Final, FD (Fair Disclosure) Wire (Feb. 6, 2019).
Regeneron announces two-year results from Phase 3 Panorama evaluating Eylea, Theflyonthewall.com (Feb. 9, 2020).
Regeneron Announces Positive Two Year Eylea Results in Patients with Diabetic Retinopathy at Angiogenesis, Exudation, and Degeneration 2020 Meeting, Newstex Blogs, Benzinga (Feb. 8, 2020).
Regeneron Pharmaceuticals (REGN) Earnings Report: Q1 2016 Conference Call Transcript, TheStreet.com (May 6, 2016).
Regeneron Pharmaceuticals (REGN) Earnings Report: Q4 2015 Conference Call Transcript, TheStreet.com (Feb. 9, 2016).
Regeneron Pharmaceuticals Inc Annual Shareholders Meeting—Final, FD (Fair Disclosure) Wire (Jun. 14, 2019).
Regeneron Pharmaceuticals Inc at Barclays Biopharmaceuticals CEO/CFO Conference Call Series—Final, FD (Fair Disclosure) Wire (May 17, 2019).
Regeneron Pharmaceuticals, Inc.—Eylea Injection Improves Diabetic Retinopathy and Reduces Vision-Threatening Complications in Phase 3 Trial, ENP Newswire (Oct. 26, 2018).
Regeneron Pharmaceuticals, Inc.—FDA Approves EYLEA Injection for Diabetic Retinopathy, ENP Newswire (May 14, 2019).
Regeneron Reports First Quarter 2020 Financial and Operating Results, PR Newswire (May 5, 2020).
Regeneron Reports Fourth Quarter and Full Year 2017 Financial and Operating Results, Plus Company Updates (PCU) (Feb. 13, 2018).
Regeneron Reports Third Quarter 2018 Financial and Operating Results, PR Newswire (Nov. 6, 2018).
Regeneron's Eylea Soars, But Praluent Is Slow Out Of The Gate, The Pink Sheet Daily (Feb. 9, 2016).
Regeneron Reports Third Quarter 2017 Financial and Operating Results (Nov. 8, 2017).
Regeneron (REGN) to Report Q3 Earnings: Is a Beat in Store?, Zacks Investment Research (Nov. 1, 2018).
Regeneron announces phase 3 Panorama trial evaluating Eylea in moderately severe to severe NPDR met its 24-week primary . . . , PharmaBiz (Mar. 20, 2018).
Regeneron Pharmaceuticals Inc at J.P. Morgan 2019 Spring Biotech Conference Call—Final, FD (Fair Disclosure) Wire (Mar. 15, 2019).
Regeneron Pharmaceuticals Inc at JPMorgan Global Healthcare Conference—Final, FD (Fair Disclosure) Wire (Jan. 7, 2019).
Regeneron Reports First Quarter 2018 Financial and Operating Results, PR Newswire (May 3, 2018).
Regeneron Reports Fourth Quarter and Full Year 2017 Financial and Operating Results, PR Newswire (Feb. 8, 2018).
Regeneron Reports Fourth Quarter and Full Year 2018 Financial and Operating Results, PR Newswire (Feb. 6, 2019).
Regeneron Reports Positive Results From Phase 3 Panorama Trial With Eylea, CE Noticias Financieras English (Mar. 19, 2018).
Regeneron Reports Second Quarter 2018 Financial and Operating Results, PR Newswire (Aug. 2, 2018).
Regeneron Reports Third Quarter 2017 Financial and Operating Results, PR Newswire (Nov. 8, 2017).
Regeneron 10-K (Feb. 9, 2017).
Regeneron Form 10-K (Dec. 31, 2016).
Regeneron Form 10-K (Dec. 31, 2017).
Regeneron Form 10-K (Dec. 31, 2018).
Regeneron Form 10-Q (Jun. 30, 2018).
Regeneron Form 10-Q (Jun. 30, 2016).
Regeneron Form 10-Q (Jun. 30, 2017).
Regeneron Form 10-Q (Mar. 31, 2017).
Regeneron Form 10-Q (Mar. 31, 2018).
Regeneron Form 10-Q (Sep. 30, 2016).
Regeneron Form 10-Q (Sep. 30, 2017).
Regeneron Form 10-Q (Sep. 30, 2018).
Regeneron 2017 Annual Report.
Regeneron 2018 Annual Report.
Regeneron 2019 Annual Report.
Regeneron 2016 Annual Report.
Regeneron 2015 Annual Report.
Stewart Michael W., "Aflibercept (VEGF-TRAP): The Next Anti-VEGF Drug", Inflammation & Allergy Drug Tar, Bentham Science Publishers, NL. vol. 10, No. 6, (Dec. 1, 2011) pp. 497-508.
United States: Eylea (aflibercept) Injection Demonstrates Positive Topline Results in Phase 3 Non-Proliferative Diabetic Retinopathy Trial, Thai News Service (Apr. 13, 2018).
Will Regeneron Pharma (REGN) Disappoint in Q3 Earnings?, Zacks Investment Research (Nov. 3, 2017).
Wykoff, Abstract: Intravitreal Aflibercept Injection (IAI) for Moderately Severe to Severe Nonproliferative Diabetic Retinopathy (NPDR): The Phase 3 Panorama Study, American Society of Retina Specialists (ASRS), 2018 Annual Meeting, Vancouver, BC (Jul. 20-24, 2018).
Wykoff, Presentation: Intravitreal Aflibercept for Moderately Severe to Severe Non-Proliferative Diabetic Retinopathy (NPDR) The Phase 3 Panorama Study, The American Society of Retina Specialists, Jul. 24, 2018.
History Changes for Study: NCT02634333, Anti-VEGF Treatment for Prevention of PDR/DME (Dec. 15, 2015).
History Changes for Study: NCT02634333, Anti-VEGF Treatment for Prevention of PDR/DME (Feb. 19, 2016).
History Changes for Study: NCT02634333, Anti-VEGF Treatment for Prevention of PDR/DME (Mar. 22, 2016).
History Changes for Study: NCT02634333, Anti-VEGF Treatment for Prevention of PDR/DME (Apr. 25, 2016).
History Changes for Study: NCT02634333, Anti-VEGF Treatment for Prevention of PDR/DME (May 13, 2016).
History Changes for Study: NCT02634333, Anti-VEGF Treatment for Prevention of PDR/DME (Jun. 14, 2016).
History Changes for Study: NCT02634333, Anti-VEGF Treatment for Prevention of PDR/DME (Jul. 14, 2016).
History Changes for Study: NCT02634333, Anti-VEGF Treatment for Prevention of PDR/DME (Aug. 25, 2016).
History Changes for Study: NCT02634333, Anti-VEGF Treatment for Prevention of PDR/DME (Sep. 8, 2016).
History Changes for Study: NCT02634333, Anti-VEGF Treatment for Prevention of PDR/DME (Dec. 9, 2016).
History Changes for Study: NCT02634333, Anti-VEGF Treatment for Prevention of PDR/DME (Jan. 19, 2017).
History Changes for Study: NCT02634333, Anti-VEGF Treatment for Prevention of PDR/DME (Feb. 16, 2017).
History Changes for Study: NCT02634333, Anti-VEGF Treatment for Prevention of PDR/DME (Mar. 16, 2017).
History Changes for Study: NCT02634333, Anti-VEGF Treatment for Prevention of PDR/DME (Dec. 15, 2015) History Changes for Study: NCT02634333, Anti-VEGF Treatment for Prevention of PDR/DME (Apr. 20, 2017).
History Changes for Study: NCT02634333, Anti-VEGF Treatment for Prevention of PDR/DME (May 18, 2017).
History Changes for Study: NCT02634333, Anti-VEGF Treatment for Prevention of PDR/DME (Jun. 14, 2017).
History Changes for Study: NCT02634333, Anti-VEGF Treatment for Prevention of PDR/DME (Jul. 20, 2017).
History Changes for Study: NCT02634333, Anti-VEGF Treatment for Prevention of PDR/DME (Aug. 22, 2017).
History Changes for Study: NCT02634333, Anti-VEGF Treatment for Prevention of PDR/DME (Sep. 29, 2017).
History Changes for Study: NCT02634333, Anti-VEGF Treatment for Prevention of PDR/DME (Oct. 16, 2017).
History Changes for Study: NCT02634333, Anti-VEGF Treatment for Prevention of PDR/DME (Oct. 27, 2017).
History Changes for Study: NCT02634333, Anti-VEGF Treatment for Prevention of PDR/DME (Jan. 25, 2018).
History Changes for Study: NCT02634333, Anti-VEGF Treatment for Prevention of PDR/DME (Feb. 23, 2018).
History Changes for Study: NCT02634333, Anti-VEGF Treatment for Prevention of PDR/DME (May 9, 2018).
History Changes for Study: NCT02634333, Anti-VEGF Treatment for Prevention of PDR/DME (Aug. 23, 2018).

(56) References Cited

OTHER PUBLICATIONS

Sella et al., "Efficacy of Topical aflibercept versus topical bevacizumab for the prevention of corneal neovascularization in a rat model" Experimental Eye Research (2016) 146:224-232.
Sato et al., "Vascular Molecular Pathology in Diabetes," *The Japanese Diabetes Society*, 48(10):713-716 (2005) (with machine translation).
Highlights of Prescribing Information for Eylea (aflibercept); revised Oct. 2016 (with English version).
"Product Development in Biotechnology," Chapter 11 in *Biotechnology Fundamentals* 3rd ed., pp. 257-280, Kahn et al. (eds.), Taylor & Francis Group, Oxfordshire (2000).
U.S. Appl. No. 16/055,847—Third Party Submissions dated May 1, 2019.
U.S. Appl. No. 16/159,282—Third Party Submissions dated May 31, 2019.
Abraham et al., "Randomized, Double-Masked, Sham-Controlled Trial of Ranibizumab for Neovascular Age-Related Macular Degeneration: PIER Study Year 2," *Am. J. Ophthalmology*, 150(3), pp. 315-324.e1 (Sep. 2010).
Adamis, "Ocular Angiogenesis: Vascular Endothelial Growth Factor and Other Factors," in *Retinal Pharmacotherapy 23*, Chapter 4, pp. 23-36, Nguyen et al., eds., Saunders Elsevier (printed in China), 19 pp. (2010).
Adhi et al., "Macular Thickness by Age and Gender in Healthy Eyes Using Spectral Domain Optical Coherence Tomography," *PLoS ONE*, 7(5):e37638, pp. 1-6(May 2012).
ADIS R&D Profile, "Aflibercept: AVE 0005, AVE 005, AVE0005, VEGF Trap—Regeneron, VEGF Trap (R1R2), VEGF Trap-Eye," Drugs R. D., 9(4):261-269 (2008).
Affidavit of Dr. Berger, 4 pp., submitted in Opposition to EP 3716992 (May 9, 2023).
Affidavit of Dr. Kirchhof, 3 pp., submitted in Opposition to EP 3716992 (May 9, 2023).
Ahmed et al., "Efficacy of Intra-Vitreal Bavacizumab Combined with Phaco-Emulsification in the Prophylaxis of Macular Edema in Patients with Non-Proliferative Diabetic Retinopathy," *APMC*, 10(2):58-62 (Apr.-Jun. 2016).
Al Qassimi et al., "Management of Diabetic Macular Edema: Guidelines from the Emirates Society of Ophthalmology," *Ophthalmol. Ther.*, 11:1937-1950 (2022).
Albini et al., ARVO Annual Meeting Abstract, "Long Term Pilot Study of OCT-guided Monthly Ranibizumab for Uveitic Cystoid Macular Edema," *Investigative Ophthalmology & Visual Sci.*, 53:1184 (Mar. 2012).
American Academy of Ophthalmology Retina/Vitreous Panel, Preferred Practice Pattern® Guidelines, "Diabetic Retinopathy," Academy of Ophthalmology, San Francisco, CA, 63 pp. (Jan. 2016).
American Academy of Ophthalmology, "Anti-VEGF Treatments," https://www.aao.org/eye-health/drugs/anti-vegf-treatments (accessed Nov. 8, 2021).
American Academy of Ophthalmology, "Bevacizumab," https://eyewiki.aao.org/Bevacizumab (accessed Nov. 2, 2021).
American Academy of Ophthalmology, "Ophthalmology Subspecialists," Jun. 6, 2016, https://www.aao.org/eye-health/tips-prevention/ophthalmology-subspecialists (accessed Sep. 26, 2022).
American Academy of Ophthalmology, "Retinal Vasculitis," https://eyewiki.aao.org/Retinal_Vasculitis (accessed Jan. 13, 2022).
American Academy of Ophthalmology, "What is a Slit Lamp," https://www.aao.org/eye-health/treatments/what-is-slit-lamp (Apr. 23, 2018) (accessed Jan. 1, 2023), submitted in IPR2023-00442 as Exhibit 1039.
American Academy of Ophthalmology, "What is Avastin," https://www.aao.org/eye-health/drugs/avastin (accessed Nov. 9, 2021).
American Academy of Ophthalmology, "What is Eylea," https://www.aao.org/eye-health/drugs/what-is-eylea (accessed Nov. 9, 2021).
American Academy of Ophthalmology, "What is Lucentis," https://www.aao.org/eye-health/drugs/lucentis (accessed Nov. 9, 2021).
American Society of Retina Specialists, "Preferences and Trends (PAT) Survey," 2010.
American Society of Retina Specialists, "About Us," https://www.asrs.org/about (accessed Dec. 6, 2021).
American Society of Retina Specialists, "Age-Related Macular Degeneration," https://www.asrs.org/patients/retinal-diseases/2/agerelated-macular-degeneration (accessed Dec. 30, 2021).
American Society of Retina Specialists, "Branch Retinal Vein Occlusion," https://www.asrs.org/patients/retinal-diseases/24/branch-retinal-vein-occlusion (accessed Dec. 30, 2021).
American Society of Retina Specialists, "Central Retinal Vein Occlusion," https://www.asrs.org/patients/retinal-diseases/22/central-retinal-vein-occlusion (accessed Dec. 30, 2021).
American Society of Retina Specialists, "Diabetic Retinopathy," https://www.asrs.org/patients/retinal-diseases/3/diabetic-retinopathy (accessed Dec. 30, 2021).
American Speech-Language-Hearing Association, "Calculating Medicare Fee Schedule Rates," https://www.asha.org/practice/reimbursement/medicare/calculating-medicare-fee-schedule-rates/ (accessed Nov. 22, 2021).
Amgen, "Fusion Protein," https://www.amgen.com/stories/2018/08/the-shape-of-drugs-to-come/fusion-protein (accessed Jan. 7, 2022).
Anderson et al., "Delivery of Anti-Angiogenic Molecular Therapies for Retinal Disease," Drug Discovery Today, 15(7/8), pp. 272-282 (Apr. 2010).
Anonymous, "Anti-VEGF 2019: The State of the Art," Review of Ophthalmology (published Aug. 5, 2019).
Anonymous, Meeting Archive Titled "PA003 Eighteen-Month Results From an Extension Study of a Phase 2, Dose- and Interval-Ranging Study of VEGF Trap-Eye in Wet AMD," presented by David S Boyer, MD at Moscone Center (Oct. 2009).
Anonymous, Meeting Archive Titled "PA040 One-Year Results of the Da Vinci Study of VEGF Trap-Eye in Diabetic Macular Edema," presented by Diana V Do, MD at Orange County Convention Center (Oct. 2011).
Anonymous, Meeting Archive Titled "PA080 One-Year Results of a Phase 2 Study of Intravitreal VEGF Trap-Eye in Patients with Neovascular Age-Related Macular Degeneration," presented by David S Boyer, MD at Georgia World Congress Center (Nov. 2008).
Anonymous, Meeting Archive Titled "PO259 OCT and Fluorescein Angiography Outcomes Through 1 Year for a Phase 2 Study of Intravitreal VEGF Trap-Eye in Neovascular AMD," presented by Peter K Kaiser, MD at Moscone Center (Oct. 2009).
Anonymous, Meeting Archive Titled "PO260 VEGF Trap-Eye Vision-Specific Quality of Life Through 52 Weeks in Patients with Neovascular AMD in Clear-It 2: A Phase 2 Clinical Trial," presented by Allen C Ho, MD at Moscone Center (Oct. 2009).
Anonymous, Meeting Archive Titled "PO492 One-Year Results of the View 1 and View 2 Studies: VEGF Trap-Eye in Wet AMD," presented by David M Brown MD at Orange County Center (Oct. 2011).
Anonymous, Meeting Archive Titled "PO549 The 6-Month (Primary Endpoint) Results of the Phase 3 Galileo Study: VEGF Trap-Eye in Central Retinal Vein Occlusion," presented by Jean-Francois Korobelnik, MD at Orange County Convention Center (Oct. 2011).
Anonymous, Meeting Archive Titled "PO571 OCT and Fluorescein Angiographic Outcomes Through 1 Year for the Phase 2 Study of Intravitreal VEGF Trap-Eye in Neovascular AMD," presented by Quan Dong Nguyen, MD at Georgia World Congress Center (Nov. 2008).
Appendix to Heier et al., "Intravitreal Aflibercept (VEGF Trap-Eye) in Wet Age-Related Macular Degeneration," *Ophthalmology*, 119:2537 (2012), as filed in IPR2023-00884 as Exhibit 2049 on Aug. 25, 2023.
Article in Retinal Physician, "Subspecialty News," available online at http://www.retinalphysician.com/printarticle.aspx?articleID=104007 (Mar. 2010).
ASRS Clinical Updates, "ASRS Fights Novitas [sic] Decision to Interpret Eylea Usage More Frequently than q8 as 'Off Label'," (May 24, 2016) (accessed Apr. 7, 2022), cited in Deposition of Dr. David M. Brown, M.D., on Apr. 26, 2022.
Association for Research in Vision & Ophthalmology, ARVO News (Summer 2007).

(56) References Cited

OTHER PUBLICATIONS

Association for Research in Vision & Ophthalmology, ARVO News (Winter/Spring 2008).
Avastin Label (revised 2004), https://www.accessdata.fda.gov/drugsatfda_docs/label/2004/125085lbl.pdf (accessed Sep. 26, 2022).
Avastin Label (Revised Dec. 2017), submitted in IPR2021-00402 as Exhibit 1024.
Avery et al., "Intravitreal bevacizumab (Avastin) for neovascular age-related macular degeneration," Ophthalmology, 113(3), pp. 363-372e5 (Mar. 2006).
Barbazetto, "Dosing Regimen And The Frequency Of Macular Hemorrhages In Neovascular Age-Related Macular Degeneration Treated With Ranibizumab," Retina, 30(9):1376-85 (Oct. 2010).
BasePair Biotechnologies, "What is an Aptamer?—Aptamers and Selex," https://www.basepairbio.com/what-is-an-aptamer/ (accessed Dec. 30, 2021).
Bashshur et al., "Intravitreal Bevacizumab for the Management of Choroidal Neovascularization in Age-Related Macular Degeneration," Am. J. Ophthalmology, 142(1), pp. 1-9 (Jul. 2006).
Batta et al., "Trends in FDA Drug Approvals Over Last 2 Decades: An Observational Study," J. Family Medicine & Primary Care, 9, pp. 105-114 (2020).
Bausch and Lomb, "Help Your Patients Obtain Access to Visudyne," https://www.bauschretinarx.com/visudyne/ecp/ordering/ (accessed Jan. 12, 2022).
Bausch and Lomb, "Visudyne," https://www.bauschretinarx.com/visudyne/ecp/about/ (accessed Dec. 2, 2021).
Bausch Health Companies, Form 10-K, 2020.
Bayer Investor News, "Bayer and Regeneron Start additional Phase 3 Study for VEGF Trap-Eye in Wet Age-related Macular Degeneration," (May 8, 2008).
Bayer Investor News, "VEGF Trap-Eye: New Data Confirm Successes in the Treatment of Age-related Macular Degeneration," (Sep. 28, 2008).
Bayer Press Release, "Bayer and Regeneron Dose First Patient in Second Phase 3 Study for VEGF Trap-Eye in Wet Age-Related Macular Degeneration," (May 8, 2008), https://investor.regeneron.com/news-releases/news-release-details/bayer-and-regeneron-dose-first-patient-second-phase-3-study-vegf (accessed Sep. 26, 2022).
Bayer Press Release, "Bayer HealthCare and Regeneron Announce Encouraging 32-Week Follow Up Results From A Phase 2 Study of VEGF Trap-Eye in Age-Related Macular Degeneration," (Apr. 28, 2008), https://newsroom.regeneron.com/news-releases/news-release-details/regeneron-and-bayer-healthcare-announce-encouraging-32-week (accessed Sep. 26, 2022).
Bayer Press Release, "Bayer HealthCare and Regeneron Announce VEGF Trap-Eye Achieved Durable Improvement in Vision Over 52 Weeks in a Phase 2 Study in Patients with Age-Related Macular Degeneration," (Aug. 19, 2008), https://newsroom.regeneron.com/news-releases/news-release-details/regeneron-and-bayer-healthcare-announce-vegf-trap-eye-achieved (accessed Sep. 26, 2022).
Bayer Press Release, "VEGF Trap-Eye Shows Positive Results in Phase II Study in Patients with Diabetic Macular Edema," (Feb. 18, 2010), https://newsroom.regeneron.com/news-releases/news-release-details/vegf-trap-eye-shows-positive-results-phase-2-study-patients (accessed Sep. 26, 2022).
BCBS Florida, "Vascular Endothelial Growth Factor Inhibitors for Ocular Neovascularization," revised Apr. 1, 2022.
BCBS Florida, "Vascular Endothelial Growth Factor Inhibitors for Ocular Neovascularization," revised Apr. 1, 2023.
BenEzra et al., "Uveitis in Children and Adolescents," Br. J. Ophthalmol., 89:444-448 (2005).
Benz et al., "Clear-It-2: Interim Results Of The Phase II, Randomized, Controlled Dose-and Interval-ranging Study Of Repeated Intravitreal VEGF Trap Administration In Patients With Neovascular Age-related Macular Degeneration (AMD)," ARVO Annual Meeting Abstract (May 2007).
Beovu Label (revised Jun. 2020), https://www.accessdata.fda.gov/drugsatfda_docs/label/2020/761125s004lbl.pdf (accessed Sep. 26, 2022).
Beovu Label (revised Oct. 2019), https://www.accessdata.fda.gov/drugsatfda_docs/label/2019/761125s000lbl.pdf (accessed Sep. 26, 2022).
Berker et al., "Surgical treatment of central retinal vein occlusion," Acta Ophthalmol., 86:245-252 (2008).
Bhatt, "Protocol deviation and violation," Perspectives Clinical Research, 3(3):117 (Jul.-Sep. 2012).
Bhisitkul et al., "Alternative anti-VEGF treatment regimens in exudative age-related macular degeneration," Expert Rev. Ophthalmol., 5(6) (Jan. 2010).
Biospace, "Bayer HealthCare AG and Regeneron Pharmaceuticals, Inc. to Collaborate on VEGF Trap for the Treatment Of Eye Diseases; Regeneron Retains U.S. Commercialization Rights, Receives $75 Million Upfront, and Eligible for up to $245 Million of Milestone Payments," (Oct. 19, 2006), https://www.biospace.com/article/releases/bayer-healthcare-ag-and-regeneron-pharmaceuticals-inc-to-collaborate-on-vegf-trap-for-the-treatment-of-eye-diseases-b-regeneron-b-retains-u-s-c/ (accessed Sep. 26, 2022).
Blinder et al., "Anti-VEGF Treatment of Diabetic Macular Edema in Clinical Practice: Effectiveness and Patterns of Use (Echo Study Report I)," Clinical Ophthalmology, 11:393-401 (2017).
BMJ Publishing Group Ltd., "Review: Ranibizumab (Lucentis) In Neovascular Age-Related Macular Degeneration: Evidence From Clinical Trials," British J. Ophthalmology, (Dec. 2020), https://bjo.bmj.com/content/94/1/2.altmetrics.
Bontempo, "Preformulation Development of Parenteral Biopharmaceuticals," Drugs and the Pharmaceutical Sciences, 85:91-108 (Jul. 25, 1997).
Bork et al., "Increasing the Sialylation of Therapeutic Glycoproteins: The Potential of the Sialic Acid Biosynthetic Pathway," J. Pharm. Sci., 98(10), pp. 3499-3508 (Oct. 2009).
Bowie et al., "Deciphering the Message in Protein Sequences: Tolerance to Amino Acid Substitutions," Science, 147:1306-1310 (Mar. 16, 1990).
Boyer, "A Phase IIIb Study to Evaluate the Safety of Ranibizumab in Subjects with Neovascular Age-related Macular Degeneration," Ophthalmology, 116(9):1731-1739 (Sep. 2009).
Bressler et al., "Change in Diabetic Retinopathy Through 2 Years. Secondary Analysis of a Randomized Clinical Trial Comparing Aflibercept, Bevacizumab, and Ranibizumab," JAMA Ophthalmology, 135(6):558-568 (published online Apr. 27, 2017).
Bressler et al., "Change in Diabetic Retinopathy Through 2 Years. Secondary Analysis of a Randomized Clinical Trial Comparing Aflibercept, Bevacizumab, and Ranibizumab," JAMA Ophthalmology, 135(6):558-568, Supplemental online content, 22 pp. (Jun. 2017).
Bressler et al., "Photodynamic therapy of subfoveal choroidal neovascularization in age-related macular degeneration with verteporfin: two-year results of 2 randomized clinical trials-tap report 2," Arch. Ophthalmol., 119(2):198-207 (2001).
Bright Focus Foundation, "Age-Related Macular Degeneration: Facts & Figures," https://www.brightfocus.org/macular/article/age-related-macular-facts-figures (accessed Nov. 5, 2021).
Brown et al., "Evaluation of Intravitreal Aflibercept for the Treatment of Severe Nonproliferative Diabetic Retinopathy. Results from the Panorama Randomized Clinical Trial," JAMA Ophthalmology, 139(9):946-955 (published online Aug. 5, 2021).
Brown et al., "Anti-VEGF Agents in the Treatment of Neovascular Age-Related Macular Degeneration: Applying Clinical Trial Results to the Treatment of Everyday Patients," Am. J. Ophthalmology, 144(4), pp. 627-637e2 (2007).
Brown et al., "Intravitreal Aflibercept Injection for Macular Edema Secondary to Central Retinal Vein Occlusion: 1-Year Results from the Phase 3 Copernicus Study", Am. J. Ophthalmol., 155, pp. 329-437 (Mar. 2013).
Brown et al., "Polypeptides and Proteins," in Organic Chemistry (Fourth Ed.), Thomson Brooks/Cole (CA), Chapter 27.3, pp. 1075-1096 (2005).
Brown et al., "Ranibizumab for Diabetic Macular Edema (DME): 24-Month Efficacy and Safety Results of RISE—a Phase 3 Randomized Controlled Trial," ARVO Annual Meeting Abstract, Investigative Ophthalmology & Visual Science, 52:6647 (Apr. 2011).

(56) References Cited

OTHER PUBLICATIONS

Brown et al., "Ranibizumab Versus Verteporfin Photodynamic Therapy for Neovascular Age-Related Macular Degeneration: Two-Year Results of the Anchor Study," *Ophthalmology*, 116(1), pp. 57-65.e5 (Jan. 2009).

Brown et al., "Sustained benefits from ranibizumab for macular edema following branch retinal vein occlusion: 12-month outcomes of a phase III study," Ophthalmology, 118(8):1594-2049 (Aug. 2011).

Brown et al., Intravitreal Aflibercept for Diabetic Macular Edema, 100-Week Results from the Vista and Vivid Studies, *American Academy of Ophthalmology*, 122(10):2044-2052 (Oct. 2015).

Brown, "Long-term Outcomes of Ranibizumab Therapy for Diabetic Macular Edema: The 36-Month Results from Two phase III Trials," Ophthalmology, 120(10):2013-2022 (Oct. 2013).

Brown, "Primary Endpoint Results of a Phase II Study of Vascular Endothelial Growth Factor Trap-Eye in Wet Age-related Macular Degeneration," Ophthalmology, 118(6):1089-1097 (Jun. 2011).

Brown, "Ranibizumab versus Verteporfin for Neovascular Age-Related Macular Degeneration," N. Engl. J. Med., 355(14):1432-1444 (Oct. 5, 2006).

Browning et al., "Aflibercept for age-related macular degeneration: a game-changer or quiet addition?" American Journal of Ophthalmology, 154(2):222-226 (Aug. 2012).

Byeon et al., Short-Term Results of Intravitreal Bevacizumab for Macular Edema with Retinal Vein Obstruction and Diabetic Macular Edema, *J. Ocular Pharmacology and Therapeutics*, 23(4):387-394 (Nov. 2007).

Calculator.net, "Sample Size Calculator," https://www.calculator.net/sample-size-calculator.html?type=2&cl2=95&ss2=200&pc2=50&ps2=3000&x=68&y=18#findci (accessed Jan. 25, 2022).

Campochiaro et al., "Antagonism of Vascular Endothelial Growth Factor for Macular Edema Caused by Retinal Vein Occlusions: Two-Year Outcomes," *Ophthalmology*, 117(12), pp. 2387-2394.e5 (Dec. 2010) (online publication).

Campochiaro et al., "Ranibizumab for Macular Edema Due to Retinal Vein Occlusions Implication of VEGF as a Critical Stimulator," Molecular Therapy, 16(4):791-799 (Apr. 2008).

Campochiaro et al., "Sustained Benefits from Ranibizumab for Macular Edema following Central Retinal Vein Occlusion: Twelve-Month Outcomes of a phase III Study," Ophthalmology, 188(10):2041-2049 (Oct. 2011).

Campochiaro, "Ranibizumab for Macular Edema following Branch Retinal Vein Occlusion: six-month primary end point results of a phase III study," Ophthalmology, 117(6):1102-1112 (Jun. 2010).

Cantu et al., "Thioesterases: A New Perspective Based on Their Primary and Tertiary Structures," *Protein Science*, 19(17), pp. 1281-1295 (Jul. 2010).

Cao et al., "Inhibition of Corneal Neovascularization and Inflammation by VEGF Trap," *Investigative Ophthalmology & Visual Science*, 43(13), pp. E- Abstract 1863 (Dec. 2002).

Cao et al., "Systemic Administration of VEGF Trap Suppresses Vascular Leak and Leukostasis in the Retinas of Diabetic Rats," *Investigative Ophthalmology & Visual Science*, 46(13), pp. E-Abstract 446 (May 2005).

Cao et al., "VEGF Trap Promotes Regression of Choroidal Neovascularization (CNV) and Inhibits Fibrosis and Inflammation in the Subretinal Matrigel CNV Model," ARVO Annual Meeting Abstract, Investigative Ophthalmology & Visual Science, 50:2979 (Apr. 2009).

Cao, "A Subretinal Matrigel Rat Choroidal Neovascularization (CNV) Model and Inhibition of CNV and Associated Inflammation and Fibrosis by VEGF Trap," Investigative Ophthalmology & Visual Science, 51(11):6009-6017 (Nov. 2010).

CAS registry for No. 862111-32-8, cited in Deposition of Dr. Alexander M. Klibanov, Ph.D., on Mar. 24, 2022.

Center for Drug Evaluation and Research Approval Package for Eylea, Application No. 125387Orig1s048, 189 pp. (Mar. 25, 2015).

Center for Drug Evaluation and Research Approval Package for Lucentis, Application No. 125156Orig1s114 (Apr. 15, 2017).

Center for Drug Evaluation and Research, "Application No. 125387Orig1s000 [Eylea] Summary Review," 29 pp., https://www.accessdata.fda.gov/drugsatfda_docs/nda/2011/125387Orig1s000SumR.pdf (accessed May 20, 2022).

Center for Drug Evaluation and Research, Application No. 21-756 Medical Review(s) (Dec. 17, 2004) <URL:https://www.accessdata.fda.gov/drugsatfda_docs/nda/2004/21-756_Macugen_medr.pdf>.

Center for Drug Evaluation and Research, Approved Labeling for BLA Application No. 125156 (Lucentis), 8 pp. (2006).

Center for Drug Evaluation and Research, BLA Application Number: 125156 Medical Review, (Jun. 2006) <URL:https://www.accessdata.fda.gov/drugsatfda_docs/nda/2006/125156s0000_Lucentis_MedR.pdf>.

Center for Drug Evaluation and Research, Medical Review for BLA Application No. 125387 (Nov. 18, 2011).

Center for Drug Evaluation and Research, Statistical Review for BLA Application No. 125387, 46 pp. (Nov. 18, 2011).

Centers for Disease Control and Prevention, "Vision Loss: A Public Health Problem," https://www.cdc.gov/visionhealth/basic_information/vision_loss.htm (accessed Jun. 12, 2020).

Centers for Medicare & Medicaid Services, "Medicare Physician & Other Practitioners—by Provider and Service," https://data.cms.gov/provider-summary-by-type-of-service/medicare-physician-other-practitioners/medicare-physician-other-practitioners-by-provider-and-service (accessed Nov. 19, 2021).

Centers for Medicare & Medicaid Services, "Payment Allowance Limits for Medicare Part B Drugs: Effective Oct. 1, 2012, through Dec. 31, 2012," (Oct. 2012), https://www.cms.gov/Medicare/Medicare-Fee-for-Service-Part-B-Drugs/McrPartBDrugAvgSalesPrice/2012ASPFiles (accessed Sep. 26, 2022).

Centers for Medicare & Medicaid Services, "Payment Allowance Limits for Medicare Part B Drugs: Effective Oct. 1, 2013, through Dec. 31, 2013," (Oct. 2013), https://www.cms.gov/Medicare/Medicare-Fee-for-Service-Part-B-Drugs/McrPartBDrugAvgSalesPrice/2013ASPFiles (accessed Sep. 26, 2022).

Centers for Medicare & Medicaid Services, "Payment Allowance Limits for Medicare Part B Drugs: Effective Oct. 1, 2014, through Dec. 31, 2014," (Oct. 2014), https://www.cms.gov/Medicare/Medicare-Fee-for-Service-Part-B-Drugs/McrPartBDrugAvgSalesPrice/2014ASPFiles (accessed Sep. 26, 2022).

Centers for Medicare & Medicaid Services, "Payment Allowance Limits for Medicare Part B Drugs: Effective Oct. 1, 2015, through Dec. 31, 2015," (Oct. 2015), https://www.cms.gov/Medicare/Medicare-Fee-for-Service-Part-B-Drugs/McrPartBDrugAvgSalesPrice/2015ASPFiles (accessed Sep. 26, 2022).

Centers for Medicare & Medicaid Services, "Payment Allowance Limits for Medicare Part B Drugs: Effective Oct. 1, 2016, through Dec. 31, 2016," (Oct. 2016), https://www.cms.gov/Medicare/Medicare-Fee-for-Service-Part-B-Drugs/McrPartBDrugAvgSalesPrice/2016ASPFiles (accessed Sep. 26, 2022).

Centers for Medicare & Medicaid Services, "Payment Allowance Limits for Medicare Part B Drugs: Effective Oct. 1, 2017, through Dec. 31, 2017," (Oct. 2017), https://www.cms.gov/Medicare/Medicare-Fee-for-Service-Part-B-Drugs/McrPartBDrugAvgSalesPrice/2017ASPFiles (accessed Sep. 26, 2022).

Centers for Medicare & Medicaid Services, "Payment Allowance Limits for Medicare Part B Drugs: Effective Oct. 1, 2018, through Dec. 31, 2018," (Oct. 2018), https://www.cms.gov/Medicare/Medicare-Fee-for-Service-Part-B-Drugs/McrPartBDrugAvgSalesPrice/2018ASPFiles (accessed Sep. 26, 2022).

Centers for Medicare & Medicaid Services, "Payment Allowance Limits for Medicare Part B Drugs: Effective Oct. 1, 2019, through Dec. 31, 2019," (Oct. 2019), https://www.cms.gov/Medicare/Medicare-Fee-for-Service-Part-B-Drugs/McrPartBDrugAvgSalesPrice/2019ASPFiles (accessed Sep. 26, 2022).

Centers for Medicare & Medicaid Services, "Payment Allowance Limits for Medicare Part B Drugs: Effective Oct. 1, 2020, through Dec. 31, 2020," (Oct. 2020), https://www.cms.gov/medicare/medicare-part-b-drug-average-sales-price/2020-asp-drug-pricing-files (accessed Sep. 26, 2022).

Centers for Medicare & Medicaid Services, "Payment Allowance Limits for Medicare Part B Drugs: Effective Oct. 1, 2021, through

(56) References Cited

OTHER PUBLICATIONS

Dec. 31, 2021," (Oct. 2021), https://www.cms.gov/medicare/medicare-part-b-drug-average-sales-price/2021-asp-drug-pricing-files (accessed Sep. 26, 2022).
Centers for Medicare & Medicaid Services, "Physician Fee Schedule," https://www.cms.gov/Medicare/Medicare-Fee-for-Service-Payment/PhysicianFeeSched (accessed Nov. 22, 2021).
Centers for Medicare & Medicare Services, "2021 ASP Drug Pricing Files," https://www.cms.gov/medicare/medicare-part-b-drug-average-sales-price/2021-asp-drug-pricing-files (accessed Nov. 22, 2021).
Centers for Medicare & Medicare Services, "Medicare Part B Drug Average Sales Price," https://www.cms.gov/Medicare/Medicare-Fee-for-Service-Part-B-Drugs/McrPartBDrugAvgSalesPrice (accessed Dec. 8, 2021).
Chakravarthy et al., "Ranibizumab versus Bevacizumab to Treat Neovascular Age-related Macular Degeneration: One-Year Findings from the IVAN Randomized Trial," *Ophthalmology*, 119(7): pp. 1399-1411 (Jul. 2012).
Charles, Steve (Guest Lecturer), "VEGF Trap Has Positive DME Data," Tenth Annual Retina Fellows Forum in Chicago dated Jan. 29-30, 2010, (Article Date Mar. 1, 2010).
Chatziralli et al., "Intravitreal aflibercept for neovascular age-related macular degeneration in patients aged 90 years or older: 2-year visual acuity outcomes," Eye 32:1523-1529 (Jun. 2018).
Chen et al., "Carboxylic ester hydrolases: Classification and database derived from their primary, secondary, and tertiary structures," *Protein Science*, 25(11), pp. 1942-1953 (Nov. 2016).
Cheung et al., "Combined anti-PIGF and anti-VEGF Therapy Ameliorates Pathological Neovascularization and Improves Retinal Revascularization in the Murine Model of Oxygen Induced Ischemic Retinopathy," ARVO Annual Meeting Abstract, Investigative Ophthalmology & Visual Science, 52:6064 (Apr. 2011).
Chi et al., "Physical Stability of Proteins in Aqueous Solution: Mechanism and Driving Forces in Nonnative Protein Aggregation" Pharmaceutical Research, 20(9):1325-1336 (Sep. 2003).
Christensen, "Methodology of Superiority vs. Equivalence Trials and Non-Inferiority Trials," *J. Hepatology*, 46(5), pp. 947-954 (May 2007) (online publication).
Chung et al., "Ziv-aflibercept: A novel angiogenesis inhibitor for the treatment of metastatic colorectal cancer," Am. J. Heath-Syst. Pharm., 70:1887-1896 (Nov. 2013).
Ciulla et al., "Antivascular Endothelial Growth Factor Therapy For Neovascular Ocular Diseases Other than Age-Related Macular Degeneration," *Current Opinion in Ophthalmology*, 20:166-174 (2009).
Ciulla et al., "Antivascular Endothelial Growth Factor Therapy For Neovascular Age-Related Macular Degeneration," *Current Opinion Ophthalmology*, 20, pp. 158-165 (May 2009).
Clark et al., "Treatment Paradigms in AMD Management: Assessing Consistent Long-Term Dosing," Retina Today Supp., pp. 1-16 (Sep. 2017), cited in Deposition of Dr. David M. Brown, M.D., on Apr. 26, 2022.
Clark, Slides entitled "Extended injection Interval (≥q12wks) Maintains Vision in Neovascular Age-related Macular Degeneration: Year 2 View Subanalysis," pp. 1-14 (Jan. 10, 2018), submitted in Office Action Response dated Feb. 23, 2023, in Canadian Patent Application No. 2,824,422.
ClinicalTrials.gov Archive, History of Changes for Study: NCT00090623, "A Study of rhuFab V2 (Ranibizumab) in Subjects With Subfoveal Choroidal Neovascularization Secondary to Age-Related Macular Degeneration (AMD)," Version 1 https://clinicaltrials.gov/ct2/history/NCT00090623?V_1=View#Study PageTop (Jun. 23, 2005) (accessed Jan. 2, 2023), submitted in IPR2023-00442 as Exhibit 1053.
ClinicalTrials.gov Archive, History of Changes for Study: NCT00320775, "Safety and Tolerability Study of Intravitreal VEGF-Trap Administration in Patients With Neovascular AMD," Version 01 (Apr. 28, 2006).
ClinicalTrials.gov Archive, History of Changes for Study: NCT00320775, "Safety and Tolerability Study of Intravitreal VEGF-Trap Administration in Patients With Neovascular AMD," Version 02 (Oct. 3, 2006).
ClinicalTrials.gov Archive, History of Changes for Study: NCT00320775, "Safety and Tolerability Study of Intravitreal VEGF-Trap Administration in Patients With Neovascular AMD," Version 03 (Jul. 25, 2007).
ClinicalTrials.gov Archive, History of Changes for Study: NCT00320775, "Safety and Tolerability Study of Intravitreal VEGF-Trap Administration in Patients With Neovascular AMD," Version 04 (Jan. 23, 2009).
ClinicalTrials.gov Archive, History of Changes for Study: NCT00320775, "Safety and Tolerability Study of Intravitreal VEGF-Trap Administration in Patients With Neovascular AMD," Version 05 (Apr. 29, 2009).
ClinicalTrials.gov Archive, History of Changes for Study: NCT00320775, "Safety and Tolerability Study of Intravitreal VEGF-Trap Administration in Patients With Neovascular AMD," Version 06 (Jan. 26, 2010).
ClinicalTrials.gov Archive, History of Changes for Study: NCT00320775, "Safety and Tolerability Study of Intravitreal VEGF-Trap Administration in Patients With Neovascular AMD," Version 07 (Jan. 25, 2011).
ClinicalTrials.gov Archive, History of Changes for Study: NCT00320775, "Safety and Tolerability Study of Intravitreal VEGF-Trap Administration in Patients With Neovascular AMD," Version 08 (Jun. 8, 2011).
ClinicalTrials.gov Archive, History of Changes for Study: NCT00320775, "Safety and Tolerability Study of Intravitreal VEGF-Trap Administration in Patients With Neovascular AMD," Version 09 (Mar. 16, 2015).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 01 (Apr. 28, 2006).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 02 (Aug. 1, 2006).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 03 (Oct. 3, 2006).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 04 (Jul. 24, 2007).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 05 (Jan. 23, 2009).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 06 (Apr. 28, 2009).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 07 (Nov. 30, 2010).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 08 (Apr. 20, 2011).

(56) References Cited

OTHER PUBLICATIONS

ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 09 (Dec. 1, 2011).
ClinicalTrials.gov Archive, History of Changes for Study: NCT00320788, "Safety and Efficacy of Repeated Intravitreal Administration of Vascular Endothelial Growth Factor (VEGF) Trap in Patients With Wet Age-Related Macular Degeneration (AMD)," Version 10 (Jan. 27, 2012).
ClinicalTrials.gov Archive, History of Changes for Study: NCT00320814, "Phase 1 Study of VEGF Trap in Patients With Diabetic Macular Edema," Version 01 (Apr. 28, 2006).
ClinicalTrials.gov Archive, History of Changes for Study: NCT00320814, "Phase 1 Study of VEGF Trap in Patients With Diabetic Macular Edema," Version 02 (Sep. 6, 2006).
ClinicalTrials.gov Archive, History of Changes for Study: NCT00320814, "Phase 1 Study of VEGF Trap in Patients With Diabetic Macular Edema," Version 03 (Jan. 5, 2009).
ClinicalTrials.gov Archive, History of Changes for Study: NCT00320814, "Phase 1 Study of VEGF Trap in Patients With Diabetic Macular Edema," Version 04 (Jan. 25, 2011).
ClinicalTrials.gov Archive, History of Changes for Study: NCT00320814, "Phase 1 Study of VEGF Trap in Patients With Diabetic Macular Edema," Version 05 (Jun. 8, 2011).
ClinicalTrials.gov Archive, History of Changes for Study: NCT00473330, "A Study of Ranibizumab Injection in Subjects With Clinically Significant Macular Edema (ME) With Center Involvement Secondary to Diabetes Mellitus (RISE)," Version 13, dated Mar. 21, 2017, submitted in IPR2021-00881 as Exhibit 2122.
ClinicalTrials.gov Archive, History of Changes for Study: NCT00473382, "A Study of Ranibizumab Injection in Subjects With Clinically Significant Macular Edema (ME) With Center Involvement Secondary to Diabetes Mellitus (RIDE)," Version 13, dated Mar. 21, 2017, submitted in IPR2021-00881 as Exhibit 2123.
ClinicalTrials.gov Archive, History of Changes for Study: NCT00485836, "A Study of the Efficacy and Safety of Ranibizumab Injection in Patients With Macular Edema Secondary to Central Retinal Vein Occlusion (CRUISE)," Version 10, dated Jun. 29, 2017, submitted in IPR2021-00881 as Exhibit 2125.
ClinicalTrials.gov Archive, History of Changes for Study: NCT00486018, "A Study of the Efficacy and Safety of Ranibizumab Injection in Patients With Macular Edema Secondary to Branch Retinal Vein Occlusion (BRAVO)," Version 12, dated Apr. 4, 2017, submitted in IPR2021-00881 as Exhibit 2124.
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Comparison of Changes from Version 08 to Version 09 (Apr. 28, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 01 (Jul. 31, 2007).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 02 (Aug. 17, 2007).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 03 (Nov. 14, 2007).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 04 (Dec. 4, 2007).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 05 (Mar. 13, 2008).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 06 (Jun. 26, 2008).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 07 (Jan. 22, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 08 (Mar. 3, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 09 (Apr. 28, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 10 (Sep. 12, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 11 (Dec. 1, 2009).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 12 (Jan. 5, 2011).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 13 (Apr. 18, 2011).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 14 (May 4, 2011).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 15 (Dec. 1, 2011).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 16 (Apr. 13, 2012).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 17 (Dec. 17, 2012).
ClinicalTrials.gov Archive, History of Changes for Study: NCT00509795, "Vascular Endothelial Growth Factor VEGF Trap-Eye: Investigation of Efficacy and Safety in Wet Age-Related Macular Degeneration (AMD) (VIEW1)," Version 18 (Dec. 20, 2012).

(56) References Cited

OTHER PUBLICATIONS

ClinicalTrials.gov Archive, History of Changes for Study: NCT00519285, "Aflibercept in Combination With Docetaxel in Metastatic Androgen Independent Prostate Cancer (VENICE)," Version 01, dated Aug. 21, 2007, submitted in IPR2021-00881 as Exhibit 2078.

ClinicalTrials.gov Archive, History of Changes for Study: NCT00527423, "Randomized, Single-Masked, Long-Term, Safety and Tolerability Study of VEGF Trap-Eye in AMD," Version 01 (Sep. 7, 2007).

ClinicalTrials.gov Archive, History of Changes for Study: NCT00527423, "Randomized, Single-Masked, Long-Term, Safety and Tolerability Study of VEGF Trap-Eye in AMD," Version 02 (Jul. 3, 2008).

ClinicalTrials.gov Archive, History of Changes for Study: NCT00527423, "Randomized, Single-Masked, Long-Term, Safety and Tolerability Study of VEGF Trap-Eye in AMD," Version 03 (Apr. 9, 2009).

ClinicalTrials.gov Archive, History of Changes for Study: NCT00527423, "Randomized, Single-Masked, Long-Term, Safety and Tolerability Study of VEGF Trap-Eye in AMD," Version 04 (Dec. 3, 2009).

ClinicalTrials.gov Archive, History of Changes for Study: NCT00527423, "Randomized, Single-Masked, Long-Term, Safety and Tolerability Study of VEGF Trap-Eye in AMD," Version 05 (Feb. 11, 2011).

ClinicalTrials.gov Archive, History of Changes for Study: NCT00527423, "Randomized, Single-Masked, Long-Term, Safety and Tolerability Study of VEGF Trap-Eye in AMD," Version 06 (Apr. 25, 2011).

ClinicalTrials.gov Archive, History of Changes for Study: NCT00527423, "Randomized, Single-Masked, Long-Term, Safety and Tolerability Study of VEGF Trap-Eye in AMD," Version 07 (Jun. 20, 2011).

ClinicalTrials.gov Archive, History of Changes for Study: NCT00527423, "Randomized, Single-Masked, Long-Term, Safety and Tolerability Study of VEGF Trap-Eye in AMD," Version 08 (Nov. 1, 2011).

ClinicalTrials.gov Archive, History of Changes for Study: NCT00527423, "Randomized, Single-Masked, Long-Term, Safety and Tolerability Study of VEGF Trap-Eye in AMD," Version 09 (May 9, 2012).

ClinicalTrials.gov Archive, History of Changes for Study: NCT00527423, "Randomized, Single-Masked, Long-Term, Safety and Tolerability Study of VEGF Trap-Eye in AMD," Version 10 (Sep. 27, 2012).

ClinicalTrials.gov Archive, History of Changes for Study: NCT00527423, "Randomized, Single-Masked, Long-Term, Safety and Tolerability Study of VEGF Trap-Eye in AMD," Version 11 (Jun. 10, 2013).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 01 (Mar. 17, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 02 (Apr. 24, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 03 (Jun. 19, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 04 (Aug. 4, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 05 (Sep. 30, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 06 (Oct. 2, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 07 (Nov. 4, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 08 (Dec. 1, 2008).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 09 (Jan. 5, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 10 (Feb. 5, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 11 (Mar. 5, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 12 (Apr. 2, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 13 (May 4, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 14 (Jun. 4, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 15 (Jul. 3, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 16 (Sep. 1, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 17 (Sep. 23, 2009).

ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 18 (Nov. 19, 2009).

ClinicalTrials.gov Archive, History of Changes for Study: NCT00637377, "Vascular Endothelial Growth Factor (VEGF) Trap-

(56) References Cited

OTHER PUBLICATIONS

Eye: Investigation of Efficacy and Safety in Wet Age-Related Macular Degeneration (AMD) (VIEW 2)," Version 19 (Feb. 19, 2010).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 20 (Jul. 9, 2010).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 21 (Oct. 6, 2010).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 22 (Nov. 30, 2010).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 23 (Feb. 21, 2011).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 24 (May 23, 2011).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 25 (Jun. 6, 2011).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 26 (Dec. 16, 2011).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 27 (Feb. 27, 2012).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 28 (Mar. 12, 2013).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 29 (Apr. 25, 2014).
ClinicalTrials.gov Archive, History of Changes for Study: NCT00637377, "Vascular Endothelial Growth Factor (VEGF) Trap-Eye: Investigation of Efficacy and Safety in Wet Age-Related Macular Degeneration (AMD) (VIEW 2)," Version 30 (Nov. 28, 2014).
ClinicalTrials.gov Archive, History of Changes for Study: NCT00644124, "Aflibercept and Standard Chemotherapy (R-CHOP) in First Line of Non Hodgkin B-Cell Lymphoma," Version 01, dated Mar. 21, 2008, submitted in IPR2021-00881 as Exhibit 2079.
ClinicalTrials.gov Archive, History of Changes for Study: NCT00685854, "Pilot Study of Intravitreal Injection of Ranibizumab for Macular Telangiectasia With Neovascularization (MACTEL 2)," Version 01 https://clinicaltrials.gov/ct2/history/NCT00685854?V1=View#StudyPageTop (May 24, 2008) (accessed Jan. 6, 2023), submitted in IPR2023-00442 as Exhibit 1032.
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 01 (Nov. 7, 2008).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 02 (Dec. 5, 2008).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 03 (Feb. 5, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 04 (Feb. 11, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 05 (Feb. 13, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 06 (Mar. 12, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 07 (Apr. 24, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 08 (May 27, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 09 (Jun. 2, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 10 (Jun. 18, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 11 (Jul. 14, 2009).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 12 (Nov. 18, 2010).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 13 (Jan. 24, 2011).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 14 (May 2, 2011).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 15 (Sep. 27, 2013).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 16 (Aug. 13, 2014).
ClinicalTrials.gov Archive, History of Changes for Study: NCT00789477, "DME And VEGF Trap-Eye [Intravitreal Aflibercept Injection (IAI;EYLEA;BAY86-5321)] Investigation of Clinical Impact (Da Vinci)," Version 17 (Aug. 28, 2014).
ClinicalTrials.gov Archive, History of Changes for Study: NCT00794417, "A Study of Aflibercept Administered in Combination With Pemetrexed and Cisplatin in Patients With Advanced Carcinoma," Version 01, dated Nov. 19, 2008, submitted in IPR2021-00881 as Exhibit 2053.

(56) References Cited

OTHER PUBLICATIONS

ClinicalTrials.gov Archive, History of Changes for Study: NCT00826618 Pilot Study of Ranibizumab (Lucentis) for Uveitic Cystoid Macular Edema (submitted Aug. 24, 2014), https://www.clinicaltrials.gov/ct2/history/NCT00826618?V_2=View#StudyPageTop, submitted in IPR2022-01225 as Exhibit 2125.
ClinicalTrials.gov Archive, History of Changes for Study: NCT00826618 Pilot Study of Ranibizumab (Lucentis) for Uveitic Cystoid Macular Edema (submitted Jan. 20, 2009), https://www.clinicaltrials.gov/ct2/history/NCT00826618?V_1=View#StudyPageTop, submitted in IPR2022-01225 as Exhibit 2123.
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 01 (Jul. 20, 2009).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 02 (Sep. 3, 2009).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 03 (Oct. 7, 2009).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 04 (Dec. 3, 2009).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 05 (Feb. 18, 2010).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 06 (Jul. 2, 2010).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 07 (Nov. 18, 2010).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 08 (Feb. 11, 2011).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 09 (May 5, 2011).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 10 (May 9, 2011).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 11 (Mar. 28, 2012).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 12 (Jun. 7, 2012).
ClinicalTrials.gov Archive, History of Changes for Study: NCT00943072, "Vascular Endothelial Growth Factor (VEGF) Trap-Eye: Investigation of Efficacy and Safety in Central Retinal Vein Occlusion (CRVO)," Version 13 (Apr. 16, 2013).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 01 (Nov. 12, 2009).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 02 (Jan. 21, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 03 (Feb. 9, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 04 (Mar. 16, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 05 (Apr. 16, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 06 (Jul. 22, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 07 (Aug. 25, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 08 (Aug. 26, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 09 (Sep. 8, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 10 (Oct. 4, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 11 (Nov. 1, 2010).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 12 (Jan. 25, 2011).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 13 (Apr. 8, 2011).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 14 (Jun. 23, 2011).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 15 (Sep. 19, 2011).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 16 (Nov. 29, 2011).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 17 (Jan. 26, 2012).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 18 (Feb. 20, 2012).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 19 (Oct. 23, 2012).
ClinicalTrials.gov Archive, History of Changes for Study: NCT01012973, "Vascular Endothelial Growth Factor (VEGF) Trap-

(56) References Cited

OTHER PUBLICATIONS

Eye: Investigation of Efficacy and Safety in Central Retinal Vein Occlusion (CRVO)(Galileo)," Version 20 (Dec. 18, 2012).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 21 (Jan. 18, 2013).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 22 (Jan. 30, 2014).
ClinicalTrials.gov Archive, History of Changes for Study: NCT01012973, "Vascular Endothelial Growth Factor (VEGF) Trap-Eye: Investigation of Efficacy and Safety in Central Retinal Vein Occlusion (CRVO)(Galileo)," Version 23 (Oct. 27, 2014).
ClinicalTrials.gov Archive, History of Changes for Study: NCT01042379, "I-Spy 2 Trial: Neoadjuvant and Personalized Adaptive Novel Agents to Treat Breast Cancer," Version 01 (Jan. 4, 2010).
ClinicalTrials.gov Archive, History of Changes for Study: NCT01148615, "A Study of Intravenous Aflibercept With Docetaxel in Chinese Patients With Solid Tumors," Version 01, dated Jun. 21, 2010, submitted in IPR2021-00881 as Exhibit 2054.
ClinicalTrials.gov Archive, History of Changes for Study: NCT01486771, "Macugen for Proliferative Diabetic Retinopathy Study With Extended Dosing (M-PDRS ED)," Version 01, dated Dec. 5, 2011, submitted in IPR2021-00881 as Exhibit 2109.
ClinicalTrials.gov Archive, History of Changes for Study: NCT01940900, "A Phase 3 Safety and Efficacy Study of Fovista (E10030) Intravitreous Administration in Combination With Lucentis Compared to Lucentis Monotherapy," Version 21, dated Aug. 13, 2018, submitted in IPR2021-00881 as Exhibit 2025.
ClinicalTrials.gov Archive, History of Changes for Study: NCT01944839, "A Phase 3 Safety and Efficacy Study of Fovista (E10030) Intravitreous Administration in Combination With Lucentis Compared to Lucentis Monotherapy," Version 27, dated Aug. 8, 2018, submitted in IPR2021-00881 as Exhibit 2024.
ClinicalTrials.gov Archive, History of Changes for Study: NCT02247479, "A Study Investigating the Efficacy and Safety of Lampalizumab Intravitreal Injections in Participants With Geographic Atrophy Secondary to Age-Related Macular Degeneration (Chroma)," Version 60, dated Jun. 17, 2019, submitted in IPR2021-00881 as Exhibit 2021.
ClinicalTrials.gov Archive, History of Changes for Study: NCT02247531, "A Study Investigating the Safety and Efficacy of Lampalizumab Intravitreal Injections in Participants With Geographic Atrophy Secondary to Age-Related Macular Degeneration (Spectri)," Version 60, dated Oct. 14, 2019, submitted in IPR2021-00881 as Exhibit 2020.
ClinicalTrials.gov Archive, History of Changes for Study: NCT03577899, "Efficacy and Safety Trial of Conbercept Intravitreal Injection for Neovascular AMD(Panda-1)," Version 06, dated Jun. 23, 2021, submitted in IPR2021-00881 as Exhibit 2023.
ClinicalTrials.gov Archive, History of Changes for Study: NCT03630952, "Efficacy and Safety Trial of Conbercept Intravitreal Injection for Neovascular AMD(Panda-2)," Version 07, dated Jun. 22, 2021, submitted in IPR2021-00881 as Exhibit 2022.
ClinicalTrials.gov, "A Study of rhuFab V2 (Ranibizumab) in Subjects With Subfoveal Choroidal Neovascularization Secondary to Age-Related Macular Degeneration (AMD)," NCT00090623, ClinicalTrials.gov (last updated Jun. 21, 2013), https://clinicaltrials.gov/ct2/show/NCT00090623, submitted in IPR2023-00442, Ex. 2348.
ClinicalTrials.gov, "A Study to Compare rhuFab V2 With Verteporfin Photodynamic in Treating Subfoveal Neovascular Macular Degeneration," NCT00061594, ClinicalTrials.gov (last updated Mar. 19, 2014), https://www.clinicaltrials.gov/ct2/show/NCT00061594, submitted in IPR2023-00442 as Exhibit 2346.
ClinicalTrials.gov, "A Study to Evaluate rhuFab V2 in Subjects With Minimally Classic or Occult Subfoveal Neovascular Macular Degeneration," NCT00056836, ClinicalTrials.gov (last updated May 16, 2014), https://clinicaltrials.gov/ct2/show/NCT00056836, submitted in IPR2023-00442 as Exhibit 2345.
ClinicalTrials.gov, "Vascular Endothelial Growth Factor (VEGF) Trap-Eye: Investigation of Efficacy and Safety in Central Retinal Vein Occlusion (CRVO)," NCT00943072 (last updated May 27, 2013), https://clinicaltrials.gov/ct2/show/NCT00943072, submitted in IPR2021-00881 as Exhibit 2126.
ClinicalTrials.gov, "1997: Congress Passes Law (FDAMA) Requiring Trial Registration," (1997), https://clinicaltrials.gov/ct2/about-site/history, submitted in IPR2023-00099 as Exhibit 1085 (last updated May 2021).
ClinicalTrials.gov, "About the Results Database," https://clinicaltrials.gov/ct2/about-site/results (Mar. 2018) (accessed Jan. 1, 2023), submitted in IPR2023-00442 as Exhibit 1050.
ClinicalTrials.gov, "Background," https://clinicaltrials.gov/ct2/about-site/background (May 2021) (accessed Jan. 1, 2023), submitted in IPR2023-00442 as Exhibit 1049.
ClinicalTrials.gov, "How to Read a Study Record," https://clinicaltrials.gov/ct2/help/how-read-study (May 2021) (accessed Jan. 1, 2023), submitted in IPR2023-00442 as Exhibit 1051.
ClinicalTrials.gov, "What Is ClinicalTrials.gov?" https://www.clinicaltrials.gov/ct2/about-site/background (accessed Jan. 20, 2021).
ClinicalTrials.gov, Study: NCT00320814, "Phase 1 Study of VEFT Trap in Patients With Diabetic Macular Edema," https://clinicaltrials.gov/study/NCT00320814 (last updated Jun. 10, 2011), submitted in IPR2023-00884 as Exhibit 2012.
ClinicalTrials.gov, Study: NCT00593450, "Comparison of Age-related Macular Degeneration Treatments Trials: Lucentis-Avastin Trial," Version 25, https://clinicaltrials.gov/ct2/show/NCT00593450 (Aug. 21, 2017) (accessed Jan. 1, 2023), submitted in IPR2023-00442 as Exhibit 1035.
ClinicalTrials.gov, Study: NCT00685854, "Ranibizumab Injections to Treat Macular Telangiectasia Without New Blood Vessel Growth," https://web.archive.org/web/20081107014243/https://clinicaltrials.gov/ct2/show/NCT00685854 (Apr. 2008) (accessed Jan. 6, 2023), submitted in IPR2023-00442 as Exhibit 1033.
ClinicalTrials.gov, Study: NCT00685854, "Ranibizumab Injections to Treat Macular Telangiectasia Without New Blood Vessel Growth," Version 23, https://clinicaltrials.gov/ct2/show/NCT00685854 (Jul. 2, 2017) (accessed Jan. 1, 2023), submitted in IPR2023-00442 as Exhibit 1044.
ClinicalTrials.gov, Study: NCT00789477, DME And VEGF Trap-Eye [Intravitreal Aflibercept Injection (IAI;EYLEA®;BAY86-5321)] Investigation of Clinical Impact (Da Vinci), https://clinicaltrials.gov/study/NCT00789477 (last updated Sep. 9, 2014), submitted in IPR2023-00884 as Exhibit 2016.
ClinicalTrials.gov, Vascular Endothelial Growth Factor (VEGF) Trap-Eye: Investigation of Efficacy and Safety in Central Retinal Vein Occlusion (CRVO) (Galileo), NCT01012973 (last updated Nov. 2, 2014), https://clinicaltrials.gov/ct2/show/NCT01012973, submitted in IPR2021-00881 as Exhibit 2127.
CloudResearch, "Determining Sample Size: How Many Survey Participants Do You Need?" https://www.cloudresearch.com/resources/guides/statistical-significance/determine-sample-size/ (accessed Jan. 25, 2022).
CMS, Local Coverage Determination (LCD) for Ranibizumab (Lucentis) (L29266, First Coast Service Options, Inc Jun. 14, 2011).
CMS.gov Medicare Coverage Database, "Billing and Coding: Aflibercept (Eylea)," https://www.cms.gov/medicare-coverage-database/view/article.aspx?articleid=53387&ver=28&keyword=&keywordType=starts&areaId=all&docType=6,3,5,1,F,P&contractOption=all&hcpcsOption=code&hcpcsStartCode=J0178&hcpcsEndCode=J0178&sortBy=title&bc=1 (accessed Apr. 22, 2021).
Cobo et al., "The Clearance of Intravitreal Gentamicin," Am. J. Ophthalmology, 92(1), pp. 59-62 (1981).
Controls in SCI experiments, RegenBase. Retrieved Jan. 6, 2021, from http://regenbase.org/control-groups.html.
Cooper et al., "Increased Renal Expression of Vascular Endothelial Growth Factor (VEGF) and Its Receptor VEGFR-2 in Experimental Diabetes," *Diabetes*, 48:2229-2239 (Nov. 1999).

(56) References Cited

OTHER PUBLICATIONS

Corcoran, "Coding Q&A: Audits Increase as Injections Increase," Retinal Physician, 16:18, 54 (Jul. 1, 2019) https://www.retinalphysician.com/issues/2019/july-august-2019/coding-q-amd;a-audits-incresaeras-injections-incr.

Corporate Finance Institute, "SEC Filings—Requirements for Public Companies & Where to Find Them," https://corporatefinanceinstitute.com/resources/data/public-filings/sec-filings/ (accessed Jan. 20, 2021).

Corrections to Kiire et al., "Managing Retinal Vein Occlusion," *BMJ*, 344(e2110):1 (2012).

Cousins, "Controversies in the Long-term Management of Neovascular AMD: The Role of Imaging in Clinical Decision Making," *Retinal Physician* (Jan. 1, 2010), https://www.retinalphysician.com/issues/2010/jan-feb/controversies-in-the-long-term-management-of-neova (accessed Sep. 26, 2022).

Croll et al., "VEGF-mediated inflammation precedes angiogenesis in adult brain," *Experimental Neurology*, 187, pp. 388-402 (Jun. 2004).

Cruz, "PIER Data Suggest a Need for Tailored Injection Schedule," Ocular Surgery News, (Sep. 1, 2006), https://www.healio.com/news/ophthalmology/20120331/pier-data-suggest-a-need-for-tailored-injection-schedule (accessed Feb. 10, 2022).

Csaky, "Safety Implications of Vascular Endothelial Growth Factor Blockade for Subjects Receiving Intravitreal Anti-Vascular Endothelial Growth Factor Therapies," Am. J. Ophthalmology, 148(5):647-656 (Nov. 2009).

Cuervo-Lozano, "Short-Term Outcomes After the Loading Phase of Intravitreal Bevacizumab and Subthreshold Macular Laser in Non-Center Involved Diabetic Macular Edema," *Int. J. Ophthalmol.*, 11(6):981-985 (Jun. 18, 2018).

Cursiefen et al., "Inhibition of hemangiogenesis and lymphangiogenesis after normal-risk corneal transplantation by neutralizing VEGF promotes graft survival," *Investigative Ophthalmology & Visual Science*, 45(8):2666-2673 (Aug. 2004).

Cursiefen et al., "VEGF-A stimulates lymphangiogenesis and hemangiogenesis in inflammatory neovascularization via macrophage recruitment," *J. Clin. Invest.*, 113(7):1040-1050 (Apr. 2004).

Dadgostar et al., "The Evolving Role of Vascular Endothelial Growth Factor Inhibitors in the Treatment of Neovascular Age-Related Macular Degeneration," *Eye*, 22:761-767 (2008).

Davis, "Risk Factors for High-Risk Proliferative Diabetic Retinopathy and Severe Visual Loss: Early Treatment Diabetic Retinopathy Study Report #18," *Invest. Ophthalmol. Vis. Sci*, 39:233-252 (1998).

Davis-Smyth et al., "The Second Immunoglobulin-like Domain of the VEGF Tyrosine Kinase Receptor Flt-1 Determines Ligand Binding and May Initiate a Signal Transduction Cascade," *EMBO Journal*, 15(18):4919-4927 (1996).

Declaration by Professor Sivaprasad, including Annex (dated May 8, 2023).

Demarest et al., "Optimization of the Antibody $C_H3$ Domain by Residue Frequency Analysis of IgG Sequences," *J. Mol. Biol.*, 335(1), pp. 41-48 (Jan. 2004).

DeVriese et al., "Antibodies against Vascular Endothelial Growth Fact Improve Early Renal Dysfunction in Experimental Diabetes," *J. Am. Soc. Nephrol.*, 12:993-1000 (May 2001).

Dhoot et al., "Baseline Factors Affecting Changes in Diabetic Retinopathy Severity Scale Score After Intravitreal Aflibercept or Laser for Diabetic Macular Edema," *Ophthalmology*, pp. 1-6 (2017), as submitted in Opposition of EP3716992 as D41 on May 10, 2023.

Dixon et al., "VEGF Trap-Eye for the treatment of neovascular age-related macular degeneration," *Expert Opin. Investig. Drugs*, 18(10):1573-1580 (Aug. 2009).

Do et al., "Incorporating the Latest Findings From Clinical Trials Into the Management of Diabetic Retinopathy for the Comprehensive Ophthalmologist," https://aao.scientificposters.com/epsView.cfm?xvTgEJiNo9X9FYlsrbBjRKZ9ICSVGWMJbEunzn9LGZqaMHKIw4tNfg%3D%3D (Oct. 25, 2009) (accessed Mar. 26, 2023), submitted in IPR2023-00739 as Exhibit 1023.

Do et al., "An exploratory study of the safety, tolerability and bioactivity of a single intravitreal injection of vascular endothelial growth factor Trap-Eye in patients with diabetic macular oedema," Br. J. Ophthalmol., 93(2):144-149 (Feb. 2009).

Do et al., "Pharmacokinetic Study of Intravitreal Aflibercept In Humans with Neovascular Age-Related Macular Degeneration," *Retina*, 00, pp. 1-5 (2019), also available as Retina, 40(4), pp. 643-647 (Apr. 2020).

Do et al., "Results of a Phase 1 Study of Intravitreal VEGF Trap in Subjects with Diabetic Macular Edema: The Clear-It DME Study," ARVO Annual Meeting Abstract (May 2007).

Do et al., "VEGF Trap-Eye Vision-specific Quality of Life through 52 Weeks in Patients with Neovascular AMD in Clear-It 2: A Phase 2 Clinical Trial," ARVO Annual Meeting Abstract (Apr. 2009).

Do, "One-Year Outcomes of the Da Vinci Study of VEGF Trap-Eye in Eyes with Diabetic Macular Edema," *Ophthalmology*, 119(8):1658-65 (Aug. 2012).

Donohue et al., "A Decade of Direct-to-Consumer Advertising of Prescription Drugs," *The New England Journal of Medicine*, 35(7), pp. 673-681 (Aug. 2007).

Donohue et al., "Effect of Direct-to-Consumer Advertising on Medication Choice: The Case of Antidepressants," Journal of Public Policy & Marketing, 23(2), pp. 115-127 (Sep. 2004).

Dreyfuss et al., "Ocular Angiogenesis," *Journal of Ophthalmology*, 2015, pp. Article ID 892043 (Sep. 2015).

Drug Vehicle (Code C927), National Cancer Institute (NCI). Retrieved Jan. 6, 2021, from https://ncithesaurus.nci.nih.gov/ncitbrowser/ConceptReport.jsp?dictionary =NCI_Thesaurus&code=C927&ns=ncit.

Drugs.com, "Eylea FDA Approval History," https://www.drugs.com/history/eylea.html (accessed Nov. 16, 2021).

Drugs.com, "FDA Approves Eylea for Wet Age-Related Macular Degeneration," (Nov. 18, 2011), https://www.drugs.com/newdrugs/fda-approves-eylea-wet-age-related-macular-degeneration-2955.html (accessed Feb. 4, 2022).

Duncan et al., "Inhibition of Vascular Endothelial Growth Factor in the Primate Ovary Up-Regulates Hypoxia-Inducible Factor-1α in the Follicle and Corpus Luteum," *Endocrinology*, 149, pp. 3313-3320 (Apr. 2008) (online publication), cited in Deposition of Dr. Alexander M. Klibanov, Ph.D., on Mar. 24, 2022.

Dunleavy, "JPM23: Regeneron Reports Disappointing Sales of Powerhouse Eylea, Says It's a 'Blip'" (Jan. 9, 2023), https://www.fiercepharma.com/pharma/regeneron-reports-disappointing-sales-powerhouse-eylea-says-its-blip, accessed Jun. 15, 2023.

Early Treatment Diabetic Retinopathy Study Research Group, "Photocoagulation for Diabetic Macular Edema—Early Treatment Diabetic Retinopathy Study Report No. 1," *Arch. Ophthalmol.*, 103:1796-1806 (Dec. 1985).

Eichten et al., "Rapid decrease in tumor perfusion following VEGF blockade predicts long-term tumor growth inhibition in preclinical tumor models," Angiogenesis, 16:429-441 (Dec. 2013).

Elman et al., "Randomized trial evaluating ranibizumab plus prompt or deferred laser or triamcinolone plus prompt laser for diabetic macular edema," *Ophthalmology*, 117(6): pp. 1064-1077.e35 (Jun. 2010).

Elvidge, "Opthotech's Fovista crashes out in wet AMD," *Biopharmadive* (Aug. 14, 2017), https://www.biopharmadive.com/news/opthotech-fovista-phase-3-failure-setback-novartis/449248/ (accessed Aug. 2, 2021).

Elyasi et al., "Diabetic Macular Edema: Diagnosis and Management," EyeNet Magazine, May 2021: 35-37 (May 2021).

Engelbert, "Long-Term Follow-Up For Type 1 (Subretinal Pigment Epithelium) Neovascularization Using A Modified 'Treat And Extend' Dosing Regiment Of Intravitreal Antivascular Endothelial Growth Factor Therapy," *Retina*, 30(9):1368-1375 (Oct. 2010).

Engelbert, "The 'Treat and Extend' Dosing Regimen of Intravitreal Anti-Vascular Endothelial Growth Factor Therapy for Neovascular Age-Related Macular Degeneration," Ophthalmology Management, Issue 42, (Jun. 2010) available at http://www.visioncareprofessional.com/emails/amdupdate/index.asp?issue=42.

Engelbert, "'Treat And Extend' Dosing Of Intravitreal Antivascular Endothelial Growth Factor Therapy For Type 3 Neovascularization/Retinal Angiomatous Proliferation,"*Retina*, 29(10):1424-1431 (Nov. 2009).

(56) References Cited

OTHER PUBLICATIONS

Eremina et al., "Glomerular-specific alterations of VEGF-A expression lead to distinct congenital and acquired renal diseases," *Journal of Clinical Investigation*, 111(5), pp. 707-716 (Mar. 2003).
Eriksson et al., "Structure, Expression and Receptor-Binding Properties of Novel Vascular Endothelial Growth Factors," Vascular Growth Factors and Angiogenesis, Springer, pp. 41-57 (1999).
Ernst et al., "Intravitreal Bevacizumab versus Panretinal Photocoagulation for Treatment-Naïve Proliferative and Sever Nonproliferative Diabetic Retinopathy," *Acta Ophthalmologica*, pp. e573-e574 (2012).
European Medicines Agency, Lucentis (ranibizumab) Label.
Ex. 99 (a)(1)(a) to Tender Offer Statement to Momenta, filed with SEC on Sep. 2, 2020.
Excerpts from J.M. Berg et al., Biochemistry ($5^{th}$ Ed. 2002).
Excerpts from J.M. Berg et al., Biochemistry, 6th ed., Freeman, New York (2006).
Excerpts from Shorter Oxford English Dictionary vol. 1 ($6^{th}$ ed. 2007).
Expert Opinion of Professor Priglinger, 15 pp. (Mar. 14, 2023).
Extended European Search Report dated Nov. 22, 2022, for EP Appln. 22181390.0, 5 pp.
Eye Care Surgery Center, "Macular Degeneration," https://www.eyecaresurgerycenterbr.com/diabetes-retina/macular-degeneration/ (accessed Nov. 18, 2021).
EyeGuru.org, "Intravitreal Injection Standard Dosing Table," https://eyeguru.org/blog/intravitreal-injection-dosing/ (accessed Dec. 6, 2021).
Eylea Approval Letter (Nov. 18, 2011).
Eylea Label (revised Aug. 2018).
Eylea Label (revised Feb. 2023), https://www.accessdata.fda.gov/drugsatfda_docs/label/2023/125387s075lbl.pdf (accessed Apr. 4, 2023).
Eylea Label (revised Mar. 2021), https://www.accessdata.fda.gov/drugsatfda_docs/label/2021/125387s069lbl.pdf (accessed Sep. 26, 2022).
Eylea Label (revised May 2016), https://www.accessdata.fda.gov/drugsatfda_docs/label/2016/125387s051lbl.pdf (accessed Sep. 26, 2022).
Eylea Label (revised May 2019).
Eylea Label (revised Oct. 2014), https://www.accessdata.fda.gov/drugsatfda_docs/label/2014/125387s043lbl.pdf (accessed Sep. 26, 2022).
Eylea Label (revised Sep. 2012), https://www.accessdata.fda.gov/drugsatfda_docs/label/2012/125387s004lbl.pdf (accessed Sep. 26, 2022).
Eylea, "Wet AMD: Dosing Flexibility," https://hcp.eylea.us/about/wet-amd-dosing/ (accessed Jan. 5, 2022).
Fauser et al., "Suppression of Intraocular Vascular Endothelial Growth Factor During Aflibercept Treatment of Age-Related Macular Degeneration," *Am. J. Ophthalmology*, 158, pp. 532-536 (2014).
FDA, "22 Case Studies Where Phase 2 and Phase 3 Trials Had Divergent Results" (Jan. 2017), submitted in IPR2021-00881 as Exhibit 1146.
FDA, "Drugs@FDA: FDA-Approved Drugs, BLA 125387," https://www.accessdata.fda.gov/scripts/cder/daf/index.cfm?event=overview.process&ApplNo=125387 (accessed May 18, 2022).
FDA, "Guidance for Industry: Expedited Programs for Serious Conditions—Drugs and Biologics" (May 2014), https://www.fda.gov/media/86377/download (accessed Sep. 26, 2022).
FDA, "Macugen Drug Approval Package Page," Mar. 23, 2005, https://www.accessdata.fda.gov/drugsatfda_docs/nda/2004/21-756_Macugen.cfm (accessed Jan. 12, 2022).
FDA, "Non-Inferiority Clinical Trials to Establish Effectiveness: Guidance for Industry" (Nov. 2016), submitted in IPR2021-00881 as Exhibit 2097.
FDA, "Purple Book Database of Licensed Biological Products," https://purplebooksearch.fda.gov/patent-list (accessed May 13, 2022).
FDA, Purple Book Database of Licensed Biological Products, https://purplebooksearch.fda.gov/patent-list https://purplebooksearch.fda.gov/patent-list, accessed Jun. 27, 2023.

Fernández-Ferreiro et al., "Preclinical PET Study of Intravitreal Injections," *Investigative Ophthalmology & Visual Science*, 58(7), pp. 2843-2851 (Jun. 2017).
Ferrara et al., "Angiogenesis as a Therapeutic Target," *Nature*, 438, pp. 967-974 (Dec. 2005).
Ferrara et al., "Clinical applications of angiogenic growth factors and their inhibitors," Nature Medicine, 5(12):1359-1364 (Dec. 1999).
Ferrara et al., "Development of ranibizumab, an anti-vascular endothelial growth factor antigen binding fragment, as therapy for neovascular age-related macular degeneration," *Retina*, 26(8), pp. 859-870 (Oct. 2006).
Ferrara, "Vascular Endothelial Growth Factor: Molecular and Biological Aspects," Advances in Organ Biology, pp. 1-30 (1999).
FiercePharma, "Beovu, Novartis," (Oct. 25, 2021), https://www.fiercepharma.com/special-report/beovu-novartis-top-10-drug-launch-disasters (accessed Dec. 30, 2021).
FiercePharma, "Novartis' Hot New Eye Drug Beovu Tied to Potential Vision Loss: Experts," (Feb. 24, 2020), https://www.fiercepharma.com/pharma/retinal-society-flags-serious-side-effect-for-novartis-beovu (accessed Dec. 30, 2021).
FiercePharma, "The Top 20 Drugs by Worldwide sales in 2020," (May 3, 2021), https://www.fiercepharma.com/special-report/top-20-drugs-by-2020-sales (accessed Sep. 26, 2022).
Flyvbjerg et al., "Amelioration of Long-Term Renal Changes in Obese Type 2 Diabetic Mice by a Neutralizing Vascular Endothelial Growth Factor Antibody," Diabetes, 51:3090-3094 (Oct. 2002).
FocusVision, "Survey Sample Size: How Much Do I Need?" (Apr. 11, 2019), https://www.focusvision.com/blog/survey-sample-size-how-much-do-i-need/ (accessed Jan. 25, 2022).
Franklin et al., "The Structural Basis for the Function of Two Anti-VEGF Receptor 2 Antibodies," *Structure* 19:1097-1107 (Aug. 10, 2011).
Fraser et al., "Single Injections of Vascular Endothelial Growth Factor Trap Block Ovulation in the Macaque and Produce a Prolonged, Dose-Related Suppression of Ovarian Function." J. Clin. Endocrinol & Metab. 90(2): 1114-1122 (Feb. 2005).
Fraser et al., "The Role of Vascular Endothelial Growth Factor and Estradiol in the Regulation of Endometrial Angiogenesis and Cell Proliferation in the Marmoset," *Endocrinology*, 149(9), pp. 4413-4420 (May 2008) (electronic publication).
Fung et al., "An Optical Coherence Tomography-Guided, Variable Dosing Regiment with Intravitreal Ranibizumab (Lucentis) for Neovascular Age-related Macular Degeneration," Am. J. Ophthalmology, 143(4):566-583 (Apr. 2007).
Gagnon et al., "The Cost of Pushing Pills: A New Estimate of Pharmaceutical Promotion Expenditures in the United States," PLoS Medicine, 5(1), pp. 29-33 (Jan. 2008).
Gale, "Complementary and Coordinated Roles of the VEGFs and Angiopoietins during Normal and Pathologic Vascular Formation," Cold Spring Harbor Symposia on Quantitative Biology, vol. LXVII., pp. 267-273 (2002).
Gallemore et al., "When Anti-VEGF Treatment Fails: Retina Specialists Are Charting New Territory and Learning How to Spot and React to Failed Anti-VEGF Therapy," *Rev. Ophthalmology*, (Mar. 2008).
Garcia-Quintanilla, "Pharmacokinetics of Intravitreal Anti-VEGF Drugs in Age-Related Macular Degeneration," *Pharmaceutics*, 11:365 (Jul. 2019).
Genentech, "Genentech Statement on Chroma, the Second Phase III Study for Lampalizumab," Press Release (Nov. 9, 2017).
Genentech, Inc., "FDA Approves Lucentis for the Treatment of Wet Age-Related Macular Degeneration," Press Release, (Jun. 30, 2006).
Genentech, Inc., "FDA Green-Lights Genentech's Lucentis for Macular Edema following Retinal Vein Occlusion," Press Release, (Jun. 23, 2010), https://www.genengnews.com/news/fda-green-lights-genentechs-lucentis-for-macular-edema-following-retinal-vein-occlusion/ (accessed Jan. 12, 2022).
Genentech, Inc., "Genentech, Inc. Submits Biologics License Application For FDA Review Of Lucentis™ In Wet Age-Related Macular Degeneration," Press Release (Dec. 30, 2005), https://www.biospace.com/article/releases/genentech-inc-submitsbiologics-license-application-

(56) References Cited

OTHER PUBLICATIONS for-fda-review-of-lucentis-tm-in-wetage- related-macular-degeneration-/ (accessed Feb. 3, 2022).
Genentech, Press Release "FDA Approves Genentech's Lucentis (Ranibizumab Injection) for Diabetic Retinopathy, the Leading Cause of Blindness Among Working Age Adults in the United States," 5 pp. (Apr. 17, 2017).
Gewaily et al., "Intravitreal steroids versus observation for macular edema secondary to central retinal vein occlusion," *Cochrane Database Syst. Rev.*, 1(CD007324):1-31 (2009).
Golan et al., "Current Treatment of Retinal Vein Occlusion," *Eur. Ophthalmic Rev.*, 5:62-68 (2011).
Gomez-Manzano et al., "VEGF Trap Induces Antiglioma Effect at Different Stages of Disease," *Neuro-Oncology*, 10, pp. 940-945 (Dec. 2008), cited in Deposition of Dr. Alexander M. Klibanov, Ph.D., on Mar. 24, 2022.
Gonzalez-Cortés, "Treatment of Diabetic Macular Edema (DME): Shifting Paradigms," *Medicina Universitaria*, 17(69):243-247 (2015).
Good Days, https://www.mygooddays.org/ (accessed May 18, 2022).
Good Days, https://www.mygooddays.org/patients/assistance-types (last visited Jun. 27, 2023).
Gragoudas et al., "Pegaptanib for Neovascular Age-Related Macular Degeneration," N. Engl. J. Med., 351(27):2805-2816, (Dec. 30, 2004).
Gross et al., "Panretinal Photocoagulation vs Intravitreous Ranibizumab for Proliferative Diabetic Retinopathy. A Randomized Clinical Trial," *JAMA*, 314(20):2137-2146 (published Nov. 13, 2015; corrected Mar. 12, 2019).
Guha et al., "The Economics of Commercial Success in Pharmaceutical Patent Litigation," *Landslide* 1(5) (2009).
Gupta et al., "A treat and extend regimen using ranibizumab for neovascular age-related macular degeneration clinical and economic impact," *Ophthalmology*, 117(11): 2134-2140 (Nov. 2010).
Gutierrez et al., "Intravitreal bevacizumab (Avastin) in the treatment of macular edema secondary to retinal vein occlusion," *Clin. Ophthalmol.*, 2(4):787,791 (Dec. 2008).
Hachiya et al., "Increase in respiratory cost at high growth temperature is attributed to high protein turnover cost in Petunia x hybrida petals," *Plant, Cell, and Environment*, 30(10), pp. 1269-1283 (Oct. 2007).
Haller et al., "VEGF Trap-Eye In CRVO: Primary Endpoint Results of the Phase 3 Copernicus Study," ARVO Annual Meeting Abstract (Apr. 2011).
Halpern et al., "Resource utilization and costs of age-related macular degeneration," *Health Care Financ. Rev.*, 27(3): pp. 37-47 (Spring 2006).
Handgraaf et al., "Molecular Dynamics Study of Onset of Water Gelation around the Collagen Triple Helix," *Proteins*, 64:711-718 (2006).
Hanhart et al., Correspondence regarding "Fellow Eye Effect of Unilateral Intravitreal Anti-VEGF Injections in Eyes with Diabetic Macular Edema," *Eye*, 29, pp. 292-293 (Nov. 2014) (online publication), cited in Deposition of Dr. Alexander M. Klibanov, Ph.D., on Mar. 24, 2022.
Hashmi et al., "Conjunctivitis," in *StatPearls*, Treasure Island (FL), StatPearls Publishing, https://www.ncbi.nlm.nih.gov/books/NBK541034/ (published online Jan. 2022, updated Dec. 6, 2022) (accessed Jan. 5, 2023), submitted in IPR2023-00442 as Exhibit 1024.
Hayes, "SEC Filings: Forms You Need To Know," *Investopedia*, https://www.investopedia.com/articles/fundamental-analysis/08/sec-forms.asp (accessed Jan. 20, 2021).
HCPCS Codes, "HCPCS Codes," https://hcpcs.codes/ (accessed Jan. 6, 2022).
Healio, "Access to Retina Providers Shows No Geographic Bias in U.S.," (Mar. 12, 2019), https://www.healio.com/news/ophthalmology/20190312/access-to-retina-providers-shows-no-geographic-bias-in-us (accessed Dec. 6, 2021).

Hecht, "Ophthalmic Preparations," *Remington: The Science and Practice of Pharmacy*, vol. II, 19th edition, Chapter 89, pp. 1563-1576 (1995) (Easton, PA).
Heier & Focus Study Group, *Abstract: Intravitreal Ranibizumab (Lucentis™) with Verteporfin Photodynamic Therapy for Neovascular Age-Related Macular Degeneration: Year One Results*, Am. Soc'y Retina Specialists Ann. Meeting 94 (2005).
Heier et al., "Clear-It 2: Phase 2, Randomized Controlled Dose and Interval-Ranging Study of Intravitreal VEFG Trap Eye in Patients with Neovascular Age-Related Macular Degeneration: Predictive Factors for Visual Acuity," ARVO Annual Meeting Abstract (Apr. 2009).
Heier et al., "Intravitreal Aflibercept (VEGF Trap-Eye) in Wet Age-related Macular Degeneration," Ophthalmology, 119:2537-2548 (Dec. 2012).
Heier et al., "Intravitreal Aflibercept (VEGF Trap-Eye) in Wet Age-related Macular Degeneration," *Ophthalmology*, 119, Appendices 2-8, pp. 1-34 (Dec. 2012), submitted in IPR2022-01524 as Exhibit 1030.
Heier et al., "Ranibizumab for Choroidal Neovascularization Secondary to Causes Other Than Age-Related Macular Degeneration: A Phase I Clinical Trial," Ophthalmology, 118(1):111-118 (Jan. 2011).
Heier et al., "Ranibizumab for macular edema due to retinal vein occlusions: long-term follow-up in the Horizon trial," Ophthalmology, 119(4):802-809 (2012).
Heier et al., "RhuFab V2 (anti-VEGF Antibody) for Treatment of Exudative AMD," Symposium 8: Experimental and Emerging Treatments for Choroidal Neovascularization, 10 pp (2002).
Heier et al., "RhuFab V2 in Wet AMD—6 Month Continued Improvement Following Multiple Intravitreal Injections," Investigative Ophthalmology & Visual Science, 44(E-Abstract):972 (2003).
Heier et al., "The 1-year Results of Clear-It 2, a Phase 2 Study of Vascular Endothelial Growth Factor Trap-Eye Dosed As-needed After 12-week Fixed Dosing," Ophthalmology 118(6):1098-1106 (Jun. 2011).
Heier et al., "The 1-year Results of Clear-It 2, a Phase 2 Study of Vascular Endothelial Growth Factor Trap-Eye Dosed As-needed After 12-week Fixed Dosing: Erratum," Ophthalmology, 118(9):1700 (Sep. 2011).
Heier, "Intravitreal Aflibercept for Diabetic Macular Edema: 148-Week Results from the Vista and Vivid Studies," Ophthalmology, 123(11):2376-2385 (2016), (published online Sep. 7, 2016).
Heier, "Intravitreal VEGF Trap for AMD: An Update," Retina Today 44 (Oct. 2009).
Heier, "VEGF Trap-Eye for Exudative AMD," *Retinal Physician*, (Apr. 2009).
Heimann, "Intravitreal Injections: Techniques and Sequelae," in *Medical Retina*, Holz & Spaide, eds., (2007) (New York, NY).
Helzner, "Lucentis After 1 Year: Doctors praise this practice-transforming therapy—but find drawbacks," *Retinal Physician* (Jul. 1, 2007), https://www.retinalphysician.com/issues/2007/july-aug/lucentis-after-1-year (accessed Sep. 26, 2022).
Herceptin Label, Sep. 1998.
Highlights of Prescribing Information for Eylea (aflibercept) Injection, for Intravitreal use, 11 pp., revised Feb. 2023.
Highlights of Prescribing Information for Eylea (aflibercept); revised Oct. 2016.
Highlights of Prescribing Information for Eylea (Revised: Jun. 2021), cited in Deposition of Dr. Richard Manning, Ph.D., on May 4, 2022, submitted in IPR2021-00881 as Exhibit 1152.
Hirokawa et al., "Tau Proteins: The Molecular Structure and Mode of Binding on Microtubules," *J. Cell Biol.*, 107(4), pp. 1449-1459 (Oct. 1988).
Ho et al., Slides entitled "VEGF Trap-Eye in Wet AMD—Clear It 2: One-Year Key Results," Retina Society, pp 1-35 (2008).
Ho, Slides entitled "VEGF Trap-Eye in Wet AMD—Clear-It 2: One-Year OCT and FA Outcomes," Clear-It 2 Study Group, pp. 1-24 (Sep. 28, 2008).
Holash et al., "Vessel Cooption, Regression, and Growth in Tumors Mediated by Angiopoietins and VEGF," Science, 284(5422):1994-1998 (Jun. 18, 1999).

(56) References Cited

OTHER PUBLICATIONS

Holash, "Inhibitors of growth factor receptors, signaling pathways and angiogenesis as therapeutic molecular agents," *Cancer Metastasis*, 25:243-252 (Jun. 2006).
Holash, "VEGF-Trap: A VEGF blocker with potent antitumor effects," PNAS, 99(17)11393-11398 (Aug. 20, 2002).
Holz et al., "VEGF Trap-Eye for Macular Oedema Secondary to Central Retinal Vein Occlusion: 6-Month Results of the Phase III Galileo Study," *British J. Ophthalmology*, 97, pp. 278-284 (Dec. 2013).
Hopkins Medicine, "Photodynamic Therapy for Age-Related Macular Degeneration," https://www.hopkinsmedicine.org/health/treatment-tests-and-therapies/photodynamic-therapy-for-agerelated-macular-degeneration (accessed Dec. 1, 2021).
Iacono et al., "Antivascular Endothelial Growth Factor in Diabetic Retinopathy," *Dev. Ophthalmol.*, 46, pp. 39-53 (2010).
International Search Report issued in International Application PCT/US2018/063025, mailed Mar. 19, 2019.
Internet Archive, "CATT Patient Eligibility Criteria," https://web.archive.org/web/20100713035617/http://www.med.upenn.edu/cpob/studies/documents/CATTEligibilityCriteria_000.pdf (Jul. 13, 2010) (accessed Dec. 8, 2022), submitted in IPR2023-00442 as Exhibit 1031.
*Intraocular Inflammation and Uveitis*, American Academy of Ophthalmology, Section 9: Basic and Clinical Science Course, Chapter 6, pp. 101-146 (2008-2009).
Ip et al., "A randomized trial comparing the efficacy and safety of intravitreal triamcinolone with observation to treat vision loss associated with macular edema secondary to central retinal vein occlusion: the Standard Care vs Corticosteroid for Retinal Vein Occlusion (SCORE) study report 5," Arch. Ophthalmol., 127(9):1101-1114 (2009).
Iqvia, "Available Iqvia Data," https://www.iqvia.com/insights/the-iqvia-institute/available-iqvia-data (accessed Jan. 18, 2022).
Iqvia, Form 10-K, 2020.
Jaffe et al., "Differential Response to Anti-VEGF Regimens in Age-Related Macular Degeneration Patients with Early Persistent Retinal Fluid," *Ophthalmology*, 123(9), pp. 1856-1864 (Sep. 2016).
Jaffe et al., *Intraocular Drug Delivery*, Taylor & Francis Group (NY) (2006).
Jager et al., "Risks of Intravitreous Injection: A Comprehensive Review," *Retina*, 24(5), pp. 676-698 (Oct. 2004) (Philadelphia, PA).
Janeway et al., "The structure of a typical antibody molecule" Immunobiology: The Immune System in Health and Disease. 5th edition. New York: Garland Science (2001).
Johnson & Johnson Services, Inc., "Johnson & Johnson Completes Acquisition of Momenta Pharmaceuticals, Inc.," Press Release, (Oct. 1, 2020), https://www.jnj.com/johnson-johnson-completes-acquisition-of-momenta-pharmaceuticals-inc (accessed Aug. 2, 2021).
Johnson & Johnson Services, Inc., "Johnson & Johnson to Acquire Momenta Pharmaceuticals, Inc., Expanding Janssen's Leadership in Novel Treatments for Autoimmune Diseases," Press Release, (Aug. 19, 2020) https://www.jnj.com/johnson-johnson-to-acquire-momenta-pharmaceuticals-inc-expanding-janssens-leadership-in-novel-treatments-for-autoimmune-diseases (accessed Aug. 2, 2021).
Kaiser Family Foundation, "A Snapshot of Sources of Coverage Among Medicare Beneficiaries in 2018," available at: https://www.kff.org/medicare/issue-brief/a-snapshot-of-sources-of-coverage-among-medicare-beneficiaries-in-2018/ (accessed Mar. 23, 2021).
Kaiser Family Foundation, "Medicare Advantage in 2021: Enrollment Update and Key Trends," https://www.kff.org/medicare/issue-brief/medicare-advantage-in-2021-enrollment-update-and-key-trends/ (accessed Jun. 21, 2021).
Kaiser, "Vascular endothelial growth factor Trap-Eye for diabetic macular oedema," Br. J. Ophthalmol., 93(2):135-136 (Feb. 2009).
Kanghong Pharmaceutical, "Announcement of Chengdu Kanghong Pharmaceutical Group Co., Ltd. on Stopping the Global Multi-center Clinical Trial of Conbercept Ophthalmic Injection," Press Release, http://epaper.zqrb.cn/html/2021-04/10/content_716426.htm?div=-1 (with English translation) (accessed Sep. 26, 2022).

Karia, "Retinal vein occlusion: pathophysiology and treatment options," *Clinical Ophthalmology*, 4:809-816 (Jul. 2010).
Keane et al., "Effect of Ranibizumab Retreatment Frequency on Neurosensory Retinal Volume in Neovascular AMD," *Retina*, 29(5), pp. 592-600 (May 2009).
Keane et al., "Retinal vein occlusion and macular edema—critical evaluation of the clinical value of ranibizumab," *Clinical Ophthalmology*, 5:771-781 (2011).
Kiire et al., "Managing retinal vein occlusion," *BMJ*, 344(e499):1-16 (Feb. 2012).
Kim et al., "A Brief History of Anti-VEGF for the Treatment of Ocular Angiogenesis," *The American Journal of Pathology*, 181(2), pp. 376-379 (Aug. 2012).
Kim et al., "Eyes that Do Not Meet the Eligibility Criteria of Clinical Trials on Age-Related Macular Degeneration: Proportions of the Real-World Patient Population and Reasons for Exclusion," *Journal of Ophthalmology*, 2021: Article ID 6635467, 8 pages (Apr. 2021).
Kim et al., "Potent VEGF Blockade Causes Regression of Coopted Vessels in a Model of Neuroblastoma," *Proc. Nat'l Acad. Sci.*, 99(17), pp. 11399-11404 (Aug. 12, 2002).
Kinge et al., "Efficacy of Ranibizumab in Patients With Macular Edema Secondary to Central Retinal Vein Occlusion: Results From the Sham-Controlled ROCC Study," *American Journal of Ophthalmology*, 150(3):310-314 (2010).
Kleiger et al., "The 1.7 Å Crystal Structure of BOI: A Study of How Two Dissimilar Amino Acid Sequences Can Adopt the Same Fold," *J. Mol. Biol.*, 299(4), pp. 1019-1034 (Jun. 2000).
Korobelnik et al., "Intravitreal Aflibercept Injection for Macular Edema Resulting from Central Retinal Vein Occlusion," *Ophthalmology*, 121(1):202-208 (Jan. 2014).
Korobelnik, "Intravitreal Aflibercept for Diabetic Macular Edema," Ophthalmology, 121(11):2247-2254 (Nov. 2014).
Kreatsoulas, "Expanding Therapeutic Options for Retinal Vein Occlusion," *Retina Today*, pp. 20-21 (Jul./Aug. 2009).
Krzystolik et al., "Prevention of Experimental Choroidal Neovascularization With Intravitreal Anti-Vascular Endothelial Growth Factor Antibody Fragment," Arch. Ophthalmol., 120(3):338-346 (Mar. 2002).
Kuepper, "The Best Investment Information Sources: Using SEC Filings, Analyst Reports, and Company Websites," *The Balance*, https://www.thebalance.com/top-best-sources-of-investor-information-1979207 (accessed Jan. 20, 2021).
Kuhlmann et al., "Lessons Learned from Biosimilar Epoetins and Insulins," *The British Journal of Diabetes & Vascular Disease*, 10(2), pp. 90-99 (Apr. 2010).
Kuo, "Comparative evaluation of the antitumor activity of antiangiogenic proteins delivered by gene transfer," PNAS, 98(8):4605-4610 (Apr. 10, 2001).
L36962: Medicare Part AB Local Coverage Determination (LCD) Comment Summary (May 2, 2014), cited in Deposition of Dr. David M. Brown, M.D., on Apr. 26, 2022, submitted in IPR2021-00881 as Exhibit 1140.
Lalwani, "A Variable-dosing Regimen with Intravitreal Ranibizumab for Neovascular Age-related Macular Degeneration: Year 2 of the PrONTO Study," Am. J. Ophthalmology, 148(1):43-58 (Jul. 2009).
Lalwani, "All About PrONTO: Study Yielded Good Results in AMD With Treatment Guided by OCT," Retina Today (May 2007).
Levine, "Macular Hemorrhage In Neovascular Age-Related Macular Degeneration After Stabilization With Antiangiogenic Therapy," *Retina*, 29(8):1074-1079 (Sep. 2009).
Li et al., "Safety and Efficacy of Conbercept in Neovascular Age-Related Macular Degeneration: Results from a 12-Month Randomized Phase 2 Study: Aurora Study," *Ophthalmology*, 121(9), pp. 1740-1747 (2014).
Li et al., "Treatment regimens for administration of anti-vascular endothelial growth factor agents for neovascular age-related macular degeneration," *Cochrane Database Syst. Rev.*, Issue 5, Article CD012208, pp. 1-91 (2020).
Ling et al., "Deregulating Direct-to-Consumer Marketing of Prescription Drugs: Effects on Prescription and Over-the-Counter Product Sales," *Journal of Law and Economics*, 45, pp. 691-723 (2002).

(56) References Cited

OTHER PUBLICATIONS

Liu et al., "A Novel Engineered VEGF Blocker with an Excellent Pharmacokinetic Profile and Robust Anti-Tumor Activity," *BMC Cancer*, 15(170), pp. 1-14 (Mar. 2015) (online publication), cited in Deposition of Dr. Alexander M. Klibanov, Ph.D., on Mar. 24, 2022.
Lobov et al., "VEGF Trap Treatment Regresses Pathological Neovessels, Improves Revascularization and Reduces Retinal Ischemia in the Murine Oxygen-Induced Retinopathy (OIR) Model," ARVO Annual Meeting Abstract, Investigative Ophthalmology & Visual Science, 52:3128 (Apr. 2011).
Lott et al., "Bevacizumab in Inflammatory Eye Disease," *American Journal of Ophthalmology*, 148(5): pp. 711-17.e2 (Nov. 2009).
Lu et al., "Identification of the Residues in the Extracellular Region of KDR Important for Interaction with Vascular Endothelial Growth Factor and Neutralizing Anti-KDR Antibodies," *J. Biol. Chem.*, 275(19):14321-14330 (May 12, 2000).
Lucentis Approval (Jun. 30, 2006).
Lucentis Label (Revised 2006).
Lucentis Label (Revised 2014), submitted in IPR2021-00402 as Exhibit 1023.
Lucentis Label (revised Apr. 2017), https://www.accessdata.fda.gov/drugsatfda_docs/label/2017/125156s114lbl.pdf (accessed Sep. 26, 2022).
Lucentis Label (revised Aug. 2012), https://www.accessdata.fda.gov/drugsatfda_docs/label/2012/125156s0069s0076lbl.pdf (accessed Sep. 26, 2022).
Lucentis Label (revised Jun. 2010), https://www.accessdata.fda.gov/drugsatfda_docs/label/2010/125156s053lbl.pdf (accessed Sep. 26, 2022).
Lucentis Label (revised Mar. 2018), https://www.accessdata.fda.gov/drugsatfda_docs/label/2018/125156s117lbl.pdf (accessed Sep. 26, 2022).
Macugen Approval Letter (Dec. 17, 2004).
Macugen Label (revised Dec. 2004), https://www.accessdata.fda.gov/drugsatfda_docs/label/2004/021756lbl.pdf (accessed Sep. 26, 2022).
Macugen Label (submitted with NDA 21-756), submitted in IPR2021-00881 as Exhibit 2038.
Macular Photocoagulation Study Group, "Laser photocoagulation of subfoveal neovascular lesions in age-related macular degeneration. Results of a randomized clinical trial," Arch. Ophthalmol., 109(9):1220-1231 (1991).
Major et al., "Da Vinci: DME and VEGF Trap-Eye: Investigation of Clinical Impact: Phase 2 Study in Patients with Diabetic Macular Edema (DME)," ARVO Annual Meeting Abstract (Apr. 2010).
Mankiw, *Principles of Microeconomics*, 5th ed., South-Western Cengage Learning (Mason, OH) (Sep. 2009).
Manning et al., "Similar Products at Different Prices: Can Biopharmaceutical Companies Segment Markets?" *International Journal of the Economics of Business*, 22(2), pp. 231-243 (Jun. 2015).
Mansour et al., "Long-term Visual Outcomes of Intravitreal Bevacizumab in Inflammatory Ocular Neovascularization," *American Journal of Ophthalmology*, 148(2): pp. 310-316.e2 (Aug. 2009).
Margolis, "Hemorrhagic Recurrence Of Neovascular Age-Related Macular Degeneration Not Predicted By Spectral Domain Optical Coherence Tomography," *Retinal Cases & Brief Reports*, 4:1-4 (Winter 2010).
Martin et al., "Ranibizumab and Bevacizumab for Treatment of Neovascular Age-related Macular Degeneration: Two-Year Results," *Ophthalmology*, 119(7): pp. 1388-1398 (Jul. 2012).
Martin et al., CATT Research Group, "Ranibizumab and Bevacizumab for Neovascular Age-Related Macular Degeneration," *N. Engl. J. Med.*, 364(20):1897-1908 (May 19, 2011).
Massin, "Anti-VEGF Therapy for Diabetic Macular Edema: An Update," *Retina Today*, 54 (Sep./Oct. 2008).
Massin, "Safety and Efficacy of Ranibizumab in Diabetic Macular Edema (Resolve Study*)," Diabetes Care, 33(11):2399-2405 (Nov. 2010).
Mathis, "Fine-Tuning Your Anti-VEGF Injection Protocols: The Second Article in Our Series Recapping Research and Analysis Presented at Our Annual Meeting," *Retinal Physician* (Oct. 1, 2009), https://www.retinalphysician.com/issues/2009/october-2009/fine-tuning-your-anti-vegf-injection-protocols (accessed Feb. 4, 2022).
Mayo Clinic, "Wet Macular Degeneration Symptoms and Causes," https://www.mayoclinic.org/diseases-conditions/wet-macular-degeneration/symptoms-causes/syc-20351107 (accessed Nov. 11, 2021).
Mayo Clinic, "Wet Macular Degeneration," https://www.mayoclinic.org/diseases-conditions/wet-macular-degeneration/diagnosis-treatment/drc-20351113 (accessed Nov. 11, 2021).
Medicare Interactive, "Medicare Part B Covered Services," https://www.medicareinteractive.org/get-answers/medicare-covered-services/medicare-coverage-overview/summary-of-part-b-covered-services (accessed Nov. 22, 2021).
Medicare Interactive, "The Parts of Medicare (A, B, C, D)," https://www.medicareinteractive.org/get-answers/medicare-basics/medicare-coverage-overview/original-medicare (accessed Nov. 30, 2021).
Medicare.gov, "Macular Degeneration Tests & Treatment," https://www.medicare.gov/coverage/macular-degeneration-tests-treatment (accessed Nov. 22, 2021).
Medicare.gov, "Medicare Advantage Plans," https://www.medicare.gov/sign-up-change-plans/types-of-medicare-health-plans/medicare-advantage-plans (accessed Dec. 31, 2021).
Medicare.gov, "When Does Medicare Coverage Start?" https://www.medicare.gov/basics/get-started-with-medicare/sign-up/when-does-medicare-coverage-start (accessed Dec. 15, 2021).
Medline Plus, "Laser Photocoagulation—Eye," https://medlineplus.gov/ency/article/007664.htm (accessed Dec. 2, 2021).
Michels et al., "Systemic bevacizumab (Avastin) therapy for neovascular age-related macular degeneration twelve-week results of an uncontrolled open-label clinical study," *Ophthalmology*, 112(6):1035-1047 (Jun. 2005).
Mihailescu et al., "A Signature of the T à R Transition in Human Hemoglobin," *Proc. Natl. Acad. Sci. USA*, 98(7):3773-3777 (Mar. 27, 2001).
Miller & Zois, LLC, "Novartis Looking to Repurpose its Dangerous Beovu Drug," Nov. 28, 2020, https://www.drugrecalllawyerblog.com/novartis-repurpose-beovu.html (accessed Sep. 23, 2021).
Miller, "Taking Advantage of the New Purple Book Patent Requirements for Biologics," (Apr. 26, 2021), https://www.morganlewis.com/pubs/2021/04/taking-advantage-of-the-new-purple-book-patent-requirements-for-biologics (accessed Sep. 26, 2022).
Mitchell et al., "Evaluating the Impact of Intravitreal Aflibercept on Diabetic Retinopathy Progression in the VIVID-DME and VISTA-DME Studies," *Ophthalmol. Retina*, 2, pp. 10 (Oct. 2018).
Mitchell et al., "Ranibizumab (Lucentis) in Neovascular Age-Related Macular Degeneration: Evidence from Clinical Trials," Brit. J. Ophthalmology, 94:2-13 (2010) (first online publication on May 20, 2009).
Mitchell, "Targeted Therapy for Metastatic Colorectal Cancer: Role of Aflibercept," *Clinical Colorectal Cancer*, 12(2):73-85 (Jun. 2013).
Mitchell, "The Restore Study, Ranibizumab Monotherapy or Combined with Laser versus Laser Monotherapy for Diabetic Macular Edema," Ophthalmology, 188(4):615-625 (Apr. 2011).
Mitra et al., "Review of anti-vascular endothelial growth factor therapy in macular edema secondary to central retinal vein occlusions," Expert Review in Ophthalmol., Taylor & Francis, GB 6(6):623-629 (Jan. 2011).
Moroney et al., "Aflibercept in Epithelial Ovarian Carcinoma," *Future Oncology*, 5(5), pp. 591-600 (Jun. 2009).
Mousa and Mousa, "Current Status of Vascular Endothelial Growth Factor Inhibition in Age-Related Macular Degeneration," Biodrugs, 24(3):183-194 (Aug. 2010).
Mueller et al., "Ocular Infection and Inflammation," Emergency Med. Clinics N. Am., 26(1), pp. 57-72 (Feb. 2008) (Philadelphia, PA).
Murphy et al., "Protein Folding, Misfolding, Stability and Aggregation: An Overview," in *Misbehaving Proteins—Protein (Mis)Folding, Aggregation, and Stability*, Murphy et al., eds., Springer, (2006) (New York, NY).

(56) References Cited

OTHER PUBLICATIONS

Mylan, "Momenta and Mylan Announce Development Strategy for M710, a Proposed Biosimilar to Eylea® (aflibercept)," Press Release (Jan. 3, 2018).
N/A, "Materials from Dec. 2011 FDA Committee Mtg.," (Dec. 1, 2011).
N/A, "Materials from Jun. 2011 FDA Committee Mtg.," (Jun. 17, 2011).
National Health Service, "Overview: Uveitis," https://www.nhs.uk/conditions/uveitis/ (Jan. 3, 2020) (accessed Jan. 5, 2023), submitted in IPR2023-00442 as Exhibit 1063.
NCT01331681, Intravitreal Aflibercept Injection in Vision Impairment Due to DME (Vivid-DME), Mar. 2016, as submitted in Opposition of EP3716992 as D36 on May 10, 2023.
NCT01363440, Study of Intravitreal Aflibercept Injection (IAI; Eylea®, BAY86-5321) in Patients with Diabetic Macular Edema (Vista DME), Apr. 2016, as submitted in Opposition of EP3716992 as D37 on May 10, 2023.
Nguyen et al., "A Phase I Study of Intravitreal Vascular Endothelial Growth Factor Trap-Eye in Patients with Neovascular Age-Related Macular Degeneration," Ophthalmology, 116(11):2141-2148 (Nov. 1, 2009).
Nguyen et al., "A phase I trial of an IV-administered vascular endothelial growth factor trap for treatment in patients with choroidal neovascularization due to age-related macular degeneration," Ophthalmology, 113(9):1522e1-1522e14 (Sep. 2006) (epub Jul. 28, 2006).
Nguyen et al., "Randomized, Double-masked, Active-controlled Phase 3 Trial of the Efficacy and Safety of Intravitreal VEGF Trap-Eye in Wet AMD: One-year Results of the View 1 Study," ARVO Annual Meeting Abstract (Apr. 2011).
Nguyen et al., "Results of a Phase I, Dose-Escalation, Safety, Tolerability, and Bioactivity Study of Intravitreous VEGF Trap in Patients with Neovascular Age-Related Macular Degeneration," ARVO Annual Meeting Abstract (May 1, 2006).
Nguyen, "Ranibizumab for Diabetic Macular Edema, Results from 2 Phase III Randomized Trials: Rise and Ride," Ophthalmology, 119(4):789-801 (Apr. 2012).
Ni et al., "Emerging Pharmacologic Therapies for Wet Age-Related Macular Degeneration," *Ophthalmologica*, 223, pp. 401-410 (May 2009) (online publication).
Nichols, "AAO: Ranibizumab (rhuRab) May Improve Vision in Age-Related Macular Degeneration," Doctor's Guide Global Edition, www.pslgroup.com/dg/23f2aa.htm, pp. 1-2 (Nov. 24, 2003).
Nieto et al., "Ocular silicon distribution and clearance following intravitreal injection of porous silicon microparticles," *Exp. Eye Res.*, 116, pp. 161-168 (Nov. 2013).
Noguera-Troise et al., "Blockade of D114 inhibits tumor growth by promoting non-productive angiogenesis," Nature, 444:1032-1037 (Dec. 2006).
Nork, et al., "Prevention of experimental choroidal neovascularization and resolution of active lesions by VEGF trap in nonhuman primates," *Arch. Ophthalmol.*, 129:1042-1052 (Aug. 2011).
Novartis Press Release, "Novartis Receives FDA Approval for Beovu, Offering Wet AMD Patients Vision Gains and Greater Fluid Reductions vs Aflibercept," (Oct. 8, 2019), https://www.novartis.com/news/media-releases/novartis-receives-fda-approval-beovu-offering-wet-amd-patients-vision-gains-and-greater-fluid-reductions-vs-aflibercept (accessed Sep. 26, 2022).
Novartis Press Release, "US FDA Approves Updated Novartis Beovu Label, to Include Additional Safety Information," (Jun. 11, 2020), https://www.novartis.com/news/media-releases/us-fda-approves-updated-novartis-beovu-label-include-additional-safety-information (accessed Sep. 26, 2022).
Novartis, Annual Report, 2020, submitted in IPR2021-00881 as Exhibit 2230.
Nucleic acid sequence alignment of SEQ ID No. 1 of the '338 and '069 patents with SEQ ID No. 15 of the '758 patent and SEQ ID No. 15 of the '959 patent, submitted in IPR2021-00881 as Exhibit 1124.
Nucleotide sequence alignment of SEQ ID No. 1 of the '338 patent with SEQ ID No. 15 of the '758 patent and SEQ ID No. 3 of Dix, submitted in IPR2022-00881 as Exhibit 1094.
Nucleotide sequence alignment of SEQ ID No. 1 of the '681 and '601 patents with SEQ ID No. 15 of the '758 patent and SEQ ID No. 1 of the '173 patent, submitted in IPR2022-01226 as Exhibit 1093.
Ohr, "Aflibercept in wet age-related macular degeneration: a perspective review," *Ther. Adv. Chronic Dis.*, 3(4):153-161 (Apr. 2012).
Oliveira et al., "VEGF Trap R1R2 suppresses experimental corneal angiogenesis," European Journal of Ophthalmology, 20(1):48-54 (Jan. 1, 2010).
Ophthotech, "Ophthotech Announces Results from Pivotal Phase 3 Trials of Fovista® in Wet Age-Related Macular Degeneration," Press Release (Dec. 12, 2016).
Optometry Pharma, Supplement to Australian Optometry, Jun. 2009.
P17948 VGFR1_Human, available at https://www.uniprot.org/uniprotkb/P17948/entry, submitted in IPR2022-01225 as Exhibit 2079 on Apr. 25, 2023.
P17948 VGFR1_Human, Entry Version 140 (txt) (Jan. 11, 2011), available at https://rest.uniprot.org/unisave/P17948?format=txt&versions=140, submitted in IPR2022-01225 as Exhibit 2080 on Apr. 25, 2023.
P35968 VGFR2_Human, available at https://www.uniprot.org/uniprotkb/P35968/entry, submitted in IPR2022-01225 as Exhibit 2084 on Apr. 25, 2023.
P35968 VGFR2_Human, Entry Version 127 (txt) (Jan. 11, 2011), available at https://rest.uniprot.org/unisave/P35968?format=txt&versions=127, submitted in IPR2022-01225 as Exhibit 2085 on Apr. 25, 2023.
Pai et al., "Current concepts in intravitreal drug therapy for diabetic retinopathy," Saudi Journal of Ophthalmology, 24(4):143-149 (Jun. 30, 2010).
Papadopoulos, "Binding and neutralization of vascular endothelial growth factor (VEGF) and related ligands by VEGF Trap, ranibizumab and bevacizumab," *Angiogenesis*, 15:171-185 (Feb. 2012).
Park et al., "New Approach to Anti-VEGF Agents for Age-Related Macular Degeneration," *Journal of Ophthalmology*, 2012:Article ID 637316 (Feb. 2012).
Parkins & Lashmar, "The formulation of biopharmaceutical products," Pharmaceutical Science & Technology Today, 3(4):129-137 (Apr. 4, 2000).
Pflugfelder et al., "Intravitreal Vancomycin: Retinal Toxicity, Clearance, and Interaction with Gentamicin," *Arch. Ophthalmol.*, 105(6), pp. 831-837 (Jun. 1987).
Phosphate buffer. Cold Spring Harbor Protocols 2006: pdb.rec8543 (2006).
Pieramici, "Intravitreal Ranibizumab for Treatment of Macular Edema Secondary to Retinal Vein Occlusion," *Retina Today*, 44-46 (Mar. 2009).
Pindyck et al., *Microeconomics*, Upper Saddle River: Prentice Hall (2013).
Piques et al., "Ribosome and transcript copy numbers, polysome occupancy and enzyme dynamics in Arabidopsis," *Molecular Systems Biology*, 5(1), pp. 314 (Jan. 2009).
Powers et al., "Recent advances in the management and understanding of diabetic retinopathy [version 1; referees: 2 approved]," F1000Research, 6(F1000Faculty Ref): 2063, 9 pp. (Nov. 29, 2017).
Prangé et al., "Exploring Hydrophobic Sites in Proteins with Xenon or Krypton," *Proteins: Structure, Function, and Genetics*, 30(1), pp. 61-73 (Jan. 1998).
Prevent Blindness, "Uveitis: What is Uveitis?" https://preventblindness.org/wp-content/uploads/2021/06/FS119-Uveitisshort.pdf (accessed Jan. 6, 2023), submitted in IPR2023-00442 as Exhibit 1023.
Publication of OIG Special Fraud Alerts, 59 Fed. Reg. 242, (Dec. 19, 1994), https://oig.hhs.gov/documents/physicians-resources/980/121994.pdf (accessed Sep. 26, 2022).
Quiram et al., "Exudative Age-Related Macular Degeneration: Current Therapies and Potential Treatments," *Clinical Medicine: Therapeutics*, 1, pp. 1003-1011 (2009) (online publication).
Raman et al., "Diabetic Macular Edema," *Sci. J. Med. & Vis. Res. Foun.*, XXXIII(2):50-56 (Jun. 2015).

(56) References Cited

OTHER PUBLICATIONS

Ramazi et al., "Post-translational modifications in proteins: resources, tools and prediction methods," *Database*, 2021(1):baab012 (Apr. 2021).
Ramirez et al., "Epidemiology of Conjunctivitis in US Emergency Departments," *JAMA Ophthalmol.*, 135(10):1119-1121 (Oct. 1, 2017).
Randolph et al., "Surfactant-Protein Interactions" Rational Design of Stable Protein Formulations pp. 159-175, Springer, Boston, MA (2002).
Raptiva Label (Final Labelling Mar. 13, 2009), submitted in IPR2021-00402 as Exhibit 1027.
Regeneron 2008 Annual Report.
Regeneron 2009 Annual Report and 10-K.
Regeneron 2010 Annual Report and 10-K.
Regeneron Form 10-K for the year ended Dec. 31, 2004.
Regeneron Form 10-K for the year ended Dec. 31, 2005, submitted in IPR2021-00881 as Exhibit 1147.
Regeneron Form 10-K for the year ended Dec. 31, 2011, submitted in IPR2021-00881 as Exhibit 1149.
Regeneron Form 10-Q for the period ended Jun. 30, 2013.
Regeneron Pharmaceuticals, Inc. at Bank of America Merrill Lynch Health Care Conference—Final, FD (Fair Disclosure) Wire (Sep. 13, 2017).
Regeneron Pharmaceuticals, Inc., "About," https://www.regeneron.com/about (accessed Nov. 3, 2021).
Regeneron Pharmaceuticals, Inc., "An Exploratory Study of the Safety, Tolerability and Biological Effect of a Single Intravitreal Administration of VEGF Trap in Patients with Diabetic Macular Edema," poster presented at the 2007 Association for Research in Vision and Ophthalmology meeting in Ft. Lauderdale, Florida (May 2007).
Regeneron Pharmaceuticals, Inc., "Bayer and Regeneron Dose First Patient in Second Phase 3 Study for VEGF Trap-Eye in Wet Age-Related Macular Degeneration," Press Release, (May 8, 2008), https://investor.regeneron.com/news-releases/news-release-details/bayer-and-regeneron-dose-first-patient-second-phase-3-study-vegf (accessed Sep. 26, 2022).
Regeneron Pharmaceuticals, Inc., "Bayer and Regeneron Extend Development Program for VEGF Trap-Eye to Include Central Retinal Vein Occlusion," Press Release, (Apr. 30, 2009), https://investor.regeneron.com/news-releases/news-release-details/bayer-and-regeneron-extend-development-program-vegf-trap-eye, submitted in IPR2023-00099 as Exhibit 1028 (accessed Nov. 4, 2022).
Regeneron Pharmaceuticals, Inc., "Bayer and Regeneron Report Positive Top-Line Results of Two Phase 3 Studies with VEGF Trap-Eye in Wet Age-related Macular Degeneration," Press Release, (Nov. 22, 2010) https://newsroom.regeneron.com/news-releases/news-release-details/bayer-and-regeneron-report-positive-top-line-results-two-phase-3 (accessed Sep. 26, 2022).
Regeneron Pharmaceuticals, Inc., "Clear-It-2: Interim Results Of The Phase II, Randomized, Controlled Dose-and Interval-ranging Study Of Repeated Intravitreal VEGF Trap Administration In Patients With Neovascular Age-related Macular Degeneration (AMD)," poster presented at the 2007 Association for Research in Vision and Ophthalmology meeting in Ft. Lauderdale, Florida (May 2007).
Regeneron Pharmaceuticals, Inc., "Enrollment Completed in Regeneron and Bayer HealthCare Phase 3 Studies of VEGF Trap-Eye in Neovascular Age-Related Macular Degeneration (Wet AMD)," Press Release, (Sep. 14, 2009) https://newsroom.regeneron.com/news-releases/news-release-details/enrollment-completed-regeneron-and-bayer-healthcare-phase-3 (accessed Sep. 26, 2022).
Regeneron Pharmaceuticals, Inc., "Eylea (aflibercept) Injection: Components of Reimbursement," 2015—[[REDACTED]].
Regeneron Pharmaceuticals, Inc., "Eylea Injection Receives FDA Approval for Macular Edema Following Retinal Vein Occlusion (RVO)," Press Release, (Oct. 6, 2014) https://investor.regeneron.com/news-releases/news-release-details/eylear-aflibercept-injection-receives-fda-approval-macular-edema (accessed Sep. 26, 2022).
Regeneron Pharmaceuticals, Inc., "Eylea Injection Receives FDA Approval for the Treatment of Diabetic Macular Edema (DME)," Press Release, (Jul. 29, 2014) https://investor.regeneron.com/news-releases/news-release-details/eylear-aflibercept-injection-receives-fda-approval-treatment (accessed Sep. 26, 2022).
Regeneron Pharmaceuticals, Inc., "Eylea," https://eylea.us/ (accessed May 18, 2022).
Regeneron Pharmaceuticals, Inc., "FDA Approves Eylea Injection for Diabetic Retinopathy," (May 13, 2019) https://investor.regeneron.com/news-releases/news-release-details/fda-approves-eylear-aflibercept-injection-diabetic-retinopathy (accessed Sep. 26, 2022).
Regeneron Pharmaceuticals, Inc., "FDA Grants Priority Review for VEGF Trap-Eye for the Treatment of Wet Age-Related Macular Degeneration," Press Release, (Apr. 18, 2011) https://newsroom.regeneron.com/news-releases/news-release-details/fda-grants-priority-review-vegf-trap-eye-treatment-wet-age#:~:text=(Nasdaq%3A%20REGN)%20today%20announced,macular%20degeneration%20(wet%20AMD) (accessed Sep. 26, 2022).
Regeneron Pharmaceuticals, Inc., "First Patient Enrolled In Regeneron And Bayer Healthcare VEGF Trap-Eye Phase 3 Program In Central Retinal Vein Occlusion," Press Release, (Jul. 23, 2009) https://newsroom.regeneron.com/news-releases/news-release-details/first-patient-enrolled-regeneron-and-bayer-healthcare-vegf-trap (accessed Sep. 26, 2022).
Regeneron Pharmaceuticals, Inc., "For the Treatment of Wet Age-Related Macular Degeneration," 2012.
Regeneron Pharmaceuticals, Inc., "History," https://www.regeneron.com/about/history (accessed Dec. 15, 2021).
Regeneron Pharmaceuticals, Inc., "Optical Coherence Tomography Outcomes of a Phase 1, Dose-Escalation, Safety, Tolerability, and Bioactivity Study of Intravitreal VEGF Trap in Patients with Neovascular Age-Related Macular Degeneration: The Clear-It 1 Study," poster presented at the 2007 Association for Research in Vision and Ophthalmology meeting in Ft. Lauderdale, Florida (May 2007).
Regeneron Pharmaceuticals, Inc., "Positive Interim Phase 2 Data Reported For VEGF Trap-Eye In Age-Related Macular Degeneration," Press Release, (Mar. 27, 2007) https://newsroom.regeneron.com/news-releases/news-release-details/positive-interim-phase-2-data-reported-vegf-trap-eye-age-related (accessed Sep. 26, 2022).
Regeneron Pharmaceuticals, Inc., "Regeneron And Bayer Announce Start Of Phase 3 Clinical Program In Diabetic Macular Edema," Press Release, (Apr. 8, 2011) https://newsroom.regeneron.com/news-releases/news-release-details/regeneron-and-bayer-announce-start-phase-3-clinical-program (accessed Sep. 26, 2022).
Regeneron Pharmaceuticals, Inc., "Regeneron and Bayer HealthCare Announce Encouraging 32-Week Follow-up Results from a Phase 2 Study of VEGF Trap-Eye in Age-Related Macular Degeneration," Press Release, (Apr. 28, 2008) https://newsroom.regeneron.com/news-releases/news-release-details/regeneron-and-bayer-healthcare-announce-encouraging-32-week (accessed Sep. 26, 2022).
Regeneron Pharmaceuticals, Inc., "Regeneron and Bayer HealthCare Announce VEGF Trap-Eye Achieved Durable Improvement in Vision over 52 Weeks in a Phase 2 Study in Patients with Age-related Macular Degeneration," Press Release, (Aug, 19, 2008) https://newsroom.regeneron.com/news-releases/news-release-details/regeneron-and-bayer-healthcare-announce-vegf-trap-eye-achieved#:~:text=00%20AM%20EDT-,Regeneron%20and%20Bayer%20HealthCare%20Announce%20VEGF%20Trap%2DEye%20Achieved%20Durable,with%20Age%2Drelated%20Macular%20Degeneration (accessed Sep. 26, 2022).
Regeneron Pharmaceuticals, Inc., "Regeneron and Bayer Healthcare Initiate Phase 3 Global Development Program for VEGF Trap-Eye In Wet Age-Related Macular Degeneration (AMD)," Press Release, (Aug. 2, 2007) https://investor.regeneron.com/news-releases/news-release-details/regeneron-and-bayer-healthcare-initiate-phase-3-global (accessed Sep. 26, 2022).
Regeneron Pharmaceuticals, Inc., "Regeneron and Bayer Initiate Phase 3 Clinical Program for the Treatment of Wet Age-Related Macular Degeneration in China," Press Release, (Nov. 28, 2011) https://newsroom.regeneron.com/news-releases/news-release-details/regeneron-and-bayer-initiate-phase-3-clinical-program-treatment (accessed Sep. 26, 2022).
Regeneron Pharmaceuticals, Inc., "Regeneron and Bayer Report Positive Results for VEGF Trap-Eye in Phase 3 Study in Central Retinal Vein Occlusion (CRVO) and in Phase 2 Study in Diabetic

(56) References Cited

OTHER PUBLICATIONS

Macular Edema (DME)," Press Release, (Dec. 20, 2010) https://newsroom.regeneron.com/news-releases/news-release-details/regeneron-and-bayer-report-positive-results-vegf-trap-eye-phase (accessed Sep. 26, 2022).

Regeneron Pharmaceuticals, Inc., "Regeneron And Bayer Start Phase 3 Trial To Extend Ophthalmology Research & Development Program For VEGF Trap-Eye In Asia," Press Release, (Jan. 18, 2011) https://investor.regeneron.com/news-releases/news-release-details/regeneron-and-bayer-start-phase-3-trial-extend-ophthalmology (accessed Sep. 26, 2022).

Regeneron Pharmaceuticals, Inc., "Regeneron Announces Clinical Presentations at ASRS 2011 Annual Meeting," Press Release, (Aug. 17, 2011) https://investor.regeneron.com/news-releases/news-release-details/regeneron-announces-clinical-presentations-asrs-2011-annual (accessed Sep. 26, 2022).

Regeneron Pharmaceuticals, Inc., "Regeneron Announces Eylea(TM) (aflibercept ophthalmic solution) Receives Unanimous Recommendation for Approval for Treatment of Wet AMD from FDA Advisory Committee," Press Release, (Jun. 17, 2011) https://www.prnewswire.com/news-releases/regeneron-announces-eylea-aflibercept-ophthalmic-solution-receives-unanimous-recommendation-for-approval-for-treatment-of-wet-amd-from-fda-advisory-committee-124081949.html?$G1Ref (accessed Sep. 26, 2022).

Regeneron Pharmaceuticals, Inc., "Regeneron Announces FDA Approval of Eylea (Aflibercept) Injection for Macular Edema Following Central Retinal Vein Occlusion," Press Release, (Sep. 21, 2012) https://investor.regeneron.com/news-releases/news-release-details/regeneron-announces-fda-approval-eylear-aflibercept-injection (accessed Sep. 26, 2022).

Regeneron Pharmaceuticals, Inc., "Regeneron Announces FDA Approval of Eylea(TM) (aflibercept) Injection for the Treatment of Wet Age-Related Macular Degeneration: Corrected" (Nov. 18, 2011).

Regeneron Pharmaceuticals, Inc., "Regeneron Announces Positive Primary Endpoint Results From A Phase 2 Study Of VEGF Trap-Eye In Age-Related Macular Degeneration," Press Release, (Oct. 1, 2007) https://newsroom.regeneron.com/news-releases/news-release-details/regeneron-announces-positive-primary-endpoint-results-phase-2#:~:text=(Nasdaq%3A%20REGN)%20and%20development,macular%20degeneration%20(wet%20AMD) (accessed Sep. 26, 2022).

Regeneron Pharmaceuticals, Inc., "Regeneron Receives $20 Million Milestone Payment for Initiation of Phase 3 Study of VEGF Trap-Eye in Wet AMD," Media Release: Aug. 13, 2007. Available from URL: http://www.regeneron.com.

Regeneron Pharmaceuticals, Inc., "Regeneron Reports First Quarter 2008 Financial and Operating Results," Press Release, (May 1, 2008) https://investor.regeneron.com/news-releases/news-release-details/regeneron-reports-first-quarter-2008-financial-and-operating (accessed Sep. 26, 2022).

Regeneron Pharmaceuticals, Inc., "Regeneron Reports Fourth Quarter and Full Year 2004 Financial and Operating Results," Press Release, (Feb. 22, 2005).

Regeneron Pharmaceuticals, Inc., "Regeneron Reports Fourth Quarter and Full Year 2005 Financial and Operating Results," Press Release, (Feb. 24, 2006).

Regeneron Pharmaceuticals, Inc., "Regeneron Reports Fourth Quarter And Full Year 2007 Financial And Operating Results," Press Release, (Feb. 27, 2008).

Regeneron Pharmaceuticals, Inc., "Regeneron Reports Fourth Quarter and Full Year 2012 Financial and Operating Results," Press Release (Feb. 14, 2013), https://investor.regeneron.com/news-releases/news-release-details/regeneron-reports-fourth-quarter-and-full-year-2012-financial (accessed Aug. 2, 2021).

Regeneron Pharmaceuticals, Inc., "Regeneron Reports Fourth Quarter and Full Year 2019 Financial and Operating Results," Press Release, (Feb. 6, 2020), https://investor.regeneron.com/news-releases/news-release-details/regeneron-reports-fourth-quarter-and-full-year-2019-financial (accessed Aug. 2, 2021).

Regeneron Pharmaceuticals, Inc., "Regeneron Reports Full Year And Fourth Quarter 2008 Financial And Operating Results," Press Release, (Feb. 26, 2009) https://investor.regeneron.com/news-releases/news-release-details/regeneron-reports-full-year-and-fourth-quarter-2008-financial (accessed Sep. 26, 2022).

Regeneron Pharmaceuticals, Inc., "Regeneron Reports Positive Phase 1 Data for the VEGF Trap in Age-Related Macular Degeneration; Preliminary Results Show Improvements in Vision and Reginal Swelling; VEGF Trap Was Well Tolerated at All Dose Levels," Media Release, (May 1, 2006).

Regeneron Pharmaceuticals, Inc., "Regeneron Reports Second Quarter Financial And Operating Results," Press Release, (Aug. 1, 2007) https://investor.regeneron.com/news-releases/news-release-details/regeneron-reports-second-quarter-financial-and-operating-results/ (accessed Sep. 26, 2022).

Regeneron Pharmaceuticals, Inc., "Regeneron Reports Third Quarter 2010 Financial Results and Business Highlights," Press Release (Oct. 28, 2010) https://investor.regeneron.com/news-releases/news-release-details/regeneron-reports-third-quarter-2010-financial-results-and, submitted in IPR2023-00099 as Exhibit 1058 (last accessed Nov. 4, 2022).

Regeneron Pharmaceuticals, Inc., "Regeneron Schedules Nov. 22, 2010 Teleconference And Webcast To Discuss Results Of Two Phase 3 Studies With VEGF Trap-Eye In Wet Age-Related Macular Degeneration," Press Release, (Nov. 19, 2010) https://investor.regeneron.com/news-releases/news-release-details/regeneron-schedules-november-22-2010-teleconference-and-webcast (accessed Sep. 26, 2022).

Regeneron Pharmaceuticals, Inc., "Regeneron Submits Biologics License Application To FDA For VEGF Trap-Eye For Treatment Of Wet Age-Related Macular Degeneration," Press Release, (Feb. 22, 2011) https://newsroom.regeneron.com/news-releases/news-release-details/regeneron-submits-biologics-license-application-fda-vegf-trap (accessed Sep. 26, 2022).

Regeneron Pharmaceuticals, Inc., "Regeneron To Webcast Investor Briefing On VEGF Trap-Eye Clinical Program On Sunday, Feb. 13 At 9 AM ET," Press Release, (Feb. 9, 2011) https://investor.regeneron.com/news-releases/news-release-details/regeneron-webcast-investor-briefing-vegf-trap-eye-clinical (accessed Sep. 26, 2022).

Regeneron Pharmaceuticals, Inc., "Regeneron's Yancopoulos Receives Columbia College's Alexander Hamilton Award," Press Release, (Nov. 22, 2019) https://www.prnewswire.com/news-releases/regenerons-yancopoulos-receives-columbia-colleges-alexander-hamilton-award-300963506.html (accessed Sep. 26, 2022), cited in Deposition of Dr. Diana V. Do, M.D., on Apr. 21, 2022.

Regeneron Pharmaceuticals, Inc., "Representative Regeneron U.S. Product Related Patents, Eylea (aflibercept) Injection," (Jan. 2022), https://www.regeneron.com/downloads/us-patent-products.pdf (accessed Sep. 26, 2022), cited in Deposition of Dr. Richard Manning, Ph.D., on May 4, 2022.

Regeneron Pharmaceuticals, Inc., "Research Areas," https://www.regeneron.com/science/research-areas (accessed Nov. 3, 2021).

Regeneron Pharmaceuticals, Inc., "Two Year Results of Phase 3 Studies with Eylea(TM) (aflibercept) Injection in wet AMD Show Sustained Improvement in Visual Acuity," Press Release, (Dec. 5, 2011) https://newsroom.regeneron.com/news-releases/news-release-details/two-year-results-phase-3-studies-eyleatm-aflibercept-injection (accessed Sep. 26, 2022).

Regeneron Pharmaceuticals, Inc., "U.S. Eylea Historical Brand P&L," May 2021, submitted in IPR2021-00881 as Exhibit 2200—[[Redacted]].

Regeneron Pharmaceuticals, Inc., "US Eylea P&L LTD," Dec. 2021, submitted in IPR2021-00881 as Exhibit 2170—[[Redacted]].

Regeneron Pharmaceuticals, Inc., "VEGF Trap-Eye Clear-It 2 Final Primary Endpoint Results," presented at the 2007 Retina Society Conference in Boston, Massachusetts (Sep. 30, 2007).

Regeneron Pharmaceuticals, Inc., "VEGF Trap-Eye Final Phase 2 Results in Age-related Macular Degeneration Presented at 2008 Retina Society Meeting," Press Release (Sep. 28, 2008) https://investor.regeneron.com/news-releases/news-release-details/vegf-trap-eye-final-phase-2-results-age-related-macular?ReleaseID=393906.

Regeneron Pharmaceuticals, Inc., "VEGF Trap-Eye Phase 2 Wet AMD Results Reported At ARVO Annual Meeting," Press Release,

(56) References Cited

OTHER PUBLICATIONS (May 9, 2007) https://newsroom.regeneron.com/news-releases/news-release-details/vegf-trap-eye-phase-2-wet-amd-results-reported-arvo-annual (accessed Sep. 26, 2022).
Regeneron Pharmaceuticals, Inc., "VEGF Trap-Eye Shows Positive Results in a Phase 2 Study in Patients With Diabetic Macular Edema," Press Release, (Feb. 18, 2010) https://newsroom.regeneron.com/news-releases/news-release-details/vegf-trap-eye-shows-positive-results-phase-2-study-patients (accessed Sep. 26, 2022).
Regeneron Pharmaceuticals, Inc., "VEGF Trap-Eye Submitted for EU Marketing Authorization for Treatment of Wet Age-Related Macular Degeneration," Press Release, (Jun. 7, 2011) https://investor.regeneron.com/news-releases/news-release-details/vegf-trap-eye-submitted-eu-marketing-authorization-treatment-wet (accessed Sep. 26, 2022).
Regeneron Pharmaceuticals, Inc., "View 1 Vascular Endothelial Growth Factor (VEGF) Trap-Eye 1-Year Results: Investigation of Efficacy and Safety in Wet Age-Related Macular Degeneration (AMD)," presented at Bascom Palmer Eye Institute's Angiogenesis, Exudation and Degeneration 2011 meeting in Miami, Florida (Feb. 12, 2011).
Regeneron Pharmaceuticals, Inc., "View 2 Vascular Endothelial Growth Factor (VEGF) Trap-Eye 1-Year Results: Investigation of Efficacy and Safety in Wet Age-Related Macular Degeneration (AMD)," presented at Bascom Palmer Eye Institute's Angiogenesis, Exudation and Degeneration 2011 meeting in Miami, Florida (Feb. 12, 2011).
Regeneron Pharmaceuticals, Inc., ATU Sales Share Data: All Indications, 2021, submitted in IPR2021-00881 as Exhibit 2279.
Regeneron Pharmaceuticals, Inc., ATU Sales Share Data: BRVO, 2021, submitted in IPR2021-00881 as Exhibit 2283.
Regeneron Pharmaceuticals, Inc., ATU Sales Share Data: CRVO, 2021, submitted in IPR2021-00881 as Exhibit 2282.
Regeneron Pharmaceuticals, Inc., ATU Sales Share Data: DME, 2021, submitted in IPR2021-00881 as Exhibit 2281.
Regeneron Pharmaceuticals, Inc., ATU Sales Share Data: DR w/o DME, 2021, submitted in IPR2021-00881 as Exhibit 2284.
Regeneron Pharmaceuticals, Inc., ATU Sales Share Data: Wet AMD, 2021, submitted in IPR2021-00881 as Exhibit 2280.
Regeneron Pharmaceuticals, Inc., Earnings Call Transcript, Apr. 26, 2012, submitted in IPR2021-00881 as Exhibit 2134.
Regeneron Pharmaceuticals, Inc., Earnings Call Transcript, Feb. 13, 2012, submitted in IPR2021-00881 as Exhibit 2133.
Regeneron Pharmaceuticals, Inc., Earnings Call Transcript, Jul. 25, 2012, submitted in IPR2021-00881 as Exhibit 2135.
Regeneron Pharmaceuticals, Inc., Eylea Gross & Net Sales P&L YTD, 2021, submitted in IPR2021-00881 as Exhibit 2285—[[Redacted]].
Regeneron Pharmaceuticals, Inc., Eylea Marketing Material, 2013, submitted in IPR2021-00881 as Exhibit 2136.
Regeneron Pharmaceuticals, Inc., Eylea Marketing Material, Nov. 2013, submitted in IPR2021-00881 as Exhibit 2137.
Regeneron Pharmaceuticals, Inc., Form 10-K, 2020, submitted in IPR2021-00881 as Exhibit 2254.
Regeneron Pharmaceuticals, Inc., Press Release, "Eylea® (Aflibercept) Injection Receives FDA Approval for the Treatment of Diabetic Macular Edema (DME)" (Jul. 29, 2014).
Regeneron Pharmaceuticals, Inc., Press Release, "Eylea® (Aflibercept) Injection Receives FDA Approval for the Treatment of Diabetic Retinopathy in Patients with Diabetic Macular Edema (DME)," 3 pp. (Mar. 25, 2015).
Regeneron SEC Form 10-K (Feb. 17, 2011).
Regeneron SEC Form 10-K (Feb. 26, 2009).
Regeneron SEC Form 10-K (Feb. 27, 2008).
Regeneron SEC Form 10-Q (Apr. 29, 2010).
Regeneron SEC Form 10-Q (Apr. 30, 2009).
Regeneron SEC Form 10-Q (Aug. 3, 2007).
Regeneron SEC Form 10-Q (Aug. 8, 2006).
Regeneron SEC Form 10-Q (Jul. 28, 2010).
Regeneron SEC Form 10-Q (Jul. 28, 2011).
Regeneron SEC Form 10-Q (May 3, 2011).
Regeneron SEC Form 10-Q (May 4, 2007).
Regeneron SEC Form 10-Q (May 8, 2006).
Regeneron SEC Form 10-Q (Nov. 3, 2009).
Regeneron SEC Form 10-Q (Nov. 6, 2006).
Regeneron SEC Form 10-Q (Nov. 7, 2007).
Regeneron SEC Form 10-Q (Oct. 27, 2011).
Regeneron SEC Form 10-Q (Oct. 28, 2010).
Regeneron SEC Form 10-Q (Sep. 30, 2009), submitted in IPR2021-00880 as Exhibit 1021.
Regeneron SEC Form 8-K Exhibit: "99(a) Slides that Regeneron Pharmaceuticals, Inc. intends to use in conjunction with meetings with investors at the J.P. Morgan 27th Annual Healthcare Conference in San Francisco on Jan. 12-15, 2009," (Jan. 9, 2009).
Regeneron SEC Form 8-K Exhibit: "Overheads for presentation at Regeneron's Annual Meeting of Shareholders to be held on Jun. 8, 2007," (Jun. 8, 2007).
Regeneron SEC Form 8-K Exhibit: "Presentation entitled VEGF Trap-Eye in CRVO: 1-year Results of the Phase 3 Copernicus Study," (Aug. 22, 2011).
Regeneron SEC Form 8-K Exhibit: "Press Release Announcing FDA Approval of Eylea(TM) (aflibercept) Injection for the Treatment of Wet Age-Related Macular Degeneration, dated Nov. 18, 2011," (Nov. 21, 2011).
Regeneron SEC Form 8-K Exhibit: "Press Release dated Apr. 30, 2009," (May 1, 2009).
Regeneron SEC Form 8-K Exhibit: "Press Release dated Feb. 17, 2011," (Feb. 18, 2011).
Regeneron SEC Form 8-K Exhibit: "Press Release dated May 1, 2008," (May 2, 2008).
Regeneron SEC Form 8-K Exhibit: "Press Release dated May 2, 2007," (May 3, 2007).
Regeneron SEC Form 8-K Exhibit: "Press Release dated May 3, 2011," (May 3, 2011).
Regeneron SEC Form 8-K Exhibit: "Press Release dated Nov. 3, 2009," (Nov. 4, 2009).
Regeneron SEC Form 8-K Exhibit: "Press Release dated Nov. 4, 2008," (Nov. 4, 2008).
Regeneron SEC Form 8-K Exhibit: "Press Release dated Nov. 6, 2007," (Nov. 6, 2007).
Regeneron SEC Form 8-K Exhibit: "Press Release dated Oct. 1, 2007," (Oct. 1, 2007).
Regeneron SEC Form 8-K Exhibit: "Press Release of Regeneron Pharmaceuticals, Inc. dated May 1, 2006," (May 2, 2006).
Regeneron SEC Form 8-K Exhibit: "Press Release of Regeneron Pharmaceuticals, Inc. dated May 3, 2006," (May 5, 2006).
Regeneron SEC Form 8-K Exhibit: "Press Release Reporting Positive Results for VEGF Trap-Eye in Phase 3 Study in Central Retinal Vein Occlusion (CRVO) and in Phase 2 Study in Diabetic Macular Edema (DME) dated Dec. 20, 2010," (Dec. 20, 2010).
Regeneron SEC Form 8-K Exhibit: "Press Release Reporting Positive Results for VEGF Trap-Eye in Second Phase 3 Study in Central Retinal Vein Occlusion, dated Apr. 27, 2011," (Apr. 27, 2011).
Regeneron SEC Form 8-K Exhibit: "Press Release, dated Jun. 17, 2011, Announcing that Eylea(TM) (aflibercept ophthalmic solution) Received Unanimous Recommendation for Approval for Treatment of Wet AMD from FDA Advisory Committee," (Jun. 21, 2011).
Regeneron SEC Form 8-K Exhibit: "Slides presented at the Company's 2006 Annual Meeting of Shareholders held on Jun. 9, 2006," (Jun. 9, 2006).
Regeneron, "Regeneron Announces FDA Acceptance of Eylea® (aflibercept) Injection Supplemental Biologics License Application for Review for Diabetic Macular Edema Indication," Press Release (Dec. 18, 2013).
Regeneron, "Regeneron Announces FDA Approval of Eylea® (Aflibercept) Injection for the Treatment of Wet Age-Related Macular Degeneration: Corrected," Press Release, 4 pp. (Nov. 18, 2011).
Regeneron, Representative Regeneron U.S. Product Related Patents, Eylea® (aflibercept) Injection, https://www.regeneron.com/downloads/us-patent-products.pdf (updated Mar. 2023).

(56) References Cited

OTHER PUBLICATIONS

Regillo et al., "Randomized, Double-Masked, Sham-Controlled Trial of Ranibizumab for Neovascular Age-related Macular Degeneration: Pier Study Year 1," American Journal of Ophthalmology, 145(2):239-248 (2008).
Reichert, "Antibody-Based Therapeutics To Watch In 2011," mAbs, 3(1), pp. 76-99 (2011).
Remicade Label (Revised Nov. 2013), submitted in IPR2021-00402 as Exhibit 1025.
Retinal Physician, "Ongoing Treatment for Patients with Neovascular AMD," (Oct. 1, 2007), https://www.retinalphysician.com/issues/2007/october-2007/ongoing-treatment-for-patients-with-neovascular-am (accessed Sep. 26, 2022).
Retinal Physician, "Retinal Physician Symposium Covers Broad Range of Topics," (Sep. 1, 2006), https://www.retinalphysician.com/issues/2006/september-2006/retinal-physician-symposium-covers-broad-range-of (accessed Feb. 4, 2022).
Retinal Physician, "Revisiting an Early Treatment for Wet AMD: Is There a Role for Thermal Laser in the Era of Anti-VEGF Therapy?" Press Release, (Sep. 1, 2011) https://www.retinalphysician.com/issues/2011/september-2011/revisiting-an-early-treatment-for-wet-amd (accessed Sep. 26, 2022).
Retinal Physician, "Steps for a Safe Intravitreal Injection Technique," https://www.retinalphysician.com/issues/2009/july-aug/steps-for-a-safe-intravitreal-injection-technique (Jul. 1, 2009) (accessed Dec. 7, 2023), submitted in IPR2023-00442 as Exhibit 1041.
Roche, "FDA Approves Lucentis for Treatment of Diabetic Macular Edema," Press Release, (Aug. 13, 2012) https://www.roche.com/investors/updates/iny-update-2012-08-13.htm (accessed Sep. 26, 2022).
Roche, "FDA Approves Roche's Lucentis for Diabetic Retinopathy, the Leading Cause of Blindness Among Working Age Adults in the United States," Press Release, (Apr. 18, 2017) https://www.roche.com/media/releases/med-cor-2017-04-18b.htm (accessed Sep. 26, 2022).
Roche, Finance Report, 2020, submitted in IPR2021-00881 as Exhibit 2256.
Rogers et al., "The prevalence of retinal vein occlusion: pooled data from population studies from the United States, Europe, Asia, and Australia," Ophthalmology, 117(2), pp. 313-319e1 (2010).
Rosenfeld et al., "Optical coherence tomography findings after an intravitreal injection of bevacizumab (avastin) for neovascular age-related macular degeneration," Ophthalmic. Surg. Lasers Imaging, 36(4):331-335 (2005).
Rosenfeld, "Lessons Learned From Avastin and OCT—The Great, the Good, the Bad, and the Ugly: The LXXV Edward Jackson Memorial Lecture," Am. J. Ophthalmology, 204:26-45 (Aug. 2019).
Rosenfeld, "Ranibizumab for Neovascular Age-Related Macular Degeneration," N. Engl. J. Med., 355(14):1419-1431 (Oct. 5, 2006).
Rowe et al., Handbook of Pharmaceutical Excipients, Cover to Preface (5th ed. 2006) (London, UK).
Rudge et al., "Clinical Development of VEGF Trap," Angiogenesis, William D. Figg & Judah Folkman, eds. (2008).
Rudge et al., "VEGF Trap as a Novel Antiangiogenic Treatment Currently in Clinical Trials for Cancer and Eye Diseases, and VelociGene-based Discovery of the Next Generation of Angiogenesis Targets," Cold Spring Harbor Symposia on Quantitative Biology, 70:411-418 (2005).
Rudge et al., "VEGF Trap complex formation measures production rates of VEFG providing a biomarker for predicting efficacious angiogenic blockade," PNAS, 104(47):18363-18370 (Nov. 20, 2007).
Saishin, et al., "VEGF-Trap(R1R2) suppresses choroidal neovascularization and VEGF-induced breakdown of the blood-retinal barrier," J. Cell. Physiol., 195:241-248 (2003).
Schachat et al., "Anti-Vascular Endothelial Growth Factor Drugs to Reduce Diabetic Retinopathy Progression," Ophthalmology Retina, 2(10):985-987 (Oct. 2018).
Schmidt-Erfurth et al., "Efficacy and Safety of Monthly versus Quarterly Ranibizumab Treatment in Neovascular Age-related Macular Degeneration: The Excite Study," Ophthalmology, 118(5)831-839 (2011).
Schmidt-Erfurth et al., "Intravitreal Aflibercept: Injection for Neovascular Age-related Macular Degeneration," Ophthalmology, 121, pp. 193-201 (2013).
Schmidt-Erfurth et al., "Primary Results of an International Phase III Study Using Intravitreal VEGF Trap-Eye Compared to Ranibizumab in Patients with Wet AMD (View 2)," ARVO Annual Meeting Abstract (Apr. 2011).
Schmidt-Erfurth, "Current Concepts in the Management of Diabetic Macular Edema," Johns Hopkins Advanced Studies in Ophthalmology, 7(2), pp. 52-59 (2010).
Schmidt-Erfurth, "Three-Year Outcomes of Individualized Ranibizumab Treatment in Patients with Diabetic Macular Edema," Ophthalmology, 121(5):1045-1053 (May 2014).
Schneider, "Nits, Grits, and Soft Information in SEC Filings," U. PA. L. REV., 121(2), pp. 254-305 (1972) (Philadelphia, PA).
Schnichels, "Comparative toxicity and proliferation testing of aflibercept, bevacizumab and ranibizumab on different ocular cells," Br. J. Ophthalmol., 97:917-923 (2013).
Schweitzer, Pharmaceutical Economics and Policy: Second Edition, Oxford University Press (2007) (New York, NY).
ScienceDaily, "FDA Approves First Angiogenesis Inhibitor to Treat Colorectal Cancer," Press Release, (Feb. 27, 2004) https://www.sciencedaily.com/releases/2004/02/040227071334.htm (accessed Sep. 26, 2022).
Scott et al., "The Folding of Spectrin Domains I: Wild-type Domains Have the Same Stability but Very Different Kinetic Properties," J. Mol. Biol., 344:195-205 (2004).
Scott et al., "A randomized trial comparing the efficacy and safety of intravitreal triamcinolone with standard care to treat vision loss associated with macular Edema secondary to branch retinal vein occlusion: the Standard Care vs Corticosteroid for Retinal Vein Occlusion (Score) study report 6," Arch. Ophthalmol., 127(9):1115-1128 & 127(12):1653 (2009).
Second Amendment to Collaboration Agreement, dated Jan. 7, 2005, available https://www.sec.gov/Archives/edgar/data/872589/000095012305000248/y04663exv10w1.htm, accessed Jun. 27, 2023.
Semeraro et al., "Aflibercept in wet AMD: specific role and optimal use," Drug Design, Development and Therapy, 7:711-722 (Aug. 2, 2013).
Shahid et al., "The Management of Retinal Vein Occlusion: is Interventional Ophthalmology the Way Forward?," Br. J. Ophthalmology, 90:627-639 (2006).
Sharma & Kaiser, "Update on VEGF Trap-Eye Clinical Trials," Retinal Physician, pp. 1-5 (Nov./Dec. 2010) <URL: https://www.retinalphysician.com/issues/2010/nov-dec/update-on-vegf-trap-eye-clinical-trials>.
Shechtman et al., "Hold 'em or Fold 'em?," Review of Optometry, 3 pp. (Apr. 15, 2018).
Shen et al., "Clearance of Intravitreal Voriconazole," Invest. Ophthalmology & Visual Sci., 45(5), pp. 2238-2241 (May 2007).
Simo and Hernandez, "Advances in Medical Treatment of Diabetic Retinopathy," Diabetes Care, 32(8):1556-1562 (Aug. 2009).
Simulect Label (May 1998), submitted in IPR2021-00402 as Exhibit 1028.
Sivaprasad et al., "Clinical efficacy and mechanistic evaluation of aflibercept for proliferative diabetic retinopathy (acronym CLARITY): a multicentre phase IIb randomised active-controlled clinical trial," BMJ Open, 5:e008405, 8 pp. (2015).
Sivaprasad et al., "Clinical efficacy of intravitreal aflibercept versus panretinal photocoagulation for best corrected visual acuity in patients with proliferative diabetic retinopathy at 52 weeks (CLARITY): a multicentre, single-blinded, randomised, controlled, phase 2b, non-inferiority trial," Lancet, 389:2193-2203 (Jun. 3, 2017).
Sivaprasad et al., "Clinical efficacy of intravitreal aflibercept versus panretinal photocoagulation for best corrected visual acuity in patients with proliferative diabetic retinopathy at 52 weeks (CLARITY): a multicentre, single-blinded, randomised, controlled, phase 2b, non-inferiority trial," Lancet, 389:2193, Supplementary Appendix (Jun. 3, 2017).
Sivaprasad, "Sustained-Release Steroid Options For DME Therapy," Retina Today, pp. 34-36 (Sep. 2021).
Slakter et al., "A Phase 2, Randomized, Controlled Dose-and Interval-Ranging Study of Intravitreal VEGF Trap-Eye in Patients

(56) References Cited

OTHER PUBLICATIONS with Neovascular Age-Related Macular Degeneration: Optical Coherence Tomography (OCT) and Fluorescein Angiography (FA) Outcomes at 1 Year," ARVO Annual Meeting Abstract (Apr. 2009).

Slakter et al., "Influence of Baseline Angiographic Classification on Outcomes in the Clear-It 2 Phase 2 Study of Intravitreal VEGF Trap-Eye in Neovascular Age-Related Macular Degeneration," ARVO Annual Meeting Abstract (Apr. 2010).

Slides for the 2008 Retina Society Meeting "VEGF Trap-Eye in Wet AMD Clear-It 2: Summary of One-Year Key Results," Sep. 28, 2008.

Solá et al., "Effects of Glycosylation on the Stability of Protein Pharmaceuticals," *Journal of Pharmaceutical Sciences*, 98(4), pp. 1223-1245 (Apr. 2009).

Sophie et al., "Aflibercept: a Potent Vascular Endothelial Growth Factor Antagonist for Neovascular Age-Related Macular Degeneration and Other Retinal Vascular Diseases," *Biol. Ther.*, 2(3):1-22 (2012).

Spaide et al., "Prospective Study of Intravitreal Ranibizumab as a Treatment for Decreased Visual Acuity Secondary to Central Retinal Vein Occlusion," *Am. J. Ophthalmology*, 147(2), pp. 298-306 (Feb. 2009).

Spaide, "Ranibizumab According to Need: A Treatment for Age-related Macular Degeneration," Am. J. Ophthalmology, 143(4):679-680 (Apr. 2007).

Spielberg et al., "Intravitreal Bevacizumab for Myopic Choroidal Neovascularization: Short-Term and 1-Year Results," *Bulletin Societe Belge D'Ophtalmologie*, 312, pp. 17-27 (2009).

Stefanini et al., "Increase of Plasma VEGF after Intravenous Administration of Bevacizumab Is Predicted by a Pharmacokinetic Model," *Cancer Research*, 70(23), pp. 9886-9894 (Dec. 2010), cited in Deposition of Dr. Alexander M. Klibanov, Ph.D., on Mar. 24, 2022.

Steinbrook, "The Price of Sight—Ranibizumab, Bevacizumab, and the Treatment of Macular Degeneration," *N. Eng. J. Med.*, 355(14), pp. 1409-1412 (Oct. 2006).

Stewart et al., "Predicted biological activity of intravitreal VEGF Trap," *British Journal of Ophthalmology*, 92(5):667-668 (May 2008).

Stewart, "A Review of Ranibizumab for the Treatment of Diabetic Retinopathy," *Ophthalmol. Ther.*, 6:33-47 (2017).

Stewart, "The Clinical Utility of Aflibercept for Diabetic Macular Edema," *Diabetes Metab. Syndr. Obes.* 8:473-482 (2015)

Stewart, "Treatment of Diabetic Retinopathy: Recent Advances and Unresolved Challenges," *World J. Diabetes*, 7(16):333-341 (Aug. 25, 2016).

Stewart, "Aflibercept," Nature Reviews: Drug Discovery, 11:269-270 (Apr. 1, 2012).

Stewart, "The expanding role of vascular endothelial growth factor inhibitors in ophthalmology,"Mayo Clin Proc., 87(1):77-88 (Jan. 2012).

Tannock et al., "Aflibercept versus placebo in combination with docetaxel and prednisone for treatment of men with metastatic castration-resistant prostate cancer (Vencie): a phase 3, double-blind randomized trial," *Lancet Oncol.*, 14:760-768 (Jul. 2013).

The Branch Vein Occlusion Study, G., "Argon laser photocoagulation for macular edema in branch vein occlusion," *Am. J. Ophthalmology*, 98(3):271-282 (Sep. 1984).

The Central Vein Occlusion Study, G., "Evaluation of grid pattern photocoagulation for macular edema in central vein occlusion. The Central Vein Occlusion Study Group M report," *Ophthalmology*, 102(10):1425-1433 (Oct. 1995).

The Eyetech Study Group, "Anti-Vascular Endothelial Growth Factor Therapy for Subfoveal Choroidal Neovascularization Secondary to Age-related Macular Degeneration," Ophthalmology, 110(5):979-986 (May 2003).

Thomas et al., "Comparative Effectiveness of Aflibercept for the Treatment of Patients with Neovascular Age-related Macular Degeneration," *Clinical Ophthalmology*, 7, pp. 495-501 (Mar. 2013).

Thomson Reuters Integrity, "VEGF Trap-Eye final phase II results in age-related macular degeneration," presented at 2008 Retina Society Meeting (Sep. 28, 2008).

Thomson Reuters, "Thomson Reuters Links Discovery and Literature Citation Databases," Press Release (Jan. 4, 2010).

Thurston, "Complementary actions of VEGF and Angiopoietin-1 on blood vessel growth and leakage," *J. Anat.*, 200:575-580 (Jun. 2002).

Thurston, "Vascular endothelial growth factor and other signaling pathways in developmental and pathologic angiogenesis," *International Journal of Hematology*, 80:7-20 (Jul. 2004).

Tolentino et al., "One-year Results Of The Da Vinci Study of VEGF Trap-Eye In DME," ARVO Annual Meeting Abstract, Investigative Ophthalmology & Visual Science, 52:6646 (Apr. 2011).

U.S. Department of Health and Human Services (ASPE), "Medicare Part B Reimbursement of Prescription Drugs," Jun. 2014, available at: https://aspe.hhs.gov/sites/default/files/private/pdf/106966/ib_mprpd.pdf (accessed Sep. 26, 2022).

U.S. Department of Health and Human Services, Food and Drug Administration, "Guidance for industry Q1A(R2) stability testing of new drug substances and products," Rockville, MD (Nov. 2003).

U.S. Department of Health and Human Services, National Institute of Health, National Eye Institute, "Age-Related Macular Degeneration: What You Should Know," (Sep. 2015) https://www.nei.nih.gov/sites/default/files/healthpdfs/WYSK_AMD_English_Sept2015_PRINT.pdf.

U.S. Department of Health and Human Services, National Institute of Health, National Eye Institute, "Diabetic Retinopathy: What You Should Know," (Sep. 2015) https://www.nei.nih.gov/sites/default/files/2019-06/Diabetic-Retinopathy-What-You-Should-Know-508.pdf.

U.S. Department of Health and Human Services, Office of Inspector General, "Questionable Billing for Medicare Ophthalmology Services" Sep. 2015 OEI-04-12-00280.

United Healthcare, "Ophthalmologic Policy: VEGF Inhibitors," effective Apr. 1, 2023.

United Healthcare, "Ophthalmologic Policy: VEGF Inhibitors," effective Jan. 1, 2022, submitted in IPR2021-00881 as Exhibit 1167.

United States' Statement of Facts, filed Apr. 14, 2023. *United States of America* vs. *Regeneron Pharmaceuticals, Inc.*, in the United States District Court for the District of Massachusetts (20-cv-11217).

USC-Brookings, "Medicare Payment for Physician-Administered (Part B) Drugs: The Interim Final Rule and a Better Way Forward," https://www.brookings.edu/blog/usc-brookings-schaeffer-on-health-policy/2021/02/10/medicare-payment-for-physician-administered-part-b-drugs/ (accessed Sep. 26, 2022).

Van Beek et al., "The Molecular Structure of Spider Dragline Silk: Folding and Orientation of the Protein Backbone," *Proc. Natl. Acad. Sci. USA*, 99(16):10266-10271 (Aug. 6, 2002).

Van Bruggen et al., "VEGF antagonism reduces edema formation and tissue damage after ischemia/reperfusion injury in the mouse brain," The Journal of clinical investigation, 104(11):1613-1620 (1999).

Vanderkam, "George Yancopoulos: Doing Well by Trying to Do Good," *Scientific American*, https://www.scientificamerican.com/article/george-yancopoulos-westinghouse/ (accessed Apr. 14, 2022), cited in Deposition of Dr. Diana V. Do, M.D., on Apr. 21, 2022.

Verywell Health, "Macular Degeneration: Timeline of Vision Loss Progression," https://www.verywellhealth.com/macular-degeneration-timeline-5069947 (accessed Mar. 21, 2021).

Vestrum Health, "Pharmaceutical Companies," https://www.vestrumhealth.com/pharma.php (accessed Jan. 3, 2022).

Vestrum Health, "Homepage," https://www.vestrumhealth.com/index.php (accessed Jan. 3, 2022).

Virgili et al., Cochrane Library, Cochrane Database of Systematic Reviews, "Anti-vascular endothelial growth factor for diabetic macular oedema: a network meta-analysis (Review)," 156 pp., John Wiley & Sons, Ltd. (2017).

Visudyne Label (revised Apr. 2016), https://www.accessdata.fda.gov/drugsatfda_docs/label/2016/021119s027lbl.pdf (accessed Sep. 26, 2022).

(56) References Cited

OTHER PUBLICATIONS

Volkin et al., "Alterations in the Structure of Proteins that Cause Their Irreversible Inactivation," *Developments in Biological Standardization*, 74, pp. 73-81 (1992) (Basel, SI).
Wachsberger, "VEGF trap in combination with radiotherapy improves tumor control in u87 glioblastoma," *Int. J. Radiation Oncology Biol Phys.*, 67(5):1526-1537 (Apr. 2007).
Wall Street Journal, "Genentech's Big Drug for Eyes Faces a Rival" (2007).
Wang et al., "Anti-Angiogenic Properties of a New VEGF Antagonist, VEGF Trap, in a Mouse Model of Retinal Neovascularization," *Investigative Ophthalmology & Visual Science*, vol. 43. E-Abstract. 3714 (Dec. 2002).
Weidner et al., "Observations Regarding the Average Sales Price Reimbursement Methodology," *Evidence-Based Oncology*, 27(4), pp. 156-160 (2021).
Wells et al., "Aflibercept, Bevacizumab, or Ranibizumab for Diabetic Macular Edema," *The New England Journal of Medicine*, 372(13), pp. 1193-1203 (2015).
WHO Drug Information, "International Nonproprietary Names for Pharmaceutical Substances (INN)," 20(2):115-119 (2006).
Wiesmann et al., "Crystal Structure at 1.7 Å Resolution of VEGF in Complex with Domain 2 of the Flt-1 Receptor," *Cell*, 91:695-704 (Nov. 28, 1997).
Wilhelmus, "The Red Eye, Infectious Conjunctivitis, Keratitis, Endophthalmitis, and Periocular Cellulitis," *Infectious Disease Clinics N. AM.*, 2(1), pp. 99-116 (Mar. 1988) (Philadelphia, PA).
Wirbelauer, "Management of the Red Eye for the Primary Care Physician," *Am. J. Med.*, 119(4), pp. 302-306 (Apr. 2006) (online publication).
Wolfson, "Regeneron Focuses on Age-Related Macular Degeneration," Chemistry & Biology, 15:303-304 (Apr. 2008).
World Health Organization, "Blindness and Vision Impairment Fact Sheet," Press Release, (Oct. 14, 2021) https://www.who.int/news-room/fact-sheets/detail/blindness-and-visual-impairment (accessed Sep. 26, 2022).
World Health Organization, "International Nonproprietary Names for Pharmaceutical Substances (INN)," *WHO Drug Information*, 20, pp. 118-119 (2006), cited in Deposition of Dr. Alexander M. Klibanov, Ph.D., on Mar. 24, 2022.
Writing Committee for the Diabetic Retinopathy Clinical Research Network, "Panretinal Photocoagulation vs Intravitreous Ranibizumab for Proliferative Diabetic Retinopathy. A Randomized Clinical Trial," *JAMA*, 314(20):2137-2146 (2015).
Writing Committee for the Diabetic Retinopathy Clinical Research Network, "Panretinal Photocoagulation vs Intravitreous Ranibizumab for Proliferative Diabetic Retinopathy. A Randomized Clinical Trial," *JAMA*, 314(20):2137-2146, Supplementary Online Content, 61 pp. (2015).
Wu et al., "Comparison Of Two Doses Of Intravitreal Bevacizumab (Avastin) For Treatment Of Macular Edema Secondary To Branch Retinal Vein Occlusion," *Retina*, 28:212-219 (2008).
Wulff et al., "Prevention of Thecal Angiogenesis, Antral Follicular Growth, and Ovulation in the Primate by Treatment with Vascular Endothelial Growth Factor Trap R1R2" Endocrinology, 143(7): 2797-2807 (Jul. 2002).
Xia et al., "Transgenic delivery of VEGF to mouse skin leads to an inflammatory condition resembling human psoriasis," Blood, 103(1):161-168 (Jul. 1, 2003).
Xolair Label (2003), submitted in IPR2021-00402 as Exhibit 1026.
Yahoo Finance, "Beovu Now Publicly Reimbursed in Ontario and New Brunswick for the Treatment of Neovascular Wet AMD," Press Release, (Dec. 17, 2021) https://finance.yahoo.com/news/beovu-brolucizumab-injection-now-publicly-120000109.html (accessed Dec. 30, 2021).
Yancopoulos Presentation, "VEGF Trap : Scientific Background, BSP / REGN Kick-Off" (Feb. 16, 2007), as filed in IPR2023-00884 as Exhibit 2007 on Aug. 25, 2023.
Yancopoulos, "Clinical Application of Therapies Targeting VEGF," Cell, 143:13-16 (Oct. 1, 2010).
Yancopoulos, "Vascular-specific growth factors and blood vessel formation," Nature, 407:242-48 (Sep. 14, 2000).
Yang, "Comparison of Binding Characteristics and in vitro Activities of Three Inhibitors of Vascular Endothelial Growth Factor A," *Molecular Pharmaceutics*, 11(10), pp. 3421-3429 (Oct. 2014), cited in Deposition of Dr. Alexander M. Klibanov, Ph.D., on Mar. 24, 2022.
Yorston, "Anti-VEGF Drugs in the Prevention of Blindness," *Community Eye Health Journal*, 27(87), pp. 44-46 (2014).
Yu et al., "Relationship of Protein Molecular Structure to Metabolisable Proteins in Different Types of Dried Distillers Grains with Solubles: a Novel Approach," *British Journal of Nutrition*, 104:1429-1437 (Jul. 2, 2010).
Yung, "Moving Toward the Next Steps in Angiogenesis Therapy?" Neuro-Oncology, 10(6):939 (Dec. 2008).
Zarbin et al., "Pathway-Based Therapies for Age-Related Macular Degeneration: An Integrated Survey of Emerging Treatment Alternatives," *Retina*, 30(9), pp. 1350-1367 (Oct. 2010).
Zucchi, "Edgar: Investors' One-Stop-Shop For Company Filings," *YAHOO!LIFE*, https://www.yahoo.com/lifestyle/tagged/health/edgar-investors-one-stop-shop-170000800.html (accessed Jan. 20, 2021).
Boyer et al., "Treating Diabetic Retinopathy by Restoring Activation of the Tie2 Pathway with AKB-9778. New treatments aim to reduce vision loss and treatment burden," *Retinal Physician*, vol. 14, Issue Jul./Aug. 2017, pp. 59, 60, 62, 64, retrieved from <https://www.retinaphysician.com/issues/2017/july-august-2017/treating-diabetic-retinoathy-by-restoring-activat>, 8 pp. (Jul. 1, 2017).
Cai et al., "Aflibercept, bevacizumab or ranibizumab for diabetic macular oedema: recent clinically relevant findings from DRCR.net Protocol T," *Curr. Opin. Ophthalmol.*, 28:636-643 (Nov. 2017).
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 1, 12 pp. (Oct. 23, 2017), <https://classic.clinicaltrials.gov/ct2/history/NCT03321513?V_1=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 2, 13 pp. (Dec. 15, 2017), <https://classic.clinicaltrials.gov/ct2/history/NCT03321513?V_2=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 3, 16 pp. (Jan. 25, 2018), <https://classic.clinicaltrials.gov/ct2/history/NCT03321513?V_3=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 4, 16 pp. (Feb. 23, 2018), <https://classic.clinicaltrials.gov/ct2/history/NCT03321513?V_4=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 5, 17 pp. (Mar. 13, 2018), <https://classic.clinicaltrials.gov/ct2/history/NCT03321513?V_5=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 6, 19 pp. (Jun. 27, 2018), <https://classic.clinicaltrials.gov/ct2/history/NCT03321513?V_6=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 7, 21 pp. (Aug. 22, 2018), <https://classic.clinicaltrials.gov/ct2/history/NCT03321513?V_7=View>.
ClinicalTrials.gov, Archive, History of Changes for Study: NCT003321513, "DRCR.Net Aflibercept vs. Bevacizumab + Deferred Aflibercept for the Treatment of CI-DME (DRCR AC)," Version 8, 21 pp. (Oct. 24, 2018), <https://classic.clinicaltrials.gov/ct2/history/NCT03321513?V_8=View>.
ClinicalTrials.gov, Archive, History of Changes for Study: NCT01627249, "Comparative Effectiveness Study of Intravitreal Aflibercept, Bevacizumab, and Ranibizumab for DME (Protocol

(56) References Cited

OTHER PUBLICATIONS

T)," Version 1, 10 pp. (Jun. 22, 2012), <https://classic.clinicaltrials.gov/ct2/history/NCT01627249?V_1=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 10, 51 pp. (Aug. 25, 2016), <https://classic.clinicaltrials.gov/ct2/history/NCT01627249?V_10=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 11, 51 pp. (Feb. 24, 2017), <https://classic.clinicaltrials.gov/ct2/history/NCT01627249?V_11=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 12, 51 pp. (Jul. 3, 2017), <https://classic.clinicaltrials.gov/ct2/history/NCT01627249?V_12=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 13, 51 pp. (Aug. 22, 2018), >https://classic.clinicaltrials.gov/ct2/history/NCT01627249?V_13=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 2, 10 pp. (Jun. 25, 2012), <https://classic.clinicaltrials.gov/ct2/history/NCT01627249?V_2=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 3, 11 pp. (Jul. 17, 2012), <https://classic.clinicaltrials.gov/ct2/history/NCT01627249?V_3=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 4, 11 pp. (Aug. 21, 2012), <https://classic.clinicaltrials.gov/ct2/history/NCT01627249?V_4=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 5, 15 pp. (Feb. 21, 2013), <https://classic.clinicaltrials.gov/ct2/history/NCT01627249?V_5=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 6, 17 pp. (Sep. 4, 2013), <https://classic.clinicaltrials.gov/ct2/history/NCT01627249?V_6=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 7, 17 pp. (Dec. 1, 2014), <https://classic.clinicaltrials.gov/ct2/history/NCT01627249?V_7=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 8, 50 pp. (Nov. 12, 2015), <https://classic.clinicaltrials.gov/ct2/history/NCT01627249?V_8=View>.
ClinicalTrials.gov, Archive, History of Changes for Study: NCT01627249, "Comparative Effectiveness Study of Intravitreal Aflibercept, Bevacizumab, and Ranibizumab for DME (Protocol T)," Version 9, 51 pp. (May 19, 2016), <https://classic.clinicaltrials.gov/ct2/history/NCT01627249?V_9=View>.
ClinicalTrials.gov, Archive, History of Changes for Study: NCT01909791, "Treatment of rCI-DME in Eyes with Very Good VA Study (Protocol V)," Version 1, 11 pp. (Jul. 26, 2013), <https://classic.clinicaltrials.gov/ct2/history/NCT01909791?V_1=View>.
ClinicalTrials.gov, Archive, History of Changes for Study: NCT01909791, "Treatment of rCI-DME in Eyes with Very Good VA Study (Protocol V)," Version 10, 23 pp. (Jul. 14, 2016), <https://classic.clinicaltrials.gov/ct2/history/NCT01909791?V_10=View>.
ClinicalTrials.gov, Archive, History of Changes for Study: NCT01909791, "Treatment of rCI-DME in Eyes with Very Good VA Study (Protocol V)," Version 11, 23 pp. (Aug. 25, 2016), <https://classic.clinicaltrials.gov/ct2/history/NCT01909791?V_11=View>.
ClinicalTrials.gov, Archive, History of Changes for Study: NCT01909791, "Treatment of rCI-DME in Eyes with Very Good VA Study (Protocol V)," Version 12, 24 pp. (Dec. 9, 2016), <https://classic.clinicaltrials.gov/ct2/history/NCT01909791?V_12=View>.
ClinicalTrials.gov, Archive, History of Changes for Study: NCT01909791, "Treatment of rCI-DME in Eyes with Very Good VA Study (Protocol V)," Version 13, 24 pp. (Feb. 27, 2018), <https://classic.clinicaltrials.gov/ct2/history/NCT01909791?V_13=View>.
ClinicalTrials.gov, Archive, History of Changes for Study: NCT01909791, "Treatment of rCI-DME in Eyes with Very Good VA Study (Protocol V)," Version 3, 14 pp. (Nov. 20, 2013), <https://classic.clinicaltrials.gov/ct2/history/NCT01909791?V_3=View>.
ClinicalTrials.gov, Archive, History of Changes for Study: NCT01909791, "Treatment of rCI-DME in Eyes with Very Good VA Study (Protocol V)," Version 4, 14 pp. (Feb. 6, 2014), <https://classic.clinicaltrials.gov/ct2/history/NCT01909791?V_4=View>.
ClinicalTrials.gov, Archive, History of Changes for Study: NCT01909791, "Treatment of rCI-DME in Eyes with Very Good VA Study (Protocol V)," Version 5, 16 pp. (Aug. 25, 2014), <https://classic.clinicaltrials.gov/ct2/history/NCT01909791?V_5=View>.
ClinicalTrials.gov, Archive, History of Changes for Study: NCT01909791, "Treatment of rCI-DME in Eyes with Very Good VA Study (Protocol V)," Version 6, 22 pp. (Dec. 1, 2014), <https://classic.clinicaltrials.gov/ct2/history/NCT01909791?V_6=View>.
ClinicalTrials.gov, Archive, History of Changes for Study: NCT01909791, "Treatment of rCI-DME in Eyes with Very Good VA Study (Protocol V)," Version 7, 22 pp. (Apr. 28, 2015), <https://classic.clinicaltrials.gov/ct2/history/NCT01909791?V_7=View>.
ClinicalTrials.gov, Archive, History of Changes for Study: NCT01909791, "Treatment of rCI-DME in Eyes with Very Good VA Study (Protocol V)," Version 8, 22 pp. (Nov. 30, 2015), <https://classic.clinicaltrials.gov/ct2/history/NCT01909791?V_8=View>.
ClinicalTrials.gov, Archive, History of Changes for Study: NCT01909791, "Treatment of rCI-DME in Eyes with Very Good VA Study (Protocol V)," Version 9, 22 pp. (Jun. 1, 2016), <https://classic.clinicaltrials.gov/ct2/history/NCT01909791?V_9=View>.
ClinicalTrials.gov, Archive, History of Changes for Study: NCT02858076, "Anti-VEGF vs. Prompt Vitrectomy for VH from PDF (AB)," Version 1, 11 pp. (Aug. 3, 2016), <https://classic.clinicaltrials.gov/ct2/history/NCT02858076?V_1=View>.
ClinicalTrials.gov, Archive, History of Changes for Study: NCT02858076, "Anti-VEGF vs. Prompt Vitrectomy for VH from PDF (AB)," Version 10, 16 pp. (Jul. 20, 2017), <https://classic.clinicaltrials.gov/ct2/history/NCT02858076?V_10=View>.
ClinicalTrials.gov, Archive, History of Changes for Study: NCT02858076, "Anti-VEGF vs. Prompt Vitrectomy for VH from PDF (AB)," Version 11, 17 pp. (Aug. 22, 2017), <https://classic.clinicaltrials.gov/ct2/history/NCT02858076?V_11=View>.
ClinicalTrials.gov, Archive, History of Changes for Study: NCT02858076, "Anti-VEGF vs. Prompt Vitrectomy for VH from PDF (AB)," Version 12, 18 pp. (Sep. 29, 2017), <https://classic.clinicaltrials.gov/ct2/history/NCT02858076?V_12=View>.
ClinicalTrials.gov, Archive, History of Changes for Study: NCT02858076, "Anti-VEGF vs. Prompt Vitrectomy for VH from PDF (AB)," Version 2, 11 pp. (Aug. 25, 2016), <https://classic.clinicaltrials.gov/ct2/history/NCT02858076?V_2=View>.
ClinicalTrials.gov, Archive, History of Changes for Study: NCT02858076, "Anti-VEGF vs. Prompt Vitrectomy for VH from PDF (AB)," Version 3, 11 pp. (Nov. 4, 2016), <https://classic.clinicaltrials.gov/ct2/history/NCT02858076?V_3=View>.

(56) References Cited

OTHER PUBLICATIONS

ClinicalTrials.gov, Archive, History of Changes for Study: NCT02858076, "Anti-VEGF vs. Prompt Vitrectomy for VH from PDF (AB)," Version 4, 13 pp. (Dec. 9, 2016), <https://classic.clinicaltrials.gov/ct2/history/NCT02858076?V_4=View>.
ClinicalTrials.gov, Archive, History of Changes for Study: NCT02858076, "Anti-VEGF vs. Prompt Vitrectomy for VH from PDF (AB)," Version 5, 13 pp. (Jan. 19, 2017), <https://classic.clinicaltrials.gov/ct2/history/NCT02858076?V_5=View>.
ClinicalTrials.gov, Archive, History of Changes for Study: NCT02858076, "Anti-VEGF vs. Prompt Vitrectomy for VH from PDF (AB)," Version 6, 13 pp. (Feb. 16, 2017), <https://classic.clinicaltrials.gov/ct2/history/NCT02858076?V_6=View>.
ClinicalTrials.gov, Archive, History of Changes for Study: NCT02858076, "Anti-VEGF vs. Prompt Vitrectomy for VH from PDF (AB)," Version 7, 14 pp. (Apr. 20, 2017), <https://classic.clinicaltrials.gov/ct2/history/NCT02858076?V_7=View>.
ClinicalTrials.gov, Archive, History of Changes for Study: NCT02858076, "Anti-VEGF vs. Prompt Vitrectomy for VH from PDF (AB)," Version 8, 15 pp. (May 19, 2017), <https://classic.clinicaltrials.gov/ct2/history/NCT02858076?V_8=View>.
ClinicalTrials.gov, Archive, History of Changes for Study: NCT02858076, "Anti-VEGF vs. Prompt Vitrectomy for VH from PDF (AB)," Version 9, 15 pp. (Jun. 14, 2017), <https://classic.clinicaltrials.gov/ct2/history/NCT02858076?V_9=View>.
Elman et al., "Randomized trial evaluating ranibizumab plus prompt or deferred laser or triamcinolone plus prompt laser for diabetic macular edema," *Ophthalmology*, 117(6):1064-1077.e35 (Jun. 2010), published Apr. 28 2010, available at https://www.aaojournal.org/article/S0161-6420(10)00243-5/fulltext.
Ferrucci et al., "Improving the Identification and Care of Patients with Diabetic Retinopathy—A Clinical Exchange Program for Optometrists," *Review Education Group*, 16 pp., downloaded from <https://www.revieweducationgroup.com/ce/improving-the-identification-and-care-of-patients-with-diabetic-retinopathy> (retrieved on Oct. 3, 2023) (release date Jul. 31, 2018).
Glassman et al., "Five-Year Outcomes after Initial Aflibercept, Bevacizumab, or Ranibizumab Treatment for Diabetic Macular Edema (Protocol T Extension Study)," *Ophthalmology*, 127(9):1201-1210 (Sep. 2020), author manuscript (available Sep. 1, 2021), 18 pp.
Kumar et al., "What Vascular Changes May Tell Us About Macular Edema and Disease Burden," *Retinal Specialist*, pp. 22-25 (Sep. 2017).
Midena et al., "Impact of Baseline Central Retinal Thickness on Outcomes in the Vivid-DME and Vista-DME Studies," *J. Ophthalmol.*, vol. 2018, Article ID 3640135, 9 pp., <https://doi.org/10.1155/2018/3640135> (2018).
Regillo et al., "Randomized, double-masked, sham-controlled trial of ranibizumab for neovascular age-related macular degeneration: Pier Study year 1," *Am J Ophthalmol.*, 145(2):239-248 (2008), published Dec. 3, 2007, available at https://www.ajo.com/article/S0002-9394(07)00881-1/fulltext.
Retina Society, Fifty-First Scientific Meeting, Scientific Program, 270 pp., San Francisco, CA, Sep. 12-15, 2018.
Retina Society, Fifty-Second Scientific Meeting, Scientific Program, 270 pp., London, UK, Sep. 11-15, 2019.
Retina Society, The 50th Annual Scientific Meeting, Scientific Program, 15 pp., Boston, MA, Oct. 5-8, 2017.
Staurenghi et al., "Impact of baseline Diabetic Retinopathy Severity Scale scores on visual outcomes in the VIVID-DME and VISTA-DME studies," *Br. J. Ophthalmol.*, 102:954-958 (2018).
Terry, "Regeneron's Eylea Shows Promising Data for Diabetic Retinopathy," *BioSpace*, 2 pp., downloaded from <https://www.biospace.com/article/regeneron-s-eylea-shows-promising-data-for-diabetic-retinopathy/> (published Mar. 19, 2018).
Wykoff et al., "Longitudinal Retinal Perfusion Status in Eyes with Diabetic Macular Edema Receiving Intravitreal Aflibercept or Laser in VISTA Study," *Ophthalmology*, 126:1171-1180 (2019).

Zhao et al., "The role of anti-vascular endothelial growth factor (anti-VEGF) in the management of proliferative diabetic retinopathy," *Drugs in Context*, 7:212532, 10 pp. (2018).
Albini et al., "Immunologic Processes in Disease," in *Pathobiology of Ocular Disease*, Gordon K. Klintworth & Alec Garner, eds., Informa Healthcare USA, Inc., New, York, NY, pp. 47-67 (2008).
Anonymous, "Study Population," in *Fundamentals of Clinical Trials*, 4th ed., Lawrence M. Friedman et al., eds., Springer, New York, pp. 55-66 (2010).
Bashshur et al., "Intravitreal Bevacizumab for Treatment of Neovascular Age-related Macular Degeneration: A One-year Prospective Study," *Am. J. Ophthalmology*, 145(2):249-256, 256.e1, and 256.e2 (Feb. 2008).
Bodaghi et al., "Chronic Severe Uveitis: Etiology and Visual Outcome in 927 Patents from a Single Center," *Medicine*, 80:263-270 (2001).
Boston Children's Hospital, "Orbital Cellulitis (Periorbital Cellulitis)," https://www.childrenshospital.org/conditions/orbital-cellulitis#:~:text=The%20terms%20orbital%20cellulitis%20and,area%20that%20encloses%20the%20eye, submitted in IPR2023-00442 as Exhibit 2382 on Oct. 13, 2023.
Brown et al., Panel Discussion, "Ophthalmic Formulations: Safety and Efficacy of VEGF-Neutralizing Drugs," *Supplement to Retina Today*, pp. 10-14 (Jan.-Feb. 2012).
Buyse, "Phase III Design: Principles," *Chinese Clinical Oncology*, 5(1):10, 13 pp. (2016).
Caspi, "A Look at Autoimmunity & Inflammation in the Eye," *J. Clin. Invest.*, 120(9):3073-3083 (Sep. 2010).
Center for Drug Evaluation and Research Approval Package for Eylea, Application No. 125387Orig1s053, 70 pp. (Oct. 28, 2016).
Center for Drug Evaluation and Research Approval Package for Eylea, Application No. 125387Orig1s060, 60 pp. (Aug. 12, 2019).
Center for Drug Evaluation and Research Approval Package for Eylea, Application No. 125387Orig1s061, 146 pp. (May 13, 2019).
D'Amico et al., VEGF Inhibition Study in Ocular Neovascularization (V.I.S.I.O.N.) Clinical Trial Group, "Pegaptanib Sodium for Neovascular Age-Related Macular Degeneration: Two-Year Safety Results of the Two Prospective, Multicenter, Controlled Clinical Trials," *Ophthalmology*, 113(6):992-1001 (Jun. 2006).
Excerpts from *Merriam-Webster's Medical Desk Dictionary*, Merriam-Webster, Inc., Springfield, Massachusetts, pp. 11, 143, and 144 (2005).
FDA Advisory Committee Briefing Document for BLA 125387/S-075, 64 pp. (Jan. 9, 2023).
Getz et al., "Measuring the Incidence, Causes, and Repercussions of Protocol Amendments," *Drug Information Journal*, 45:265-275 (2011).
*Intraocular Inflammation and Uveitis*, American Academy of Ophthalmology (Singapore), Section 9: Basic and Clinical Science Course, Chapter 9, "Endophthalmitis," pp. 293-310 (2008-2009).
Mayo Clinic, "Stye (sty), Overview," https://www.mayoclinic.org/diseases-conditions/sty/symptoms-causes/syc-20378017, submitted in IPR2023-00442 as Exhibit 2381 on Oct. 13, 2023.
Toy et al., "Treatment of Non-Neovascular Idiopathic Macular Telangiectasia Type 2 with Intravitreal Ranibizumab: Results of a Phase II Clinical Trial," *Retina*, 32(5):996-1006 (May 2012).
Turbert, "What Is Macular Telangiectasia?," American Academy of Ophthalmology, 3 pp., available at: https://www.aao.org/eye-health/diseases/macular-telangiectasia, submitted in IPR2023-00442 as Exhibit 2375 on Oct. 13, 2023.
U.S. Dept. of Health & Human Services, Approval of Research with Conditions: OHRP Guidance (2010), available at https://www.hhs.gov/ohrp/regulations-and-policy/guidance/guidance-on-irb-approval-of-research-with-conditions-2010/index.html (Nov. 10, 2010).
U.S. Food & Drug Administration, "Step 3: Clinical Research," https://www.fda.gov/patients/drug-development-process/step-3-clinical-research#phases, 7 pp., submitted in IPR2023-00442 as Exhibit 2385 on Oct. 13, 2023.
ClinicalTrials.gov, Archive, History of Changes for Study: NCT01909791, "Treatment for CI-DME in Eyes with Very Good VA Study (Protocol V)," Version 2, 5 pp. (Oct. 7, 2013), <https://classic.clinicaltrials.gov/ct2/history/NCT01909791?V_2=View>.

(56) References Cited

OTHER PUBLICATIONS

Wykoff et al., "Intravitreal Aflibercept Injection in Eyes With Substantial Vision Loss After Laser Photocoagulation for Diabetic Macular Edema: Subanalysis of the VISTA and VIVID Randomized Clinical Trials," *JAMA Ophthalmol.*, 135(2):107-114 (Feb. 1, 2017).
Regeneron Pharmaceuticals, Inc., "FDA to Review Eylea® (Aflibercept) Injection for the Treatment of Diabetic Retinopathy," Press Release, (Sep. 13, 2018).
Antiplatelet Trialists' Collaboration, "Collaborative Overview of Randomised Trials of Antiplatelet Therapy—II: Maintenance of Vascular Graft or Arterial Patency by Antiplatelet Therapy," *Br. Med. J.*, 308:158-168 (Jan. 15, 1994).
Baigent et al., Antithrombotic Trialists' Collaboration, "Collaborative meta-analysis of randomised trials of antiplatelet therapy for prevention of death, myocardial infarction, and stroke in high risk patients," *Br. Med. J.*, 324:71-86 (Jan. 12, 2002).
Declaration of Karen Chu dated Nov. 30, 2023, submitted in EPO Opposition Proceedings against EP 3716992.
Declaration of Robert L. Vitti, M.D., M.B.A. dated Nov. 30, 2023, submitted in EPO Opposition Proceedings against EP 3716992.
European Search Report from EP Application 23187537 completed Jan. 5, 2024.
Klein et al., "Changes in Retinal Vessel Diameter and Incidence and Progression of Diabetic Retinopathy," *Arch. Opthalmol.*, 130(6):749-755 (2012).
Powell et al., "Compendium of Excipients for Parenteral Formulations," *J. Pharm. Sci. Technol.*, 52:238-311 (1998).
Andersen et al., "Recombinant protein expression for therapeutic applications," *Current Opinion in Biotechnology*, 13:117-123 (Apr. 2002).
Proprietor's Letter to EPO in response to EPO communication of May 4, 2021, in European Patent Application No. 18825837.0-1112, 5 pp., dated Sep. 6, 2021.
American Academy of Ophthalmology 2018 Meeting Program (Oct. 27-30, 2018), 184 pp.
Anonymous, "FDA Refuses to Approve Regeneron's Eylea Pre-Filled Syringe," Pharmaceutical Business Review, 7 pp. (published online on Oct. 26, 2018).
Chan et al., "DRCR.net Protocol Review," Insert to *Retina Today*, 16 pp. (Apr. 2016).
ClinicalTrials.gov Archive, History of Changes for Study: NCT01331681, "VEGF Trap-Eye in Vision Impairment Due to Diabetic Macular Edema (DME) (VIVID-DME)," version 1, 10 pages (Apr. 7, 2011).
ClinicalTrials.gov Archive, History of Changes for Study: NCT01331681, "VEGF Trap-Eye in Vision Impairment Due to Diabetic Macular Edema (DME) (VIVID-DME)," version 2, 10 pages (May 5, 2011).
ClinicalTrials.gov Archive, History of Changes for Study: NCT01331681, "VEGF Trap-Eye in Vision Impairment Due to Diabetic Macular Edema (DME) (VIVID-DME)," version 3, 12 pages (May 19, 2011).
ClinicalTrials.gov Archive, History of Changes for Study: NCT01331681, "VEGF Trap-Eye in Vision Impairment Due to Diabetic Macular Edema (DME) (VIVID-DME)," version 4, 12 pages (Jun. 11, 2011).
ClinicalTrials.gov Archive, History of Changes for Study: NCT01331681, "VEGF Trap-Eye in Vision Impairment Due to Diabetic Macular Edema (DME) (VIVID-DME)," version 5, 12 pages (Jul. 5, 2011).
ClinicalTrials.gov Archive, History of Changes for Study: NCT01331681, "VEGF Trap-Eye in Vision Impairment Due to Diabetic Macular Edema (DME) (VIVID-DME)," version 6, 12 pages (Aug. 2, 2011).
ClinicalTrials.gov Archive, History of Changes for Study: NCT01331681, "VEGF Trap-Eye in Vision Impairment Due to Diabetic Macular Edema (DME) (VIVID-DME)," version 7, 12 pages (Aug. 30, 2011).
ClinicalTrials.gov Archive, History of Changes for Study: NCT01331681, "VEGF Trap-Eye in Vision Impairment Due to Diabetic Macular Edema (DME) (VIVID-DME)," version 8, 12 pages (Sep. 28, 2011).
ClinicalTrials.gov Archive, History of Changes for Study: NCT01331681, "VEGF Trap-Eye in Vision Impairment Due to Diabetic Macular Edema (DME) (VIVID-DME)," version 9, 13 pages (Oct. 26, 2011).
ClinicalTrials.gov Archive, History of Changes for Study: NCT01331681, "VEGF Trap-Eye in Vision Impairment Due to Diabetic Macular Edema (DME) (VIVID-DME)," version 10, 13 pages (Nov. 23, 2011).
ClinicalTrials.gov Archive, History of Changes for Study: NCT01331681, "VEGF Trap-Eye in Vision Impairment Due to Diabetic Macular Edema (DME) (VIVID-DME)," version 11, 13 pages (Dec. 19, 2011).
ClinicalTrials.gov Archive, History of Changes for Study: NCT01331681, "VEGF Trap-Eye in Vision Impairment Due to Diabetic Macular Edema (DME) (VIVID-DME)," version 12, 13 pages (Jan. 17, 2012).
ClinicalTrials.gov Archive, History of Changes for Study: NCT01331681, "VEGF Trap-Eye in Vision Impairment Due to Diabetic Macular Edema (DME) (VIVID-DME)," version 13, 13 pages (Feb. 14, 2012).
ClinicalTrials.gov Archive, History of Changes for Study: NCT01331681, "VEGF Trap-Eye in Vision Impairment Due to Diabetic Macular Edema (DME) (VIVID-DME)," version 14, 13 pages (Mar. 14, 2012).
ClinicalTrials.gov Archive, History of Changes for Study: NCT01331681, "VEGF Trap-Eye in Vision Impairment Due to Diabetic Macular Edema (DME) (VIVID-DME)," version 15, 13 pages (Apr. 11, 2012).
ClinicalTrials.gov Archive, History of Changes for Study: NCT01331681, "VEGF Trap-Eye in Vision Impairment Due to Diabetic Macular Edema (DME) (VIVID-DME)," version 16, 13 pages (May 2, 2012).
ClinicalTrials.gov Archive, History of Changes for Study: NCT01331681, "VEGF Trap-Eye in Vision Impairment Due to Diabetic Macular Edema (DME) (VIVID-DME)," version 17, 11 pages (Jun. 18, 2012).
ClinicalTrials.gov Archive, History of Changes for Study: NCT01331681, "VEGF Trap-Eye in Vision Impairment Due to Diabetic Macular Edema (DME) (VIVID-DME)," version 18, 11 pages (Sep. 5, 2012).
ClinicalTrials.gov Archive, History of Changes for Study: NCT01331681, "VEGF Trap-Eye in Vision Impairment Due to Diabetic Macular Edema (DME) (VIVID-DME)," version 19, 11 pages (Dec. 10, 2012).
ClinicalTrials.gov Archive, History of Changes for Study: NCT01331681, "VEGF Trap-Eye in Vision Impairment Due to Diabetic Macular Edema (DME) (VIVID-DME)," version 20, 11 pages (Mar. 8, 2013).
ClinicalTrials.gov Archive, History of Changes for Study: NCT01331681, "VEGF Trap-Eye in Vision Impairment Due to Diabetic Macular Edema (DME) (VIVID-DME)," version 21, 12 pages (Jun. 12, 2013).
ClinicalTrials.gov Archive, History of Changes for Study: NCT01331681, "VEGF Trap-Eye in Vision Impairment Due to Diabetic Macular Edema (DME) (VIVID-DME)," version 22, 12 pages (Sep. 9, 2013).
ClinicalTrials.gov Archive, History of Changes for Study: NCT01331681, "VEGF Trap-Eye in Vision Impairment Due to Diabetic Macular Edema (DME) (VIVID-DME)," version 23, 12 pages (Nov. 14, 2013).
ClinicalTrials.gov Archive, History of Changes for Study: NCT01331681, "VEGF Trap-Eye in Vision Impairment Due to Diabetic Macular Edema (DME) (VIVID-DME)," version 24, 12 pages (Feb. 10, 2014).
ClinicalTrials.gov Archive, History of Changes for Study: NCT01331681, "VEGF Trap-Eye in Vision Impairment Due to Diabetic Macular Edema (DME) (VIVID-DME)," version 25, 12 pages (Apr. 30, 2014).

(56) References Cited

OTHER PUBLICATIONS

ClinicalTrials.gov Archive, History of Changes for Study: NCT01331681, "VEGF Trap-Eye in Vision Impairment Due to Diabetic Macular Edema (DME) (VIVID-DME)," version 26, 12 pages (May 28, 2014).
ClinicalTrials.gov Archive, History of Changes for Study: NCT01331681, "VEGF Trap-Eye in Vision Impairment Due to Diabetic Macular Edema (DME) (VIVID-DME)," version 27, 43 pages (Aug. 29, 2014).
ClinicalTrials.gov Archive, History of Changes for Study: NCT01331681, "VEGF Trap-Eye in Vision Impairment Due to Diabetic Macular Edema (DME) (VIVID-DME)," version 28, 43 pages (Dec. 8, 2014).
ClinicalTrials.gov Archive, History of Changes for Study: NCT01331681, "VEGF Trap-Eye in Vision Impairment Due to Diabetic Macular Edema (DME) (VIVID-DME)," version 29, 43 pages (Feb. 12, 2015).
ClinicalTrials.gov Archive, History of Changes for Study: NCT01331681, "VEGF Trap-Eye in Vision Impairment Due to Diabetic Macular Edema (DME) (VIVID-DME)," version 30, 43 pages (Apr. 26, 2015).
ClinicalTrials.gov Archive, History of Changes for Study: NCT01331681, "VEGF Trap-Eye in Vision Impairment Due to Diabetic Macular Edema (DME) (VIVID-DME)," version 31, 43 pages (Dec. 11, 2015).
ClinicalTrials.gov Archive, History of Changes for Study: NCT01331681, "VEGF Trap-Eye in Vision Impairment Due to Diabetic Macular Edema (DME) (VIVID-DME)," version 32, 47 pages (Mar. 20, 2016).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 1, 9 pages (May 31, 2011).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 2, 9 pages (Jun. 11, 2011).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 3, 9 pages (Sep. 15, 2011).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 4, 8 pages (Jan. 13, 2012).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 5, 9 pages (Feb. 13, 2012).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 6, 9 pages (Nov. 9, 2012).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 7, 9 pages (Jun. 10, 2013).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 8, 9 pages (Nov. 19, 2013).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 9, 10 pages (Feb. 11, 2014).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 10, 33 pages (Apr. 2, 2015).
ClinicalTrials.gov Archive, History of Changes for Study: NCT01363440, "Study of Intravitreal Administration of VEGF Trap-Eye (BAY86-5321) in Patients with Diabetic Macular Edema (VISTA DME)," version 11, 51 pages (Apr. 25, 2016).
Dhoot et al., "Functional Outcomes of Sustained Improvement on Diabetic Retinopathy Severity Scale with Intravitreal Aflibercept in the VISTA and VIVID Trials," *Eye*, 37:2020-2025 (2023).
Regeneron Form 8-K, Exhibit 99, presentation titled "JP Morgan 2017 Growth Through Innovation," 47 pp., Jan. 9, 2017 (retrieved from sec.gov/Archives/edgar/data/872589/000110465917001558/a17-1670_18k.htm on Feb. 22, 2024).
Regeneron, Presentation entitled "JP Morgan 2018," 35 pp. (Jan. 8, 2018), Exhibit 99.1 from Regeneron SEC Form 8-K (retrieved from sec.gov/Archives/edgar/data/872589/000110465918001100/a18-2403_1ex99d1.htm on Mar. 20, 2024).
Regeneron, Schedule 14A, Regeneron 2017 Annual Report, 31 pp. (retrieved from sec.gov/Archives/edgar/data/872589/000110465918025868/a18-5919_7defa14a.htm on Mar. 20, 2024).
Wykoff, Slide Deck Presentation: "Intravitreal Aflibercept for Moderately Severe to Severe Non-Proliferative Diabetic Retinopathy (NPDR) The Phase 3 Panorama Study," The American Society of Retina Specialists, 20 pp., Jul. 24, 2018.
Regeneron Press Release, "Eylea® (aflibercept) Injection Improves Diabetic Retinopathy and Reduces Vision-Threatening Complications in Phase 3 Trial," PRNewswire, 3 pp. (Oct. 25, 2018).
Lim, Abstract: Intravitreal Aflibercept Injection for Nonproliferative Diabetic Retinopathy: Year 2 Results from the Panorama Study, Assoc. for Res. in Vision and Ophthalmology (ARVO), 2020 Annual Meeting, *Investigative Ophthalmology & Visual Science*, vol. 61, 1381 (Jun. 2020), e-publication—Mar. 4, 2020.
Brown, Abstract: "Treatment of Moderately Severe to Severe Nonproliferative Diabetic Retinopathy with Intravitreal Aflibercept Injection: Results from the Phase 3 Panorama Study," 2019 Macula Society Meeting; Bonita Springs, Florida, 3 pp. (Feb. 13-16, 2019).
Heier, Presentation: "Intravitreal Aflibercept Injection for Moderately Severe to Severe Nonproliferative Diabetic Retinopathy: The Phase 3 Panorama Study," Retina Society Annual Meeting, 18 pp. (Sep. 13, 2018).
Regeneron, United States Securities and Exchange Commission, Schedule 14A, Proxy Statement Pursuant to Section 14(a) of the Securities Exchange Act of 1934 (DEFA14a), including "Regeneron 2017 Annual Report," 47 pp., filed Apr. 23, 2018 (retrieved from sec.gov/Archives/edgar/data/872589/000110465917001558/a17-1670_18k.htm on Feb. 22, 2024).
Wykoff, Abstract: Intravitreal Aflibercept Injection (IAI) for Moderately Severe to Severe Nonproliferative Diabetic Retinopathy (NPDR): The Phase 3 Panorama Study, American Society of Retina Specialists (ASRS), 2018 Annual Meeting, Vancouver, British Columbia (Jul. 20-24, 2018), e-publication Jul. 25, 2018.
Arabi et al., "Update on Management of Non-proliferative Diabetic Retinopathy without Diabetic Macular Edema; Is There a Paradigm Shift?," *J Ophthalmic Vis. Res.*, 17(1):108-117 (Jan. 21, 2022).
Lechner et al., "The pathology associated with diabetic retinopathy," *Vision Research*, 139:7-14 (2017), available online Apr. 29, 2017.
Clinicaltrials.gov posting NCT01363440, Study of Intravitreal Aflibercept Injection (IAI; Eylea®; BAY86-5321) in Patients With Diabetic Macular Edema (VISTA DME), May 30, 2016.
Clinicaltrials.gov posting NCT00509795, Vascular Endothelial Growth Factor VEGF Trap-Eye: Investigation of Efficacy and Safety in Wet Age-Related Macular Degeneration (Amd) (VIEW1), Dec. 28, 2012.
Ip et al., "Long-Term Effects of Therapy with Ranibizumab on Diabetic Retinopathy Severity and Baseline Risk Factors for Worsening Retinopathy," *Ophthalmology*, 122(2):367-374 (Feb. 1, 2015).
Brown, Abstract: "Diabetic Retinopathy (NPDR): The Phase 3 Panorama Study," Assoc. for Res. In Vision and Ophthalmology), 2018 Annual Meeting, Honolulu, Hawaii (Apr. 29-May 3, 2018) (published online Mar. 6, 2018) Previously submitted (item 8 in IDS submitted Mar. 24, 2021).
Brown, Abstract: "Intravitreal Aflibercept Injection (IAI) for Moderately Severe to Severe Nonproliferative Diabetic Retinopathy (NPDR): The Phase 3 Panorama Study," Assoc. for Res. In Vision and Ophthalmology (ARVO), 2018 Annual Meeting, Honolulu,

(56) References Cited

OTHER PUBLICATIONS

Hawaii (Apr. 29-May 3, 2018) (published online in *Investigative Ophthalmology & Visual Science*, vol. 59, 1889 on Mar. 6, 2018) Previously submitted (item 9 in IDS submitted Mar. 24, 2021).
Heier, "Intravitreal Aflibercept for Diabetic Macular Edema: 148-Week Results from the Vista and Vivid Studies," Ophthalmology, 123(11):2376-2385 (e-publication Sep. 17, 2016) Previously submitted (item 520 in IDS submitted Oct. 13, 2023).
Higgins, Abstract: "The Phase 3 Panorama Study of Intravitreal Aflibercept for Moderately Severe to Severe Non-Proliferative Diabetic Retinopathy," American Academy of Optometry (AAOpt), 2018 Annual Meeting, Chicago, Illinois (e-publication Oct. 8, 2018) Previously submitted (item 42 in IDS submitted Mar. 24, 2021).
Higgins, Presentation: "The Phase 3 Panorama Study of Intravitreal Aflibercept for Moderately Severe to Severe Non-Proliferative Diabetic Retinopathy," American Academy of Optometry (AAOpt), 14 pp. (Nov. 7-10, 2018) Previously submitted (item 41 in IDS submitted Mar. 24, 2021).
Lim, Abstract: "Intravitreal Aflibercept Injection for Nonproliferative Diabetic Retinopathy: Year 2 Results from the Panorama Studdy," Assoc. for Res. In Vision and Ophthalmology (ARVO), 2018 Annual Meeting, Honolulu, Hawaii (Apr. 29-May 3, 2018) (published online Mar. 6, 2018) Previously submitted (item 45 in IDS submitted Mar. 24, 2021).
Regeneron, United States Securities and Exchange Commission, Schedule 14A, Proxy Statement Pursuant to Section 14(a) of the Securities Exchange Act of 1934 (DEFA14a), including "Regeneron 2017 Annual Report," 31 pp., filed Apr. 23, 2018 (retrieved from https://www.sec.gov/Archives/edgar/data/872589/000110465918025868/a18-5919_7defa14a.htm on Mar. 20, 2024) Previously submitted (item 54 in IDS filed May 3, 2024).
Regeneron Pharmaceuticals, Inc., "EYLEA® (aflibercept) Injection Improves Diabetic Retinopathy and Reduces Vision-Threatening Complications in Phase 3 Trial," (Oct. 25, 2018) Previously submitted (item 69 in IDS filed Mar. 24, 2021).
Wykoff, Slide Deck Presentation: "Intravitreal Aflibercept for Moderately Severe to Severe Non-Proliferative Diabetic Retinopathy (NPDR) The Phase 3 Panorama Study," The American Society of Retina Specialists 2018 Annual Meeting, 20 pp. (Jul. 20-25, 2018) Previously submitted (item 58 in IDS submitted May 3, 2024).
Wykoff et al., "Intravitreal Aflibrecept Injection in Eyes With Substanial Vision Loss After Laser Photocagulation for Diabetic Macular Edema: Sybanalysis of the Vista and Vivid Randomized Clinical Trial," *JAMA Ophthalmol.*, 135(2):107-114 (Feb. 1, 2017), e-publication Dec. 22, 2016. Previously submitted (item 2 in IDS submitted Dec. 14, 2023).
Adair et al., "Angiogenesis," Colloquium Series in Integrated Systems Physiology: From Molecule to Function, Granger et al. (eds.), 85 pp., Morgan & Claypool Life Sciences (2011).
Arevalo et al., "Intravitreal bevacizumab (Avastin) for proliferative diabetic retinopathy: 6-months follow-up," *Eye*, 23(1):117-123 (2009) (published online Sep. 21, 2007).
BioSpace, "Opko Health, Inc. Announces Update on Phase III Clinical Triial of Bevasiranib; Company Decided to Terminate Clinical Study," Press Release, 4 pp. (Mar. 6, 2009).
Chan et al., "Normal macular thickness measurements in healthy eyes using Stratus optical coherence tomography," *Archives of Ophthalmology*, 124(2):193-198 (Feb. 2006).
ClinicalTrials.gov, "How to Read a Study Record," https://clinicaltrials.gov/study-basics/how-to-read-study-record#record-history-tab (last updated Jan. 9, 2024).
ClinicalTrials.gov, Archive: NCT0047330, "A Study of Ranibizumab Injection in Subjects With Clinically Significant Macular Edema With Center Involvement Secondary to Diabetes Mellitus (RISE)," https://web.archive.org/web/20100609131649/https:/www.clinicaltrials.gov/ct2/show/NCT00473330 (last updated Nov. 7, 2009).
ClinicalTrials.gov, Record History for NCT00473330, "A Study of Ranibzumab Injection in Subjects With Clinically Significant Macular Edema (ME) With Center Involvement Secondary to Diabetes Mellitus (RISE) (RISE)," Version 9, dated Nov. 11, 2010, https://www.clinicaltrials.gov/study/NCT00473330?tab=history&a=9.
ClinicalTrials.gov, Record History for NCT00473382, "A Study of Ranibizumab Injection in Subjects With Clinically Significant Macular Edema (ME) With Center Involvement Secondary to Diabetes Mellitus (RIDE) (RIDE)," version 9, dated Nov. 11, 2010, 13 pp., https://www.clinicaltrials.gov/study/NCT00473382.
ClinicalTrials.gov, Record History for NCT00485836, "A Study of the Efficacy and Safety of Ranibizumab Injection in Patients With Macular Edema Secondary to Central Retinal Vein Occulusion (CRUISE) (CRUISE)," version 7, dated May 5, 2010, 11 pp., https://www.clinicaltrials.gov/study/NCT00485836.
ClinicalTrials.gov, Record History for NCT00486018, "A Study of the Efficacy and Safety of Ranibizumab Injection in Patients With Macular Edema Secondary to Branch Retinal Vein Occlusion (Bravo) (BRAVO)," version 8, dated May 5, 2010, 11 pp., https://www.clinicaltrials.gov/study/NCT00486018.
Conberecept (Kangbeicept) Eye Injection (Langmu), https://www.cnkh.com/productnew/17146.htm (published Jun. 26, 2015).
Department of Health & Human Services, Avastin Approval Letter (DHHS STN: BL 125085/0), 8 pp. (Feb. 26, 2004) [Redacted].
Department of Health & Human Services, BLA 125156/S-114, Lucentis Supplement Approval Letter, 4 pp. (Apr. 15, 2017).
Department of Health & Human Services, BLA 125387/48, EYLEA Supplement Approval Letter, 4 pp. (Mar. 25, 2015).
Department of Health & Human Services, BLA 125387/S-061, EYLEA Supplement Approval Letter, 4 pp. (May 13, 2019).
Diabetic Retinopathy Study Research Group, "Photocoagulation treatment of proliferative diabetic retinopathy: clinical application of Diabetic Retinopathy Study (DRS) finds, DRS Report Number 8," *Ophthalomology*, 88 (7):583-600 (Jul. 1981).
Dombrow et al., "Ocular Angiogenesis: The Science Behind the Symptoms," *Retinal Physician*, 12 pp. (Jan. 1, 2011).
Drugs.com Website, "Eylea FDA Approval History," 2 pp., https://www.drugs.com/history/eylea.html (accessed Jan. 15, 2024).
Drugs.com Website, "Eylea FDA Approval History," 2 pp., https://www.drugs.com/history/eylea.html (accessed Jan. 16, 2024).
Early Treatment Diabetic Retinopathy Study Research Group "Fundus photographic risk factors for progression of diabetic retinopathy: ETDRS report number 12," *Opthalmology*, 98(5):823-833 (May 1991).
Early Treatment Diabetic Retinopathy Study Research Group, "Early photocoagulation for diabetic retinopathy: ETDRS Report Number 9," *Ophthalmology*, 98(5):766-785 (May 1991).
FDA, "Step 3: Clinical Research," https://www.fda.gov/patients/drug-development-process/step-3- clinical-research (last accessed Aug. 23, 2023.
FDA, Department of Health & Human Services, "Indications and Usage Section of Labeling for Human Prescription Drug Biological Products—Content and Format. Guidance for Industry," 20 pp. (Jul. 2018), presented by Exhibit 2096 in IPR2023-00739 on Jan. 26, 2024.
Fong et al., "Diabetic Retinopathy," *Diabetes Care*, 27(10):2540-2553 (Oct. 2004).
Genentech, "FDA Approves Genentech's Lucentis (Ranibizumab Injection) Prefilled Syringe," Press Release, 5 pp. (Oct. 14, 2016).
Gonzalez et al., "Use of Pegaptanib Sodium (Macugen®) for the Regression of Proliferative Diabetic Retinopathy," *Investigative Ophthalmology & Visual Science*, 47(13):2329, 2 pp., ARVO Annual Meeting Abstract (May 2006).
Highlights of Prescribing Information for Beovu (brolucizumab-dbII) Injection, 15 pp. (Revised Dec. 2022), available at https://www.accessdata.fda.gov/drugsatfda_doc/label/2022/761125s0171b1.pdf.
Highlights of Prescribing Information for Susvimo™ (ranibizumab injection) for intravitreal use via Susvimo ocular implant (revised Apr 2022), 73 pp., available at https://www.accessdata.fda.gov/drugsatfda_docs/label/2022/76119 7s00b1b1.pdf.
Highlights of Prescribing Information for Susvimo™ (ranibizumab injection) for intravitreal use via Susvimo ocular implant (revised Oct. 2021), 87 pp., available at https://www.accessdata.fda.gov/drugsatfda docs/label/2021/76119 7s0001b1.pdf.

(56) References Cited

OTHER PUBLICATIONS

Highlights of Prescribing Information for Vabysmo™ (faricimab-svoa) injection (revised Jan. 2022), 17 pp., available at https://www.accessdata.fda.gov/drugsatfda_docs/label/2022/76123 5s0001b1.pdf.
Highlights of Prescribing Information for Vabysmo™ (faricimab-svoa) injection (revised Jan. 2023), 17 pp., available at https://www.accessdata.fda.gov/drugsatfda_docs/label/2022/76123 s0011b1.pdf.
Holz et al., Abstract, "Safety and Efficacy of RanibizumabTreatment in Patients with Neovascular Age-Related Macular Degeneration: 12-MonthResults of the Sustain Study," *Investigative Ophthalmology & Visual Science*, 50(13):3095, ARVO Annual Meeting Abstract (Apr. 2009).
Major et al., Abstract, "Da Vinci: DME and VEGF Trap-Eye: INvestigation of Clinical Impact: Phase 2 study in patients with Diabetic Macular Edema (DME)," ARVO, Control/Tracking No. 10-LB-8576-ARVO (Mar. 3, 2010).
Michaelides et al., "A Prospective Randomized Trial of Intravitreal Bevacizumab or Laser Therapy in the Management of Diabetic Macular Edema (BOLT study): 12-month data: report 2," *Ophthalmology*, 117(6):1078-1086 and 1086.e1-e2 (2010).
Miller, "VEGF: From Discovery to Therapy: The Champalimaud Award Lecture," *Translational Vision Science & Technology*, 5(2):9 (Mar. 11, 2016).
Musat et al., "Diabetic Macular edema," *Romanian Journal of Ophthalmology*, 59(3):133-136 (Jul.-Sep. 2015).
National Cancer Institute, "Second-Line Therapy," 1 p., https://www.cancer.gov/publications/dictionaries/cancer-terms/def/second-line-therapy (accessed Jan. 16, 2024).
Nguyen et al., "Two-year Outcomes of the Ranibizumab for Edema of the mAcula in diabetes (READ-2) study," *Ophthalmology*, 117(11):2146-2151 (201).
Nguyen et al., "Vascular endothelial growth factor is a critical stimulus for diabetic macular edema," *Am J Ophthalmol.*, 142(6):961-969 (Dec. 2006).
Opko Health, "Opko Health Initiates Phase 3 Trial of Bevasiranib for the Treatment of AMD," Press Release, 3 pp. (Jul. 11, 2007).
Opko Health, "OPKO's Bbevasiranib Named One of Most Promising Drugs Recently Entering Phase III Trials," Press Release, 2 pp. (Dec. 6, 2007).
Parikh et al., "Trends Of Anti-Vascular Endothelial Growth Factor Use in Ophthalmology Among Privately Insured and Medicare Advantage Patients," *Ophthalmology*, 124(3):352-358 (2017).
Prasad, "The DRCR Network Aids DR Treatment: The Government-sponsored network allows clinical researchers to communicate effectively," *Review of Ophthalmology*, 6 pp. (Oct. 15, 2006).
Regeneron Pharmaceuticals, Inc., "Bayer HealthCare and Regeneron to Collaborate on VEGF Trap for the Trewatment of Eye Diseases," Press Release 3 pp. (Oct. 18, 2006).
Regeneron Website, "History: A 35 Year Journey with a Relentless Focus on Science," https://www.regeneron.com/about/history (accessed Jan. 15, 2024).
Regeneron, "US Eylea P&L LTD, " 2 pp. (2001) [redacted], submitted as Exhibit 2214 in IPR2023-00884 on Feb. 23, 2024.
Romero-Aroca et al., "Laser treatment for diabetic macular edema in the 21st century," *Current Diabetes Review*, 10(2):100-112 (Apr. 2, 2014).
Sharma et al., "Mechanisms of Acquired Resistance to Anti-VEGF Therapy for Neovascular Eye Disease," *Investigative Ophthalmology & Visual Science*, 64(5):28, 12 pp. (May 30, 2023).
Spaide et al., "Intravitreal bevacizumab (Avastin) treatment of proliferative diabetic retinopathy complicated by vitreous hemorrhage," *Retina*, 26(3):275-278 (Mar. 2006).
Tolentino et al., "Intravitreous Injections of Vascular Endothelial Growth Factor Produce Retinal Ischemia and Microangiopathy in an Adult Primate," *Ophthalmology*, 103(11):1820-1828 (Jun. 1996).
Treatment of Age-Related Macular Degeneration with Photodynamic Therapy (TAP) Study Group, "Photodynamic therapy of subfoveal choroidal neovascularization in age-related macular degeneration with verteporfin: one-year results of 2 randomized clinical trials—TAP report 1," *Archives of Ophthalmology*, 117(10):1329-1345 (Oct. 1999).
Wang et al., "Diabetic Retinopathy: Pathophysiology and Treatments," *International Journal of Molecular Sciences*, 19(6):1816, 14 pp. (Jun. 20, 2018).
Whelan, "What is Angiogenesis?, " Technology Networks, 10 pp. (Jul. 6, 2022).
Whelan, "What is Angiogenesis?, " Technology Networks, 11 pp. (Jul. 6, 2022).
World Health Organization, "Blindness and Vision Impairment Fact Sheet," 8 pp. (Aug. 10, 2023), https://www.who.int/news-room/fact- sheets/detail/blindness-and-visual-impairment.
Yancopoulos, Screenshots of Database [Redacted], submitted as Exhibit 2092 in IPR2023-00884 on Feb. 23, 2024.
Yang et al., "Observation of Intravitreal Injection of Conbercept for Treatment of Diabetic Macular Edema," China Medical Journal, 18(10):1028-1029 (Oct. 31, 2016).
Zhu et al., "Efficacy of Intravitreal Injection of Conbercept on Treatment of Diabetic Retinopathy," *Southwest National Defense Medicine* 26(10):1121-1123 (Oct. 31, 2016), with machine translation.

\* cited by examiner

PANORAMA Dosing Schedule

| Week: | BL | 4 | 8 | 12 | 16 | 20 | 24 | 28 | 32 | 36 | 40 | 44 | 48 | 52 | 56 | ...100 |
|---|---|---|---|---|---|---|---|---|---|---|---|---|---|---|---|---|
| SHAM* | O | O | O | O | O | O | O | O | O | O | O | O | O | O | O | ...O |
| Group 1* | X | X | X | O | X | O | O | O | X | O | O | O | X | O | O | ...⋮ |
| Group 2* | X | X | X | X | X | X | X | X | X | X | X | X | X | X | + | ...⋮ |

Only 1 dose difference between Group 1 and Group 2 through week 24

+Group 2 (Q8) group continues PRN through Week 100 based on DRSS level

*Patients progressing to PDR/ASNV or CI-DME were eligible for rescue treatment (IAI or laser) at the discretion of the investigator. Data for patients receiving rescue treatment was censored from the time of rescue.

X=active injection, O=sham injection

FIG. 4

Disposition and Baseline Demographics

| | — Sham | ---- Group 1 | — Group 2 | --- All IAI | — Total |
|---|---|---|---|---|---|
| Number of Patients who Completed at Week 24 | 119 (89.5%) | 129 (95.6%) | 132 (98.5%) | 261 (97.0%) | 380 (94.5%) |
| N (FAS/SAF) | 133 | 135 | 134 | 269 | 402 |
| Age (years (SD)) | 55.8 (10.31) | 55.4 (11.13) | 55.8 (10.19) | 55.6 (10.66) | 55.7 (10.53) |
| Women # (%) | 64 (48.1%) | 60 (44.4%) | 53 (39.6%) | 113 (42.0%) | 177 (44.0%) |
| Race # (%) | | | | | |
| White | 107 (80.5%) | 99 (73.3%) | 104 (77.6%) | 203 (75.5%) | 310 (77.1%) |
| Black or African American | 13 (9.8%) | 16 (11.9%) | 12 (9.0%) | 28 (10.4%) | 41 (10.2%) |
| Asian | 4 (3.0%) | 12 (8.9%) | 7 (5.2%) | 19 (7.1%) | 23 (5.7%) |
| Other | 9 (6.8%) | 8 (5.9%) | 11 (8.2%) | 19 (7.1%) | 28 (7.0%) |
| Hemoglobin A1C (%) | 8.5 (1.54) | 8.6 (1.69) | 8.4 (1.64) | 8.5 (1.66) | 8.5 (1.62) |
| Duration of Diabetes (years (SD)) | 15.5 (9.34) | 13.7 (8.61) | 14.0 (9.69) | 13.8 (9.15) | 14.4 (9.24) |
| Diabetes Type 2 | 123 (92.5%) | 121 (89.6%) | 124 (92.5%) | 245 (91.1%) | 368 (91.5%) |

FIG. 5

Baseline Disease Characteristics

| | Sham | Group 1 | Group 2 | All IAI | Total |
|---|---|---|---|---|---|
| N (FAS/SAF) | 133 | 135 | 134 | 269 | 402 |
| ETDRS BCVA (letters) Mean (SD) Snellen Equivalent | 82.7 (6.03) 20/25 | 82.2 (6.63) 20/25 | 82.3 (5.15) 20/25 | 82.3 (5.93) 20/25 | 82.4 (5.96) 20/25 |
| CRT (microns) Mean (SD) | 249.4 (38.41) | 246.0 (34.34) | 246.8 (31.59) | 246.4 (32.94) | 247.4 (34.82) |
| Diabetic Retinopathy Severity Score (DRSS) | | | | | |
| Level 47 | 99 (74.4%) | 102 (75.6%) | 101 (75.4%) | 203 (75.5%) | 302 (75.1%) |
| Level 53 | 34 (25.6%) | 33 (24.4%) | 33 (24.6%) | 66 (24.5%) | 100 (24.9%) |

FIG. 6

Ocular TEAEs in Study Eye through Week 24
(≥3%)

| | — Sham | --- All IAI |
|---|---|---|
| N (FAS/SAF) | 133 | 269 |
| Number of Patients ≥ 1 AE, n (%) | 44 (33.1%) | 77 (28.6%) |
| Eye disorders | 42 (31.6%) | 76 (28.3%) |
| Conjunctival haemorrhage | 4 (3.0%) | 32 (11.9%) |
| Vitreous floaters | 1 (0.8%) | 14 (5.2%) |
| Diabetic retinal oedema | 18 (13.5%) | 11 (4.1%) |
| Eye pain | 2 (1.5%) | 11 (4.1%) |
| Diabetic retinopathy | 4 (3.0%) | 1 (0.4%) |

FIG. 13

Ocular Serious TEAEs in Study Eye through Week 24

| | — Sham | --- All IAI |
|---|---|---|
| N (FAS/SAF) | 133 | 269 |
| Number of Patients with ≥ 1 AE, n (%) | 1 (0.8%) | 0 |
| Iris neovascularisation | 1 (0.8%) | 0 |

FIG. 14

Ocular Inflammation in Study Eye through Week 24

| | — Sham | --- All IAI |
|---|---|---|
| N (FAS/SAF) | 133 | 269 |
| # of injection | 0 | 1182 |
| Vitreal cells | 0 | 1 (0.4%) (0.08% per injection) |

FIG. 15

APTC Events through Week 24

| | — Sham | --- All IAI |
|---|---|---|
| N (FAS/SAF) | 133 | 269 |
| Number of Patients with ≥ 1 AE, n (%) | 2 (1.5%) | 1 (0.4%) |
| Non Fatal Stroke | 0 | 1 (0.4%) |
| Cerebrovascular accident | 0 | 1 (0.4%) |
| Vascular Death | 2 (1.5%) | 0 |
| Cardiac arrest | 1 (0.8%) | 0 |
| Myocardial infarction | 1 (0.8%) | 0 |

FIG. 16

Deaths through Week 24

| Treatment Group | Patient Age /Sex /Race | Days from First Treatment to Death | Days from Last Treatment to Death | AE Preferred Term with Fatal Outcome | Rescue/ FE Treatment |
|---|---|---|---|---|---|
| Sham | 43/F/W | 52 | 23 | Acute respiratory failure Pulmonary hypertension | No rescue/ No FE treatment |
| Sham | 65/M/W | 73 | 13 | Cardiac arrest | No rescue/ No FE treatment |
| Sham | 73/M/W | 86 | 4 | Myocardial infarction | No rescue/ 2 FE treatments |

FIG. 17

International Clinical Diabetic Retinopathy Disease
Severity Scale Detailed Table

| LEVEL | SEVERITY |
|---|---|
| 10 | DR absent |
| 20 | Microaneurysms only |
| 35 | Mild NPDR |
| 43 | Moderate NPDR |
| 47 | Moderately severe NPDR |
| 53 | Severe NPDR |
| 61 | Mild PDR |
| 65 | Moderate PDR |
| 71 | High Risk PDR |
| 75 | High Risk PDR |
| 81 | Advanced PDR, fundus partially obscured, center of macula attached |
| 85 | Advanced PDR, posterior fundus obscured or center of macula detached |
| 90 | Cannot grade, even sufficiently for level 81 or 85 |

ETDRS Group, #12 1991

DRSS grading scale was derived from the ETDRS and is used to grade severity of DR and describe the change in severity over time.

FIG. 18

Ocular TEAEs in Study Eye through Week 52 (≥3%)

| | — Sham | ---- 2q16 | — 2q8 |
|---|---|---|---|
| N (FAS/SAF) | 133 | 135 | 134 |
| Number of Patients ≥ 1 AE, n (%) | 67 (50.4%) | 58 (43.0%) | 60 (44.8%) |
| Eye disorders | 64 (48.1%) | 57 (42.2%) | 59 (44.0%) |
| Conjunctival haemorrhage | 7 (5.3%) | 16 (11.9%) | 23 (17.2%) |
| Diabetic retinal oedema | 32 (24.1%) | 8 (5.9%) | 12 (9.0%) |
| Vitreous floaters | 3 (2.3%) | 6 (4.4%) | 12 (9.0%) |
| Eye pain | 4 (3.0%) | 10 (7.4%) | 5 (3.7%) |
| Retinal exudates | 5 (3.8%) | 5 (3.7%) | 7 (5.2%) |
| Blepharitis | 1 (0.8%) | 2 (1.5%) | 6 (4.5%) |
| Vitreous detachment | 1 (0.8%) | 4 (3.0%) | 4 (3.0%) |
| Cataract | 1 (0.8%) | 3 (2.2%) | 4 (3.0%) |
| Dry eye | 4 (3.0%) | 3 (2.2%) | 4 (3.0%) |
| Diabetic retinopathy | 13 (9.8%) | 2 (1.5%) | 3 (2.2%) |
| Visual impairment | 0 | 1 (0.7%) | 4 (3.0%) |

FIG. 28

Ocular Serious TEAEs in Study Eye through Week 52

| | Sham | 2q16 | 2q8 |
|---|---|---|---|
| N (FAS/SAF) | 133 | 135 | 134 |
| # of Patients with ≥ 1 AE, n (%) | 1 (0.8%) | 0 | 1 (0.7%) |
| Visual acuity reduced | 0 | 0 | 1 (0.7%) |
| Vitreous haemorrhage | 0 | 0 | 1 (0.7%) |
| Iris neovascularisation | 1 (0.8%) | 0 | 0 |

FIG. 29

Ocular Inflammation in Study Eye through Week 52

| | Sham | 2q16 | 2q8 |
|---|---|---|---|
| N (FAS/SAF) | 133 | 135 | 134 |
| # of injections | 0 | 749 | 1158 |
| # of Patients with ≥ 1 AE, n (%) | 0 | 1 (0.7%) (0.13% per injection) | 1 (0.7%) (0.09% per injection) |
| Anterior chamber flare | 0 | 0 | 1 (0.7%) |
| Iritis | 0 | 1 (0.7%) | 0 |

FIG. 30

APTC Events through Week 52

| | Sham | 2q16 | 2q8 |
|---|---|---|---|
| N (FAS/SAF) | 133 | 135 | 134 |
| Number of Patients with at Least One Such AE, n (%) | 5 (3.8%) | 4 (3.0%) | 2 (1.5%) |
| Non Fatal Stroke | 2 (1.5%) | 3 (2.2%) | 1 (0.7%) |
| Non Fatal MI | 0 | 1 (0.7%) | 0 |
| Vascular Death | 3 (2.3%) | 0 | 1 (0.7%) |

FIG. 31

USE OF A VEGF RECEPTOR-BASED FUSION PROTEIN ANTAGONIST TO TREAT NONPROLIFERATIVE DIABETIC RETINOPATHY

This application claims the benefit of U.S. provisional patent application Nos. 62/593,033, filed Nov. 30, 2017; 62/644,425, filed Mar. 17, 2018; and 62/748,782, filed Oct. 22, 2018; each of which is herein incorporated by reference in its entirety.

FIELD OF THE INVENTION

The present invention relates to the field of therapeutic treatments of eye disorders. More specifically, the invention relates to the administration of VEGF antagonists to treat eye disorders caused by or associated with angiogenesis.

BACKGROUND

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness. Yet another eye disorder associated with abnormal angiogenesis is central retinal vein occlusion (CRVO). CRVO is caused by obstruction of the central retinal vein that leads to a back-up of blood and fluid in the retina. The retina can also become ischemic, resulting in the growth of new, inappropriate blood vessels that can cause further vision loss and more serious complications. Release of vascular endothelial growth factor (VEGF) contributes to increased vascular permeability in the eye and inappropriate new vessel growth. Thus, inhibiting the angiogenic-promoting properties of VEGF appears to be an effective strategy for treating angiogenic eye disorders.

FDA-approved treatments of angiogenic eye disorders such as AMD and CRVO include the administration of an anti-VEGF antibody called ranibizumab (Lucentis®, Genentech, Inc.) on a monthly basis by intravitreal injection.

Methods for treating eye disorders using VEGF antagonists are mentioned in, e.g., U.S. Pat. Nos. 7,303,746; 7,306,799; 7,300,563; 7,303,748; and US 2007/0190058. Nonetheless, there remains a need in the art for new administration regimens for angiogenic eye disorders, especially those which allow for less frequent dosing while maintaining a high level of efficacy.

BRIEF SUMMARY OF THE INVENTION

The present invention provides methods for treating angiogenic eye disorders (e.g., diabetic retinopathy, e.g., nonproliferative diabetic retinopathy). The methods of the invention comprise sequentially administering multiple doses of a VEGF antagonist to a patient over time. In particular, the methods of the invention comprise sequentially administering to the patient a single initial dose of a VEGF antagonist, followed by one or more secondary doses of the VEGF antagonist, followed by one or more tertiary doses of the VEGF antagonists. The present inventors have surprisingly discovered that beneficial therapeutic effects can be achieved in patients suffering from angiogenic eye disorders by administering a VEGF antagonist to a patient at a frequency of once every 8 or more weeks, especially when such doses are preceded by about three doses administered to the patient at a frequency of about 2 to 4 weeks. Thus, according to the methods of the present invention, each secondary dose of VEGF antagonist is administered 2 to 4 weeks after the immediately preceding dose, and each tertiary dose is administered at least 8 weeks after the immediately preceding dose. An example of a dosing regimen of the present invention is shown in FIG. 1. One advantage of such a dosing regimen is that, for most of the course of treatment (i.e., the tertiary doses), it allows for less frequent dosing (e.g., once every 8 weeks) compared to prior administration regimens for angiogenic eye disorders which require monthly administrations throughout the entire course of treatment. (See, e.g., prescribing information for Lucentis® [ranibizumab], Genentech, Inc.).

The methods of the present invention can be used to treat any angiogenic eye disorder, including, e.g., age related macular degeneration, diabetic retinopathy, diabetic macular edema, central retinal vein occlusion, corneal neovascularization, etc.

The methods of the present invention comprise administering any VEGF antagonist to the patient (e.g., by intravitreal injection). In one embodiment, the VEGF antagonist comprises one or more VEGF receptor-based chimeric molecule(s), (also referred to herein as a "VEGF-Trap" or "VEGFT"). An exemplary VEGF antagonist that can be used in the context of the present invention is a multimeric VEGF-binding protein comprising two or more VEGF receptor-based chimeric molecules referred to herein as "VEGFR1R2-FcΔC1(a)" or "aflibercept."

Various administration routes are contemplated for use in the methods of the present invention, including, e.g., topical administration or intraocular administration (e.g., intravitreal administration).

Aflibercept (EYLEA™, Regeneron Pharmaceuticals, Inc) was approved by the FDA in November 2011, for the treatment of patients with neovascular (wet) age-related macular degeneration, with a recommended dose of 2 mg administered by intravitreal injection every 4 weeks for the first three months, followed by 2 mg administered by intravitreal injection once every 8 weeks.

The present invention provides a method for treating diabetic retinopathy of any severity level, for example, nonproliferative diabetic retinopathy (NPDR) (e.g., moderately severe to severe NPDR, for example, characterized by a Diabetic Retinopathy Severity Scale level of about 47-53, e.g., 47 or 53) in a patient (e.g., a human, for example, 18 years of age or older, e.g., having type 1 or 2 diabetes) in need of such treatment, said method comprising administering (e.g., by intravitreal injection), to an eye of the patient, (i) 3 monthly doses followed by one or more secondary doses every 16 weeks, wherein the first secondary dose initiates 8 weeks after the third monthly dose (week 16) and continues thereafter every 16 weeks (e.g., wherein a dose is given at week 32, 48, 64, etc.) (see e.g., FIG. 2), or (ii) 3 or 4 or 5 monthly doses followed by one or more secondary doses every 8 weeks, wherein the secondary doses initiate 8 weeks after the final of the 3 or 4 or 5 monthly doses and continues with a dose given every 8 weeks thereafter;

of about 2 mg of VEGF antagonist which is, for example, a VEGF receptor-based chimeric molecule, for example, that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2. For example, in an embodiment of the invention, the VEGF antagonist is Aflibercept. In an embodiment of the invention, the VEGF antagonist comprises VEGFR1 R2-FcΔC1(a) encoded by the nucleic acid sequence of SEQ ID NO:1. In an embodiment of the invention, the patient is characterized as not suffering from diabetic macular edema; having a baseline best-corrected visual acuity (BCVA) ETDRS letter score of 69 or greater; having vision characterized by a Snellen visual acuity of 20/40 or better; does not suffer from retinal neovascularization; does not suffer from anterior segment neovascularization (ASNV); does not suffer from vitreous hemorrhage; and/or does not suffer from tractional retinal detachment. In an embodiment of the invention, "treating" NPDR in a patient, as discussed herein, refers to bringing about at least a 2-step improvement in DRSS (Diabetic Retinopathy Severity Scale) from baseline (before the first VEGF antagonist administration), for example, by week 24 or 48 or 52 (relative to commencement of first VEGF antagonist administration).

The present invention provides a method for treating or preventing proliferative diabetic retinopathy (PDR) in a patient (e.g., a human) in need of such treatment or prevention; or for preventing progression of non-proliferative diabetic retinopathy (NPDR) to proliferative diabetic retinopathy, anterior segment neovascularization (ASNV), diabetic macular edema (DME) or center involved diabetic macular edema (CI-DME), wherein the patient is initially treated for non-proliferative diabetic retinopathy (e.g., wherein the patient has type 1 or 2 diabetes; has a hemoglobin A1c of about 8.5; has an ETDRA BCVA score of about 82; has a central retinal thickness of about 247 m; has a diabetic retinopathy severity score of 47 or 53; and/or is about 56 years of age), said method comprising administering, to an eye of the patient (e.g., by intravitreal injection), (i) 3 monthly doses followed by one or more secondary doses every 16 weeks, wherein the first secondary dose initiates 8 weeks after the third monthly dose (week 16), or (ii) 3 or 4 or 5 monthly doses followed by one or more secondary doses every 8 weeks; of about 2 mg of VEGF antagonist, e.g., that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2 (e.g., aflibercept). For example, in an embodiment of the invention, the patient is treated for at least about 24 weeks, 52 weeks or 100 weeks, e.g., wherein the patient receives about 3 to about 5 injections over the 24 week period. In an embodiment of the invention, the patient is treated, e.g., for about 24 or more weeks, and achieves one or more of the following benefits:

(i) at least a 2 step improvement from baseline in diabetic retinopathy severity scale (DRSS) score;

(ii) at least a 3 step improvement from baseline in diabetic retinopathy severity scale (DRSS) score;

(iii) an improvement in best corrected visual acuity of at least about 1.9 letters;

(iv) does not experience a reduction in best corrected visual acuity of any more than 4 letters;

(v) does not develop diabetic macular edema;

(vi) does not develop center involved diabetic macular edema;

(vii) does not experience a vision threatening complication;

(viii) does not develop proliferative diabetic retinopathy;

(ix) does not develop anterior segment neovascularization;

and/or (x) experiences a reduction in central retinal thickness of about 19 m. Thus, the present invention also provides methods for causing a patient with non-proliferative diabetic retinopathy to achieve one or more of the following benefits (i) at least a 2 step improvement from baseline in diabetic retinopathy severity scale (DRSS) score;

(ii) at least a 3 step improvement from baseline in diabetic retinopathy severity scale (DRSS) score;

(iii) an improvement in best corrected visual acuity of at least about 1.9 letters;

(iv) does not experience a reduction in best corrected visual acuity of any more than 4 letters;

(v) does not develop diabetic macular edema;

(vi) does not develop center involved diabetic macular edema;

(vii) does not experience a vision threatening complication;

(viii) does not develop proliferative diabetic retinopathy;

(ix) does not develop anterior segment neovascularization;

and/or (x) experiences a reduction in central retinal thickness of about 19 m; by administering a VEGF antagonist according to the dosing regimen set forth above.

For example, the present invention provides a method for causing a reduction or preventing an increase in the Diabetic Retinopathy Severity Scale (DRSS) level (see e.g., FIG. 18) (e.g., by at least 2 or 3 levels) of nonproliferative diabetic retinopathy in a patient comprising administering, to an eye of the patient (e.g., by intravitreal injection), (i) 3 monthly doses followed by one or more secondary doses every 16 weeks, wherein the first secondary dose initiates 8 weeks after the third monthly dose (week 16), or (ii) 3 or 4 or 5 monthly doses followed by one or more secondary doses every 8 weeks;

of about 2 mg of VEGF antagonist, e.g., that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2 (e.g., aflibercept).

The present invention also provides a method for treating or preventing the occurrence or re-occurrence of a vision threating complication or blindness in the eye of a subject (e.g., a human) whose eye has nonproliferative diabetic retinopathy comprising administering (e.g., by intravitreal injection), to an eye of the subject (e.g., by intravitreal injection), (i) 3 monthly doses followed by one or more secondary doses every 16 weeks, wherein the first secondary dose initiates 8 weeks after the third monthly dose (week 16), or (ii) 3 or 4 or 5 monthly doses followed by one or more secondary doses every 8 weeks; of about 2 mg of VEGF antagonist that is a VEGF receptor-based chimeric molecule. Optionally, the other eye of the subject is also administered the VEGF antagonist even if not so afflicted, afflicted with DRSS of a lower level or afflicted with another angiogenic eye disorder. For example, in an embodiment of the invention, the VEGF antagonist is a VEGF receptor-based chimeric molecule which (i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2; (ii) comprises (1) an immunoglobin-like (Ig) domain 2 of a first VEGF receptor and (2) Ig domain 3 of a second VEGF receptor, and (3) a multimerizing component; (iii) is aflibercept; or (iv) is conbercept.

One aspect of the invention is a package, comprising:
a drug container; and
instructions for using the drug for treating or preventing diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

Another aspect of the invention is a package wherein the instructions indicate the drug is administered by intravitreal injection.

Another aspect of the invention is a package wherein the instructions indicate the drug is administered 3 or 5 monthly doses followed by one or more doses every 8 weeks.

Another aspect of the invention is a package wherein the instructions indicate the drug is administered 3 monthly doses followed by one or more secondary doses every 16 weeks, wherein the first secondary dose initiates 8 weeks after the third monthly dose (week 16).

Another aspect of the invention is a package wherein the instructions indicate the drug is administered one dose every 8 weeks.

An aspect of the invention is a package, comprising: a drug container; and instructions for using the drug for treating or preventing proliferative diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

Other embodiments of the present invention will become apparent from a review of the ensuing detailed description.

BRIEF DESCRIPTION OF THE FIGURES

FIG. 4 summarizes the PANORAMA dosing schedule of the sham, Group 1 and Group 2 groups. X=Active injections; O=sham injections.

FIG. 5 describes the baseline disposition and demographics of the PANORAMA study population in each dosing group including: sham, Group 1, Group 2 and the combination of Group 1 and Group 2 (All IAI). IAI=Intravitreal aflibercept injection.

FIG. 6 describes the baseline disease characteristics of the PANORAMA study population in each dosing group including: sham, Group 1, Group 2 and the combination of Group 1 and Group 2 (All IAI).

FIG. 13 summarizes the study eye ocular treatment emergent adverse events (TEAEs) in the sham and All IAI (combined Group 1 and Group 2) PANORAMA groups through week 24. FAS/SAF=full analysis set/safety analysis set FIG. 14 summarizes the study eye ocular serious treatment emergent adverse events (TEAEs) in the sham and All IAI (combined Group 1 and Group 2) PANORAMA groups through week 24. FAS/SAF=full analysis set/safety analysis set.

FIG. 15 summarizes the study eye intra-ocular inflammation experienced by the sham and All IAI (combined Group 1 and Group 2) PANORAMA groups through week 24.

FIG. 16 summarizes the anti-platelet trialists' collaboration (APTC) events experienced by sham and All IAI (combined Group 1 and Group 2) PANORAMA groups through week 24.

FIG. 17 summarizes the deaths of PANORAMA subjects through week 24.

FIG. 18 is an International Clinical Diabetic Retinopathy Disease Severity Scale (DRSS) Detailed Table.

FIG. 28 summarizes the incidence of ocular treatment-emergent adverse events (TEAEs) experienced by subjects, in the treatment eye, in each treatment group (sham, 2q16 and 2q8) after 52 weeks.

FIG. 29 summarizes the incidence of serious ocular treatment-emergent adverse events (TEAEs) experienced by subjects, in the treatment eye, in each treatment group (sham, 2q16 and 2q8) after 52 weeks.

FIG. 30 summarizes the incidence of ocular inflammation experienced by subjects, in the treatment eye, in each treatment group (sham, 2q16 and 2q8) after 52 weeks. 1 additional event of vitreal cells was included in the IOI table, but it was determined not to be an IOI event.

FIG. 31 summarizes the incidence of anti-platelet trialists' collaboration (APTC) events experienced by subjects, in the treatment eye, in each treatment group (sham, 2q16 and 2q8) after 52 weeks.

DETAILED DESCRIPTION

Figure 1:
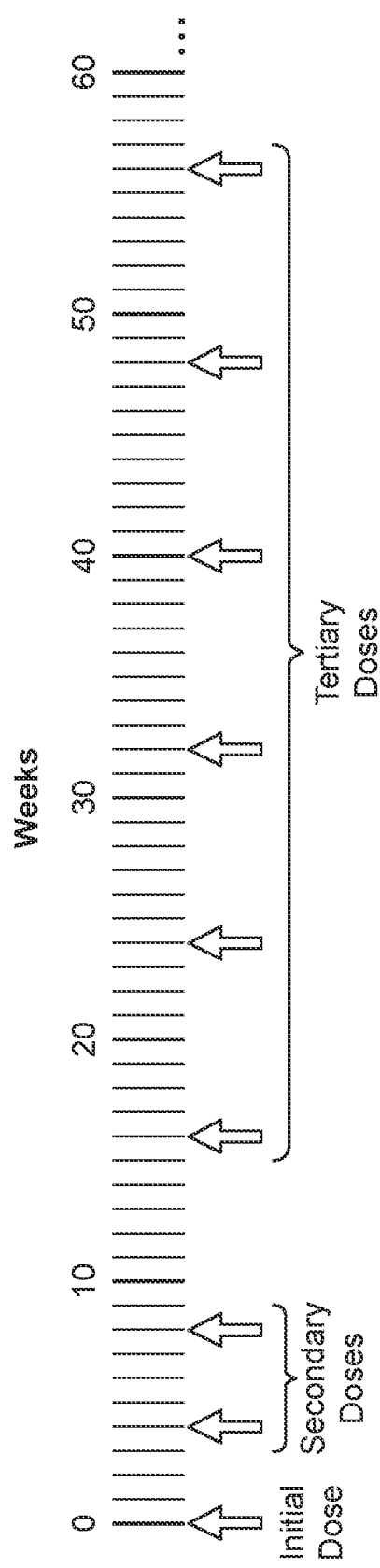
FIG. 1 shows an exemplary dosing regimen of the present invention. In this regimen, a single "initial dose" of VEGF antagonist ("VEGFT") is administered at the beginning of the treatment regimen (i.e. at "week 0"), two "secondary doses" are administered at weeks 4 and 8, respectively, and at least six "tertiary doses" are administered once every 8 weeks thereafter, i.e., at weeks 16, 24, 32, 40, 48, 56, etc.). This VEGF antagonist dosage regimen forms part of the present invention.

The present invention includes an exceptionally effective method for preventing the progression of non-proliferative diabetic retinopathy without diabetic macular edema in a patient to more advanced and vision threatening disorders such as proliferative diabetic retinopathy, diabetic macular edema and/or anterior segment neovascularization of the eye. Indeed, moderately severe to severe non-proliferative diabetic retinopathy patients on the aflibercept dosing regimens of the present invention experienced a reversal of disease progression achieving a two or more step improvement in DRSS level. The eyes of subjects on the dosing regimens of the present invention also experienced a reduction in the occurrence of vision threatening complications relative to untreated eyes. This prevention can be achieved by administration of a VEGF antagonist, such as aflibercept, to the eye of a patient using the dosing regimens set forth herein.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

A subject or a patient can be a mammal, for example a human (e.g., a human 50, 55, 60, 65 or 70 years of age or older), rabbit, mouse, non-human primate, monkey or rat. In an embodiment of the invention, the subject or patient previously received a different treatment for DR, e.g., PDR (e.g., panretinal photocoagulation (laser) therapy). In an embodiment of the invention, the previous treatment failed to sufficiently treat the DR. In an embodiment of the invention, the patient or subject does not suffer from DME and/or CI-DME. In an embodiment of the invention, the subject or patient has diabetes (e.g., type 1 or type 2).

Dosing Regimens

The present invention provides methods for treating angiogenic eye disorders such as diabetic retinopathy of any severity level, for example, proliferative or nonproliferative diabetic retinopathy (NPDR), e.g., moderately severe NPDR or severe NPDR. The methods of the invention comprise sequentially administering to the eye of a subject or patient (e.g., a human such as a human 18 years of age or older) multiple doses of a VEGF antagonist (e.g., aflibercept). In an embodiment of the invention, the patient has diabetes (e.g., type 1 or type 2). As used herein, "sequentially administering" means that each dose of VEGF antagonist is administered to the eye of a patient at a different point in time, e.g., on different days separated by a predetermined interval (e.g., hours, days, weeks or months). The present invention includes methods which comprise sequentially administering to the eye of a patient a single initial dose of a VEGF antagonist, followed by one or more secondary doses of the VEGF antagonist, followed by one or more tertiary doses of the VEGF antagonist.

The present invention provides methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, comprising administering, to the eye of the subject, three or four or five initial monthly doses of VEGF antagonist (e.g., aflibercept) followed by one or more secondary doses every eight weeks. In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye. The present invention, thus, provides methods including administering a 0.5 or 2 mg dose of VEGF antagonist (e.g., by intravitreal injection) to an eye of a subject (e.g., a human) as 3 or 4 or 5 monthly doses followed by a dose every 8 weeks counted from the last of the initial 3 or 4 or 5 monthly doses. In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye. In one exemplary embodiment of the present invention, a single initial dose of a VEGF antagonist (e.g., 2 mg) is administered to a patient's eye (e.g., by intravitreal injection) on the first day of the treatment regimen (i.e., at week 0), followed by two secondary doses, each administered four weeks after the immediately preceding dose (i.e., at week 4 and at week 8), followed by at least 5 tertiary doses, each administered eight weeks after the immediately preceding dose (i.e., at weeks 16, 24, 32, 40 and 48). The tertiary doses may continue (at intervals of 8 or more weeks) indefinitely during the course of the treatment regimen. This exemplary administration regimen is depicted graphically in FIG. 1.

Figure 2:
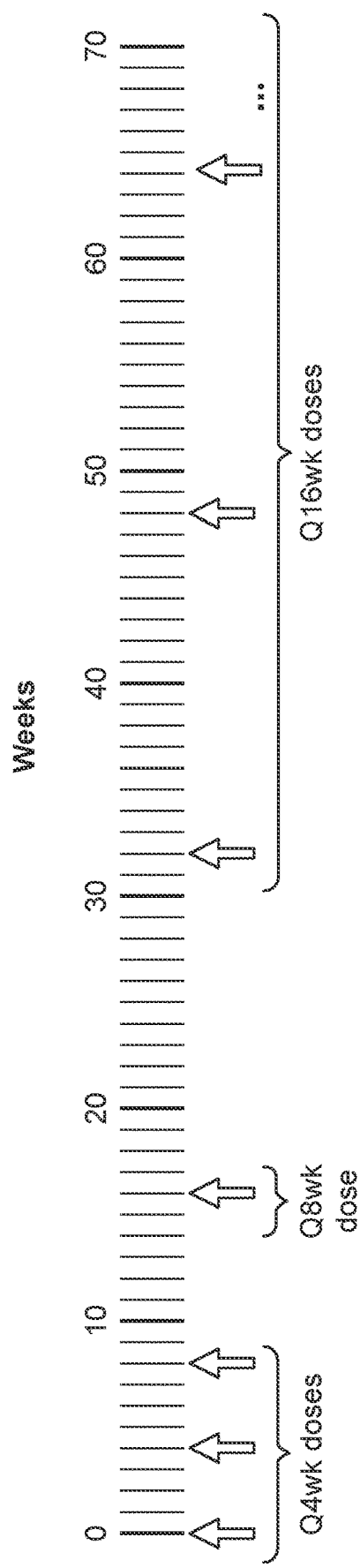
FIG. 2 shows a second exemplary dosing regimen of the present invention. In this regimen, three monthly doses ("Q4wk doses") of a VEGF antagonist are administered at the beginning of the treatment regimen (i.e., at weeks 0, 4 and 8), a single dose is then administered 8 weeks after the last Q4wk dose ("Q8wk dose") (i.e., at week 16), followed by three or more additional doses administered 16 weeks after the Q8wk dose and once every 16 weeks thereafter ("Q16wk doses") (i.e., at weeks 32, 48, 64, etc.). This VEGF antagonist dosage regimen forms part of the present invention.

The present invention also includes methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, the methods comprising administering (e.g., by intravitreal injection) to an eye of the subject:

(A) three initial monthly doses (e.g., once every 4 weeks or "Q4wk") of a VEGF antagonist (e.g., 2 mgs); followed by (B) administering to the eye of the subject a single dose (e.g., 2 mg) of the VEGF antagonist 8 weeks after the immediately preceding dose ("Q8wk"); followed by (C) administering to the eye of the subject one or more further (maintenance) doses (e.g., 2 mg) of the VEGF antagonist (e.g., aflibercept) 16 weeks after the immediately preceding dose and once every 16 weeks ("Q16wk") thereafter (at weeks 32, 48 and 64, etc., counted from the first of the initial monthly doses). See, for example, FIG. 2. A method of the present invention comprises administering a VEGF antagonist as (i) 3 monthly doses followed by one or more secondary doses every 16 weeks, wherein the first secondary dose initiates 8 weeks after the third monthly dose (week 16). In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye.

In one exemplary embodiment of the present invention, following an initial primary dose, each secondary dose is administered 2 to 4 (e.g., 2, 2½, 3, 3½, or 4) weeks after the immediately preceding dose, and each tertiary dose is administered at least 8 (e.g., 8, 8½, 9, 9½, 10, 10½, 11, 11½, 12, 12½, 13, 13½, 14, 14½, or more) weeks after the immediately preceding dose. Alternatively, following the secondary doses, the VEGF antagonist is administered on an as needed/pro re nata (PRN) basis, based on visual and/or anatomical outcomes as assessed by a physician or other qualified medical professional.

The present invention also includes methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, the methods comprising administering (e.g., by intravitreal injection) to an eye of the subject:

(A) three initial monthly doses (e.g., once every 4 weeks or "Q4wk") of a VEGF antagonist (e.g., aflibercept or conbercept, e.g., 0.5 mg or 2.0 mg); followed by (B)
administering the VEGF antagonist to the eye of the subject one or more doses of the VEGF antagonist 3 months after the immediately preceding dose (or every 12 weeks or quarterly); or
administering the VEGF antagonist to the eye of the subject on an as needed/pro re nata (PRN) basis, based on visual and/or anatomical outcomes as assessed by a physician or other qualified medical professional.

The terms "initial dose," "secondary doses," and "tertiary doses," refer to the temporal sequence of administration of the VEGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of VEGF antagonist, but will generally differ from one another in terms of frequency of administration. In certain embodiments, however, the amount of VEGF antagonist contained in the initial, secondary and/or tertiary doses will vary from one another (e.g., adjusted up or down as appropriate) during the course of treatment.

The phrase "the immediately preceding dose," as used herein, means, in a sequence of multiple administrations, the dose of VEGF antagonist which is administered to the eye of a patient prior to the administration of the very next dose in the sequence with no intervening doses.

In an embodiment of the invention, the VEGF antagonist dosing regimen is conducted over the course of 24, 48, 52, 96 or 100 weeks (or more).

In an embodiment of the invention, patients (e.g., suffering from NPDR) receiving such a dosing regimen exhibit at least a 2-step improvement in DRSS (Diabetic Retinopathy Severity Scale) from baseline (before treatment commences) at week 24 or 48 or 52 in the eye. In an embodiment of the invention, a 3-step improvement is experienced in the eye.

The methods of the invention may comprise administering to the eye of a patient any number of secondary and/or tertiary doses of a VEGF antagonist. For example, in certain embodiments, only a single secondary dose is administered to the patient's eye. In other embodiments, two or more (e.g., 2, 3, 4, 5, 6, 7, 8, or more) secondary doses are administered to the patient's eye. Likewise, in certain embodiments, only a single tertiary dose is administered to the patient's eye. In other embodiments, two or more (e.g., 2, 3, 4, 5, 6, 7, 8, or more) tertiary doses are administered to the patient's eye.

In embodiments involving multiple secondary doses, each secondary dose may be administered at the same frequency as the other secondary doses. For example, each secondary dose may be administered to the patient's eye 4 weeks after the immediately preceding dose. Similarly, in embodiments involving multiple tertiary doses, each tertiary dose may be administered at the same frequency as the other tertiary doses. For example, each tertiary dose may be administered to the patient's eye 8 weeks after the immediately preceding dose. Alternatively, the frequency at which the secondary and/or tertiary doses are administered to a patient's eye can vary over the course of the treatment regimen. For example, the present invention includes methods which comprise administering to the patient's eye a single initial dose of a VEGF antagonist, followed by one or more secondary doses of the VEGF antagonist, followed by at least 5 tertiary doses of the VEGF antagonist, wherein the first four tertiary doses are administered 8 weeks after the immediately preceding dose, and wherein each subsequent tertiary dose is administered from 8 to 12 (e.g., 8, 8½, 9, 9½, 10, 10½, 11, 11½, 12) weeks after the immediately preceding dose. The frequency of administration may also be adjusted during the course of treatment by a physician depending on the needs of the individual patient following clinical examination.

In an embodiment of the invention, a VEGF antagonist is administered to a subject according to a dosing regimen of the present invention in association with a further therapeutic agent (e.g., a vitamin or dietary supplement) or therapeutic procedure (e.g. laser therapy or surgery). For example, in an embodiment or the invention, the subject receives laser therapy, such as pan-retinal photocoagulation (laser) therapy, in association with the VEGF antagonist. In an embodiment of the invention, the subject received the laser therapy previously, for example to treat DR (e.g., PDR), but switched to a VEGF antagonist dosing regimen according to the present invention.

The term "in association with" indicates that the components, a VEGF antagonist along with a further therapeutic agent can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route.

VEGF Antagonists

The methods of the present invention comprise administering to a patient's eye a VEGF antagonist according to specified dosing regimens set forth herein. As used herein, the expression "VEGF antagonist" means any molecule that blocks, reduces or interferes with the normal biological activity of VEGF.

VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies and antigen-binding fragments thereof (e.g., Fab or F(ab)$_2$), anti-VEGF receptor antibodies and antigen-binding fragments thereof, anti-VEGF and anti-VEGF receptor single chain antibodies, anti-VEGF and anti-VEGF receptor bispecific antibodies and antigen-binding fragments thereof, anti-VEGF and anti-VEGF receptor DARPins (designed ankyrin repeat proteins) and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1 R2-FcΔC1(a) which is encoded by the nucleic acid sequence of SEQ ID NO:1. VEGFR1 R2-FcΔC1(a) comprises three components: (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acid of SEQ ID NO:2 [i.e., K458] which may or may not be included in the VEGF antagonist used in the methods of the invention; see e.g., U.S. Pat. No. 7,396,664). Amino acids 1-26 of SEQ ID NO: 2 are the signal sequence.

The VEGF antagonist used in the Examples set forth herein below is a molecule comprising the VEGFR1 R2-FcΔC1(a) molecule (e.g., a homodimer thereof) and is referred to herein as "VEGFT." Additional VEGF receptor-based chimeric molecules which can be used in the context of the present invention are disclosed in U.S. Pat. Nos. 7,396,664, 7,303,746 and WO 00/75319.

In an embodiment of the invention, the VEGF antagonist is a VEGF receptor based chimeric molecule that is a polypeptide (or a homodimer thereof) that comprises:
(1) an immunoglobin-like (Ig) domain 2 of a first VEGF receptor (e.g., VEGFR1);
(2) Ig domain 3 of a second VEGF receptor (e.g., VEGFR2); and
(3) a multimerizing component (e.g., an Fc or variant thereof).

In an embodiment of the invention, the VEGF antagonist is a VEGF receptor based chimeric molecule that is a polypeptide (or homodimer thereof) that comprises:
(1) an immunoglobin-like (Ig) domain 2 of a first VEGF receptor (e.g., VEGFR1);
(2) Ig domain 3 of a second VEGF receptor (e.g., VEGFR2);
(3) an immunoglobulin-like (Ig) domain 4 of the second VEGF receptor (e.g., VEGFR2); and
(4) a multimerizing component (e.g., an Fc or variant thereof).

Exemplary VEGF antagonists that can be used in the context of the present invention include, e.g., VEGF mini-Trap (see e.g., U.S. Pat. No. 7,087,411), aflibercept, an anti-VEGF DARPin such as the Abicipar Pegol DARPin), a single chain (e.g., VL-VH) anti-VEGF antibody such as brolucizumab (RTH258), a monospecific, multispecific or bispecific anti-VEGF antibody or antigen-binding fragment thereof, e.g., which also binds to ANG2, such as RG7716, ranibizumab (LUCENTIS), or bevacizumab (AVASTIN), and conbercept.

Angiogenic Eye Disorders

The methods of the present invention can be used to treat or prevent any angiogenic eye disorder by administering to the eye of the subject, a therapeutically effective amount of VEGF antagonist (e.g., 2 mg aflibercept) according to a dosing regimen which is set forth herein. The expression "angiogenic eye disorder," as used herein, means any disease of the eye which is caused by or associated with the growth or proliferation of blood vessels or by blood vessel leakage. Non-limiting examples of angiogenic eye disorders that are treatable using the methods of the present invention include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy and diabetic retinopathies such as nonproliferative diabetic retinopathy and proliferative diabetic retinopathy.

Diabetic retinopathy is a progressive condition that can occur in people who have diabetes. Typically, it causes progressive damage to the retina, the light-sensitive lining at the back of the eye. Diabetic retinopathy is a serious sight-threatening complication of diabetes. Over time, diabetes damages the blood vessels in the retina and diabetic retinopathy occurs when these tiny blood vessels leak blood and other fluids. The condition typically affects both eyes. The longer a person has diabetes, the more likely they will develop diabetic retinopathy. If left untreated, diabetic retinopathy can cause blindness.

Symptoms of diabetic retinopathy may include:
Seeing spots or floaters
Blurred vision
Having a dark or empty spot in the center of your vision
Difficulty seeing well at night Thus, in order to preserve vision, it is critical to halt or impede progression of diabetic retinopathy to its more sight-threatening later stages, e.g., proliferative diabetic retinopathy, diabetic macular edema and/or anterior segment neovascularization (ASNV). Klein et al., Changes in Retinal Vessel Diameter and Incidence and Progression of Diabetic Retinopathy, Arch. Opthamol. 130(6): 749-755 (2012).

Anterior segment neovascularization is neovascularization of the iris, and/or definitive neovascularization of the iridocorneal angle.

As diabetic retinopathy progresses, it reaches more advanced stages including:
1. Mild nonproliferative retinopathy. This stage is characterized by small areas of balloon-like swelling in the retina's tiny blood vessels, called microaneurysms. These microaneurysms may leak fluid into the retina; then
2. Moderate nonproliferative retinopathy. As the disease progresses, blood vessels that nourish the retina may swell and distort. They may also lose their ability to transport blood. Both conditions cause characteristic changes to the appearance of the retina and may contribute to diabetic macular edema; then
3. Severe nonproliferative retinopathy. In this stage, many more blood vessels are blocked, depriving blood supply to areas of the retina. These areas secrete growth factors that signal the retina to grow new blood vessels; and then
4. Proliferative diabetic retinopathy (PDR). See below.

Nonproliferative diabetic retinopathy (NPDR) is an early retinopathy in diabetic patients which is not characterized by neovascularization and whose stage may also be graded according to the Diabetic Retinopathy Severity Scale (DRSS). Grades of NPDR include, for example, early, moderate, moderately severe and severe. In an embodiment of the invention, moderately severe to severe NPDR is accorded a severity level of 47 to 53 (e.g., 47 or 53). In an embodiment of the invention, a moderately severe to severe NPDR patient (e.g., a human, for example 18 years of age or older with type 1 or type 2 diabetes) is characterized with one or more of the following:
without macular edema (e.g., threatening the center of the macula);
can safely defer panretinal photocoagulation for at least 6 months;
has a baseline best-corrected visual acuity (BCVA) ETDRS letter score of 69 or greater (e.g., Snellen visual acuity of 20/40 or better);
without retinal neovascularization;
without anterior segment neovascularization (ASNV);
without vitreous hemorrhage; and/or
without tractional retinal detachment.

Proliferative diabetic retinopathy (PDR) is the more advanced form of diabetic retinopathy. At this stage, new fragile blood vessels can begin to grow in the retina and into the vitreous, the gel-like fluid that fills the back of the eye. The new blood vessel may leak blood into the vitreous, clouding vision.

Thus, the present invention includes methods for treating or preventing diabetic retinopathy in a subject's eye, whether the subject's eye has moderately severe NPDR (nonproliferative diabetic retinopathy) or severe NPDR (e.g., moderately severe to severe NPDR) or PDR (proliferative diabetic retinopathy), e.g., where the DRSS for the subjects diabetic retinopathy is 47 or 53, by administering a VEGF antagonist (e.g., 2 mg of aflibercept) to the subject's eye under a dosing regimen set forth herein. In an embodiment of the invention, the subject does not suffer from diabetic macular edema (DME) and/or center-involved diabetic macular edema (CI-DME). In a patient with a nonproliferative diabetic retinopathy, the dosing regimens set forth herein may be used to prevent the progression of the patient to a more severe form of NPDR or to a proliferative diabetic retinopathy, ASNV, DME and/or CI-DME. Indeed, the dosing regimens of the present invention may be used to reverse an increase in (or prevent an increase in) DRSS in a patient suffering from NPDR (e.g., who does not suffer from DME and/or CI-DME) by as much as, for example, 2 levels or more, e.g., 3 levels.

The International Clinical Diabetic Retinopathy Disease Severity Scale (DRSS), including levels thereof, is detailed in a table set forth in FIG. 18.

Subjects suffering from NPDR are at risk of suffering from various vision threatening complications or events (VTCs) and blindness (e.g., blindness secondary to such a VTC). Vision threatening complications are defined as composite outcome of PDR (inclusive of patients who have vitreous hemorrhage or tractional retinal detachment believed to be due to PDR) and ASNV. ASNV is defined as neovascularization of the iris (at least 2 cumulative clock hours), and/or definitive neovascularization of the iridocorneal angle. The dosing regimens reduce incidence of such VTCs and/or blindness in subjects suffering from NPDR. Thus, the present invention provides methods for preventing the occurrence or re-occurrence (following one or more initial occurrences) of a VTC and/or blindness in a subject who, for example, suffers from NPDR or PDR by administering, to the subject's eye, a VEGF antagonist (aflibercept, e.g., 2.0 mg) under a dosing regimen set forth herein. Such methods may include not only the step of treating one eye suffering a VTC, but also treating the other eye even if no VTC and/or blindness has occurred in the other eye so as to prevent a VTC and/or blindness.

Pharmaceutical Formulations

The present invention includes methods in which the VEGF antagonist that is administered to the patient's eye is contained within a pharmaceutical formulation. The pharmaceutical formulation may comprise the VEGF antagonist along with at least one inactive ingredient such as, e.g., a pharmaceutically acceptable carrier. Other agents may be incorporated into the pharmaceutical composition to provide improved transfer, delivery, tolerance, and the like. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the antibody is administered. A multitude of appropriate formulations can be found in the formulary known to all pharmaceutical chemists: Remington's Pharmaceutical Sciences (15$^{th}$ ed, Mack Publishing Company, Easton, Pa., 1975), particularly Chapter 87 by Blaug, Seymour, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in the context of the methods of the present invention, provided that the VEGF antagonist is not inactivated by the formulation and the formulation is physiologically compatible and tolerable with the route of administration. See also Powell et al. PDA (1998) J Pharm Sci Technol. 52:238-311 and the citations therein for additional information related to excipients and carriers well known to pharmaceutical chemists.

Pharmaceutical formulations useful for administration by injection in the context of the present invention may be prepared by dissolving, suspending or emulsifying a VEGF antagonist in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there may be employed, e.g., sesame oil, soybean oil, etc., which may be used in combination with a solubilizing agent such as benzyl benzoate, benzyl alcohol, etc. The injection thus prepared can be filled in an appropriate ampoule if desired.

In an embodiment of the invention, the pharmaceutical formulation administered to a subject comprises aflibercept, e.g., about 40 mg/mL aflibercept, in 10 mM sodium phosphate, 40 mM sodium chloride, 0.03% polysorbate 20, and 5% sucrose, pH 6.2.

In an embodiment of the invention, the pharmaceutical formulation administered to a subject comprises a VEGF antagonist (e.g., aflibercept or conbercept, for example, 40 mg/ml thereof) and:

(a) pyrophosphate (e.g., 5 mM-250 mM). In an embodiment of the invention, the formulation further includes NaCl, sodium citrate, citric acid, mannitol and polysorbate 80, e.g., pH 5.2;

(b) a buffer such as a histidine salt such as histidine-HCl or histidine-acetate (e.g., at 10 mM to 50 mM), e.g., pH 5.7 to 6.2; a sugar such as sucrose, trehalose, mannitol, or glucose (e.g., more than 6%, but not more than 10%, for example, 2.5% to 10%); and a surfactant such as polysorbate 20 and polysorbate 80 (e.g., 0% or 0.01% to 0.03%);

(c) a histidine containing buffer such as L-histidine/ histidine hydrochloride; a non-ionic surfactant such as polysorbate 20 (e.g., 0.03%), an inorganic salt such as NaCl (e.g., 40 mM), and a carbohydrate such as sucrose (e.g., 5%), e.g. pH 6.0-6.5 (e.g., 6.2 or 6.5);

(d) a buffer consisting of a histidine salt (e.g., wherein the histidine salt is histidine-HCl or histidine-acetate, for example, 10 mM to 50 mM) and having pH ranging from 5.7 to 6.2; a sugar selected from the group consisting of sucrose, trehalose, mannitol, and glucose (e.g., more than 6%, but not more than 10%); a surfactant selected from the group consisting of polysorbate 20 and polysorbate 80 (e.g., 0% to 0.1%);

(e) citric acid (e.g., 5 mM, 10 mM, 15 mM, 20 mM, 25 mM or 30 mM), sucrose (e.g., 1%, 2%, 3%, 4%, 5%, 6%, 7%, 8%, 9% or 10%), arginine (e.g., 5 mM, 10 mM, 15 mM, 20 mM, 25 mM, 30 mM, 35 mM, 40 mM, 45 mM or 50 mM or 100 mM), and polysorbate 20 (e.g., 0.01%, 0.02%, 0.03%, 0.04%, 0.05%, 0.06%, 0.07%, 0.08%, 0.09% or 0.10%);

(f) a buffer such as phosphate, histidine, acetate, succinate, citrate, glutamate, and/or lactate (e.g., at 5-20 or 5-50 mM); a non-ionic surfactant such as a polysorbate (e.g., PS20 or PS80), a polyethylene glycol dodecyl ether, a poloxamer, 4-(1,1,3,3-Tetramethylbutyl)phenyl-polyethylene glycol, an alkylsaccharide or an alkylglycoside, a tonicifying agent such as a polyol or an amino acid, for example, sucrose, trehalose, sorbitol, mannitol, glycerol, proline, arginine, methionine, glycine, or lysine, wherein the formulation has a final osmolality of about 300 mOsm/kg, and wherein the concentration of chloride anion is less than about 10 mM; pH 5.0-6.5;

(g) sodium acetate (e.g., 10-15 mM); sucrose (e.g., 7%) or trehalose (e.g., 8%); and polysorbate 20 (e.g., 0.03%), pH 5.5; or (h) any of: 10 mM sodium phosphate, 40 mM sodium chloride, 5% (w/v) sucrose, 0.03% (w/v) polysorbate 20, pH6.2; 10 mM sodium phosphate, 9% (w/v) sucrose, 0.03% (w/v) polysorbate 20, pH 6.2; 10 mM sodium phosphate, 40 mM sodium chloride, 2% (w/v) proline, 0.03% (w/v) polysorbate 20, pH6.2; 10 mM sodium phosphate, 3% (w/v) proline, 0.03% (w/v) polysorbate 20, pH 6.2; 10 mM sodium phosphate, 9% (w/v) Trehalose, 0.03% (w/v) polysorbate 20, pH 6.2; 10 mM histidine, 3% (w/v) proline, 0.03% (w/v) polysorbate 20, pH 6.2; 10 mM histidine, 9% (w/v) sucrose, 0.03% (w/v) polysorbate 20, pH 6.2; or 10 mM acetate, 9% (w/v) sucrose, 0.03% (w/v) polysorbate 20, pH 5.2.

Modes of Administration

The VEGF antagonist (or pharmaceutical formulation comprising the VEGF antagonist) may be administered to the patient by any known delivery system and/or administration method. In certain embodiments, the VEGF antagonist is administered to the patient by ocular, intraocular, intravitreal or subconjunctival injection. In other embodiments, the VEGF antagonist can be administered to the patient by topical administration, e.g., via eye drops or other liquid, gel, ointment or fluid which contains the VEGF antagonist and can be applied directly to the eye. Administration to a patient's or subject's eye refers to any acceptable method for delivering a VEGF antagonist (e.g., aflibercept) to the tissues of the eye of the patient or subject (e.g., intravitreal injection). In an embodiment of the invention, administration to the subject's or patient's eye refers to delivering a VEGF antagonist to an eye suffering an angiogenic eye disorder (e.g., as discussed herein), such as NPDR, and, optionally, to delivery to the other eye even if not so afflicted. In an embodiment of the invention, the administration is intravitreal injection using a syringe with a 30-gauge, ½-inch injection needle. For example, in an embodiment of the invention, about 50 µl is intravitreally injected to deliver about 2 mg of VEGF antagonist (e.g., aflibercept; for example, in a pharmaceutical formulation including aflibercept, e.g., about 40 mg/mL aflibercept, in 10 mM sodium phosphate, 40 mM sodium chloride, 0.03% polysorbate 20, and 5% sucrose, pH 6.2). In an embodiment of the invention, 0.5 or 2.0 mg of conbercept in a pharmaceutical formulation comprising conbercept, citric acid, sucrose, arginine and polysorbate 20 is injected into the eye.

Other possible routes of administration include, e.g., intradermal, intramuscular, intraperitoneal, intravenous, subcutaneous, intranasal, epidural, and oral. If such a route of administration is used, delivery is not to the eye, but to another tissue such as the skin, muscular tissue, peritoneum, vein, subcutis, nasal passage, dura or mouth.

Amount of VEGF Antagonist Administered

Each dose of VEGF antagonist (e.g., 0.5 mg or 2 mg, for example of aflibercept) administered to the patient's eye over the course of the treatment regimen may contain the same, or substantially the same, amount of VEGF antagonist. Alternatively, the quantity of VEGF antagonist contained within the individual doses may vary over the course of the treatment regimen. For example, in certain embodiments, a first quantity of VEGF antagonist is administered in the initial dose, a second quantity of VEGF antagonist is administered in the secondary doses, and a third quantity of VEGF antagonist is administered in the tertiary doses. The present invention contemplates dosing schemes in which the quantity of VEGF antagonist contained within the individual doses increases over time (e.g., each subsequent dose contains more VEGF antagonist than the last), decreases over time (e.g., each subsequent dose contains less VEGF antagonist than the last), initially increases then decreases, initially decreases then increases, or remains the same throughout the course of the administration regimen.

The amount of VEGF antagonist administered to the patient's eye in each dose (e.g., 0.5 mg or 2 mg, for example of aflibercept or conbercept) is, in most cases, a therapeutically effective amount. As used herein, the phrase "therapeutically effective amount" means a dose of VEGF antagonist that results in a detectable improvement in one or more symptoms or indicia of an angiogenic eye disorder, or a dose of VEGF antagonist that inhibits, prevents, lessens, or delays the progression of an angiogenic eye disorder. In the case of an anti-VEGF antibody or a VEGF receptor-based chimeric molecule such as VEGFR1 R2-FcΔC1(a), a therapeutically effective amount can be from about 0.05 mg to about 5 mg, e.g., about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 3.0 mg, about 3.5 mg, about 4.0 mg, about 4.5 mg, or about 5.0 mg of the antibody or receptor-based chimeric molecule.

The amount of VEGF antagonist contained within the individual doses may be expressed in terms of milligrams of antibody per kilogram of patient body weight (i.e., mg/kg). For example, the VEGF antagonist may be administered to a patient at a dose of about 0.0001 to about 10 mg/kg of patient body weight.

Treatment Population and Efficacy

The methods of the present invention are useful for treating angiogenic eye disorders in patients that have been diagnosed with or are at risk of being afflicted with an angiogenic eye disorder. Generally, the methods of the present invention demonstrate efficacy within 104 weeks of the initiation of the treatment regimen (with the initial dose administered at "week 0"), e.g., by the end of week 16, by the end of week 24, by the end of week 32, by the end of week 40, by the end of week 48, by the end of week 52, by the end of week 56, etc.

In an embodiment of the invention, in the context of methods for treating angiogenic eye disorders such as DR, PDR, NPDR, AMD, CRVO, and DME, "efficacy" means that, from the initiation of treatment, the patient exhibits:

a loss of 15 or fewer (e.g., 14, 13, 12, 11, 10, 9, 8, 7, 6, 5, 4, 3, 2 or 1) letters on the Early Treatment Diabetic Retinopathy Study (ETDRS) visual acuity chart;

a gain of one or more (e.g., 1, 2, 3, 4, 5, 6, 7, 8, 9, 10, 11 or more) letters on the ETDRS chart;

maintenance of or an improvement in DRSS score, e.g., reduction in DRSS by 2 or 3 steps;

a reduction in the incidence or the prevention of vision threatening complications (VTC) and/or blindness and/or center involved diabetic macular edema; and/or a reduction in or maintenance of central retinal thickness; for example, wherein one or more of such goals are achieved within about 24 or 52 weeks of treatment initiation.

Packages

One aspect of the invention is a package, comprising:
a drug container; and
instructions for using the drug for treating or preventing diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

Another aspect of the invention is a package wherein the instructions indicate the drug is administered by intravitreal injection.

Another aspect of the invention is a package wherein the instructions indicate the drug is administered 3 or 5 monthly doses followed by one or more doses every 8 weeks.

Another aspect of the invention is a package wherein the instructions indicate the drug is administered 3 monthly doses followed by one or more secondary doses every 16 weeks, wherein the first secondary dose initiates 8 weeks after the third monthly dose (week 16).

Another aspect of the invention is a package wherein the instructions indicate the drug is administered one dose every 8 weeks.

An aspect of the invention is a package, comprising:
a drug container; and
instructions for using the drug for treating or preventing proliferative diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary VEGF antagonist used in all Examples set forth below is (unless otherwise indicated) a dimeric molecule having two functional VEGF binding units. Each functional binding unit is comprised of Ig domain 2 from VEGFR1 fused to Ig domain 3 from VEGFR2, which in turn is fused to the hinge region of a human IgG1 Fc domain (VEGFR1 R2-FcΔC1(a); encoded by SEQ ID NO:1). This VEGF antagonist is referred to in the examples below as "VEGFT". For purposes of the following Examples, "monthly" dosing is equivalent to dosing once every four weeks.

Example 1: Phase I Clinical Trial of Intravitreally Administered VEGF Receptor-Based Chimeric Molecule (VEGFT) in Subjects with Neovascular AMD In this Phase I study, 21 subjects with neovascular AMD received a single intravitreal (IVT) dose of VEGFT. Five groups of three subjects each received either 0.05, 0.15, 0.5, 2 or 4 mg of VEGFT, and a sixth group of six subjects received 1 mg. No serious adverse events related to the study drug, and no identifiable intraocular inflammation was reported. Preliminary results showed that, following injection of VEGFT, a rapid decrease in foveal thickness and macular volume was observed that was maintained through 6 weeks. At Day 43 across all dose groups, mean excess retinal thickness [excess retinal thickness=(retinal thickness−179µ)] on optical coherence tomography (OCT) was reduced from 119µ to 27µ as assessed by Fast Macular Scan and from 194µ to 60µ as assessed using a single Posterior Pole scan. The mean increase in best corrected visual acuity (BCVA) was 4.75 letters, and BCVA was stable or improved in 95% of subjects. In the 2 highest dose groups (2 and 4 mg), the mean increase in BCVA was 13.5 letters, with 3 of 6 subjects demonstrating improvement of ≥3 lines.

Example 2: Phase II Clinical Trial of Repeated Doses of Intravitreally Administered VEGF Receptor-Based Chimeric Molecule (VEGFT) in Subjects with Neovascular AMD This study was a double-masked, randomized study of 3 doses (0.5, 2, and 4 mg) of VEGFT tested at 4-week and/or 12-week dosing intervals. There were 5 treatment arms in this study, as follows: 1) 0.5 mg every 4 weeks, 2) 0.5 mg every 12 weeks, 3) 2 mg every 4 weeks, 4) 2 mg every 12 weeks and 5) 4 mg every 12 weeks. Subjects were dosed at a fixed interval for the first 12 weeks, after which they were evaluated every 4 weeks for 9 months, during which additional doses were administered based on pre-specified criteria. All subjects were then followed for one year after their last dose of VEGFT. Preliminary data from a pre-planned interim analysis indicated that VEGFT met its primary endpoint of a statistically significant reduction in retinal thickness after 12 weeks compared with baseline (all groups combined, decrease of 135µ, p<0.0001). Mean change from baseline in visual acuity, a key secondary endpoint of the study, also demonstrated statistically significant improvement (all groups combined, increase of 5.9 letters, p<0.0001). Moreover, patients in the dose groups that received only a single dose, on average, demonstrated a decrease in excess retinal thickness (p<0.0001) and an increase in visual acuity (p=0.012) at 12 weeks. There were no drug-related serious adverse events, and treatment with the VEGF antagonists was generally well-tolerated. The most common adverse events were those typically associated with intravitreal injections.

Example 3: Phase I Clinical Trial of Systemically Administered VEGF Receptor-Based Chimeric Molecule (VEGFT) in Subjects with Neovascular AMD This study was a placebo-controlled, sequential-group, dose-escalating safety, tolerability and bioeffect study of VEGFT by IV infusion in subjects with neovascular AMD. Groups of 8 subjects meeting eligibility criteria for subfoveal choroidal neovascularization (CNV) related to AMD were assigned to receive 4 IV injections of VEGFT or placebo at dose levels of 0.3, 1, or 3 mg/kg over an 8-week period.

Most adverse events that were attributed to VEGFT were mild to moderate in severity, but 2 of 5 subjects treated with 3 mg/kg experienced dose-limiting toxicity (DLT) (one with Grade 4 hypertension and one with Grade 2 proteinuria); therefore, all subjects in the 3 mg/kg dose group did not enter the study. The mean percent changes in excess retinal thickness were: −12%, −10%, −66%, and −60% for the placebo, 0.3, 1, and 3 mg/kg dose groups at day 15 (ANOVA p<0.02), and −5.6%, +47.1%, and −63.3% for the placebo, 0.3, and 1 mg/kg dose groups at day 71 (ANOVA p<0.02). There was a numerical improvement in BCVA in the subjects treated with VEGFT. As would be expected in such a small study, the results were not statistically significant.

Example 4: Phase III Clinical Trials of the Efficacy, Safety, and Tolerability of Repeated Doses of Intravitreal VEGFT in Subjects with Neovascular Age-Related Macular Degeneration A. Objectives, Hypotheses and Endpoints Two parallel Phase III clinical trials were carried out to investigate the use of VEGFT to treat patients with the neovascular form of age-related macular degeneration (Study 1 and Study 2). The primary objective of these studies was to assess the efficacy of IVT administered VEGFT compared to ranibizumab (Lucentis®, Genentech, Inc.), in a non-inferiority paradigm, in preventing moderate vision loss in subjects with all subtypes of neovascular AMD.

The secondary objectives were (a) to assess the safety and tolerability of repeated IVT administration of VEGFT in subjects with all sub-types of neovascular AMD for periods up to 2 years; and (b) to assess the effect of repeated IVT administration of VEGFT on Vision-Related Quality of Life (QOL) in subjects with all sub-types of neovascular AMD.

The primary hypothesis of these studies was that the proportion of subjects treated with VEGFT with stable or improved BCVA (<15 letters lost) is similar to the proportion treated with ranibizumab who have stable or improved BCVA, thereby demonstrating non-inferiority.

The primary endpoint for these studies was the prevention of vision loss of greater than or equal to 15 letters on the ETDRS chart, compared to baseline, at 52 weeks. Secondary endpoints were as follows: (a) change from baseline to Week 52 in letter score on the ETDRS chart; (b) gain from baseline to Week 52 of 15 letters or more on the ETDRS chart; (c) change from baseline to Week 52 in total NEI VFQ-25 score; and (d) change from baseline to Week 52 in CNV area.

B. Study Design

For each study, subjects were randomly assigned in a 1:1:1:1 ratio to 1 of 4 dosing regimens: (1) 2 mg VEGFT administered every 4 weeks (2Q4); (2) 0.5 mg VEGFT administered every 4 weeks (0.5Q4); (3) 2 mg VEGFT administered every 4 weeks to week 8 and then every 8 weeks (with sham injection at the interim 4-week visits when study drug was not administered (2Q8); and (4) 0.5 mg ranibizumab administered every 4 weeks (RQ4). Subjects assigned to (2Q8) received the 2 mg injection every 4 weeks to week 8 and then a sham injection at interim 4-week visits (when study drug is not to be administered) during the first 52 weeks of the studies. (No sham injection were given at Week 52).

The study duration for each subject was scheduled to be 96 weeks plus the recruitment period. For the first 52 weeks (Year 1), subjects received an IVT or sham injection in the study eye every 4 weeks. (No sham injections were given at Week 52). During the second year of the study, subjects will be evaluated every 4 weeks and will receive IVT injection of study drug at intervals determined by specific dosing criteria, but at least every 12 weeks. (During the second year of the study, sham injections will not be given.) During this period, injections may be given as frequently as every 4 weeks, but no less frequently than every 12 weeks, according to the following criteria: (i) increase in central retinal thickness of ≥100 μm compared to the lowest previous value as measured by optical coherence tomography (OCT); or (ii) a loss from the best previous letter score of at least 5 ETDRS letters in conjunction with recurrent fluid as indicated by OCT; or (iii) new or persistent fluid as indicated by OCT; or (iv) new onset classic neovascularization, or new or persistent leak on fluorescein angiography (FA); or (v) new macular hemorrhage; or (vi) 12 weeks have elapsed since the previous injection. According to the present protocol, subjects must receive an injection at least every 12 weeks.

Subjects were evaluated at 4 weeks intervals for safety and best corrected visual acuity (BCVA) using the 4 meter ETDRS protocol. Quality of Life (QOL) was evaluated using the NEI VFQ-25 questionnaire. OCT and FA examinations were conducted periodically.

Approximately 1200 subjects were enrolled, with a target enrollment of 300 subjects per treatment arm.

To be eligible for this study, subjects were required to have subfoveal choroidal neovascularization (CNV) secondary to AMD. "Subfoveal" CNV was defined as the presence of subfoveal neovascularization, documented by FA, or presence of a lesion that is juxtafoveal in location angiographically but affects the fovea. Subject eligibility was confirmed based on angiographic criteria prior to randomization.

Only one eye was designated as the study eye. For subjects who met eligibility criteria in both eyes, the eye with the worse VA was selected as the study eye. If both eyes had equal VA, the eye with the clearest lens and ocular media and least amount of subfoveal scar or geographic atrophy was selected. If there was no objective basis for selecting the study eye, factors such as ocular dominance, other ocular pathology and subject preference were considered in making the selection.

Inclusion criteria for both studies were as follows: (i) signed Informed consent; (ii) at least 50 years of age; (iii) active primary subfoveal CNV lesions secondary to AMD, including juxtafoveal lesions that affect the fovea as evidenced by FA in the study eye; (iv) CNV at least 50% of total lesion size; (v) early treatment diabetic retinopathy study (ETDRS) best-corrected visual acuity of: 20/40 to 20/320 (letter score of 73 to 25) in the study eye; (vi) willing, committed, and able to return for all clinic visits and complete all study-related procedures; and (vii) able to read, understand and willing to sign the informed consent form (or, if unable to read due to visual impairment, be read to verbatim by the person administering the informed consent or a family member).

Exclusion criteria for both studies were as follows: 1. Any prior ocular (in the study eye) or systemic treatment or surgery for neovascular AMD except dietary supplements or vitamins. 2. Any prior or concomitant therapy with another investigational agent to treat neovascular AMD in the study eye, except dietary supplements or vitamins. 3. Prior treatment with anti-VEGF agents as follows: (a) Prior treatment with anti-VEGF therapy in the study eye was not allowed; (b) Prior treatment with anti-VEGF therapy in the fellow eye with an investigational agent (not FDA approved, e.g. bevacizumab) was allowed up to 3 months prior to first dose in the study, and such treatments were not allowed during the study. Prior treatment with an approved anti-VEGF therapy in the fellow eye was allowed; (c) Prior systemic anti-VEGF therapy, investigational or FDA/Health Canada approved, was only allowed up to 3 months prior to first dose, and was not allowed during the study. 4. Total lesion size >12 disc areas (30.5 mm2, including blood, scars and neovascularization) as assessed by FA in the study eye. 5. Subretinal hemorrhage that is either 50% or more of the total lesion area, or if the blood is under the fovea and is 1 or more disc areas in size in the study eye. (If the blood is under the fovea, then the fovea must be surrounded 270 degrees by visible CNV.) 6. Scar or fibrosis, making up >50% of total lesion in the study eye. 7. Scar, fibrosis, or atrophy involving the center of the fovea. 8. Presence of retinal pigment epithelial tears or rips involving the macula in the study eye. 9. History of any vitreous hemorrhage within 4 weeks prior to Visit 1 in the study eye. 10. Presence of other causes of CNV, including pathologic myopia (spherical equivalent of −8 diopters or more negative, or axial length of 25 mm or more), ocular histoplasmosis syndrome, angioid streaks, choroidal rupture, or multifocal choroiditis in the study eye. 11. History or clinical evidence of diabetic retinopathy, diabetic macular edema or any other vascular disease affecting the retina, other than AMD, in either eye. 12. Prior vitrectomy in the study eye. 13. History of retinal detachment or treatment or surgery for retinal detachment in the study eye. 14. Any history of macular hole of stage 2 and above in the study eye. 15. Any intraocular or periocular surgery within 3 months of Day 1 on the study eye, except lid surgery, which may not have taken place within 1 month of day 1, as long as it was unlikely to interfere with the injection. 16. Prior trabeculectomy or other filtration surgery in the study eye. 17. Uncontrolled glaucoma (defined as intraocular pressure greater than or equal to 25 mm Hg despite treatment with anti-glaucoma medication) in the study eye. 18. Active intraocular inflammation in either eye. 19. Active ocular or periocular infection in either eye. 20. Any ocular or periocular infection within the last 2 weeks prior to Screening in either eye. 21. Any history of uveitis in either eye. 22. Active scleritis or episcleritis in either eye. 23. Presence or history of scleromalacia in either eye. 24. Aphakia or pseudophakia with absence of posterior capsule (unless it occurred as a result of a yttrium aluminum garnet [YAG] posterior capsulotomy) in the study eye. 25. Previous therapeutic radiation in the region of the study eye. 26. History of corneal transplant or corneal dystrophy in the study eye. 27. Significant media opacities, including cataract, in the study eye which might interfere with visual acuity, assessment of safety, or fundus photography. 28. Any concurrent intraocular condition in the study eye (e.g. cataract) that, in the opinion of the investigator, could require either medical or surgical intervention during the 96 week study period. 29. Any concurrent ocular condition in the study eye which, in the opinion of the investigator, could either increase the risk to the subject beyond what is to be expected from standard procedures of intraocular injection, or which otherwise may interfere with the injection procedure or with evaluation of efficacy or safety. 30. History of other disease, metabolic dysfunction, physical examination finding, or clinical laboratory finding giving reasonable suspicion of a disease or condition that contraindicates the use of an investigational drug or that might affect interpretation of the results of the study or render the subject at high risk for treatment complications. 31. Participation as a subject in any clinical study within the 12 weeks prior to Day 1. 32. Any systemic or ocular treatment with an investigational agent in the past 3 months prior to Day 1. 33. The use of long acting steroids, either systemically or intraocularly, in the 6 months prior to day 1. 34. Any history of allergy to povidone iodine. 35. Known serious allergy to the fluorescein sodium for injection in angiography. 36. Presence of any contraindications indicated in the FDA Approved label for ranibizumab (Lucentis®). 37. Females who were pregnant, breastfeeding, or of childbearing potential, unwilling to practice adequate contraception throughout the study. Adequate contraceptive measures include oral contraceptives (stable use for 2 or more cycles prior to screening); IUD; Depo-Provera®; Norplant® System implants; bilateral tubal ligation; vasectomy; condom or diaphragm plus either contraceptive sponge, foam or jelly.

Subjects were not allowed to receive any standard or investigational agents for treatment of their AMD in the study eye other than their assigned study treatment with VEGFT or ranibizumab as specified in the protocol until they completed the Completion/Early Termination visit assessments. This includes medications administered locally (e.g., IVT, topical, juxtascleral or periorbital routes), as well as those administered systemically with the intent of treating the study and/or fellow eye.

The study procedures are summarized as follows:

Best Corrected Visual Acuity: Visual function of the study eye and the fellow eye were assessed using the ETDRS protocol (The Early Treatment Diabetic Retinopathy Study Group) at 4 meters. Visual Acuity examiners were certified to ensure consistent measurement of BCVA. The VA examiners were required to remain masked to treatment assignment.

Optical Coherence Tomography: Retinal and lesion characteristics were evaluated using OCT on the study eye. At the Screen Visit (Visit 1) images were captured and transmitted for both eyes. All OCT images were captured using the Zeiss Stratus OCT™ with software Version 3 or greater. OCT images were sent to an independent reading center where images were read by masked readers at visits where OCTs were required. All OCTs were electronically archived at the site as part of the source documentation. A subset of OCT images were read. OCT technicians were required to be certified by the reading center to ensure consistency and quality in image acquisition. Adequate efforts were made to ensure that OCT technicians at the site remained masked to treatment assignment.

Fundus Photography and Fluorescein Angiography (FA): The anatomical state of the retinal vasculature of the study eye was evaluated by funduscopic examination, fundus photography and FA. At the Screen Visit (Visit 1) funduscopic examination, fundus photography and FA were captured and transmitted for both eyes. Fundus and angiographic images were sent to an independent reading center where images were read by masked readers. The reading center confirmed subject eligibility based on angiographic criteria prior to randomization. All FAs and fundus photographs were archived at the site as part of the source documentation. Photographers were required to be certified by the reading center to ensure consistency and quality in image acquisition. Adequate efforts were made to ensure that all photographers at the site remain masked to treatment assignment.

Vision-Related Quality of Life: Vision-related QOL was assessed using the National Eye Institute 25-Item Visual Function Questionnaire (NEI VFQ-25) in the interviewer-administered format. NEI VFQ-25 was administered by certified personnel at a contracted call center. At the screening visit, the sites assisted the subject and initiated the first call to the call center to collect all of the subject's contact information and to complete the first NEI VFQ-25 on the phone prior to randomization and IVT injection. For all subsequent visits, the call center called the subject on the phone, prior to IVT injection, to complete the questionnaire.

Intraocular Pressure: Intraocular pressure (IOP) of the study eye was measured using applanation tonometry or Tonopen. The same method of IOP measurement was used in each subject throughout the study.

C. Results Summary (52 Week Data)

The primary endpoint (prevention of moderate or severe vision loss as defined above) was met for all three VEGFT groups (2Q4, 0.5Q4 and 2Q8) in this study. The results from both studies are summarized in Table 1.

TABLE 1

|  | Ranibizumab 0.5 mg monthly (RQ4) | VEGFT 0.5 mg monthly (0.5Q4) | VEGFT 2 mg monthly (2Q4) | VEGFT 2 mg every 8 weeks[a] (2Q8) |
|---|---|---|---|---|
| Maintenance of vision* (% patients losing <15 letters) at week 52 versus baseline | | | | |
| Study 1 | 94.4% | 95.9%** | 95.1%** | 95.1%** |
| Study 2 | 94.4% | 96.3%** | 95.6%** | 95.6%** |
| Mean improvement in vision* (letters) at 52 weeks versus baseline (p-value vs RQ4)*** | | | | |
| Study 1 | 8.1 | 6.9 (NS) | 10.9 (p < 0.01) | 7.9 (NS) |
| Study 2 | 9.4 | 9.7 (NS) | 7.6 (NS) | 8.9 (NS |

[a]Following three initial monthly doses
*Visual acuity was measured as the total number of letters read correctly on the Early Treatment Diabetic Retinopathy Study (ETDRS) eye chart.
**Statistically non-inferior based on a non-inferiority margin of 10%, using confidence interval approach (95.1% and 95% for Study 1 and Study 2, respectively)
***Test for superiority
NS = non-significant In Study 1, patients receiving VEGFT 2 mg monthly (2Q4) achieved a statistically significant greater mean improvement in visual acuity at week 52 versus baseline (secondary endpoint), compared to ranibizumab 0.5 mg monthly (RQ4); patients receiving VEGFT 2 mg monthly on average gained 10.9 letters, compared to a mean 8.1 letter gain with ranibizumab 0.5 mg dosed every month (p<0.01). All other dose groups of VEGFT in Study 1 and all dose groups in Study 2 were not statistically different from ranibizumab in this secondary endpoint.

A generally favorable safety profile was observed for both VEGFT and ranibizumab. The incidence of ocular treatment emergent adverse events was balanced across all four treatment groups in both studies, with the most frequent events associated with the injection procedure, the underlying disease, and/or the aging process. The most frequent ocular adverse events were conjunctival hemorrhage, macular degeneration, eye pain, retinal hemorrhage, and vitreous floaters. The most frequent serious non-ocular adverse events were typical of those reported in this elderly population who receive intravitreal treatment for wet AMD; the most frequently reported events were falls, pneumonia, myocardial infarction, atrial fibrillation, breast cancer, and acute coronary syndrome. There were no notable differences among the study arms.

Example 5: Phase II Clinical Trial of VEGFT in Subjects with Diabetic Macular Edema (DME)

In this study, 221 patients with clinically significant DME with central macular involvement were randomized, and 219 patients were treated with balanced distribution over five groups. The control group received macular laser therapy at baseline, and patients were eligible for repeat laser treatments, but no more frequently than at 16 week intervals. The remaining four groups received VEGFT by intravitreal injection as follows: Two groups received 0.5 or 2 mg of VEGFT once every four weeks throughout the 12-month dosing period (0.5Q4 and 2Q4, respectively). Two groups received three initial doses of 2 mg VEGFT once every four weeks (i.e., at baseline, and weeks 4 and 8), followed through week 52 by either once every 8 weeks dosing (2Q8) or as needed dosing with very strict repeat dosing criteria (PRN). Mean gains in visual acuity versus baseline were as shown in Table 2:

TABLE 2

|  | n | Mean change in visual acuity at week 24 versus baseline (letters) | Mean change in visual acuity at week 52 versus baseline (letters) |
|---|---|---|---|
| Laser | 44 | 2.5 | −1.3 |
| VEGFT 0.5 mg monthly (0.5Q4) | 44 | 8.6** | 11.0** |
| VEGFT 2 mg monthly (2Q4) | 44 | 11.4** | 13.1** |
| VEGFT 2 mg every 8 weeks[a] (2Q8) | 42 | 8.5** | 9.7** |
| VEGFT 2 mg as needed[a] (PRN) | 45 | 10.3** | 12.0** |

[a]Following three initial monthly doses
**p < 0.01 versus laser

In this study, the visual acuity gains achieved with VEGFT administration at week 24 were maintained or numerically improved up to completion of the study at week 52 in all VEGFT study groups, including 2 mg dosed every other month As demonstrated in the foregoing Examples, the administration of VEGFT to patients suffering from angiogenic eye disorders (e.g., AMD and DME) at a frequency of once every 8 weeks, following a single initial dose and two secondary doses administered four weeks apart, resulted in significant prevention of moderate or severe vision loss or improvements in visual acuity.

Example 6: A Randomized, Multicenter, Double-Masked Trial in Treatment Naïve Patients with Macular Edema Secondary to CRVO In this randomized, double-masked, Phase 3 study, patients received 6 monthly injections of either 2 mg intravitreal VEGFT (114 patients) or sham injections (73 patients). From Week 24 to Week 52, all patients received 2 mg VEGFT as-needed (PRN) according to retreatment criteria. Thus, "sham-treated patients" means patients who received sham injections once every four weeks from Week 0 through Week 20, followed by intravitreal VEGFT as needed from Week 24 through Week 52. "VEGFT-treated patients" means patients who received VEGFT intravitreal injections once every four weeks from Week 0 through Week 20, followed by intravitreal VEGFT as needed from Week 24 through Week 52. The primary endpoint was the proportion of patients who gained ≥15 ETDRS letters from baseline at Week 24. Secondary visual, anatomic, and Quality of Life NEI VFQ-25 outcomes at Weeks 24 and 52 were also evaluated.

At Week 24, 56.1% of VEGFT-treated patients gained ≥15 ETDRS letters from baseline vs 12.3% of sham-treated patients (P<0.0001). Similarly, at Week 52, 55.3% of VEGFT-treated patients gained ≥15 letters vs 30.1% of sham-treated patients (P<0.01). At Week 52, VEGFT-treated patients gained a mean of 16.2 letters vs 3.8 letters for sham-treated patients (P<0.001). Mean number of injections was 2.7 for VEGFT-treated patients vs 3.9 for sham-treated patients. Mean change in central retinal thickness was −413.0 μm for VEGFT-treated patients vs −381.8 μm for sham-treated patients. The proportion of patients with ocular neovascularization at Week 24 were 0% for VEGFT-treated patients and 6.8% for sham-treated patients, respectively; at Week 52 after receiving VEGFT PRN, proportions were 0% and 6.8% for VEGFT-treated and sham-treated. At Week 24, the mean change from baseline in the VFQ-25 total score was 7.2 vs 0.7 for the VEGFT-treated and sham-treated groups; at Week 52, the scores were 7.5 vs 5.1 for the VEGFT-treated and sham-treated groups.

This Example confirms that dosing monthly with 2 mg intravitreal VEGFT injection resulted in a statistically significant improvement in visual acuity at Week 24 that was maintained through Week 52 with PRN dosing compared with sham PRN treatment. VEGFT was generally well tolerated and had a generally favorable safety profile.

Example 7: Dosing Regimens

Specific, non-limiting examples of dosing regimens within the scope of the present invention are as follows:

VEGFT 2 mg (0.05 mL) administered by intravitreal injection once every 4 weeks (monthly).

VEGFT 2 mg (0.5 mL) administered by intravitreal injection once every 4 weeks for the first 8 weeks, followed by 2 mg (0.05 mL) via intravitreal injection once every 8 weeks.

VEGFT 2 mg (0.5 mL) administered by intravitreal injection once every 4 weeks for the first 8 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 8 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection once every 8 weeks.

VEGFT 2 mg (0.5 mL) administered by intravitreal injection once every 4 weeks for the first 12 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection once every 8 weeks.

VEGFT 2 mg (0.5 mL) administered by intravitreal injection once every 4 weeks for the first 16 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection once every 8 weeks.

VEGFT 2 mg (0.5 mL) administered by intravitreal injection once every 4 weeks for the first 20 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection once every 8 weeks.

VEGFT 2 mg (0.5 mL) administered by intravitreal injection once every 4 weeks for the first 24 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection once every 8 weeks.

VEGFT 2 mg (0.5 mL) administered by intravitreal injection once every 4 weeks for the first 28 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection administered pro re nata (PRN) based on visual and/or anatomical outcomes (as assessed by a physician or other qualified medical professional).

VEGFT 2 mg (0.05 mL) administered by intravitreal injection as a single initial dose, followed by additional doses administered pro re nata (PRN) based on visual and/or anatomical outcomes (as assessed by a physician or other qualified medical professional).

Variations on the above-described dosing regimens would be appreciated by persons of ordinary skill in the art and are also within the scope of the present invention. For example, the amount of VEGFT and/or volume of formulation administered to a patient may be varied based on patient characteristics, severity of disease, and other diagnostic assessments by a physician or other qualified medical professional.

Any of the foregoing administration regimens may be used for the treatment of, e.g., age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, etc.

Example 8: Phase 3, Double-Masked, Randomized Study of the Efficacy and Safety of Intravitreal IAI in Patients with Moderately Severe to Severe NPDR (PANORAMA)-Week 24 and 52 Results This was a phase 3, double-masked, randomized study of the efficacy and safety of IVT (intravitreal injection) aflibercept (IAI) for the improvement of moderately severe to severe non-proliferative diabetic retinopathy (NPDR). These data relate to results achieved after 24 weeks and 52 weeks.

Eligible patients were enrolled into 1 of 3 treatment groups in a 1:1:1 randomization scheme, and are stratified based on their Diabetic Retinopathy Severity Scale (DRSS) score (level 47 vs. level 53) (see FIG. 5 and FIG. 6). Only 1 eye was selected as the study eye.

Study Design

The primary outcome measure of the study is the proportion of patients who improved by ≥2 steps from baseline on the DRSS in the combined 2Q8 and 2Q16 groups at week 24, and in each group separately at week 52.

Patients are evaluated for efficacy (best corrected visual acuity [BCVA] using the 4-meter Early Treatment Diabetic Retinopathy Study [ETDRS] protocol, spectral domain optical coherence tomography [SD OCT], and fluorescein angiography [FA]/fundus photography [FP]) and for ocular and systemic safety (including ophthalmic exams, visual field testing, and laboratory assessments) through week 100.

The secondary outcome measures are also tested at week 52 and are as follows:
 (1) Proportion of patients developing a vision threatening complication (VTC) due to diabetic retinopathy through week 52. Vision threatening complications are defined as composite outcome of PDR (inclusive of patients who have vitreous hemorrhage or tractional retinal detachment believed to be due to PDR) and ASNV. ASNV is defined as neovascularization of the iris (at least 2 cumulative clock hours), and/or definitive neovascularization of the iridocorneal angle
 (2) Proportion of patients who develop CI DME through week 52
 (3) Time to development of a vision threatening complication through week 52
 (4) Time to development of CI DME (center-involved DME) through week 52
 (5) Proportion of patients who receive PRP (panretinal photocoagulation) through week 52, inclusive of patients undergoing vitrectomy with endolaser
 (6) Area under the curve (AUC) for change in BCVA from baseline at week 52.

Study Timeline

Day −21 to −1: Screening visit (visit 1)
Day 1: Baseline visit (visit 2)
Week 24: Primary Outcome Measure (2Q8 & 2Q16 combined) (visit 7)
Week 52: Primary Outcome Measure (2Q8 & 2Q16 separately) and all secondary outcome measures (visit 11)
Week 100: End of Study (visit 18)

Exclusion criteria: Patients who met any of the following criteria at either the screening visit or at day 1 were excluded from the study:

(1) Presence of DME threatening the center of the macula (within 1,000 microns of the foveal center) in the study eye;
 (2) Evidence of retinal neovascularization on clinical examination or FA (fluorescein angiography);
 (3) Any prior focal or grid laser photocoagulation (within 1,000 microns of the foveal center) or any prior PRP in the study eye;
 (4) Any prior systemic anti-VEGF treatment or IVT anti-VEGF treatment in the study eye;
 (5) Any prior intraocular steroid in the study eye; periocular steroid in the study eye within 120 days of day 1;
 (6) History of vitreoretinal surgery in the study eye;
 (7) Intraocular pressure (IOP)≥25 mm Hg in the study eye;
 (8) Evidence of active infectious blepharitis, keratitis, scleritis, or conjunctivitis in either eye;
 (9) Any intraocular inflammation or infection in either eye within 3 months of the screening visit;
 (10) Current ASNV, vitreous hemorrhage, or tractional retinal detachment visible at the screening assessments in the study eye;
 (11) Ocular media of insufficient quality to obtain fundus and optical coherence tomography (OCT) images in the study eye; allergy to fluorescein precluding ability to perform fluorescein angiography;
 (12) Hemoglobin A1c (HbA1c)>12%, or if HbA1c is ≤12%, diabetes mellitus is uncontrolled in the opinion of the investigator;
 (13) Uncontrolled blood pressure (defined as systolic >160 mm Hg or diastolic >95 mm Hg while patient is sitting);
 (14) History of cerebrovascular accident or myocardial infarction within 180 days of day 1;
 (15) Renal failure, dialysis, or history of renal transplant;
 (16) Women who are breastfeeding or who have a positive serum hCG/urine pregnancy test at the screening or baseline visit;
 (17) Any concurrent ocular condition in the study eye which, in the opinion of the investigator, could either increase the risk to the patient beyond what is to be expected from standard procedures of IVT injections, or which otherwise may interfere with the injection procedure or with evaluation of efficacy or safety;
 (18) History of other disease, metabolic dysfunction, physical examination finding, or clinical laboratory finding giving reasonable suspicion of a disease or condition that contraindicates the use of an investigational drug or that might affect interpretation of the results of the study or render the patient at high risk for treatment complications;
 (19) Participation as a patient in any interventional clinical study within the 12 weeks prior to day 1 of the study;
 (20) Sexually active men* or women of childbearing potential** who are unwilling to practice adequate contraception prior to the initial dose/start of the first treatment, during the study, and for at least 3 months after the last dose. Adequate contraceptive measures include stable use of oral contraceptives or other prescription pharmaceutical contraceptives for 2 or more menstrual cycles prior to screening; intrauterine device; bilateral tubal ligation; vasectomy; condom plus contraceptive sponge, foam, or jelly, or diaphragm plus contraceptive sponge, foam, or jelly.

\* Contraception is not required for men with documented vasectomy.

\*\* Postmenopausal women must be amenorrheic for at least 12 months in order not to be considered of childbearing potential. Pregnancy testing and contraception are not required for women with documented hysterectomy or tubal ligation.

(21) Patients who are on systemic anti-VEGF treatment (i.e., bevacizumab, ziv-aflibercept) for oncology treatment (if a patient requires systemic anti-VEGF treatment during the study, the patient will be withdrawn)

Treatment regimen: The 3 treatment groups have the following dosing regimens scheduled from day 1 to week 48:

2Q8: aflibercept 2 mg Q8 to week 48 (after 5 initial monthly doses), followed by a flexible treatment regimen with aflibercept 2 mg after week 52;

2Q16: aflibercept 2 mg Q16 to week 96 (after 3 initial monthly doses and 1 Q8 interval);

Sham: sham injections every 4 weeks (Q4) to week 16, followed by sham injections Q8 to week 96.

Data herein may refer to the 2Q16 dosing group as "Group 1"; the 208 dosing group as "Group 2" and the sham group as "Sham".

Figure 3:
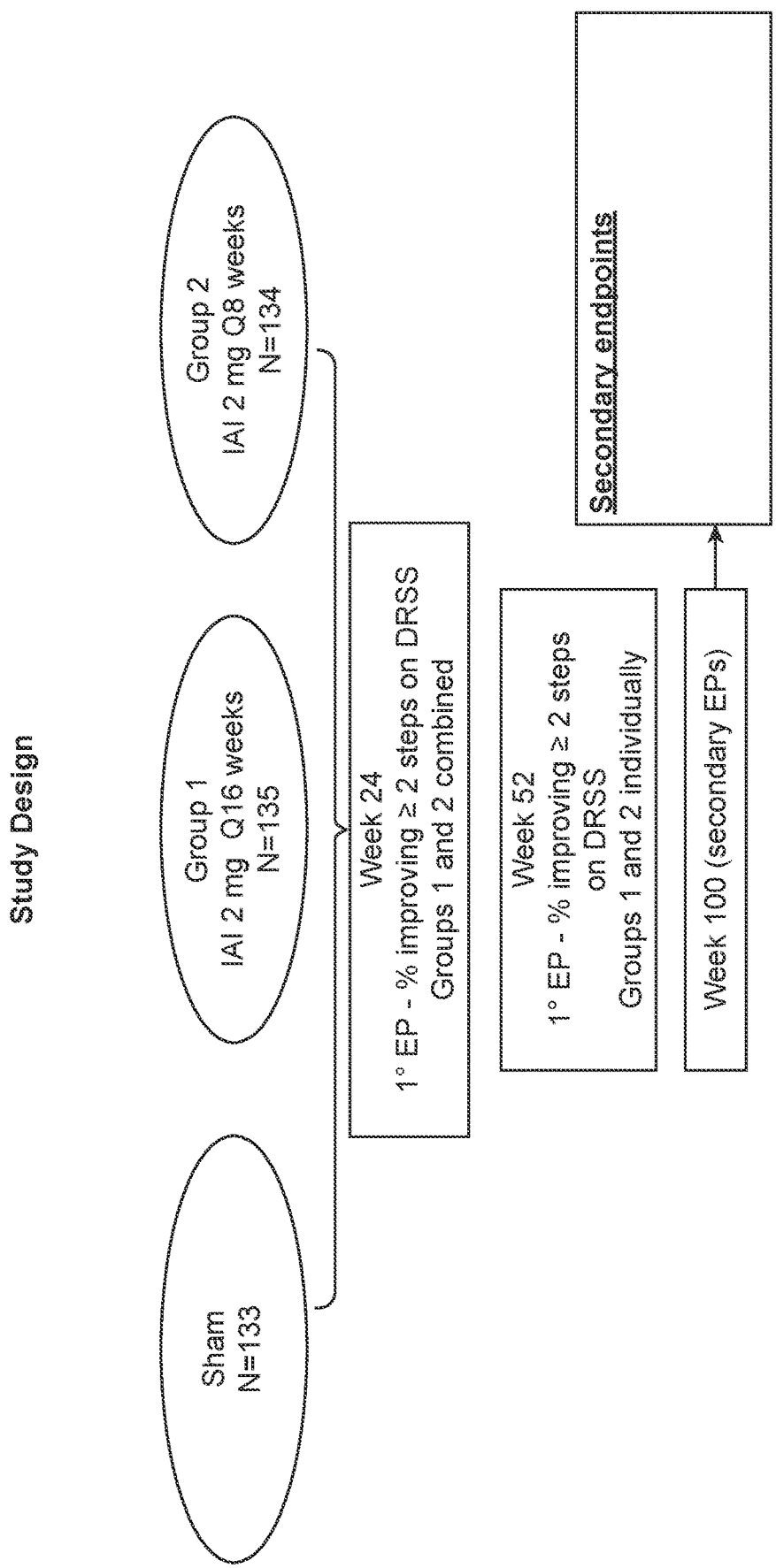
FIG. 3 summarizes the PANORAMA study design: Phase 3, Double-masked, randomized, controlled-IVT Aflibercept vs. Sham-Patients with moderately severe to severe NPDR (DRSS Level 47 and 53)-N=402. Patients with moderately severe to severe NPDR received (i) a sham injection ("sham"), (ii) 3 monthly doses followed by one or more secondary doses every 16 weeks, wherein the first secondary dose initiates 8 weeks after the third monthly dose (week 16) ("Group 1"), or (iii) 5 monthly doses followed by one or more secondary doses every 8 weeks ("Group 2"). Secondary endpoints: % developing Vision-threatening complication: PDR, ASNV; % developing CI-DME; Time to development of PDR/ASNV or CI-DME; % receiving PRP; and Area under the curve for change in BCVA from BL. Patients will be stratified by baseline DRSS level.

See FIG. 3 and FIG. 4.

Figure 7:
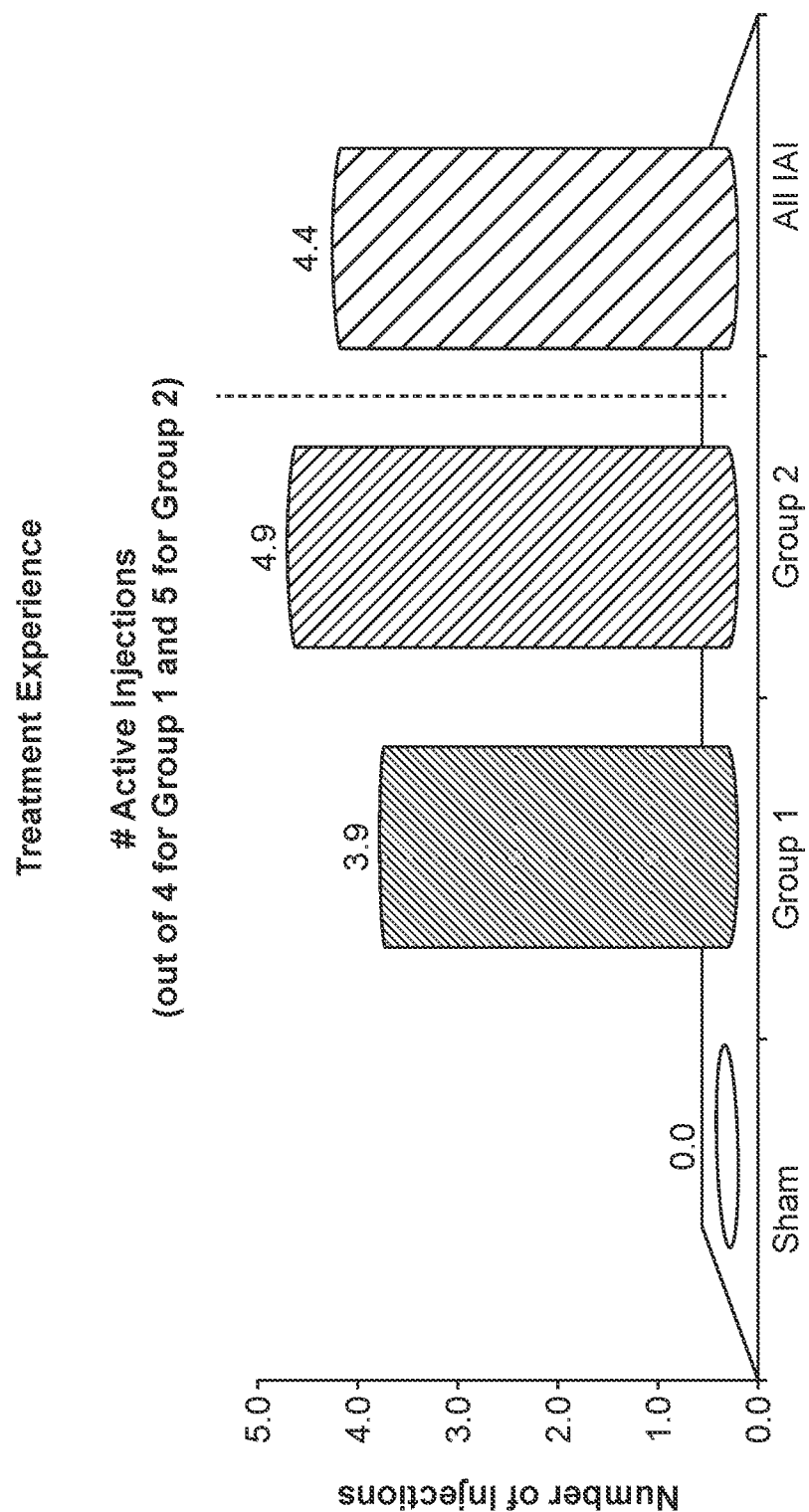
FIG. 7 sets forth the number of injections received by PANORAMA subjects in each dosing group (sham, Group 1, Group 2 and the combination of Group 1 and Group 2: "All IAI"). Sham n=133, Group 1 n=135, Group 2 n=134, All IAI n=269
Figure 8:
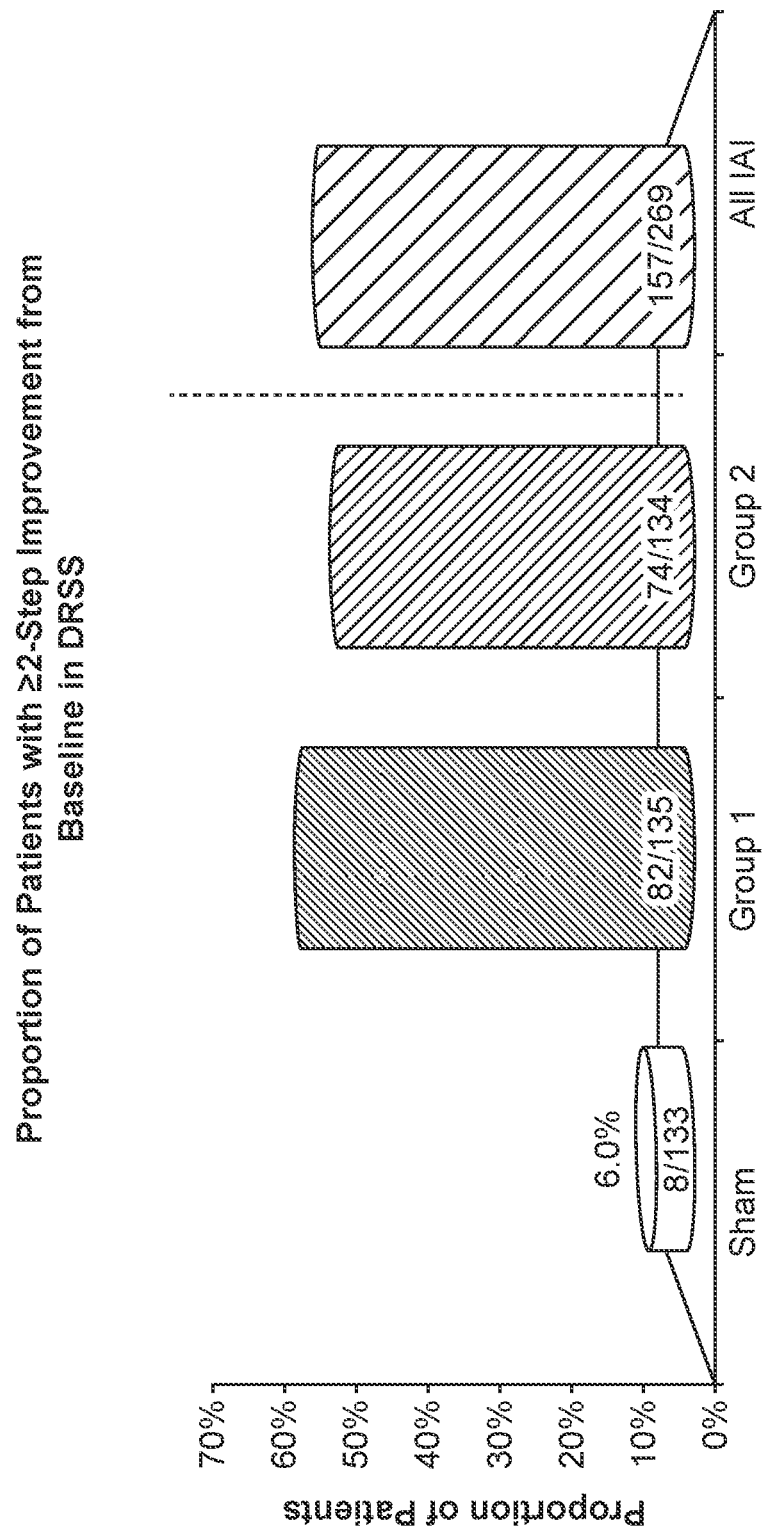
FIG. 8 shows the proportion (%) of PANORAMA patients in each dosing group (sham, Group 1, Group 2 and All IAI (combined Group 1 and Group 2)) achieving ≥2-step improvement from baseline on the diabetic retinopathy severity scale (DRSS). LOCF; Sham n=133, Group 1 n=135, Group 2 n=134, All IAI n=269. *p<0.0001 vs. sham.
Figure 20:
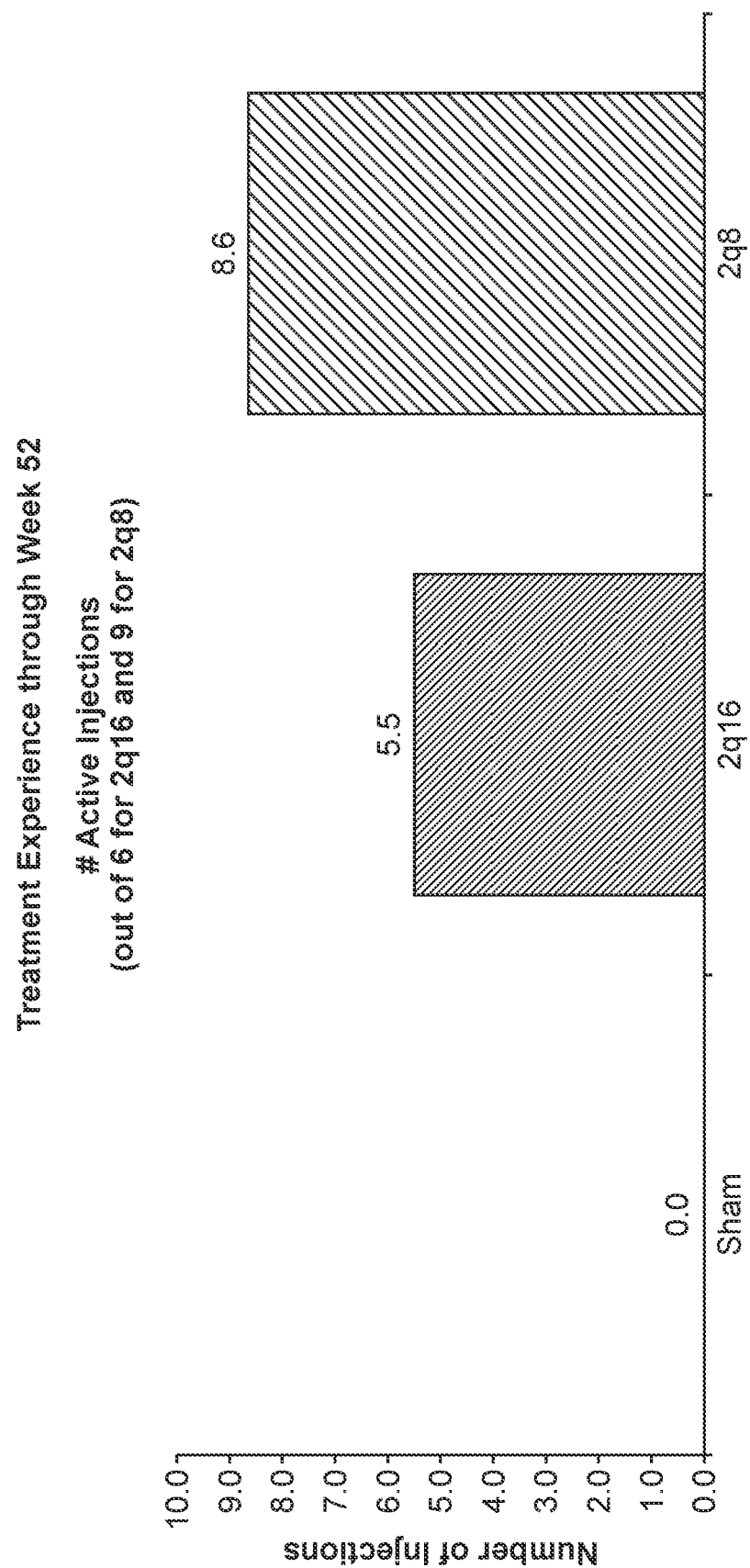
FIG. 20 summarizes the number of active injections given to subjects in treatment groups sham, 2q16 (out of 6) and 2q8 (out of 9) through week 52. Sham n=133, 2q16 n=135, 2q8 n=134.
Figure 21:
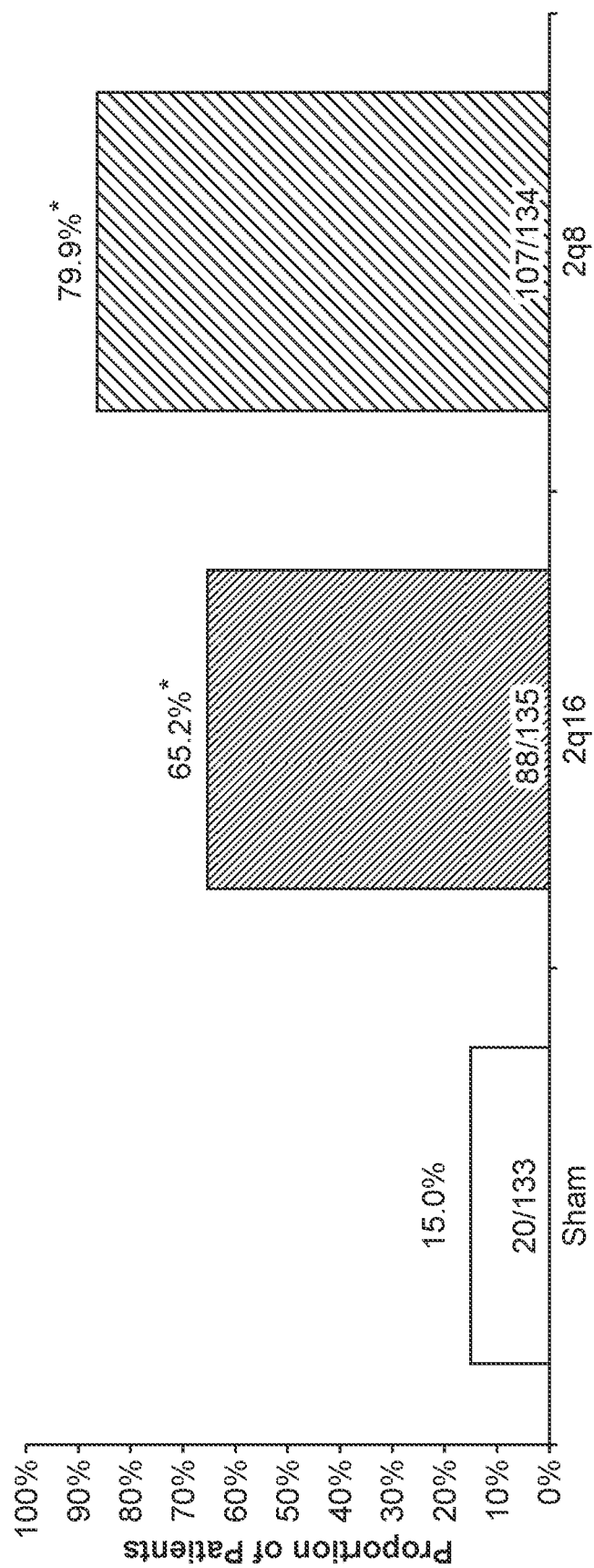
FIG. 21 summarizes the proportion of patients, in the sham, 2q16 and 2q8 groups, with at least a 2 step improvement, from baseline in DRSS at week 52. LOCF=last observation carried forward through week 52. LOCF; Sham n=133, 2q16 n=135, 2q8 n=134. *p<0.0001 vs. sham.
Figure 22:
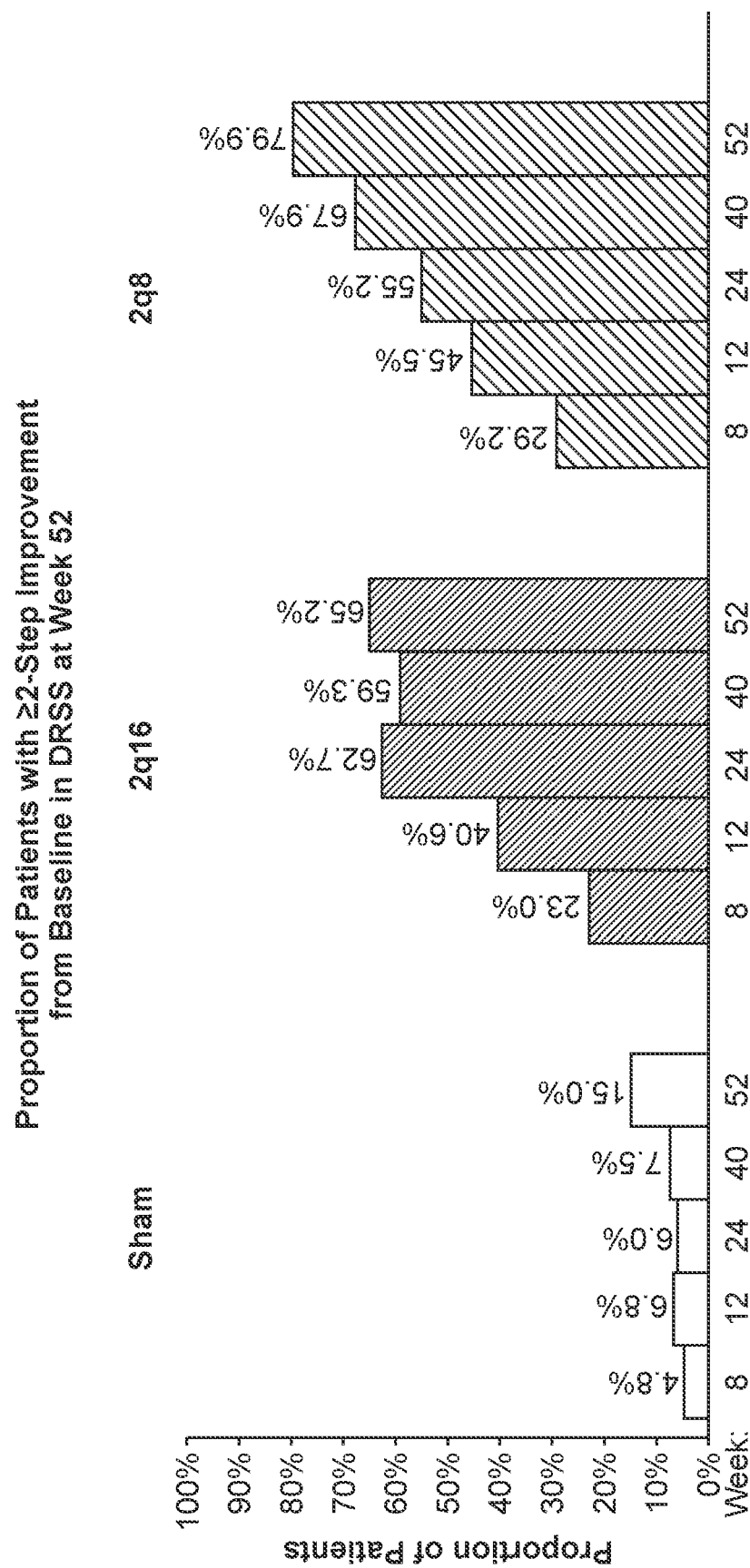
FIG. 22 summarizes the percentage of subjects in each treatment group (sham, 2q16 and 2q8) with at least a 2 step improvement, from baseline in DRSS at weeks 8, 12, 24, 40 and 52. LOCF; Sham n=133, 2q16 n=135, 2q8 n=134.

The number of injections received by each dose group after 24 weeks is shown in FIG. 7 and the number of injections after 52 weeks is shown in FIG. 20.

To preserve the masking, sham injections are performed for the 2Q8 and 2016 groups at treatment visits in which patients will not receive an active injection through week 96, and at all treatment visits for the sham group from baseline to week 96. Masking is maintained to the end of the study (week 100).

Rescue treatment in the study eye: Patients who develop PDR, ASNV, or center-involved DME (CI DME) in the study eye are treated, if deemed appropriate by the masked physician. For any of these complications, an FP (fundus photography) is performed before rescue treatment is given.

Patients who develop CI DME receive IVT aflibercept or laser photocoagulation, and no longer receive their randomized treatment. Rescue treatment is given by the masked or unmasked physician.

Patients who develop PDR and/or ASNV receive PRP or vitrectomy with endolaser, if necessary, but remain on their randomized treatment schedule. Panretinal photocoagulation or surgical intervention is performed by either the masked or unmasked physician. In addition, 1 injection of aflibercept is given, which must be administered by the unmasked physician.

If treatment for DME, ASNV, or PDR is given, patient data is censored from the time of treatment for the primary analysis.

Study Population 402 patients were enrolled. The patient population included men or women with type 1 or 2 diabetes mellitus who had moderately severe to severe NPDR (without DME threatening the center of the macula), in whom PRP can be safely deferred for at least 6 months. See FIG. 5 and FIG. 6. About 75% of patients had a DRSS of 47 and about 25% had a DRSS of 53.

For patients who meet eligibility criteria in both eyes, the eye with the most severe DRSS score is selected as the study eye. If both eyes have equivalent scores, factors such as ocular dominance and patient preference are considered in making the selection.

Ocular Procedures (Efficacy and Safety)

Best Corrected Visual Acuity (BCVA): Visual function of the study eye and the fellow eye is assessed using the ETDRS protocol (The Early Treatment Diabetic Retinopathy Study Group 1985) at 4 meters at each study visit. Visual acuity examiners are certified to ensure consistent measurement of BCVA. The VA examiner remains masked to treatment assignment. Best corrected visual acuity is done before any other ocular procedures are performed.

Intraocular Pressure (IOP): Intraocular pressure of the study eye is measured at every visit using Goldmann applanation tonometry or Tono Pen™. The same method of IOP measurement is used throughout the study for each individual patient. Intraocular pressure is measured pre-dose (bilateral) by the masked physician (or designee), and at approximately 30 minutes post-dose (study eye) by the unmasked physician (or designee).

Slit Lamp Examination: Patients' anterior eye structure and ocular adnexa is examined bilaterally pre-dose at each study visit using a slit lamp by the masked investigator.

Gonioscopy: Patients are evaluated for the development of neovascularization of the iridocorneal angle by gonioscopy in conjunction with slit lamp biomicroscopy. The examination is performed in the study eye only before the application of mydriatic agents or if frank rubeosis is present.

Indirect Ophthalmoscopy: Patients' posterior pole and peripheral retina are examined by indirect ophthalmoscopy at each study visit pre-dose (bilateral) by the masked investigator and post-dose (study eye) by the unmasked investigator. Post-dose evaluation is performed immediately after injection (active drug or sham).

Fundus Photography (FP)/Fluorescein Angiography (FA): The anatomical state of the retinal vasculature and the DRSS level is evaluated by FA and FP.

Spectral Domain Optical Coherence Tomography (SD-OCT): Retinal characteristics are evaluated at every visit using SD-OCT. Images are captured and transmitted for both eyes. Images are sent to an independent reading center where they are read by masked readers. All OCTs are electronically archived at the study sites as part of the source documentation. Optical coherence tomography technicians are certified by the reading center to ensure consistency and quality in image acquisition. Every effort is made to ensure that OCT technicians at the study site remain masked to treatment assignment.

Visual Field Testing: Visual field testing is assessed in the study eye using the Humphrey Visual Field Analyzer by sites who have access to this machine. Technicians are certified to ensure consistency and quality testing procedures. Every effort is made to ensure that visual field technicians at the study site remain masked to treatment assignment.

Adverse Events (AEs)

Overall safety was assessed by evaluation of treatment-emergent adverse events (TEAEs), physical examinations, electrocardiograms (ECGs), vital signs, and clinical safety laboratory tests (hematology, blood chemistry, hemoglobin A1c [HbA1c], and urinalysis) at various time points.

A TEAE is defined as an event (or an exacerbation of a preexisting event during the treatment period) that is observed or reported after the first administration of study drug, and no later than 30 days after last administration of study drug (active or sham injection).

The investigator (or designee) records all AEs that occur from the time the informed consent is signed until the end of study. All serious adverse events (SAEs), regardless of assessment of causal relationship to study drug must be reported within 24 hours.

Other events requiring reporting within 24 hours include symptomatic overdose of study drug (accidental or intentional overdose of at least 2 times the intended dose of study drug within the intended therapeutic window, if associated with an AE) and pregnancy.

The severity of AEs will be graded according to the following scale:

Mild: Does not interfere in a significant manner with the patient's normal functioning level. It may be an annoyance. Prescription drugs are not ordinarily needed for relief of symptoms, but may be given because of personality of the patient.

Moderate: Produces some impairment of functioning but is not hazardous to health. It is uncomfortable or an embarrassment. Treatment for symptom may be needed.

Severe: Produces significant impairment of functioning or incapacitation and is a definite hazard to the patient's health. Treatment for symptom may be given and/or patient hospitalized.

Results and Conclusions

Figure 9:
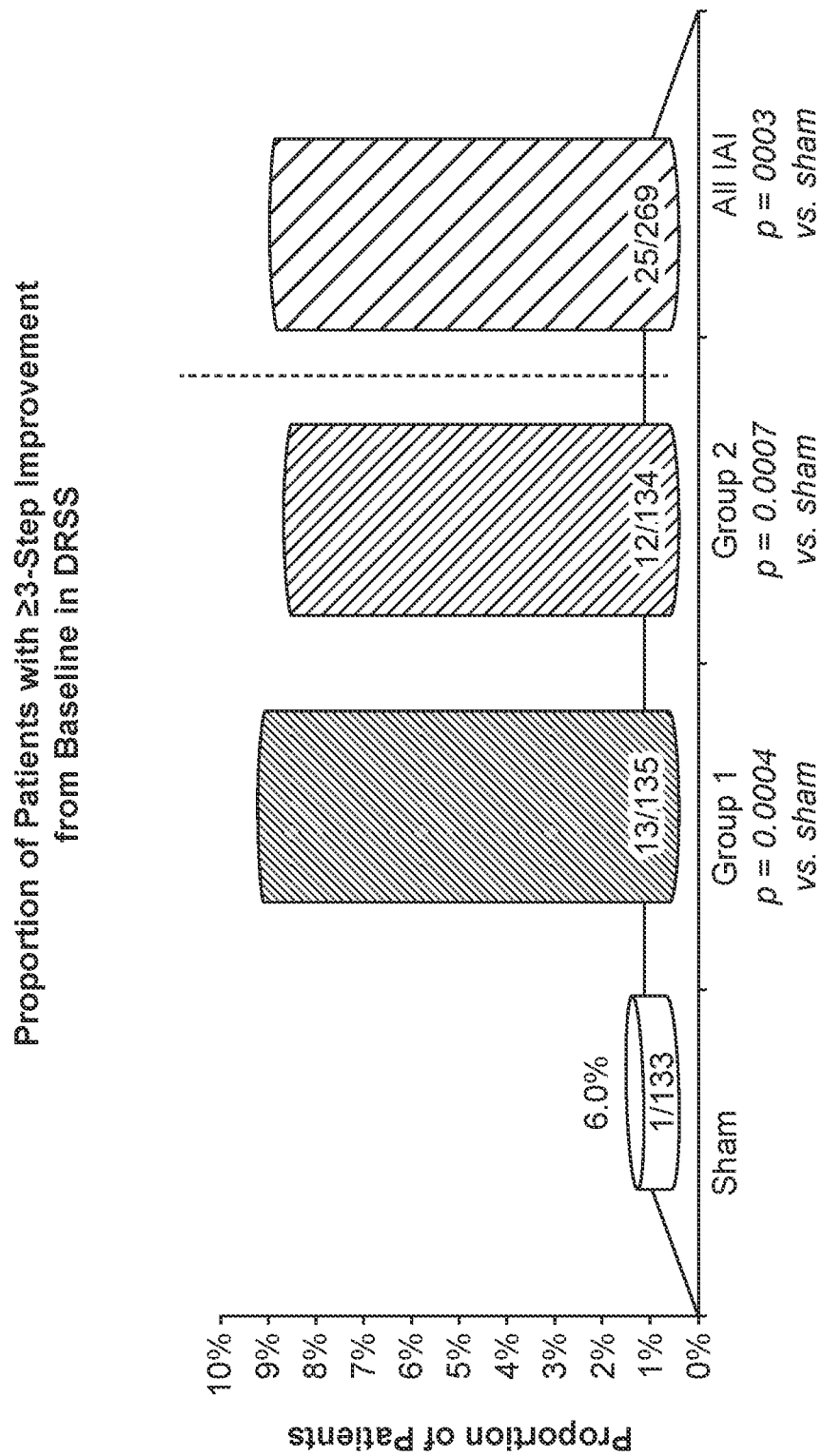
FIG. 9 shows the proportion (%) of PANORAMA patients in each dosing group (sham, Group 1, Group 2 and All IAI (combined Group 1 and Group 2)) achieving ≥3-step improvement from baseline on the diabetic retinopathy severity scale (DRSS). Sham n=133, Group 1 n=135, Group 2 n=134, All IAI n=269
Figure 32:
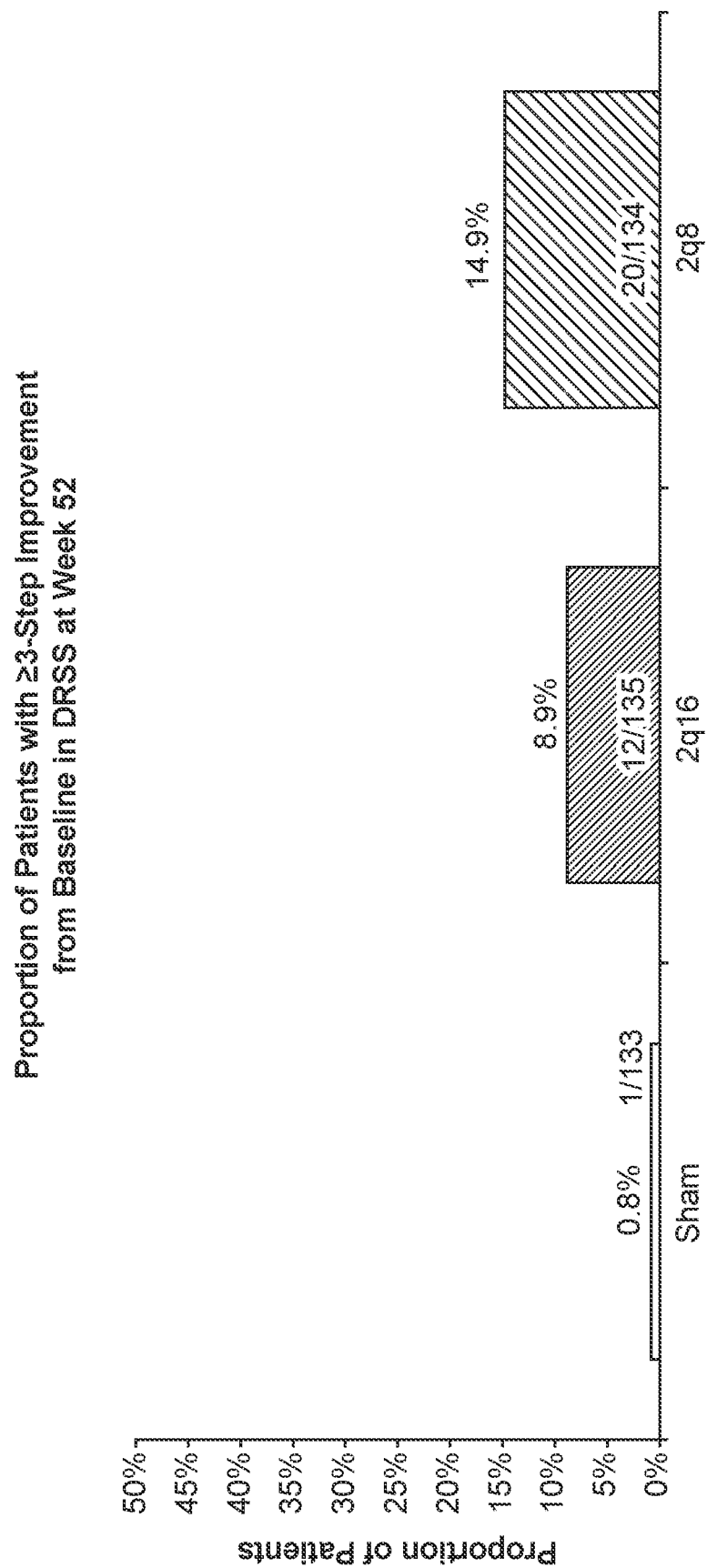
FIG. 32 summarizes the proportion of patents with a three step improvement or more in each treatment group (sham, 2q16 and 2q8) after 52 weeks. LOCF; Sham n=133, 2q16 n=135, 2q8 n=134. *nominal p<0.001 vs. sham.

The proportion of patients with ≥2-step improvement in the DRSS was significantly greater in the IA groups vs sham. See FIGS. 8, 19, 21 and 22. Patients also achieved ≥3-step improvement in the IA groups vs. Sham. See FIGS. 9 and 32.

Figure 10:
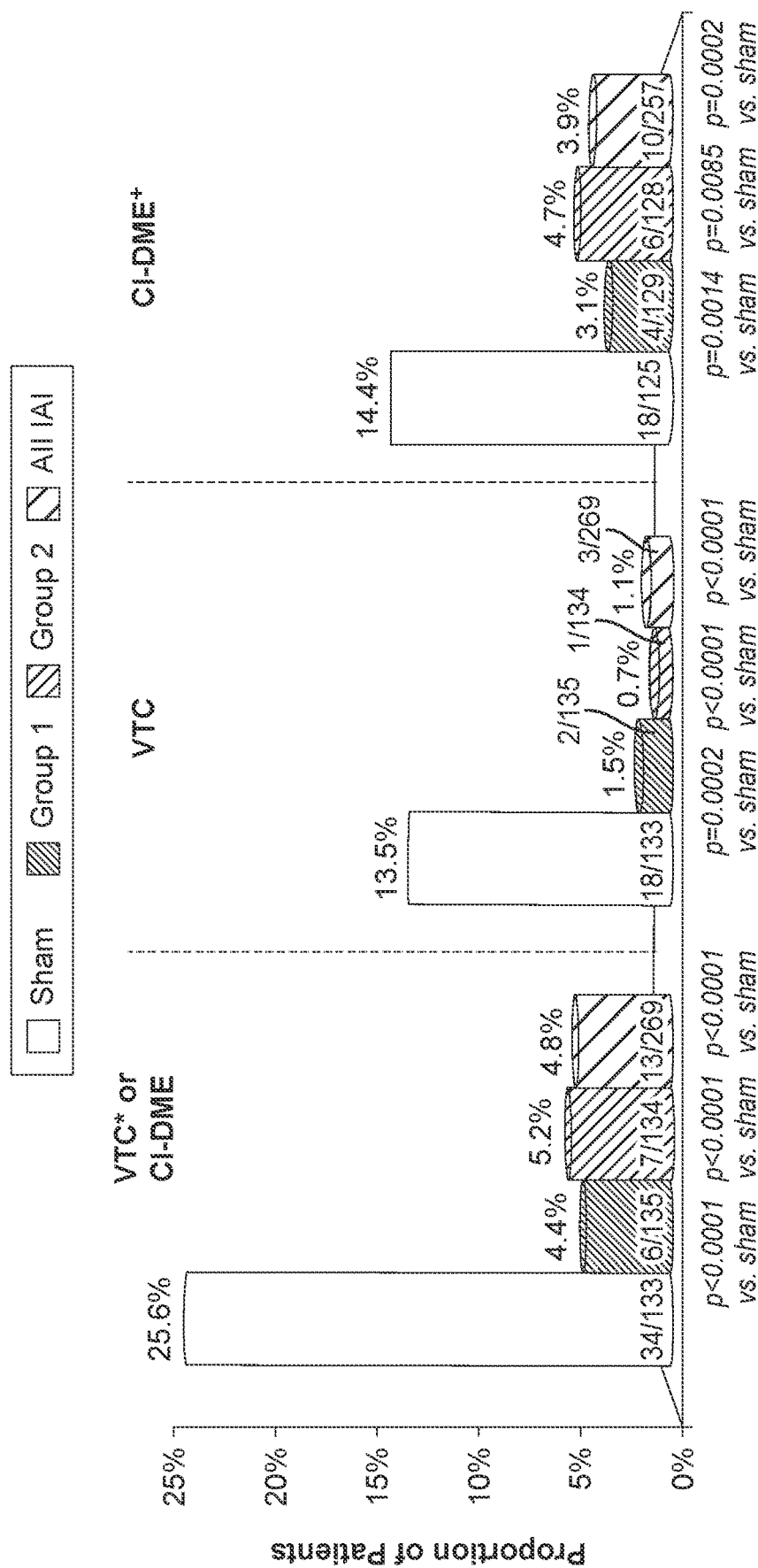
FIG. 10 shows the proportion (%) of PANORAMA patients in each dosing group (sham, Group 1, Group 2 and All IAI (combined Group 1 and Group 2)) experiencing vision threatening complications (VTC; proliferative diabetic retinopathy (PDR)/anterior segment neovascularization (ASNV))) and/or center involved diabetic macular edema (CI-DME) through week 24. +CI-DME evaluable set excludes patients who at baseline had CRT>300 μm and had qualitative evidence of CI-DME as assessed by the reading center.
Figure 23:
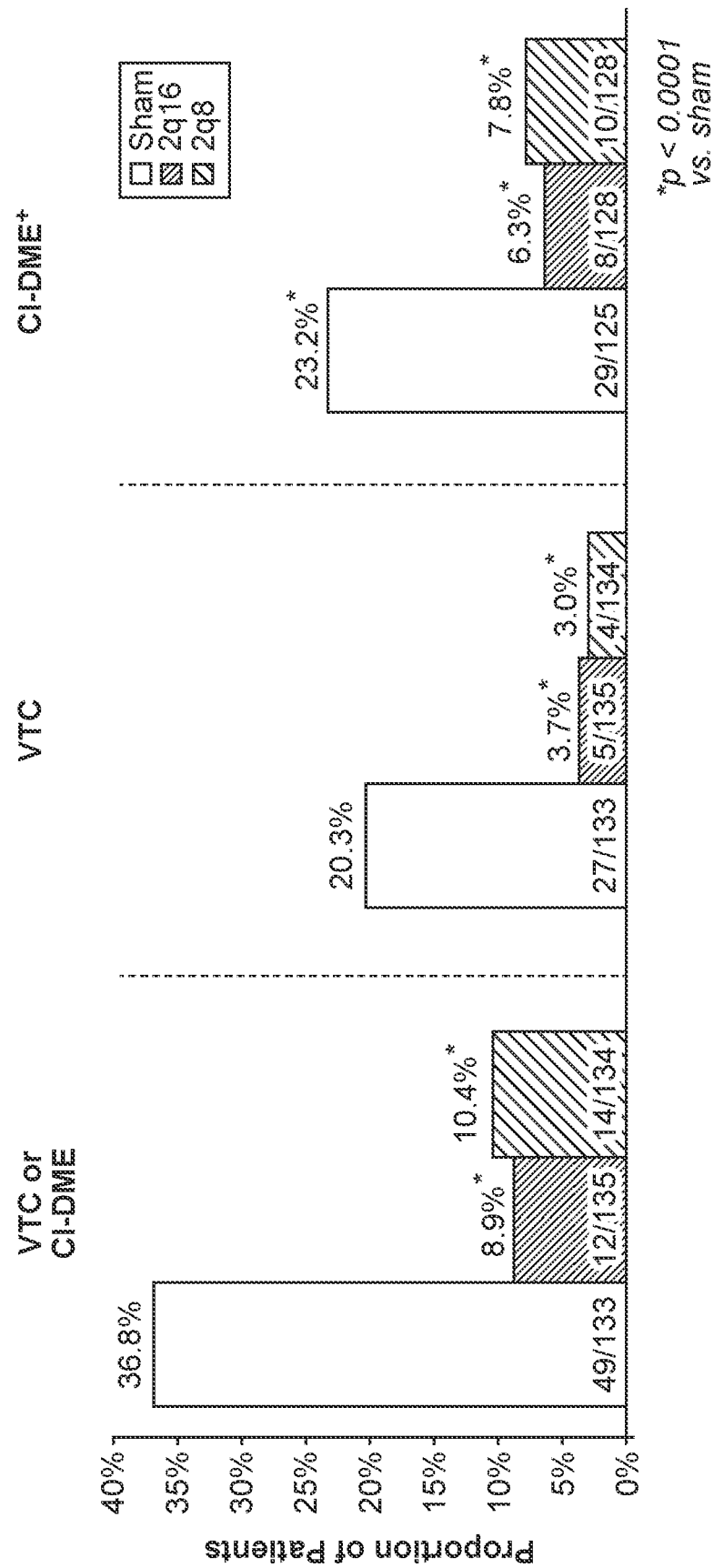
FIG. 23 summarizes the percentage of patients in each treatment group (sham, 2q16 and 2q8) developing a vision threatening complication (VTC; such as PDR/ASNV) and/or center-involved diabetic macular edema (CI-DME) through week 52. *CI-DME evaluable set excluded patients who, at baseline, both had CRT>300 μm and qualitative evidence of CI-DME as assessed by the reading center. *p<0.001, vs. sham.
Figure 24:
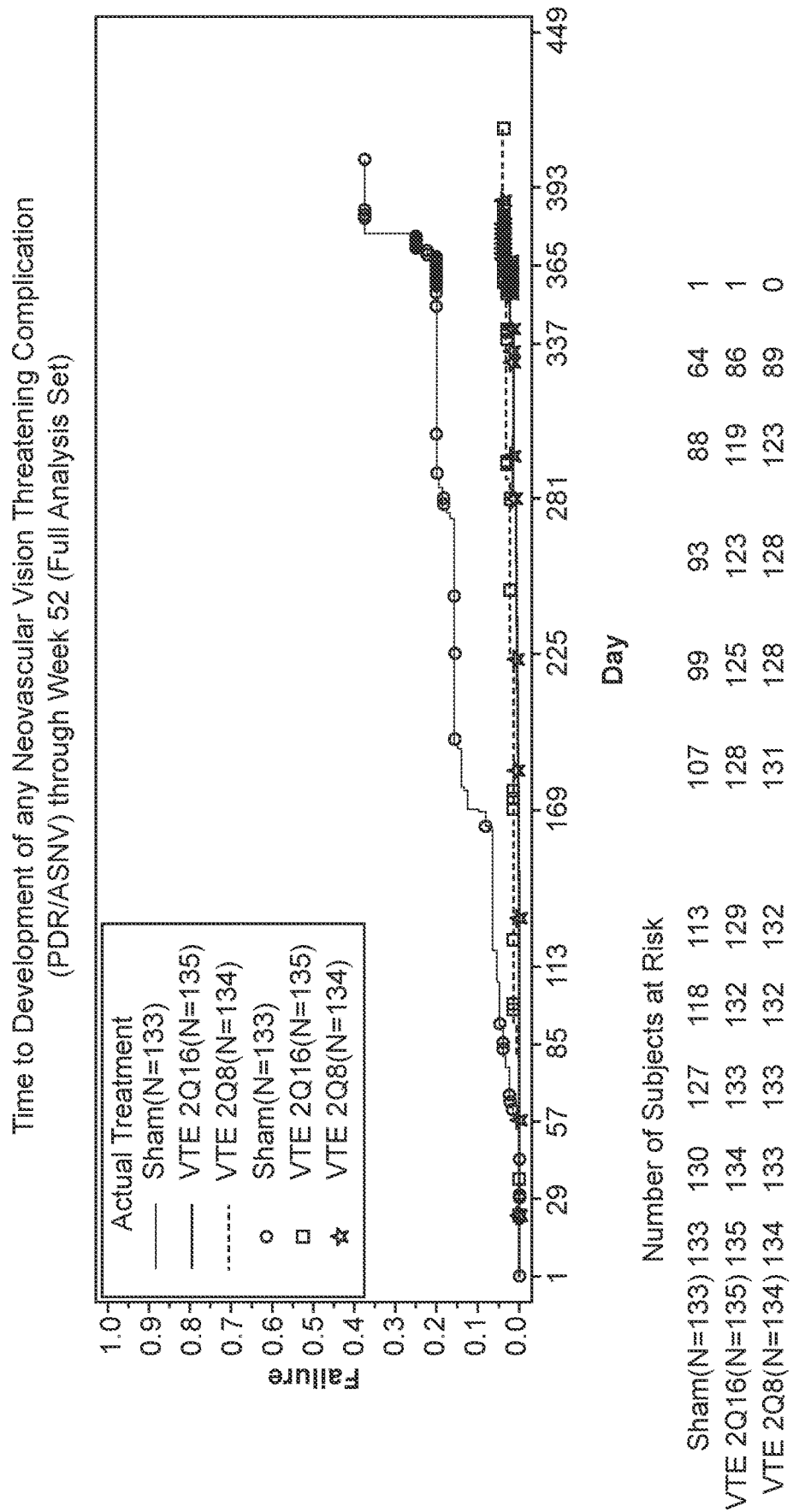
FIG. 24 is a Kaplan-Meier plot of the probability of developing a vision threatening complication over time for subjects in each treatment group (sham, 2q16 and 2q8). VTE=VEGF Trap eye. VTC=vision threatening complication, PDR/ASNV. +CI-DME evaluable set excluded patients who, at baseline, both had CRT>300 μm and qualitative evidence of CI-DME as assessed by the reading center. Note: VTE 2Q8: aflibercept 2 mg Q8 to week 45 after 5 initial monthly doses; VTE 2Q16: aflibercept 2 mg Q16 after 3 initial monthly doses and 1 8-week interval. Patients who did not have an event were considered at their last visit at or before the Week 52 visit.
Figure 25:
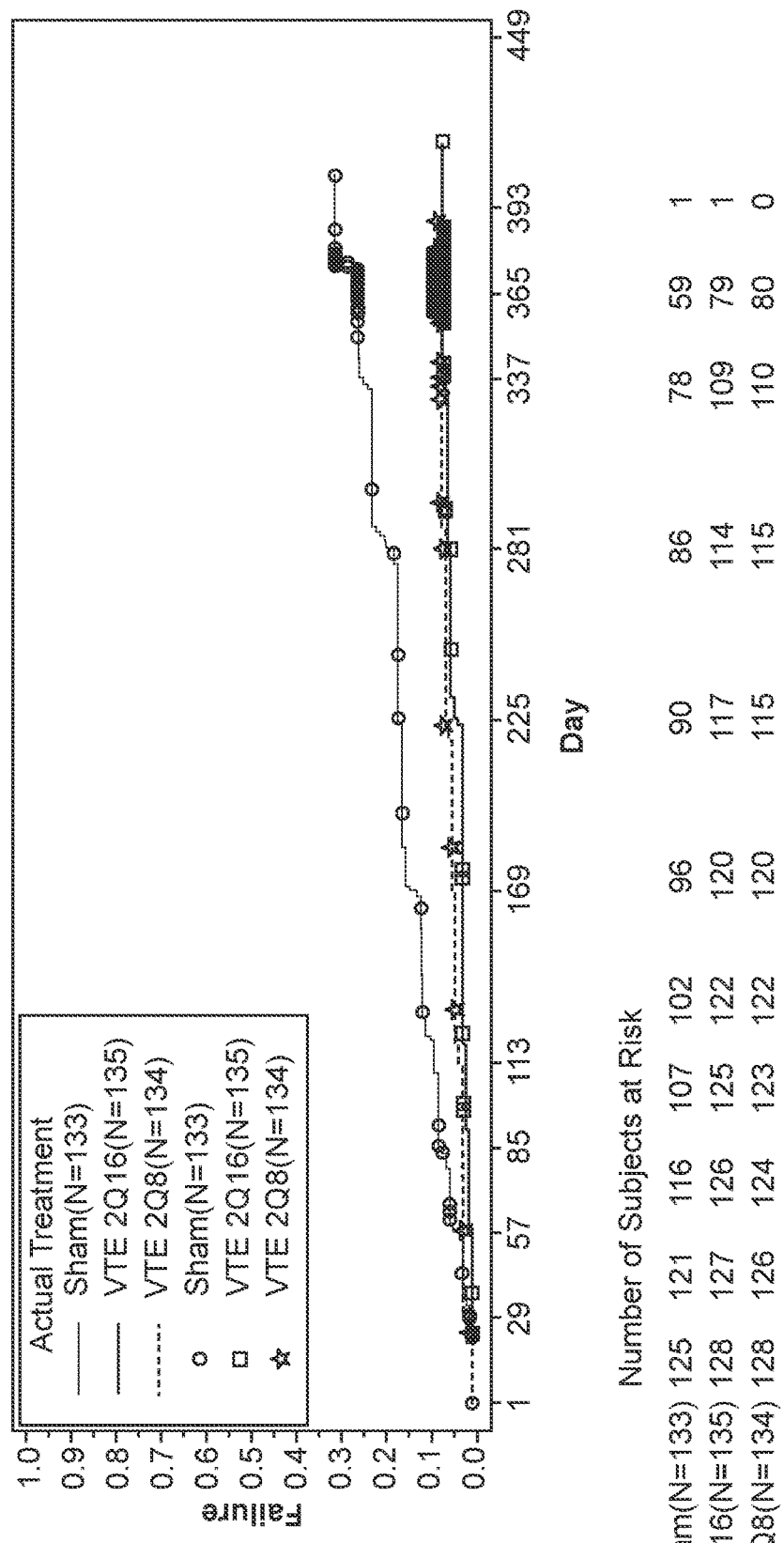
FIG. 25 summarizes the time for subjects in each treatment group (sham, 2q16 and 2q8) to develop CI-DME. Note: VTE 2Q8: aflibercept 2 mg Q8 to week 48 after 5 initial monthly doses; VTE 2Q16: aflibercept 2 mg Q16 after 3 initial monthly doses and 1 8-week interval. Includes all FAS patients who did not develop CI-DME before first study treatment and satisfied any of the following conditions: 1. CRT<=300 nM at baseline; 2.CRT>300 uM at baseline and intraretinal fluid is not 'definite, center subfield involved' and cystoid spaces is not 'definite, center subfield involved' and subretinal fluid (SSRD) is not 'present' as assessed by reading Center. Patients who did not have an event were censored at their last visit at or before the Week 52 visit. VTC=Vision threatening complication, PDR/ASNV. +CI-DME evaluable set excluded patients who, at baseline, both had CRT>300 μm and qualitative evidence of CI-DME as assessed by the reading center.

IA reduced the number of patients who developed a VTC and CI-DME. At 24 and 52 weeks, the proportion of patients experiencing a VTC and/or DME is summarized in FIGS. 10 and 23. A Kaplan-Meier analysis of the probability of developing a VTC or CI-DME in patients in each treatment group over time is set forth in FIGS. 24 and 25. A vision threatening complication (VTC) is progression to proliferative diabetic retinopathy (PDR) and anterior segment neovascularization (ASNV).

Figure 11:
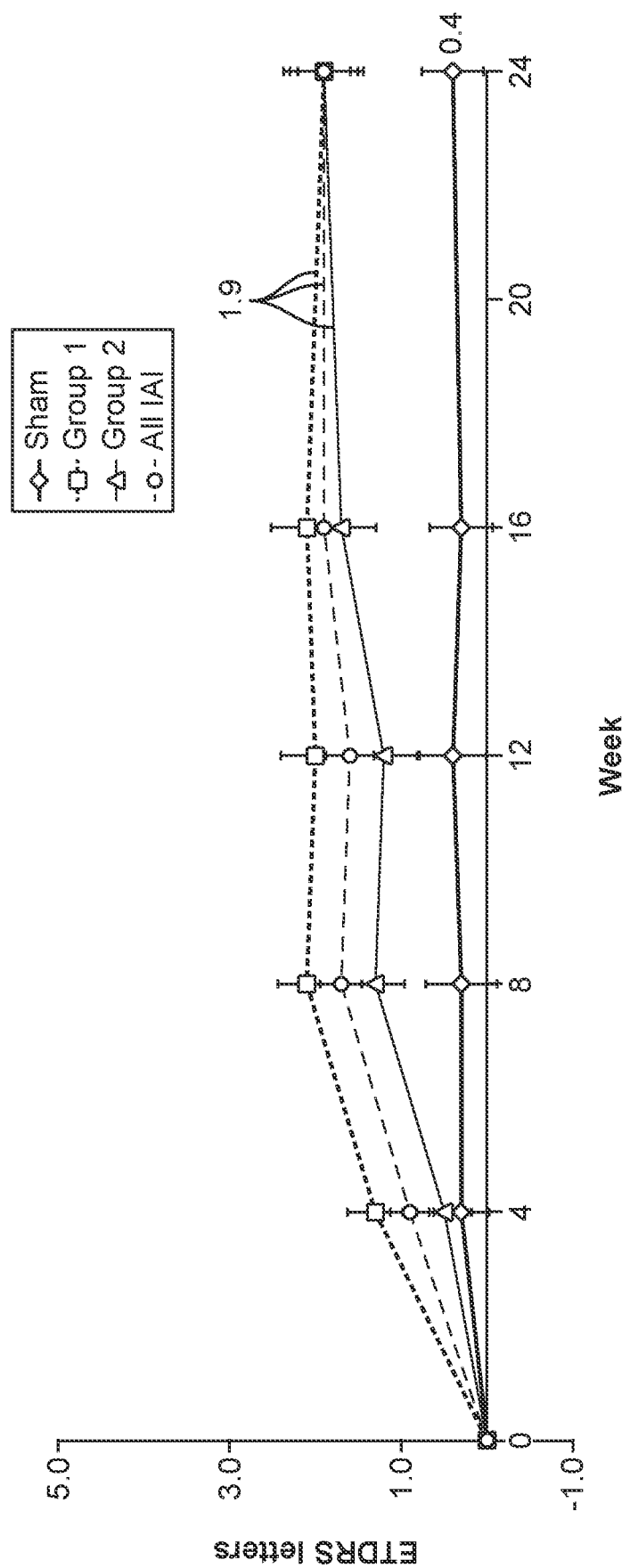
FIG. 11 summarizes the mean change in best corrected visual acuity (BCVA) score (early treatment diabetic retinopathy study (ETDRS) letters) of each PANORAMA dosing group (sham, Group 1, Group 2 and the combination of Group 1 and Group 2: "All IAI") up to 24 weeks. LOCF.; Sham n=133, Group 1 n=135, Group 2 n=134, All IAI n=269. p=0.0057 All IAI vs. sham; p=0.0194 Group 1 vs. sham; p=0.0139 Group 2 vs. sham.
Figure 12:
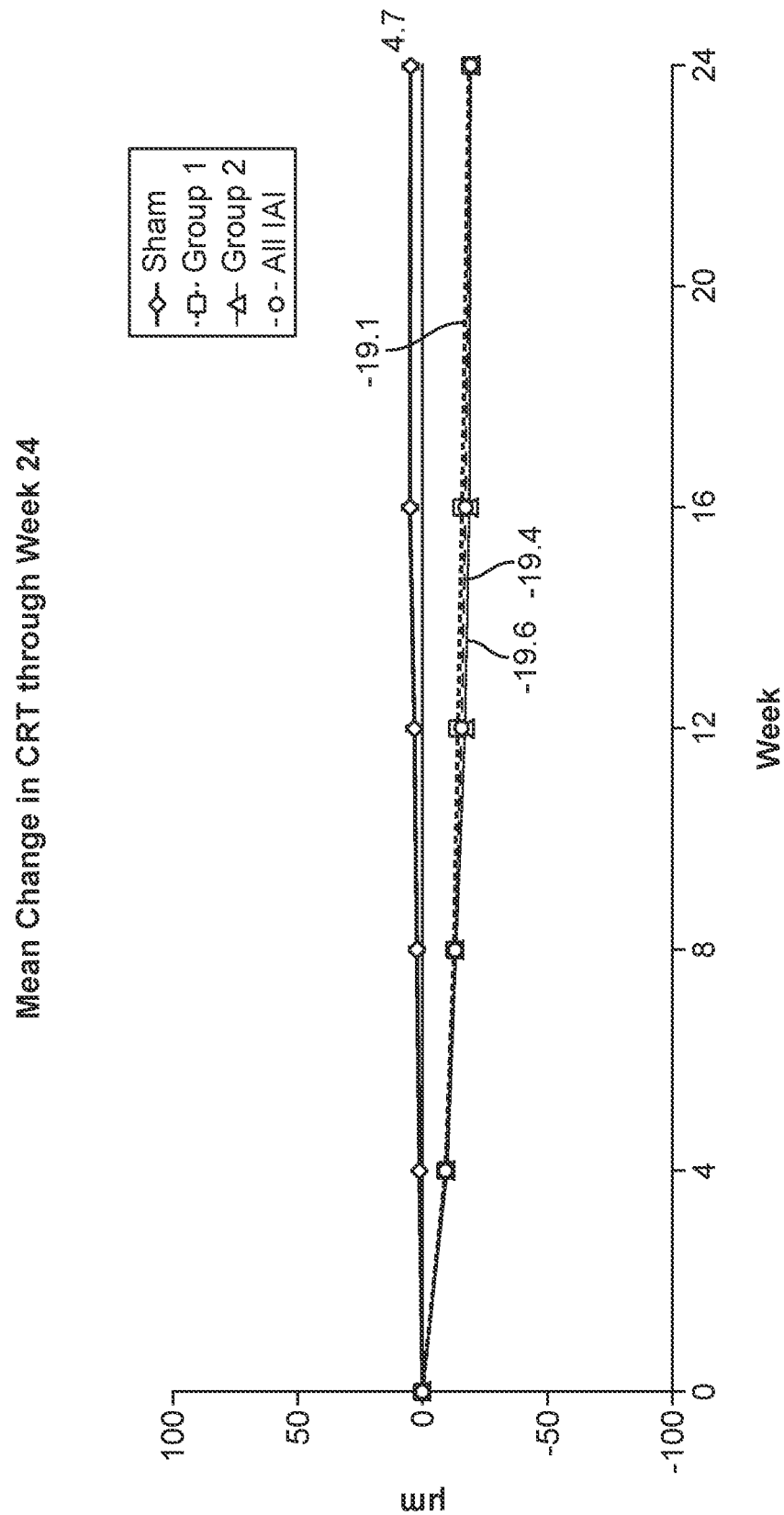
FIG. 12 summarizes the mean change in central retinal thickness (CRT, m) of each PANORAMA dosing group (sham, Group 1, Group 2 and All IAI (combined Group 1 and Group 2)) through Week 24. LOCF; Sham n=133, Group 1 n=135, Group 2 n=134, All IAI n=269. p<0.0001, All vs. sham.
Figure 19:
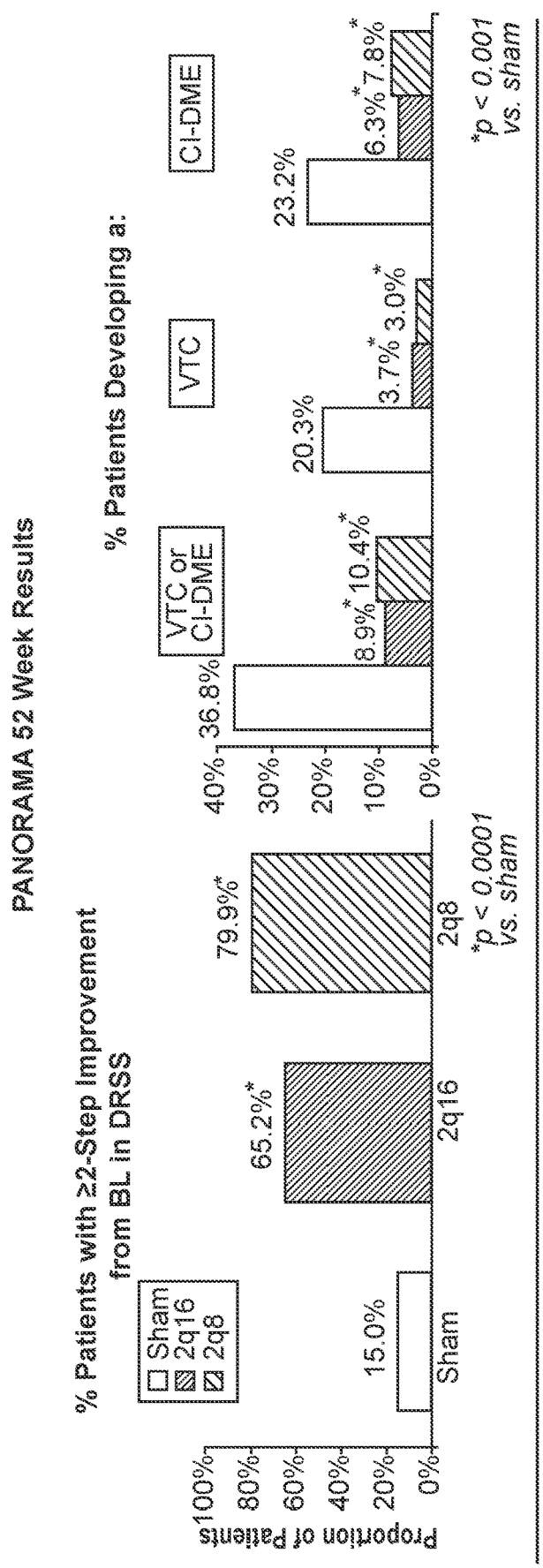
FIG. 19 is a summary of the results of the PANORAMA trial after 52 weeks-percentage of patients in each treatment group experiencing at least a 2 step improvement in DRSS and the percentage of subjects developing a vision threatening complication (VTC) and/or center-involved diabetic macular edema (CI-DME). The proportion of patients with ≥2-step DRSS improvement was significantly greater with aflibercept vs sham; Rate was greater in 2q8 group compared with 2q16. Vision threatening complications (PDR/ASNV) and CI-DME occurred in a substantially greater proportion of sham patients; Rates were similar between the 2q16 and 2q8 treatment groups. No new safety signals identified. LOCF; Sham n=133, 2q16 n=135, 2q8 n=134.
Figure 26:
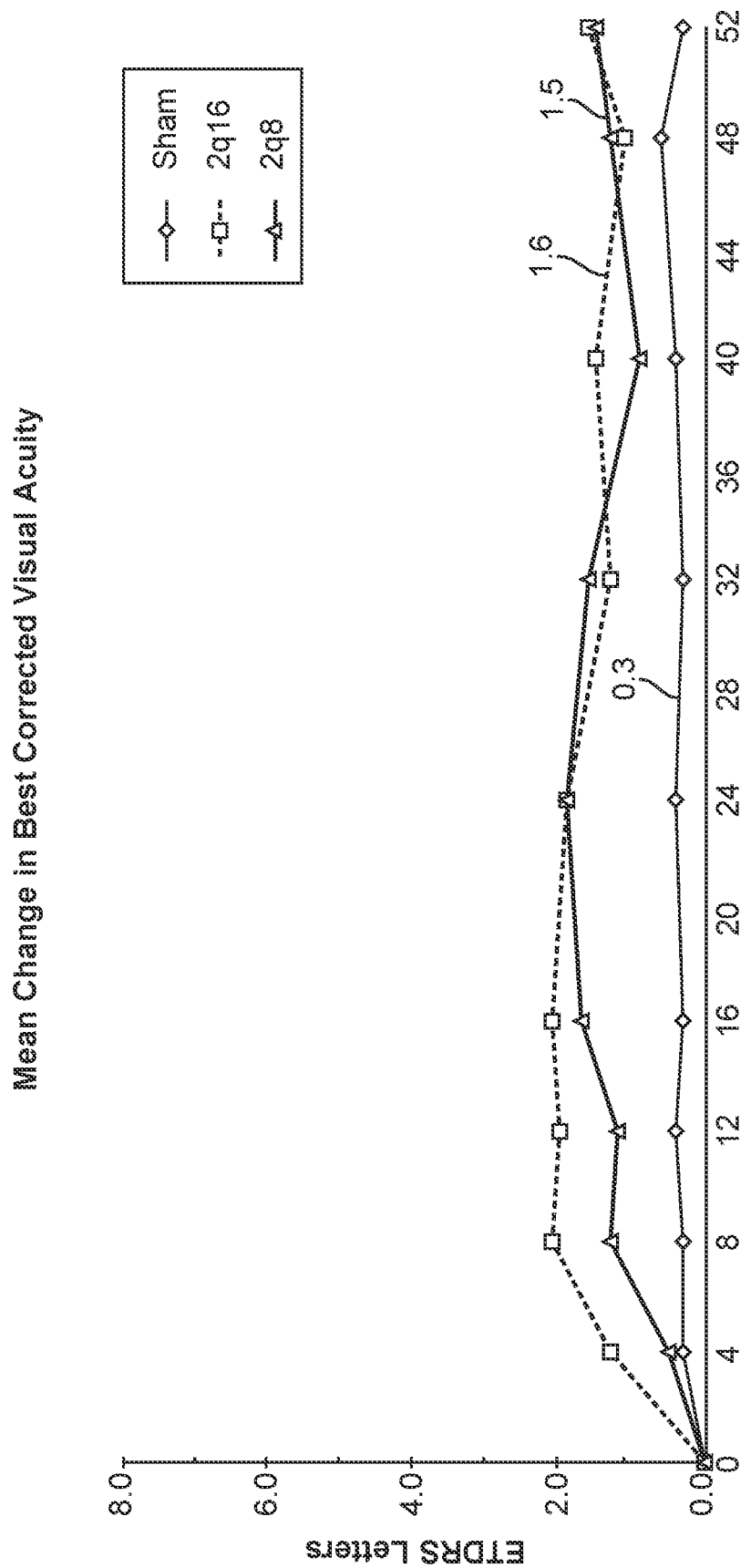
FIG. 26 summarizes the mean change in best corrected visual acuity (ETDRS letters) for subjects in each treatment group (sham, 2q16 and 2q8) over 52 weeks. LOCF; Sham n=133, 2q16 n=135, 2q8 n=134. p=0.0494 2q16 vs. sham; p=0.0895 2q8 vs. sham.
Figure 27:
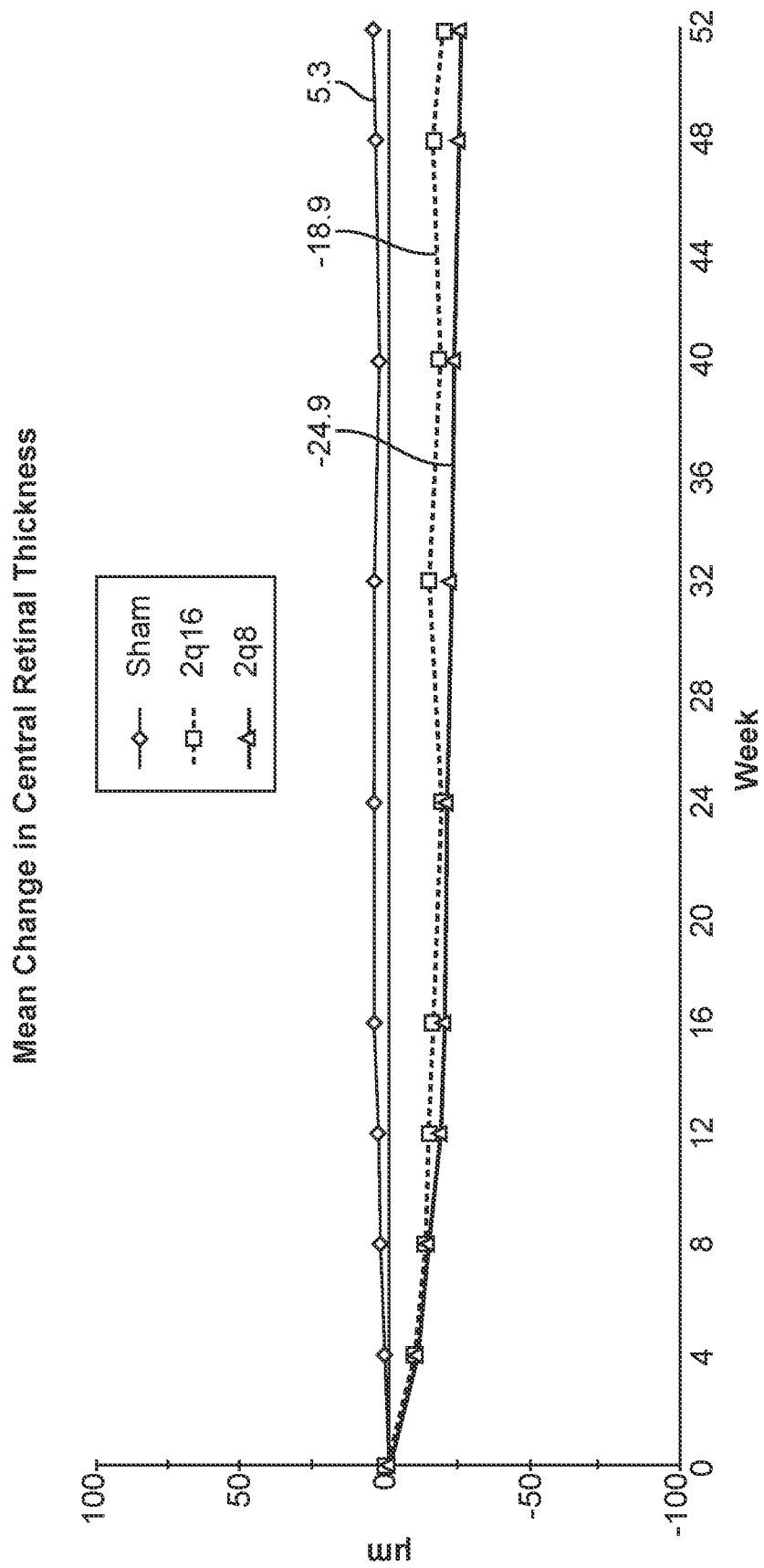
FIG. 27 summarizes the central retinal thickness (m) for subjects in each treatment group (sham, 2q16 and 2q8) over 52 weeks. LOCF; Sham n=133, 2q16 n=135, 2q8 n=134. p<0.0001, 2q16 and 2q8 vs. sham.

The changes in best corrected visual acuity (BCVA) experienced by patients in each treatment group at 24 and 52 weeks are summarized FIGS. 11 and 26. The changes to central retinal thickness of each treatment group is summarized in FIGS. 12 and 27.

Efficacy outcomes were similar in the 2Q16 (Group 1) and the 208 (Group 2) groups.

Ocular treatment emergent adverse events at 24 and 52 weeks (TEAEs) (FIGS. 13 and 28, respectively), ocular serious TEAEs at 24 and 52 weeks (FIGS. 14 and 29, respectively), intra-ocular inflammation at 24 and 52 weeks (FIGS. 15 and 30, respectively), and Anti-Platelet Trialists' Collaboration (APTC) events at 24 and 52 weeks (FIGS. 16 and 31, respectively) and deaths at 24 weeks (FIG. 17) are provided. At 52 weeks, there was a total of 7 deaths (7 in the sham treatment group and 1 in the q8w treatment group). (APTC: See Antithrombotic Trialists' Collaboration. Collaborative overview of randomized trial of antiplatelet therapy—II: Maintenance of vascular graft or arterial patency by antiplatelet therapy. Br Med J 1994; 308:168-171; and Antithrombotic Trialists' Collaboration. Collaborative meta-analysis of randomised trials of antiplatelet therapy for prevention of death, myocardial infarction, and stroke in high risk patients. Br Med J 2002; 324:71-86).

Sequences

SEQ ID NO: 1 (DNA sequence having 1377 nucleotides):
ATGGTCAGCTACTGGGACACCGGGGTCCTGCTGTGCGCGCTGCTCAGCTG

TCTGCTTCTCACAGGATCTAGTTCCGGAAGTGATACCGGTAGACCTTTCG

TAGAGATGTACAGTGAAATCCCCGAAATTATACACATGACTGAAGGAAGG

GAGCTCGTCATTCCCTGCCGGGTTACGTCACCTAACATCACTGTTACTTT

-continued
AAAAAAGTTTCCACTTGACACTTTGATCCCTGATGGAAAACGCATAATCT

GGGACAGTAGAAAGGGCTTCATCATATCAAATGCAACGTACAAAGAAATA

GGGCTTCTGACCTGTGAAGCAACAGTCAATGGGCATTTGTATAAGACAAA

CTATCTCACACATCGACAAACCAATACAATCATAGATGTGGTTCTGAGTC

CGTCTCATGGAATTGAACTATCTGTTGGAGAAAAGCTTGTCTTAAATTGT

ACAGCAAGAACTGAACTAAATGTGGGGATTGACTTCAACTGGGAATACCC

TTCTTCGAAGCATCAGCATAAGAAACTTGTAAACCGAGACCTAAAAACCC

AGTCTGGGAGTGAGATGAAGAAATTTTTGAGCACCTTAACTATAGATGGT

GTAACCCGGAGTGACCAAGGATTGTACACCTGTGCAGCATCCAGTGGGCT

GATGACCAAGAAGAACAGCACATTTGTCAGGGTCCATGAAAAGGACAAAA

CTCACACATGCCCACCGTGCCCAGCACCTGAACTCCTGGGGGGACCGTCA

GTCTTCCTCTTCCCCCCAAAACCCAAGGACACCCTCATGATCTCCCGGAC

CCCTGAGGTCACATGCGTGGTGGTGGACGTGAGCCACGAAGACCCTGAGG

TCAAGTTCAACTGGTACGTGGACGGCGTGGAGGTGCATAATGCCAAGACA

AAGCCGCGGGAGGAGCAGTACAACAGCACGTACCGTGTGGTCAGCGTCCT

CACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCT

CTACAGCAAGCTCACCGTGGACAAGAGCAGGTGGCAGCAGGGGAACGTCT

TCTCATGCTCCGTGATGCATGAGGCTCTGCACAACCACTACACGCAGAAG

AGCCTCTCCCTGTCTCCGGGTAAATGA

SEQ ID NO: 2 (polypeptide sequence having 458 amino acids):
MVSYWDTGVLLCALLSCLLLTGSSSGSDTGRPFVEMYSEIPEIIHMTEGR

ELVIPCRVTSPNITVTLKKFPLDTLIPDGKRIIWDSRKGFIISNATYKEI

GLLTCEATVNGHLYKTNYLTHRQTNTIIDVVLSPSHGIELSVGEKLVLNC

TARTELNVGIDFNWEYPSSKHQHKKLVNRDLKTQSGSEMKKFLSTLTIDG

VTRSDQGLYTCAASSGLMTKKNSTFVRVHEKDKTHTCPPCPAPELLGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for achieving a reduction of at least 2 steps in a Diabetic Retinopathy Severity Scale (DRSS) in a patient in need thereof with moderately severe to severe nonproliferative diabetic retinopathy without center-involved diabetic macular edema comprising administering, by intravitreal injection to an eye of the patient, 5 doses about once a month followed by one or more secondary doses about once every 8 weeks; of about 2 mg of VEGF receptor-based chimeric fusion protein; and wherein the patient achieves a reduction of at least 2 steps in the DRSS.

2. The method of claim 1 wherein the VEGF receptor-based chimeric fusion protein comprises:
   a VEGFR1 component comprising amino acids 27 to 129 of SEQ ID NO:2;
   a VEGFR2 component comprising amino acids 130-231 of SEQ ID NO:2; and
   a multimerization component comprising amino acids 232-457 of SEQ ID NO:2.

3. The method of claim 1 wherein the VEGF receptor-based chimeric fusion protein is aflibercept.

4. The method of claim 3 wherein the aflibercept is in a pharmaceutical formulation comprising histidine buffer.

5. The method of claim 4 wherein the aflibercept is in a pharmaceutical formulation comprising histidine buffer, a sugar, and a surfactant.

6. The method of claim 5 wherein the aflibercept in the pharmaceutical formulation is at a concentration of about 40 mg/ml.

7. The method of claim 6 wherein the aflibercept is administered by intravitreal injection from a 30-gauge needle to an eye of the patient.

8. The method of claim 3 wherein the patient achieves a gain of one or more letters on the ETDRS chart within about 24 weeks from the initiation of treatment.

9. The method of claim 3 wherein the patient achieves a reduction in central retinal thickness within about 24 weeks from the initiation of treatment.

10. The method of claim 3 wherein the patient in need thereof is administered the aflibercept and achieves, within 24 weeks from the initiation of treatment, one or more of:
    (i) an improvement in best corrected visual acuity of at least about 1.9 letters;
    (ii) does not experience a reduction in best corrected visual acuity of any more than 4 letters;
    (iii) does not develop diabetic macular edema;
    (iv) does not experience a vision threatening complication;
    (v) does not develop anterior segment neovascularization; and
    (vi) experiences a reduction in central retinal thickness of about 19 μm.

11. The method of claim 3 wherein the patient in need thereof is administered the aflibercept and achieves, within 52 weeks from the initiation of treatment, one or more of:
    (i) an improvement in best corrected visual acuity of at least about 1.9 letters;
    (ii) does not experience a reduction in best corrected visual acuity of any more than 4 letters;
    (iii) does not develop diabetic macular edema;
    (iv) does not experience a vision threatening complication;
    (v) does not develop anterior segment neovascularization; and
    (vi) experiences a reduction in central retinal thickness of about 19 μm.

12. The method of claim 1 wherein the patient in need thereof achieves the reduction within about 24 weeks from initiation of treatment.

13. The method of claim 1 wherein the patient in need thereof achieves the reduction within about 52 weeks from initiation of treatment.

14. The method of claim 1 wherein the patient achieves a reduction of at least 3 steps in the Diabetic Retinopathy Severity Scale (DRSS).

15. The method of claim 1 further comprising achieving in the patient a reduction of at least 3 steps in the Diabetic Retinopathy Severity Scale (DRSS) at about 24 weeks from initiation of treatment.

16. The method of claim 1 further comprising achieving in the patient a reduction of at least 3 steps in the Diabetic Retinopathy Severity Scale (DRSS) at about 52 weeks from initiation of treatment.

17. A method for achieving a reduction of at least 2 steps in a Diabetic Retinopathy Severity Scale (DRSS) in a patient in need thereof with moderately severe to severe nonproliferative diabetic retinopathy without center-involved diabetic macular edema comprising:
    administering, by intravitreal injection to an eye of the patient, 5 doses about once a month followed by one or more secondary doses about once every 8 weeks of about 2 mg of a VEGF receptor-based chimeric fusion protein,
    measuring DRSS of the patient at least once between the initial dose and 52 weeks following the initial dose, and wherein the patient achieves a reduction of at least 2 steps in the DRSS.

18. The method of claim 17 wherein the VEGF receptor-based chimeric fusion protein comprises (1) an immunoglobulin-like (Ig) domain 2 of VEGFR1 and (2) Ig domain 3 of VEGFR2, and (3) a multimerizing component.

19. The method of claim 17 wherein the VEGF receptor-based chimeric fusion protein comprises:
    a VEGFR1 component comprising amino acids 27 to 129 of SEQ ID NO:2;
    a VEGFR2 component comprising amino acids 130-231 of SEQ ID NO:2; and
    a multimerization component comprising amino acids 232-457 of SEQ ID NO:2.

20. The method of claim 17 wherein the patient in need thereof is administered the VEGF receptor-based chimeric fusion protein, which is aflibercept, and achieves, within about 24 weeks from initiation of treatment, one or more of:
    (i) an improvement in best corrected visual acuity of at least about 1.9 letters;
    (ii) does not experience a reduction in best corrected visual acuity of any more than 4 letters;
    (iii) does not develop diabetic macular edema;
    (iv) does not experience a vision threatening complication;
    (v) does not develop anterior segment neovascularization; and
    (vi) experiences a reduction in central retinal thickness of about 19 μm.

21. The method of claim 17 wherein the VEGF receptor-based chimeric fusion protein is aflibercept.

22. The method of claim 21 wherein the aflibercept is in a pharmaceutical formulation comprising histidine buffer.

23. The method of claim 21 wherein the aflibercept is in a pharmaceutical formulation comprising histidine buffer, a sugar, and a surfactant.

24. The method of claim 23 wherein the aflibercept in the pharmaceutical formulation is at a concentration of about 40 mg/ml.

25. The method of claim 24 wherein the aflibercept is administered by intravitreal injection from a 30-gauge needle to an eye of the patient.

26. The method of claim 21 wherein the patient achieves a gain of one or more letters on the ETDRS chart within about 24 weeks from the initiation of treatment.

27. The method of claim 21 wherein the patient achieves a reduction in central retinal thickness within about 24 weeks from the initiation of treatment.

28. The method of claim 17 wherein the patient in need thereof achieves the reduction within about 24 weeks from initiation of treatment.

29. The method of claim 17 wherein the patient in need thereof achieves the reduction within about 52 weeks from initiation of treatment.

30. The method of claim 17, further comprising achieving in the patient a reduction of at least 3 steps in the DRSS.

31. The method of claim 17 further comprising achieving in the patient a reduction of at least 3 steps in the Diabetic Retinopathy Severity Scale (DRSS) at about 24 weeks from initiation of treatment.

32. The method of claim 17 further comprising achieving in the patient a reduction of at least 3 steps in the Diabetic Retinopathy Severity Scale (DRSS) at about 52 weeks from initiation of treatment.

33. The method of claim 17 wherein the patient in need thereof prior to said administering has one or more of:
   (i) diabetes;
   (ii) a hemoglobin A1c of about 8.5;
   (iii) an Early Treatment Diabetic Retinopathy Study Best Corrected Visual Acuity score of about 82;
   (iv) a central retinal thickness of about 247 μm;
   (v) a Diabetic Retinopathy Severity Score of 47;
   (vi) a Diabetic Retinopathy Severity Score of 53; and
   (vii) is about 56 years of age.

* * * * *

UNITED STATES PATENT AND TRADEMARK OFFICE
CERTIFICATE OF CORRECTION

PATENT NO. : 12,280,093 B2
APPLICATION NO. : 17/148039
DATED : April 22, 2025
INVENTOR(S) : Robert L. Vitti et al.

Page 1 of 1

It is certified that error appears in the above-identified patent and that said Letters Patent is hereby corrected as shown below:

On the Title Page

Item "(73) Assignee:": Please replace "REGENRON" with --REGENERON--

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 2

<210> SEQ ID NO 1
<211> LENGTH: 1377
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| atggtcagct | actgggacac | cggggtcctg | ctgtgcgcgc | tgctcagctg | tctgcttctc | 60 |
| acaggatcta | gttccggaag | tgataccggt | agaccttcg | tagagatgta | cagtgaaatc | 120 |
| cccgaaatta | tacacatgac | tgaaggaagg | gagctcgtca | ttccctgccg | ggttacgtca | 180 |
| cctaacatca | ctgttacttt | aaaaaagttt | ccacttgaca | ctttgatccc | tgatggaaaa | 240 |
| cgcataatct | gggacagtag | aaagggcttc | atcatatcaa | atgcaacgta | caagaaaata | 300 |
| gggcttctga | cctgtgaagc | aacagtcaat | gggcatttgt | ataagacaaa | ctatctcaca | 360 |
| catcgacaaa | ccaatacaat | catagatgtg | gttctgagtc | cgtctcatgg | aattgaacta | 420 |
| tctgttggag | aaaagcttgt | cttaaattgt | acagcaagaa | ctgaactaaa | tgtggggatt | 480 |
| gacttcaact | gggaataccc | ttcttcgaag | catcagcata | agaaacttgt | aaaccgagac | 540 |
| ctaaaaccc | agtctgggag | tgagatgaag | aaatttttga | gcaccttaac | tatagatggt | 600 |
| gtaacccgga | gtgaccaagg | attgtacacc | tgtgcagcat | ccagtgggct | gatgaccaag | 660 |
| aagaacagca | catttgtcag | ggtccatgaa | aaggacaaaa | ctcacacatg | cccaccgtgc | 720 |
| ccagcacctg | aactcctggg | gggaccgtca | gtcttcctct | tccccccaaa | acccaaggac | 780 |
| accctcatga | tctcccggac | ccctgaggtc | acatgcgtgg | tggtggacgt | gagccacgaa | 840 |
| gaccctgagg | tcaagttcaa | ctggtacgtg | gacggcgtgg | aggtgcataa | tgccaagaca | 900 |
| aagccgcggg | aggagcagta | caacagcacg | taccgtgtgg | tcagcgtcct | caccgtcctg | 960 |
| caccaggact | ggctgaatgg | caaggagtac | aagtgcaagg | tctccaacaa | agccctccca | 1020 |
| gcccccatcg | agaaaaccat | ctccaaagcc | aagggcagc | ccgagaacc | acaggtgtac | 1080 |
| accctgcccc | catcccggga | tgagctgacc | aagaaccagg | tcagcctgac | ctgcctggtc | 1140 |
| aaaggcttct | atcccagcga | catcgccgtg | gagtgggaga | gcaatgggca | gccggagaac | 1200 |
| aactacaaga | ccacgcctcc | cgtgctggac | tccgacggct | ccttcttcct | ctacagcaag | 1260 |
| ctcaccgtgg | acaagagcag | gtggcagcag | gggaacgtct | tctcatgctc | cgtgatgcat | 1320 |
| gaggctctgc | acaaccacta | cacgcagaag | agcctctccc | tgtctccggg | taaatga | 1377 |

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

```
Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```